United States Patent
Yang et al.

(10) Patent No.: US 12,415,858 B2
(45) Date of Patent: Sep. 16, 2025

(54) ANTI-TIGIT ANTIBODIES, MULTISPECIFIC ANTIBODIES COMPRISING THE SAME, AND METHODS OF USING THE SAME

(71) Applicant: SHANGHAI HENLIUS BIOTECH, INC., Shanghai (CN)

(72) Inventors: Ming Yang, Shanghai (CN); Wenfeng Xu, Shanghai (CN); Wei-Dong Jiang, Shanghai (CN); Jie Xue, Shanghai (CN)

(73) Assignee: SHANGHAI HENLIUS BIOTECH, INC., Shanghai (CN)

( * ) Notice: Subject to any disclaimer, the term of this patent is extended or adjusted under 35 U.S.C. 154(b) by 704 days.

(21) Appl. No.: 17/811,541

(22) Filed: Jul. 8, 2022

(65) Prior Publication Data

US 2023/0037911 A1    Feb. 9, 2023

Related U.S. Application Data

(63) Continuation of application No. PCT/CN2021/070899, filed on Jan. 8, 2021.

(30) Foreign Application Priority Data

Jan. 10, 2020    (WO) ................ PCT/CN2020/071340

(51) Int. Cl.
*C07K 16/18* (2006.01)
*A61K 47/68* (2017.01)
*A61P 35/00* (2006.01)
*C07K 16/28* (2006.01)
*A61K 39/00* (2006.01)

(52) U.S. Cl.
CPC ...... *C07K 16/2827* (2013.01); *A61K 47/6843* (2017.08); *A61K 47/6849* (2017.08); *A61P 35/00* (2018.01); *C07K 16/18* (2013.01); *A61K 2039/505* (2013.01); *C07K 2317/24* (2013.01); *C07K 2317/31* (2013.01); *C07K 2317/35* (2013.01); *C07K 2317/565* (2013.01); *C07K 2317/569* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| | | |
|---|---|---|
| CN | 107207594 A | 9/2017 |
| CN | 108290946 A | 7/2018 |

(Continued)

OTHER PUBLICATIONS

Zhenwei Zhong, et al., "Development of a bispecific antibody targeting PD-L1 and TIGIT with optimal cytotoxicity," *Scientific Reports*, 12:18011, pp. 1-11 (2022).

(Continued)

*Primary Examiner* — Aurora M Fontainhas
(74) *Attorney, Agent, or Firm* — Finnegan, Henderson, Farabow, Garrett & Dunner, LLP

(57) ABSTRACT

Provided are anti-TIGIT antibodies that bind to "T cell immunoreceptor with Ig and ITIM domains (TIGIT)", including multispecific anti-TIGIT antibodies with binding specificity for TIGIT and one or more additional antigen, and methods of using the same. In certain embodiments, the anti-TIGIT antibodies comprises a single domain antibody that binds to TIGIT. In certain embodiments, the one or more additional antigen comprises Programmed cell death ligand 1 (PDL1).

21 Claims, 29 Drawing Sheets

Specification includes a Sequence Listing.

(56) References Cited

FOREIGN PATENT DOCUMENTS

| | | |
|---|---|---|
| CN | 109966487 A | 7/2019 |
| CN | 110818795 A | 2/2020 |
| JP | 2017520512 A | 7/2017 |
| JP | 2019528083 A | 10/2019 |
| WO | WO 2016/106302 | 6/2016 |
| WO | WO 2017/053748 | 3/2017 |
| WO | WO 2017/220990 A1 | 12/2017 |
| WO | WO 2018/128939 A1 | 7/2018 |
| WO | WO 2019/096121 A1 | 5/2019 |

OTHER PUBLICATIONS

Qing Zhang et al., "Blockade of the checkpoint receptor TIGIT prevents NK cell exhaustion and elicits potent anti-tumor immunity," *Nature Immunology*, vol. 19, pp. 723-732 (2018).

International Search Report for International Application No. PCT/CN2021/070899 mailed Mar. 26, 2021, (6 pages).

Johnston, R.J. et al., "The immunoreceptor TIGIT regulates antitumor and antiviral CD8(+)T cell effector function," Cancer Cell, vol. 26, Dec. 8, 2014 pp. 923-937 and supporting information (20 pages).

Ma, L. et al., "A novel bispecific nanobody with PD-L1 TIGIT dual immune checkpoint blockade," BBRC, vol. 531, No. 2, Oct. 15, 2020, pp. 144-151.

h-FcγRIIIA binding h-FcγRIIB binding m-FcγRIV binding

Anti-TIGIT x anti-PDL1-HCC

Anti-TIGIT x anti-PDL1-HCN

Tumor cells express both PDL1 & PVR

Tumor cells express PVR only

Tumor cells express PDL1

ANTI-TIGIT ANTIBODIES, MULTISPECIFIC ANTIBODIES COMPRISING THE SAME, AND METHODS OF USING THE SAME

CROSS-REFERENCE TO RELATED APPLICATIONS

This application is a continuation of International Application No. PCT/CN2021/070899, filed Jan. 8, 2021, which claims priority to International Patent Application No. PCT/CN2020/071340, filed Jan. 10, 2020, the contents of each of which are incorporated by reference in their entireties.

STATEMENT REGARDING SEQUENCE LISTING

The sequence listing associated with this application is provided in xml format and is hereby incorporated by reference in its entirety into the specification. The name of the xml file containing the sequence listing is FPCH22160189US_sequence_listing.xml; the xml file is 398 KB and was created on Aug. 23, 2022. The xml file is being submitted via Patent Center with the filing of the specification.

FIELD

The present invention relates to antibodies that bind to T cell immunoreceptor with Ig and ITIM domains (TIGIT), including multispecific anti-TIGIT antibodies with binding specificity for TIGIT and one or more additional antigen, and methods of using the same. In certain embodiments, the one or more additional antigen comprises Programmed cell death ligand 1 (PDL1).

BACKGROUND

T cell immunoreceptor with Ig and ITIM domains (TIGIT) is an immune checkpoint receptor expressed by immune cells such as activated T cells and Natural Killer cells (NK cells) and mediates immunosuppression. The ligands of TIGIT includes PVR (CD155), which has been identified on dendritic cells (DCs), macrophages as well as many human cancer cells and have been shown to down-regulate T cell activation and cytokine secretion upon binding to TIGIT. Inhibition of the TIGIT/PVR interaction can mediate potent antitumor activity of immune cells. Given the significant role for TIGIT in immune checkpoint regulation, there remains a need in the art for the development of therapeutic molecules and methods to modulate TIGIT-mediated immune cell regulation for immune therapy and cancer treatment.

Programmed cell death ligand-1 (PDL1) is expressed on antigen-presenting cells as well as many human cancer cells and have been shown to downregulate T cell activation and cytokine secretion upon binding to Programmed cell death protein 1 (PD1). PD1 primarily functions in peripheral tissues where activated T-cells may encounter the immunosuppressive PDL1/PDL2 ligands expressed by tumor and/or stromal cells. Upregulation of PDL1 can allow cancer cells to evade the host immune system, whereas inhibition of the PD1/PDL1 interaction can mediate potent antitumor activity in preclinical models. Gobbini et al., Crit Rev Oncol Hematol. 2019 December; 144:102816. Although PDL1 inhibitors are in development as immunooncology therapies, there remain a need for the development of anticancer therapeutics targeting PDL1.

SUMMARY OF THE INVENTION

The present disclosure provides isolated monoclonal antibodies that bind specifically to TIGIT with high affinity, including multispecific antibodies that binds to TIGIT and one or more additional target. In certain embodiments, the anti-TIGIT antibody comprises a single domain antibody that binds to TIGIT. In certain embodiments, the additional target is PDL1. This disclosure further provides methods of making and using the antibodies, immunoconjugates and pharmaceutical compositions comprising the antibodies, e.g., for treating diseases and disorders, e.g., cancer. The invention is based, in part, on the discovery of single domain anti-TIGIT antibodies that bind to TIGIT and multispecific antibodies that bind to both TIGIT and PDL1, which antibodies can increase an immune response in immune cells and provide improved anti-tumor efficacy.

The present disclosure provides multispecific antibodies that bind to TIGIT and PDL1. In certain embodiments, a multispecific antibody disclosed herein comprise: i) a first antigen-binding moiety comprising an anti-TIGIT antibody comprising a single domain antibody that binds to TIGIT; and ii) a second antigen-binding moiety comprising an anti-PDL1 antibody that binds to PDL1.

In certain embodiments, the single domain antibody comprises a VHH. In certain embodiments, the single domain antibody or the VHH comprises a heavy chain variable region (VH). In certain embodiments, the single domain antibody binds to TIGIT with a KD of $1\times10^{-7}$ M or less. In certain embodiments, the single domain antibody binds to TIGIT with a KD of $1\times10^{-8}$ M or less. In certain embodiments, the single domain antibody binds to TIGIT with a KD of $3\times10^{-9}$ M or less. In certain embodiments, the single domain antibody binds to TIGIT with a KD of $2\times10^{-9}$ M or less.

In certain embodiments, the single domain antibody cross-competes for binding to TIGIT with a reference anti-TIGIT single domain antibody comprising a heavy chain variable region comprising:

a) a heavy chain variable region CDR1 comprising amino acids having the sequence set forth in SEQ ID NO: 94, a heavy chain variable region CDR2 comprising amino acids having the sequence set forth in SEQ ID NO: 95, and a heavy chain variable region CDR3 comprising amino acids having the sequence set forth in SEQ ID NO: 96, b) a heavy chain variable region CDR1 comprising amino acids having the sequence set forth in SEQ ID NO: 98, a heavy chain variable region CDR2 comprising amino acids having the sequence set forth in SEQ ID NO: 99, and a heavy chain variable region CDR3 comprising amino acids having the sequence set forth in SEQ ID NO: 100, c) a heavy chain variable region CDR1 comprising amino acids having the sequence set forth in SEQ ID NO: 102, a heavy chain variable region CDR2 comprising amino acids having the sequence set forth in SEQ ID NO: 103, and a heavy chain variable region CDR3 comprising amino acids having the sequence set forth in SEQ ID NO: 104, d) a heavy chain variable region CDR1 comprising amino acids having the sequence set forth in SEQ ID NO: 106, a heavy chain variable region CDR2 comprising amino acids having the sequence set forth in SEQ ID NO: 107, and a heavy chain variable region CDR3 comprising amino acids having the sequence set forth in SEQ ID NO: 108, e) a heavy chain variable region CDR1 comprising amino acids having the sequence set forth in SEQ ID NO: 110, a heavy chain variable region CDR2 comprising amino acids having the sequence set forth in SEQ ID NO: 111, and a heavy chain variable region CDR3 comprising amino acids having the sequence set forth in SEQ ID NO: 112, f) a heavy chain variable region CDR1 comprising amino acids having the sequence set forth in SEQ ID NO: 114, a heavy chain variable region CDR2 comprising amino acids having the sequence set forth in SEQ ID NO: 115, and a heavy chain variable region CDR3 comprising amino acids having the sequence set forth in SEQ ID NO: 116, g) a heavy chain variable region CDR1 comprising amino acids having the sequence set forth in SEQ ID NO: 118, a heavy chain variable region CDR2 comprising amino acids having the sequence set forth in SEQ ID NO: 119, and a heavy chain variable region CDR3 comprising amino acids having the sequence set forth in SEQ ID NO: 120, h) a heavy chain variable region CDR1 comprising amino acids having the sequence set forth in SEQ ID NO: 122, a heavy chain variable region CDR2 comprising amino acids having the sequence set forth in SEQ ID NO: 123, and a heavy chain variable region CDR3 comprising amino acids having the sequence set forth in SEQ ID NO: 124, i) a heavy chain variable region CDR1 comprising amino acids having the sequence set forth in SEQ ID NO: 126, a heavy chain variable region CDR2 comprising amino acids having the sequence set forth in SEQ ID NO: 127, and a heavy chain variable region CDR3 comprising amino acids having the sequence set forth in SEQ ID NO: 128, j) a heavy chain variable region CDR1 comprising amino acids having the sequence set forth in SEQ ID NO: 130, a heavy chain variable region CDR2 comprising amino acids having the sequence set forth in SEQ ID NO: 131, and a heavy chain variable region CDR3 comprising amino acids having the sequence set forth in SEQ ID NO: 132, k) a heavy chain variable region CDR1 comprising amino acids having the sequence set forth in SEQ ID NO: 134, a heavy chain variable region CDR2 comprising amino acids having the sequence set forth in SEQ ID NO: 135, and a heavy chain variable region CDR3 comprising amino acids having the sequence set forth in SEQ ID NO: 136, l) a heavy chain variable region CDR1 comprising amino acids having the sequence set forth in SEQ ID NO: 138, a heavy chain variable region CDR2 comprising amino acids having the sequence set forth in SEQ ID NO: 139, and a heavy chain variable region CDR3 comprising amino acids having the sequence set forth in SEQ ID NO: 140, m) a heavy chain variable region CDR1 comprising amino acids having the sequence set forth in SEQ ID NO: 142, a heavy chain variable region CDR2 comprising amino acids having the sequence set forth in SEQ ID NO: 143, and a heavy chain variable region CDR3 comprising amino acids having the sequence set forth in SEQ ID NO: 144, n) a heavy chain variable region CDR1 comprising amino acids having the sequence set forth in SEQ ID NO: 146, a heavy chain variable region CDR2 comprising amino acids having the sequence set forth in SEQ ID NO: 147, and a heavy chain variable region CDR3 comprising amino acids having the sequence set forth in SEQ ID NO: 148, o) a heavy chain variable region CDR1 comprising amino acids having the sequence set forth in SEQ ID NO: 150, a heavy chain variable region CDR2 comprising amino acids having the sequence set forth in SEQ ID NO: 151, and a heavy chain variable region CDR3 comprising amino acids having the sequence set forth in SEQ ID NO: 152, p) a heavy chain variable region CDR1 comprising amino acids having the sequence set forth in SEQ ID NO: 154, a heavy chain variable region CDR2 comprising amino acids having the sequence set forth in SEQ ID NO: 155, and a heavy chain variable region CDR3 comprising amino acids having the sequence set forth in SEQ ID NO: 156, q) a heavy chain variable region CDR1 comprising amino acids having the sequence set forth in SEQ ID NO: 158, a heavy chain variable region CDR2 comprising amino acids having the sequence set forth in SEQ ID NO: 159, and a heavy chain variable region CDR3 comprising amino acids having the sequence set forth in SEQ ID NO: 160, r) a heavy chain variable region CDR1 comprising amino acids having the sequence set forth in SEQ ID NO: 162, a heavy chain variable region CDR2 comprising amino acids having the sequence set forth in SEQ ID NO: 163, and a heavy chain variable region CDR3 comprising amino acids having the sequence set forth in SEQ ID NO: 164, s) a heavy chain variable region CDR1 comprising amino acids having the sequence set forth in SEQ ID NO: 166, a heavy chain variable region CDR2 comprising amino acids having the sequence set forth in SEQ ID NO: 167, and a heavy chain variable region CDR3 comprising amino acids having the sequence set forth in SEQ ID NO: 168, t) a heavy chain variable region CDR1 comprising amino acids having the sequence set forth in SEQ ID NO: 170, a heavy chain variable region CDR2 comprising amino acids having the sequence set forth in SEQ ID NO: 171, and a heavy chain variable region CDR3 comprising amino acids having the sequence set forth in SEQ ID NO: 172, u) a heavy chain variable region CDR1 comprising amino acids having the sequence set forth in SEQ ID NO: 174, a heavy chain variable region CDR2 comprising amino acids having the sequence set forth in SEQ ID NO: 175, and a heavy chain variable region CDR3 comprising amino acids having the sequence set forth in SEQ ID NO: 176, v) a heavy chain variable region CDR1 comprising amino acids having the sequence set forth in SEQ ID NO: 178, a heavy chain variable region CDR2 comprising amino acids having the sequence set forth in SEQ ID NO: 179, and a heavy chain variable region CDR3 comprising amino acids having the sequence set forth in SEQ ID NO: 180, w) a heavy chain variable region CDR1 comprising amino acids having the sequence set forth in SEQ ID NO: 182, a heavy chain variable region CDR2 comprising amino acids having the sequence set forth in SEQ ID NO: 183, and a heavy chain variable region CDR3 comprising amino acids having the sequence set forth in SEQ ID NO: 184, x) a heavy chain variable region CDR1 comprising amino acids having the sequence set forth in SEQ ID NO: 186, a heavy chain variable region CDR2 comprising amino acids having the sequence set forth in SEQ ID NO: 187, and a heavy chain variable region CDR3 comprising amino acids having the sequence set forth in SEQ ID NO: 188, or y) a heavy chain variable region CDR1 comprising amino acids having the sequence set forth in SEQ ID NO: 190, a heavy chain variable region CDR2 comprising amino acids having the sequence set forth in SEQ ID NO: 191, and a heavy chain variable region CDR3 comprising amino acids having the sequence set forth in SEQ ID NO: 192.

In certain embodiments, the single domain antibody comprises a heavy chain variable region comprising:

a) a heavy chain variable region CDR1 comprising an amino acid sequence of any one of SEQ ID NOs: 94, 98, 102, 106, 110, 114, 118, 122, 126, 130, 134, 138, 142, 146, 150, 154, 158, 162, 166, 170, 174, 178, 182, 186 and 190, or a variant thereof comprising up to about 3 amino acid substitutions;

b) a heavy chain variable region CDR2 comprising an amino acid sequence of any one of SEQ ID NOs: 95, 99, 103, 107, 111, 115, 119, 123, 127, 131, 135, 139, 143, 147, 151, 155, 159, 163, 167, 171, 175, 179, 183, 187 and 191, or a variant thereof comprising up to about 3 amino acid substitutions; and c) a heavy chain variable region CDR3 comprising an amino acid sequence of any one of SEQ ID NOs: 96, 100, 104, 108, 112, 116, 120, 124, 128, 132, 136, 140, 144, 148, 152, 156, 160, 164, 168, 172, 176, 180, 184, 188 and 192, or a variant thereof comprising up to about 3 amino acid substitutions.

In certain embodiments, the single domain antibody comprises a heavy chain variable region that comprises a CDR1 domain, a CDR2 domain and a CDR3 domain, wherein the CDR1 domain, the CDR2 domain and the CDR3 domain respectively comprise a CDR1 domain, a CDR2 domain and a CDR3 domain comprised in a reference heavy chain variable region comprising the amino acid sequence selected from the group consisting of SEQ ID NOs: 97, 101, 105, 109, 113, 117, 121, 125, 129, 133, 137, 141, 145, 149, 153, 157, 161, 165, 169, 173, 177, 181, 185, 189 and 193.

In certain embodiments, the single domain antibody comprises a heavy chain variable region CDR1 comprising amino acids having the sequence set forth in SEQ ID NO: 94, a heavy chain variable region CDR2 comprising amino acids having the sequence set forth in SEQ ID NO: 95, and a heavy chain variable region CDR3 comprising amino acids having the sequence set forth in SEQ ID NO: 96. In certain embodiments, the single domain antibody comprises a heavy chain variable region CDR1 comprising amino acids having the sequence set forth in SEQ ID NO: 98, a heavy chain variable region CDR2 comprising amino acids having the sequence set forth in SEQ ID NO: 99, and a heavy chain variable region CDR3 comprising amino acids having the sequence set forth in SEQ ID NO: 100. In certain embodiments, the single domain antibody comprises a heavy chain variable region CDR1 comprising amino acids having the sequence set forth in SEQ ID NO: 102, a heavy chain variable region CDR2 comprising amino acids having the sequence set forth in SEQ ID NO: 103, and a heavy chain variable region CDR3 comprising amino acids having the sequence set forth in SEQ ID NO: 104. In certain embodiments, the single domain antibody comprises a heavy chain variable region CDR1 comprising amino acids having the sequence set forth in SEQ ID NO: 106, a heavy chain variable region CDR2 comprising amino acids having the sequence set forth in SEQ ID NO: 107, and a heavy chain variable region CDR3 comprising amino acids having the sequence set forth in SEQ ID NO: 108. In certain embodiments, the single domain antibody comprises a heavy chain variable region CDR1 comprising amino acids having the sequence set forth in SEQ ID NO: 110, a heavy chain variable region CDR2 comprising amino acids having the sequence set forth in SEQ ID NO: 111, and a heavy chain variable region CDR3 comprising amino acids having the sequence set forth in SEQ ID NO: 112. In certain embodiments, the single domain antibody comprises a heavy chain variable region CDR1 comprising amino acids having the sequence set forth in SEQ ID NO: 114, a heavy chain variable region CDR2 comprising amino acids having the sequence set forth in SEQ ID NO: 115, and a heavy chain variable region CDR3 comprising amino acids having the sequence set forth in SEQ ID NO: 116. In certain embodiments, the single domain antibody comprises a heavy chain variable region CDR1 comprising amino acids having the sequence set forth in SEQ ID NO: 118, a heavy chain variable region CDR2 comprising amino acids having the sequence set forth in SEQ ID NO: 119, and a heavy chain variable region CDR3 comprising amino acids having the sequence set forth in SEQ ID NO: 120. In certain embodiments, the single domain antibody comprises a heavy chain variable region CDR1 comprising amino acids having the sequence set forth in SEQ ID NO: 122, a heavy chain variable region CDR2 comprising amino acids having the sequence set forth in SEQ ID NO: 123, and a heavy chain variable region CDR3 comprising amino acids having the sequence set forth in SEQ ID NO: 124. In certain embodiments, the single domain antibody comprises a heavy chain variable region CDR1 comprising amino acids having the sequence set forth in SEQ ID NO: 126, a heavy chain variable region CDR2 comprising amino acids having the sequence set forth in SEQ ID NO: 127, and a heavy chain variable region CDR3 comprising amino acids having the sequence set forth in SEQ ID NO: 128. In certain embodiments, the single domain antibody comprises a heavy chain variable region CDR1 comprising amino acids having the sequence set forth in SEQ ID NO: 130, a heavy chain variable region CDR2 comprising amino acids having the sequence set forth in SEQ ID NO: 131, and a heavy chain variable region CDR3 comprising amino acids having the sequence set forth in SEQ ID NO: 132. In certain embodiments, the single domain antibody comprises a heavy chain variable region CDR1 comprising amino acids having the sequence set forth in SEQ ID NO: 134, a heavy chain variable region CDR2 comprising amino acids having the sequence set forth in SEQ ID NO: 135, and a heavy chain variable region CDR3 comprising amino acids having the sequence set forth in SEQ ID NO: 136. In certain embodiments, the single domain antibody comprises a heavy chain variable region CDR1 comprising amino acids having the sequence set forth in SEQ ID NO: 138, a heavy chain variable region CDR2 comprising amino acids having the sequence set forth in SEQ ID NO: 139, and a heavy chain variable region CDR3 comprising amino acids having the sequence set forth in SEQ ID NO: 140. In certain embodiments, the single domain antibody comprises a heavy chain variable region CDR1 comprising amino acids having the sequence set forth in SEQ ID NO: 142, a heavy chain variable region CDR2 comprising amino acids having the sequence set forth in SEQ ID NO: 143, and a heavy chain variable region CDR3 comprising amino acids having the sequence set forth in SEQ ID NO: 144. In certain embodiments, the single domain antibody comprises a heavy chain variable region CDR1 comprising amino acids having the sequence set forth in SEQ ID NO: 146, a heavy chain variable region CDR2 comprising amino acids having the sequence set forth in SEQ ID NO: 147, and a heavy chain variable region CDR3 comprising amino acids having the sequence set forth in SEQ ID NO: 148. In certain embodiments, the single domain antibody comprises a heavy chain variable region CDR1 comprising amino acids having the sequence set forth in SEQ ID NO: 150, a heavy chain variable region CDR2 comprising amino acids having the sequence set forth in SEQ ID NO: 151, and a heavy chain variable region CDR3 comprising amino acids having the sequence set forth in SEQ ID NO: 152. In certain embodiments, the single domain antibody comprises a heavy chain variable region CDR1 comprising amino acids having the sequence set forth in SEQ ID NO: 154, a heavy chain variable region CDR2 comprising amino acids having the sequence set forth in SEQ ID NO: 155, and a heavy chain variable region CDR3 comprising amino acids having the sequence set forth in SEQ ID NO: 156. In certain embodiments, the single domain antibody comprises a heavy chain variable region CDR1 comprising amino acids having the sequence set forth in SEQ ID NO: 158, a heavy chain variable region CDR2 comprising amino acids having the sequence set forth in SEQ ID NO: 159, and a heavy chain variable region CDR3 comprising amino acids having the sequence set forth in SEQ ID NO: 160. In certain embodiments, the single domain antibody comprises a heavy chain variable region CDR1 comprising amino acids having the sequence set forth in SEQ ID NO: 162, a heavy chain variable region CDR2 comprising amino acids having the sequence set forth in SEQ ID NO: 163, and a heavy chain variable region CDR3 comprising amino acids having the sequence set forth in SEQ ID NO: 164. In certain embodiments, the single domain antibody comprises a heavy chain variable region CDR1 comprising amino acids having the sequence set forth in SEQ ID NO: 166, a heavy chain variable region CDR2 comprising amino acids having the sequence set forth in SEQ ID NO: 167, and a heavy chain variable region CDR3 comprising amino acids having the sequence set forth in SEQ ID NO: 168. In certain embodiments, the single domain antibody comprises a heavy chain variable region CDR1 comprising amino acids having the sequence set forth in SEQ ID NO: 170, a heavy chain variable region CDR2 comprising amino acids having the sequence set forth in SEQ ID NO: 171, and a heavy chain variable region CDR3 comprising amino acids having the sequence set forth in SEQ ID NO: 172. In certain embodiments, the single domain antibody comprises a heavy chain variable region CDR1 comprising amino acids having the sequence set forth in SEQ ID NO: 174, a heavy chain variable region CDR2 comprising amino acids having the sequence set forth in SEQ ID NO: 175, and a heavy chain variable region CDR3 comprising amino acids having the sequence set forth in SEQ ID NO: 176. In certain embodiments, the single domain antibody comprises a heavy chain variable region CDR1 comprising amino acids having the sequence set forth in SEQ ID NO: 178, a heavy chain variable region CDR2 comprising amino acids having the sequence set forth in SEQ ID NO: 179, and a heavy chain variable region CDR3 comprising amino acids having the sequence set forth in SEQ ID NO: 180. In certain embodiments, the single domain antibody comprises a heavy chain variable region CDR1 comprising amino acids having the sequence set forth in SEQ ID NO: 182, a heavy chain variable region CDR2 comprising amino acids having the sequence set forth in SEQ ID NO: 183, and a heavy chain variable region CDR3 comprising amino acids having the sequence set forth in SEQ ID NO: 184. In certain embodiments, the single domain antibody comprises a heavy chain variable region CDR1 comprising amino acids having the sequence set forth in SEQ ID NO: 186, a heavy chain variable region CDR2 comprising amino acids having the sequence set forth in SEQ ID NO: 187, and a heavy chain variable region CDR3 comprising amino acids having the sequence set forth in SEQ ID NO: 188. In certain embodiments, the single domain antibody comprises a heavy chain variable region CDR1 comprising amino acids having the sequence set forth in SEQ ID NO: 190, a heavy chain variable region CDR2 comprising amino acids having the sequence set forth in SEQ ID NO: 191, and a heavy chain variable region CDR3 comprising amino acids having the sequence set forth in SEQ ID NO: 192.

In certain embodiments, the single domain antibody comprises a heavy chain variable region comprising an amino acid sequence having at least about 90% sequence identity to the amino acid sequence selected from the group consisting of SEQ ID NOs: 97, 101, 105, 109, 113, 117, 121, 125, 129, 133, 137, 141, 145, 149, 153, 157, 161, 165, 169, 173, 177, 181, 185, 189 and 193.

In certain embodiments, the single domain antibody comprises a heavy chain variable region comprising the amino acid sequence set forth in SEQ ID NO: 97. In certain embodiments, the single domain antibody comprises a heavy chain variable region comprising the amino acid sequence set forth in SEQ ID NO: 101. In certain embodiments, the single domain antibody comprises a heavy chain variable region comprising the amino acid sequence set forth in SEQ ID NO: 105. In certain embodiments, the single domain antibody comprises a heavy chain variable region comprising the amino acid sequence set forth in SEQ ID NO: 109. In certain embodiments, the single domain antibody comprises a heavy chain variable region comprising the amino acid sequence set forth in SEQ ID NO: 113. In certain embodiments, the single domain antibody comprises a heavy chain variable region comprising the amino acid sequence set forth in SEQ ID NO: 117. In certain embodiments, the single domain antibody comprises a heavy chain variable region comprising the amino acid sequence set forth in SEQ ID NO: 121. In certain embodiments, the single domain antibody comprises a heavy chain variable region comprising the amino acid sequence set forth in SEQ ID NO: 125. In certain embodiments, the single domain antibody comprises a heavy chain variable region comprising the amino acid sequence set forth in SEQ ID NO: 129. In certain embodiments, the single domain antibody comprises a heavy chain variable region comprising the amino acid sequence set forth in SEQ ID NO: 133. In certain embodiments, the single domain antibody comprises a heavy chain variable region comprising the amino acid sequence set forth in SEQ ID NO: 137. In certain embodiments, the single domain antibody comprises a heavy chain variable region comprising the amino acid sequence set forth in SEQ ID NO: 141. In certain embodiments, the single domain antibody comprises a heavy chain variable region comprising the amino acid sequence set forth in SEQ ID NO: 145. In certain embodiments, the single domain antibody comprises a heavy chain variable region comprising the amino acid sequence set forth in SEQ ID NO: 149. In certain embodiments, the single domain antibody comprises a heavy chain variable region comprising the amino acid sequence set forth in SEQ ID NO: 153. In certain embodiments, the single domain antibody comprises a heavy chain variable region comprising the amino acid sequence set forth in SEQ ID NO: 157. In certain embodiments, the single domain antibody comprises a heavy chain variable region comprising the amino acid sequence set forth in SEQ ID NO: 161. In certain embodiments, the single domain antibody comprises a heavy chain variable region comprising the amino acid sequence set forth in SEQ ID NO: 165. In certain embodiments, the single domain antibody comprises a heavy chain variable region comprising the amino acid sequence set forth in SEQ ID NO: 169. In certain embodiments, the single domain antibody comprises a heavy chain variable region comprising the amino acid sequence set forth in SEQ ID NO: 173. In certain embodiments, the single domain antibody comprises a heavy chain variable region comprising the amino acid sequence set forth in SEQ ID NO: 177. In certain embodiments, the single domain antibody comprises a heavy chain variable region comprising the amino acid sequence set forth in SEQ ID NO: 181. In certain embodiments, the single domain antibody comprises a heavy chain variable region comprising the amino acid sequence set forth in SEQ ID NO: 185. In certain embodiments, the single domain antibody comprises a heavy chain variable region comprising the amino acid sequence set forth in SEQ ID NO: 189. In certain embodiments, the single domain antibody comprises a heavy chain variable region comprising the amino acid sequence set forth in SEQ ID NO: 193.

In certain embodiments, the single domain antibody cross-competes for binding to TIGIT with a reference anti-TIGIT single domain antibody comprising a heavy chain variable region comprising:

(a) a heavy chain variable region CDR1 comprising amino acids having the sequence set forth in SEQ ID NO: 1, a heavy chain variable region CDR2 comprising amino acids having the sequence set forth in SEQ ID NO: 2, and a heavy chain variable region CDR3 comprising amino acids having the sequence set forth in SEQ ID NO: 3, (b) a heavy chain variable region CDR1 comprising amino acids having the sequence set forth in SEQ ID NO: 5, a heavy chain variable region CDR2 comprising amino acids having the sequence set forth in SEQ ID NO: 6, and a heavy chain variable region CDR3 comprising amino acids having the sequence set forth in SEQ ID NO: 7, (c) a heavy chain variable region CDR1 comprising amino acids having the sequence set forth in SEQ ID NO: 9, a heavy chain variable region CDR2 comprising amino acids having the sequence set forth in SEQ ID NO: 10, and a heavy chain variable region CDR3 comprising amino acids having the sequence set forth in SEQ ID NO: 11, (d) a heavy chain variable region CDR1 comprising amino acids having the sequence set forth in SEQ ID NO: 13, a heavy chain variable region CDR2 comprising amino acids having the sequence set forth in SEQ ID NO: 14, and a heavy chain variable region CDR3 comprising amino acids having the sequence set forth in SEQ ID NO: 15, (e) a heavy chain variable region CDR1 comprising amino acids having the sequence set forth in SEQ ID NO: 17, a heavy chain variable region CDR2 comprising amino acids having the sequence set forth in SEQ ID NO: 18, and a heavy chain variable region CDR3 comprising amino acids having the sequence set forth in SEQ ID NO: 19, (f) a heavy chain variable region CDR1 comprising amino acids having the sequence set forth in SEQ ID NO: 21, a heavy chain variable region CDR2 comprising amino acids having the sequence set forth in SEQ ID NO: 22, and a heavy chain variable region CDR3 comprising amino acids having the sequence set forth in SEQ ID NO: 23, (g) a heavy chain variable region CDR1 comprising amino acids having the sequence set forth in SEQ ID NO: 25, a heavy chain variable region CDR2 comprising amino acids having the sequence set forth in SEQ ID NO: 26, and a heavy chain variable region CDR3 comprising amino acids having the sequence set forth in SEQ ID NO: 27, (h) a heavy chain variable region CDR1 comprising amino acids having the sequence set forth in SEQ ID NO: 29, a heavy chain variable region CDR2 comprising amino acids having the sequence set forth in SEQ ID NO: 30, and a heavy chain variable region CDR3 comprising amino acids having the sequence set forth in SEQ ID NO: 31, (i) a heavy chain variable region CDR1 comprising amino acids having the sequence set forth in SEQ ID NO: 33, a heavy chain variable region CDR2 comprising amino acids having the sequence set forth in SEQ ID NO: 34, and a heavy chain variable region CDR3 comprising amino acids having the sequence set forth in SEQ ID NO: 35, (j) a heavy chain variable region CDR1 comprising amino acids having the sequence set forth in SEQ ID NO: 37, a heavy chain variable region CDR2 comprising amino acids having the sequence set forth in SEQ ID NO: 38, and a heavy chain variable region CDR3 comprising amino acids having the sequence set forth in SEQ ID NO: 39, (k) a heavy chain variable region CDR1 comprising amino acids having the sequence set forth in SEQ ID NO: 41, a heavy chain variable region CDR2 comprising amino acids having the sequence set forth in SEQ ID NO: 42, and a heavy chain variable region CDR3 comprising amino acids having the sequence set forth in SEQ ID NO: 43, (l) a heavy chain variable region CDR1 comprising amino acids having the sequence set forth in SEQ ID NO: 45, a heavy chain variable region CDR2 comprising amino acids having the sequence set forth in SEQ ID NO: 46, and a heavy chain variable region CDR3 comprising amino acids having the sequence set forth in SEQ ID NO: 47, (m) a heavy chain variable region CDR1 comprising amino acids having the sequence set forth in SEQ ID NO: 49, a heavy chain variable region CDR2 comprising amino acids having the sequence set forth in SEQ ID NO: 50, and a heavy chain variable region CDR3 comprising amino acids having the sequence set forth in SEQ ID NO: 51, (n) a heavy chain variable region CDR1 comprising amino acids having the sequence set forth in SEQ ID NO: 53, a heavy chain variable region CDR2 comprising amino acids having the sequence set forth in SEQ ID NO: 54, and a heavy chain variable region CDR3 comprising amino acids having the sequence set forth in SEQ ID NO: 55, (o) a heavy chain variable region CDR1 comprising amino acids having the sequence set forth in SEQ ID NO: 57, a heavy chain variable region CDR2 comprising amino acids having the sequence set forth in SEQ ID NO: 58, and a heavy chain variable region CDR3 comprising amino acids having the sequence set forth in SEQ ID NO: 59, (p) a heavy chain variable region CDR1 comprising amino acids having the sequence set forth in SEQ ID NO: 61, a heavy chain variable region CDR2 comprising amino acids having the sequence set forth in SEQ ID NO: 62, and a heavy chain variable region CDR3 comprising amino acids having the sequence set forth in SEQ ID NO: 63, (q) a heavy chain variable region CDR1 comprising amino acids having the sequence set forth in SEQ ID NO: 65, a heavy chain variable region CDR2 comprising amino acids having the sequence set forth in SEQ ID NO: 66, and a heavy chain variable region CDR3 comprising amino acids having the sequence set forth in SEQ ID NO: 67, (r) a heavy chain variable region CDR1 comprising amino acids having the sequence set forth in SEQ ID NO: 69, a heavy chain variable region CDR2 comprising amino acids having the sequence set forth in SEQ ID NO: 70, and a heavy chain variable region CDR3 comprising amino acids having the sequence set forth in SEQ ID NO: 71, (s) a heavy chain variable region CDR1 comprising amino acids having the sequence set forth in SEQ ID NO: 73, a heavy chain variable region CDR2 comprising amino acids having the sequence set forth in SEQ ID NO: 74, and a heavy chain variable region CDR3 comprising amino acids having the sequence set forth in SEQ ID NO: 75, (t) a heavy chain variable region CDR1 comprising amino acids having the sequence set forth in SEQ ID NO: 77, a heavy chain variable region CDR2 comprising amino acids having the sequence set forth in SEQ ID NO: 78, and a heavy chain variable region CDR3 comprising amino acids having the sequence set forth in SEQ ID NO: 79, and (u) a heavy chain variable region CDR1 comprising amino acids having the sequence set forth in SEQ ID NO: 81, a heavy chain variable region CDR2 comprising amino acids having the sequence set forth in SEQ ID NO: 82, and a heavy chain variable region CDR3 comprising amino acids having the sequence set forth in SEQ ID NO: 83.

In certain embodiments, the single domain antibody comprises a heavy chain variable region comprising:

(a) a heavy chain variable region CDR1 comprising amino acids having the sequence set forth in SEQ ID NO: 1, a heavy chain variable region CDR2 comprising amino acids having the sequence set forth in SEQ ID NO: 2, and a heavy chain variable region CDR3 comprising amino acids having the sequence set forth in SEQ ID NO: 3, (b) a heavy chain variable region CDR1 comprising amino acids having the sequence set forth in SEQ ID NO: 5, a heavy chain variable region CDR2 comprising amino acids having the sequence set forth in SEQ ID NO: 6, and a heavy chain variable region CDR3 comprising amino acids having the sequence set forth in SEQ ID NO: 7, (c) a heavy chain variable region CDR1 comprising amino acids having the sequence set forth in SEQ ID NO: 9, a heavy chain variable region CDR2 comprising amino acids having the sequence set forth in SEQ ID NO: 10, and a heavy chain variable region CDR3 comprising amino acids having the sequence set forth in SEQ ID NO: 11, (d) a heavy chain variable region CDR1 comprising amino acids having the sequence set forth in SEQ ID NO: 13, a heavy chain variable region CDR2 comprising amino acids having the sequence set forth in SEQ ID NO: 14, and a heavy chain variable region CDR3 comprising amino acids having the sequence set forth in SEQ ID NO: 15, (e) a heavy chain variable region CDR1 comprising amino acids having the sequence set forth in SEQ ID NO: 17, a heavy chain variable region CDR2 comprising amino acids having the sequence set forth in SEQ ID NO: 18, and a heavy chain variable region CDR3 comprising amino acids having the sequence set forth in SEQ ID NO: 19, (f) a heavy chain variable region CDR1 comprising amino acids having the sequence set forth in SEQ ID NO: 21, a heavy chain variable region CDR2 comprising amino acids having the sequence set forth in SEQ ID NO: 22, and a heavy chain variable region CDR3 comprising amino acids having the sequence set forth in SEQ ID NO: 23, (g) a heavy chain variable region CDR1 comprising amino acids having the sequence set forth in SEQ ID NO: 25, a heavy chain variable region CDR2 comprising amino acids having the sequence set forth in SEQ ID NO: 26, and a heavy chain variable region CDR3 comprising amino acids having the sequence set forth in SEQ ID NO: 27, (h) a heavy chain variable region CDR1 comprising amino acids having the sequence set forth in SEQ ID NO: 29, a heavy chain variable region CDR2 comprising amino acids having the sequence set forth in SEQ ID NO: 30, and a heavy chain variable region CDR3 comprising amino acids having the sequence set forth in SEQ ID NO: 31, (i) a heavy chain variable region CDR1 comprising amino acids having the sequence set forth in SEQ ID NO: 33, a heavy chain variable region CDR2 comprising amino acids having the sequence set forth in SEQ ID NO: 34, and a heavy chain variable region CDR3 comprising amino acids having the sequence set forth in SEQ ID NO: 35, (j) a heavy chain variable region CDR1 comprising amino acids having the sequence set forth in SEQ ID NO: 37, a heavy chain variable region CDR2 comprising amino acids having the sequence set forth in SEQ ID NO: 38, and a heavy chain variable region CDR3 comprising amino acids having the sequence set forth in SEQ ID NO: 39, (k) a heavy chain variable region CDR1 comprising amino acids having the sequence set forth in SEQ ID NO: 41, a heavy chain variable region CDR2 comprising amino acids having the sequence set forth in SEQ ID NO: 42, and a heavy chain variable region CDR3 comprising amino acids having the sequence set forth in SEQ ID NO: 43, (l) a heavy chain variable region CDR1 comprising amino acids having the sequence set forth in SEQ ID NO: 45, a heavy chain variable region CDR2 comprising amino acids having the sequence set forth in SEQ ID NO: 46, and a heavy chain variable region CDR3 comprising amino acids having the sequence set forth in SEQ ID NO: 47, (m) a heavy chain variable region CDR1 comprising amino acids having the sequence set forth in SEQ ID NO: 49, a heavy chain variable region CDR2 comprising amino acids having the sequence set forth in SEQ ID NO: 50, and a heavy chain variable region CDR3 comprising amino acids having the sequence set forth in SEQ ID NO: 51, (n) a heavy chain variable region CDR1 comprising amino acids having the sequence set forth in SEQ ID NO: 53, a heavy chain variable region CDR2 comprising amino acids having the sequence set forth in SEQ ID NO: 54, and a heavy chain variable region CDR3 comprising amino acids having the sequence set forth in SEQ ID NO: 55, (o) a heavy chain variable region CDR1 comprising amino acids having the sequence set forth in SEQ ID NO: 57, a heavy chain variable region CDR2 comprising amino acids having the sequence set forth in SEQ ID NO: 58, and a heavy chain variable region CDR3 comprising amino acids having the sequence set forth in SEQ ID NO: 59, (p) a heavy chain variable region CDR1 comprising amino acids having the sequence set forth in SEQ ID NO: 61, a heavy chain variable region CDR2 comprising amino acids having the sequence set forth in SEQ ID NO: 62, and a heavy chain variable region CDR3 comprising amino acids having the sequence set forth in SEQ ID NO: 63, (q) a heavy chain variable region CDR1 comprising amino acids having the sequence set forth in SEQ ID NO: 65, a heavy chain variable region CDR2 comprising amino acids having the sequence set forth in SEQ ID NO: 66, and a heavy chain variable region CDR3 comprising amino acids having the sequence set forth in SEQ ID NO: 67, (r) a heavy chain variable region CDR1 comprising amino acids having the sequence set forth in SEQ ID NO: 69, a heavy chain variable region CDR2 comprising amino acids having the sequence set forth in SEQ ID NO: 70, and a heavy chain variable region CDR3 comprising amino acids having the sequence set forth in SEQ ID NO: 71, (s) a heavy chain variable region CDR1 comprising amino acids having the sequence set forth in SEQ ID NO: 73, a heavy chain variable region CDR2 comprising amino acids having the sequence set forth in SEQ ID NO: 74, and a heavy chain variable region CDR3 comprising amino acids having the sequence set forth in SEQ ID NO: 75, (t) a heavy chain variable region CDR1 comprising amino acids having the sequence set forth in SEQ ID NO: 77, a heavy chain variable region CDR2 comprising amino acids having the sequence set forth in SEQ ID NO: 78, and a heavy chain variable region CDR3 comprising amino acids having the sequence set forth in SEQ ID NO: 79, and (u) a heavy chain variable region CDR1 comprising amino acids having the sequence set forth in SEQ ID NO: 81, a heavy chain variable region CDR2 comprising amino acids having the sequence set forth in SEQ ID NO: 82, and a heavy chain variable region CDR3 comprising amino acids having the sequence set forth in SEQ ID NO: 83.

In certain embodiments, the single domain antibody comprises a heavy chain variable region having at least about 90% sequence identity to an amino acid sequence selected from the group consisting of SEQ ID NOs: 4, 8, 12, 16, 20, 24, 28, 32, 36, 40, 44, 48, 52, 56, 60, 64, 68, 72, 76, 80 and 84.

In certain embodiments, the single domain antibody comprises a humanized framework.

In certain embodiments, the second antigen-binding moiety comprises an anti-PDL1 antibody that cross-competes with a reference anti-PDL1 antibody comprising:

a) a heavy chain variable domain (VH) sequence comprising (1) a CDR-H1 comprising the amino acid sequence set forth in SEQ ID NO: 221, (2) a CDR-H2 comprising the amino acid sequence set forth in SEQ ID NO: 222, and (3) a CDR-H3 comprising the amino acid sequence set forth in SEQ ID NO: 223; and a light chain variable domain (VL) sequence comprising (1) a CDR-L1 comprising the amino acid sequence set forth in SEQ ID NO: 224, (2) a CDR-L2 comprising the amino acid sequence set forth in SEQ ID NO: 225, and (3) a CDR-L3 comprising the amino acid sequence set forth in SEQ ID NO: 226;

b) a heavy chain variable domain (VH) sequence comprising (1) a CDR-H1 comprising the amino acid sequence set forth in SEQ ID NO: 229, (2) a CDR-H2 comprising the amino acid sequence set forth in SEQ ID NO: 230, and (3) a CDR-H3 comprising the amino acid sequence set forth in SEQ ID NO: 231; and a light chain variable domain (VL) sequence comprising (1) a CDR-L1 comprising the amino acid sequence set forth in SEQ ID NO: 232, (2) a CDR-L2 comprising the amino acid sequence set forth in SEQ ID NO: 233, and (3) a CDR-L3 comprising the amino acid sequence set forth in SEQ ID NO: 234;

c) a heavy chain variable domain (VH) sequence comprising (1) a CDR-H1 comprising the amino acid sequence set forth in SEQ ID NO: 237, (2) a CDR-H2 comprising the amino acid sequence set forth in SEQ ID NO: 238, and (3) a CDR-H3 comprising the amino acid sequence set forth in SEQ ID NO: 239; and a light chain variable domain (VL) sequence comprising (1) a CDR-L1 comprising the amino acid sequence set forth in SEQ ID NO: 240, (2) a CDR-L2 comprising the amino acid sequence set forth in SEQ ID NO: 241, and (3) a CDR-L3 comprising the amino acid sequence set forth in SEQ ID NO: 242;

d) a heavy chain variable domain (VH) sequence comprising (1) a CDR-H1 comprising the amino acid sequence set forth in SEQ ID NO: 245, (2) a CDR-H2 comprising the amino acid sequence set forth in SEQ ID NO: 246, and (3) a CDR-H3 comprising the amino acid sequence set forth in SEQ ID NO: 247; and a light chain variable domain (VL) sequence comprising (1) a CDR-L1 comprising the amino acid sequence set forth in SEQ ID NO: 248, (2) a CDR-L2 comprising the amino acid sequence set forth in SEQ ID NO: 249, and (3) a CDR-L3 comprising the amino acid sequence set forth in SEQ ID NO: 250;

e) a heavy chain variable domain (VH) sequence comprising (1) a CDR-H1 comprising the amino acid sequence set forth in SEQ ID NO: 253, (2) a CDR-H2 comprising the amino acid sequence set forth in SEQ ID NO: 254, and (3) a CDR-H3 comprising the amino acid sequence set forth in SEQ ID NO: 255; and a light chain variable domain (VL) sequence comprising (1) a CDR-L1 comprising the amino acid sequence set forth in SEQ ID NO: 256, (2) a CDR-L2 comprising the amino acid sequence set forth in SEQ ID NO: 257, and (3) a CDR-L3 comprising the amino acid sequence set forth in SEQ ID NO: 258;
f) a heavy chain variable domain (VH) sequence comprising (1) a CDR-H1 comprising the amino acid sequence set forth in SEQ ID NO: 261, (2) a CDR-H2 comprising the amino acid sequence set forth in SEQ ID NO: 262, and (3) a CDR-H3 comprising the amino acid sequence set forth in SEQ ID NO: 263; and a light chain variable domain (VL) sequence comprising (1) a CDR-L1 comprising the amino acid sequence set forth in SEQ ID NO: 264, (2) a CDR-L2 comprising the amino acid sequence set forth in SEQ ID NO: 265, and (3) a CDR-L3 comprising the amino acid sequence set forth in SEQ ID NO: 266;
g) a heavy chain variable domain (VH) sequence comprising (1) a CDR-H1 comprising the amino acid sequence set forth in SEQ ID NO: 269, (2) a CDR-H2 comprising the amino acid sequence set forth in SEQ ID NO: 270, and (3) a CDR-H3 comprising the amino acid sequence set forth in SEQ ID NO: 271; and a light chain variable domain (VL) sequence comprising (1) a CDR-L1 comprising the amino acid sequence set forth in SEQ ID NO: 272, (2) a CDR-L2 comprising the amino acid sequence set forth in SEQ ID NO: 273, and (3) a CDR-L3 comprising the amino acid sequence set forth in SEQ ID NO: 274;
h) a heavy chain variable domain (VH) sequence comprising (1) a CDR-H1 comprising the amino acid sequence set forth in SEQ ID NO: 277, (2) a CDR-H2 comprising the amino acid sequence set forth in SEQ ID NO: 278, and (3) a CDR-H3 comprising the amino acid sequence set forth in SEQ ID NO: 279; and a light chain variable domain (VL) sequence comprising (1) a CDR-L1 comprising the amino acid sequence set forth in SEQ ID NO: 280, (2) a CDR-L2 comprising the amino acid sequence set forth in SEQ ID NO: 281, and (3) a CDR-L3 comprising the amino acid sequence set forth in SEQ ID NO: 282;
i) a heavy chain variable domain (VH) sequence comprising (1) a CDR-H1 comprising the amino acid sequence set forth in SEQ ID NO: 285, (2) a CDR-H2 comprising the amino acid sequence set forth in SEQ ID NO: 286, and (3) a CDR-H3 comprising the amino acid sequence set forth in SEQ ID NO: 287; and a light chain variable domain (VL) sequence comprising (1) a CDR-L1 comprising the amino acid sequence set forth in SEQ ID NO: 288, (2) a CDR-L2 comprising the amino acid sequence set forth in SEQ ID NO: 289, and (3) a CDR-L3 comprising the amino acid sequence set forth in SEQ ID NO: 290; or
j) a heavy chain variable domain (VH) sequence comprising (1) a CDR-H1 comprising the amino acid sequence set forth in SEQ ID NO: 293, (2) a CDR-H2 comprising the amino acid sequence set forth in SEQ ID NO: 294, and (3) a CDR-H3 comprising the amino acid sequence set forth in SEQ ID NO: 295; and a light chain variable domain (VL) sequence comprising (1) a CDR-L1 comprising the amino acid sequence set forth in SEQ ID NO: 296, (2) a CDR-L2 comprising the amino acid sequence set forth in SEQ ID NO: 297, and (3) a CDR-L3 comprising the amino acid sequence set forth in SEQ ID NO: 298.

In certain embodiments, the second antigen-binding moiety comprises a heavy chain variable domain (VH) sequence comprising (1) a CDR-H1 comprising the amino acid sequence set forth in SEQ ID NO: 221, (2) a CDR-H2 comprising the amino acid sequence set forth in SEQ ID NO: 222, and (3) a CDR-H3 comprising the amino acid sequence set forth in SEQ ID NO: 223; and a light chain variable domain (VL) sequence comprising (1) a CDR-L1 comprising the amino acid sequence set forth in SEQ ID NO: 224, (2) a CDR-L2 comprising the amino acid sequence set forth in SEQ ID NO: 225, and (3) a CDR-L3 comprising the amino acid sequence set forth in SEQ ID NO: 226. In certain embodiments, the second antigen-binding moiety comprises a heavy chain variable domain (VH) sequence comprising (1) a CDR-H1 comprising the amino acid sequence set forth in SEQ ID NO: 229, (2) a CDR-H2 comprising the amino acid sequence set forth in SEQ ID NO: 230, and (3) a CDR-H3 comprising the amino acid sequence set forth in SEQ ID NO: 231; and a light chain variable domain (VL) sequence comprising (1) a CDR-L1 comprising the amino acid sequence set forth in SEQ ID NO: 232, (2) a CDR-L2 comprising the amino acid sequence set forth in SEQ ID NO: 233, and (3) a CDR-L3 comprising the amino acid sequence set forth in SEQ ID NO: 234. In certain embodiments, the second antigen-binding moiety comprises a heavy chain variable domain (VH) sequence comprising (1) a CDR-H1 comprising the amino acid sequence set forth in SEQ ID NO: 237, (2) a CDR-H2 comprising the amino acid sequence set forth in SEQ ID NO: 238, and (3) a CDR-H3 comprising the amino acid sequence set forth in SEQ ID NO: 239; and a light chain variable domain (VL) sequence comprising (1) a CDR-L1 comprising the amino acid sequence set forth in SEQ ID NO: 240, (2) a CDR-L2 comprising the amino acid sequence set forth in SEQ ID NO: 241, and (3) a CDR-L3 comprising the amino acid sequence set forth in SEQ ID NO: 242. In certain embodiments, the second antigen-binding moiety comprises a heavy chain variable domain (VH) sequence comprising (1) a CDR-H1 comprising the amino acid sequence set forth in SEQ ID NO: 245, (2) a CDR-H2 comprising the amino acid sequence set forth in SEQ ID NO: 246, and (3) a CDR-H3 comprising the amino acid sequence set forth in SEQ ID NO: 247; and a light chain variable domain (VL) sequence comprising (1) a CDR-L1 comprising the amino acid sequence set forth in SEQ ID NO: 248, (2) a CDR-L2 comprising the amino acid sequence set forth in SEQ ID NO: 249, and (3) a CDR-L3 comprising the amino acid sequence set forth in SEQ ID NO: 250. In certain embodiments, the second antigen-binding moiety comprises a heavy chain variable domain (VH) sequence comprising (1) a CDR-H1 comprising the amino acid sequence set forth in SEQ ID NO: 253, (2) a CDR-H2 comprising the amino acid sequence set forth in SEQ ID NO: 254, and (3) a CDR-H3 comprising the amino acid sequence set forth in SEQ ID NO: 255; and a light chain variable domain (VL) sequence comprising (1) a CDR-L1 comprising the amino acid sequence set forth in SEQ ID NO: 256, (2) a CDR-L2 comprising the amino acid sequence set forth in SEQ ID NO: 257, and (3) a CDR-L3 comprising the amino acid sequence set forth in SEQ ID NO: 258. In certain embodiments, the second antigen-binding moiety comprises a heavy chain variable domain (VH) sequence comprising (1) a CDR-H1 comprising the amino acid sequence set forth in SEQ ID NO: 261, (2) a CDR-H2 comprising the amino acid sequence set forth in SEQ ID NO: 262, and (3) a CDR-H3 comprising the amino acid sequence set forth in SEQ ID NO: 263; and a light chain variable domain (VL) sequence comprising (1) a CDR-L1 comprising the amino acid sequence set forth in SEQ ID NO: 264, (2) a CDR-L2 comprising the amino acid sequence set forth in SEQ ID NO: 265, and (3) a CDR-L3 comprising the amino acid sequence set forth in SEQ ID NO: 266. In certain embodiments, the second antigen-binding moiety comprises a heavy chain variable domain (VH) sequence comprising (1) a CDR-H1 comprising the amino acid sequence set forth in SEQ ID NO: 269, (2) a CDR-H2 comprising the amino acid sequence set forth in SEQ ID NO: 270, and (3) a CDR-H3 comprising the amino acid sequence set forth in SEQ ID NO: 271; and a light chain variable domain (VL) sequence comprising (1) a CDR-L1 comprising the amino acid sequence set forth in SEQ ID NO: 272, (2) a CDR-L2 comprising the amino acid sequence set forth in SEQ ID NO: 273, and (3) a CDR-L3 comprising the amino acid sequence set forth in SEQ ID NO: 274. In certain embodiments, the second antigen-binding moiety comprises a heavy chain variable domain (VH) sequence comprising (1) a CDR-H1 comprising the amino acid sequence set forth in SEQ ID NO: 277, (2) a CDR-H2 comprising the amino acid sequence set forth in SEQ ID NO: 278, and (3) a CDR-H3 comprising the amino acid sequence set forth in SEQ ID NO: 279; and a light chain variable domain (VL) sequence comprising (1) a CDR-L1 comprising the amino acid sequence set forth in SEQ ID NO: 280, (2) a CDR-L2 comprising the amino acid sequence set forth in SEQ ID NO: 281, and (3) a CDR-L3 comprising the amino acid sequence set forth in SEQ ID NO: 282. In certain embodiments, the second antigen-binding moiety comprises a heavy chain variable domain (VH) sequence comprising (1) a CDR-H1 comprising the amino acid sequence set forth in SEQ ID NO: 285, (2) a CDR-H2 comprising the amino acid sequence set forth in SEQ ID NO: 286, and (3) a CDR-H3 comprising the amino acid sequence set forth in SEQ ID NO: 287; and a light chain variable domain (VL) sequence comprising (1) a CDR-L1 comprising the amino acid sequence set forth in SEQ ID NO: 288, (2) a CDR-L2 comprising the amino acid sequence set forth in SEQ ID NO: 289, and (3) a CDR-L3 comprising the amino acid sequence set forth in SEQ ID NO: 290. In certain embodiments, the second antigen-binding moiety comprises a heavy chain variable domain (VH) sequence comprising (1) a CDR-H1 comprising the amino acid sequence set forth in SEQ ID NO: 293, (2) a CDR-H2 comprising the amino acid sequence set forth in SEQ ID NO: 294, and (3) a CDR-H3 comprising the amino acid sequence set forth in SEQ ID NO: 295; and a light chain variable domain (VL) sequence comprising (1) a CDR-L1 comprising the amino acid sequence set forth in SEQ ID NO: 296, (2) a CDR-L2 comprising the amino acid sequence set forth in SEQ ID NO: 297, and (3) a CDR-L3 comprising the amino acid sequence set forth in SEQ ID NO: 298.

In certain embodiments, the anti-PDL1 antibody comprises a human antibody.

In certain embodiments, the second antigen binding moiety comprises an anti-PDL1 antibody comprising two antibody heavy chains and two antibody light chains. In certain embodiments, the first antigen-binding moiety comprises two or more anti-TIGIT antibodies. In certain embodiments, the first antigen-binding moiety comprises two anti-TIGIT antibodies.

In certain embodiments, the C-terminus of at least one of the two anti-PDL1 light chains is linked to an anti-TIGIT antibody of the first antigen binding moiety. In certain embodiments, the C-terminus of each of the two anti-PDL1 light chains is linked to an anti-TIGIT antibody of the first antigen binding moiety. In certain embodiments, the N-terminus of at least one of the two anti-PDL1 light chains is linked to an anti-TIGIT antibody of the first antigen binding moiety. In certain embodiments, the N-terminus of each of the two anti-PDL1 light chains is linked to an anti-TIGIT antibody of the first antigen binding moiety. In certain embodiments, the C-terminus of at least one of the two anti-PDL1 heavy chains is linked to an anti-TIGIT antibody of the first antigen binding moiety. In certain embodiments, the C-terminus of each of the two anti-PDL1 heavy chains is linked to an anti-TIGIT antibody of the first antigen binding moiety. In certain embodiments, the N-terminus of at least one of the two anti-PDL1 heavy chains is linked to an anti-TIGIT antibody of the first antigen binding moiety. In certain embodiments, the N-terminus of each of the two anti-PDL1 heavy chains is linked to an anti-TIGIT antibody of the first antigen binding moiety.

In certain embodiments, the first antigen binding moiety is linked to the second antigen binding moiety via a linker. In certain embodiments, the linker is a peptide linker. In certain embodiments, the peptide linker comprises about four to about thirty amino acids. In certain embodiments, the peptide linker comprises an amino acid sequence selected from the group consisting of SEQ ID NOs: 195-220.

In certain embodiments, the anti-PDL1 antibody of the second antigen-binding moiety comprises an Fc region selected from the group consisting of the Fc regions of IgG, IgA, IgD, IgE and IgM. In certain embodiments, the anti-PDL1 antibody of the second antigen-binding moiety comprises an Fc region selected from the group consisting of the Fc region of IgG1, IgG2, IgG3 and IgG4. In certain embodiments, the Fc region comprises a human Fc region. In certain embodiments, the Fc region comprises an IgG1 Fc region. In certain embodiments, the Fc region comprises an IgG4 Fc region. In certain embodiments, the IgG4 Fc region comprises an S228P mutation. In certain embodiments, the multispecific antibody is a bispecific antibody.

In certain embodiments, the multispecific antibody comprises: i) a first antigen-binding moiety comprising a single domain anti-TIGIT antibody that comprises a heavy chain variable region CDR1 comprising amino acids having the sequence set forth in SEQ ID NO: 186, a heavy chain variable region CDR2 comprising amino acids having the sequence set forth in SEQ ID NO: 187, and a heavy chain variable region CDR3 comprising amino acids having the sequence set forth in SEQ ID NO: 188; and ii) a second antigen-binding moiety comprising an anti-PDL1 antibody comprising a heavy chain variable domain (VH) sequence that comprises (1) a CDR-H1 comprising the amino acid sequence set forth in SEQ ID NO: 237, (2) a CDR-H2 comprising the amino acid sequence set forth in SEQ ID NO: 238, and (3) a CDR-H3 comprising the amino acid sequence set forth in SEQ ID NO: 239; and a light chain variable domain (VL) sequence comprising (1) a CDR-L1 comprising the amino acid sequence set forth in SEQ ID NO: 240, (2) a CDR-L2 comprising the amino acid sequence set forth in SEQ ID NO: 241, and (3) a CDR-L3 comprising the amino acid sequence set forth in SEQ ID NO: 242.

In certain embodiments, the multispecific antibody comprises: i) a first antigen-binding moiety comprising a single domain anti-TIGIT antibody that comprises a heavy chain variable region CDR1 comprising amino acids having the sequence set forth in SEQ ID NO: 178, a heavy chain variable region CDR2 comprising amino acids having the sequence set forth in SEQ ID NO: 179, and a heavy chain variable region CDR3 comprising amino acids having the sequence set forth in SEQ ID NO: 180; and ii) a second antigen-binding moiety comprising an anti-PDL1 antibody comprising a heavy chain variable domain (VH) sequence that comprises (1) a CDR-H1 comprising the amino acid sequence set forth in SEQ ID NO: 253, (2) a CDR-H2 comprising the amino acid sequence set forth in SEQ ID NO: 254, and (3) a CDR-H3 comprising the amino acid sequence set forth in SEQ ID NO: 255; and a light chain variable domain (VL) sequence comprising (1) a CDR-L1 comprising the amino acid sequence set forth in SEQ ID NO: 256, (2) a CDR-L2 comprising the amino acid sequence set forth in SEQ ID NO: 257, and (3) a CDR-L3 comprising the amino acid sequence set forth in SEQ ID NO: 258.

In certain embodiments, the multispecific antibody comprises: i) a first antigen-binding moiety comprising a single domain anti-TIGIT antibody that comprises a heavy chain variable region CDR1 comprising amino acids having the sequence set forth in SEQ ID NO: 182, a heavy chain variable region CDR2 comprising amino acids having the sequence set forth in SEQ ID NO: 183, and a heavy chain variable region CDR3 comprising amino acids having the sequence set forth in SEQ ID NO: 184; and ii) a second antigen-binding moiety comprising an anti-PDL1 antibody comprising a heavy chain variable domain (VH) sequence that comprises (1) a CDR-H1 comprising the amino acid sequence set forth in SEQ ID NO: 245, (2) a CDR-H2 comprising the amino acid sequence set forth in SEQ ID NO: 246, and (3) a CDR-H3 comprising the amino acid sequence set forth in SEQ ID NO: 247; and a light chain variable domain (VL) sequence comprising (1) a CDR-L1 comprising the amino acid sequence set forth in SEQ ID NO: 248, (2) a CDR-L2 comprising the amino acid sequence set forth in SEQ ID NO: 249, and (3) a CDR-L3 comprising the amino acid sequence set forth in SEQ ID NO: 250.

In certain embodiments, the multispecific antibody comprises: i) a first antigen-binding moiety comprising a single domain anti-TIGIT antibody that comprises a heavy chain variable region CDR1 comprising amino acids having the sequence set forth in SEQ ID NO: 94, a heavy chain variable region CDR2 comprising amino acids having the sequence set forth in SEQ ID NO: 95, and a heavy chain variable region CDR3 comprising amino acids having the sequence set forth in SEQ ID NO: 96; and ii) a second antigen-binding moiety comprising an anti-PDL1 antibody comprising a heavy chain variable domain (VH) sequence that comprises (1) a CDR-H1 comprising the amino acid sequence set forth in SEQ ID NO: 293, (2) a CDR-H2 comprising the amino acid sequence set forth in SEQ ID NO: 294, and (3) a CDR-H3 comprising the amino acid sequence set forth in SEQ ID NO: 295; and a light chain variable domain (VL) sequence comprising (1) a CDR-L1 comprising the amino acid sequence set forth in SEQ ID NO: 296, (2) a CDR-L2 comprising the amino acid sequence set forth in SEQ ID NO: 297, and (3) a CDR-L3 comprising the amino acid sequence set forth in SEQ ID NO: 298.

In certain embodiments, the multispecific antibody comprises: i) a first antigen-binding moiety comprising a single domain anti-TIGIT antibody that comprises a heavy chain variable region CDR1 comprising amino acids having the sequence set forth in SEQ ID NO: 190, a heavy chain variable region CDR2 comprising amino acids having the sequence set forth in SEQ ID NO: 191, and a heavy chain variable region CDR3 comprising amino acids having the sequence set forth in SEQ ID NO: 192; and ii) a second antigen-binding moiety comprising an anti-PDL1 antibody comprising a heavy chain variable domain (VH) sequence that comprises (1) a CDR-H1 comprising the amino acid sequence set forth in SEQ ID NO: 221, (2) a CDR-H2 comprising the amino acid sequence set forth in SEQ ID NO: 222, and (3) a CDR-H3 comprising the amino acid sequence set forth in SEQ ID NO: 223; and a light chain variable domain (VL) sequence comprising (1) a CDR-L1 comprising the amino acid sequence set forth in SEQ ID NO: 224, (2) a CDR-L2 comprising the amino acid sequence set forth in SEQ ID NO: 225, and (3) a CDR-L3 comprising the amino acid sequence set forth in SEQ ID NO: 226.

In certain embodiments, the multispecific antibody comprises an anti-PDL1 antibody heavy chain linked to an anti-TIGIT antibody comprising the amino acid sequence set forth in SEQ ID NO: 309, and an anti-PDL1 antibody light chain comprising the amino acid sequence set forth in SEQ ID NO: 310. In certain embodiments, the multispecific antibody comprises an anti-PDL1 antibody heavy chain comprising the amino acid sequence set forth in SEQ ID NO: 311, and an anti-PDL1 antibody light chain linked to an anti-TIGIT antibody comprising the amino acid sequence set forth in SEQ ID NO: 312. In certain embodiments, the multispecific antibody comprises an anti-PDL1 antibody heavy chain linked to an anti-TIGIT antibody comprising the amino acid sequence set forth in SEQ ID NO: 313, and an anti-PDL1 antibody light chain comprising the amino acid sequence set forth in SEQ ID NO: 314. In certain embodiments, the multispecific antibody comprises an anti-PDL1 antibody heavy chain comprising the amino acid sequence set forth in SEQ ID NO: 315, and an anti-PDL1 antibody light chain linked to an anti-TIGIT antibody comprising the amino acid sequence set forth in SEQ ID NO: 316.

The present disclosure further provides immunoconjugates comprising any multispecific antibodies disclosed herein, linked to a therapeutic agent. In certain embodiments, the therapeutic agent is a cytotoxin. In certain embodiments, the therapeutic agent is a radioactive isotope.

The present disclosure further provides pharmaceutical compositions. In certain embodiments, the pharmaceutical composition comprises a) a multispecific antibody or a immunoconjugate disclosed herein, and b) a pharmaceutically acceptable carrier.

The present disclosure further provides nucleic acids encoding any multispecific antibodies disclosed herein. The present disclosure further provides vectors comprising any nucleic acid disclosed herein. The present disclosure further provides host cells comprising a nucleic acid or a vector disclosed herein.

The present disclosure further provides methods for preparing an multispecific antibody disclosed herein. In certain embodiments, the method comprises expressing a multispecific antibody in a host cell disclosed herein and isolating the multispecific antibody from the host cell.

The present disclosure further provides methods of reducing tumor burden in a subject. In certain embodiments, the method comprises administering to the subject an effective amount of an multispecific antibody, an immunoconjugate, or a pharmaceutical composition disclosed herein.

In certain embodiments, the method reduces the number of tumor cells. In certain embodiments, the method reduces tumor size. In certain embodiments, the method eradicates the tumor in the subject. In certain embodiments, the tumor is selected from the group consisting of mesothelioma, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, cholangiocarcinoma, head and neck cancer, blood cancer and a combination thereof.

The present disclosure further provides methods of treating and/or preventing a neoplasm in a subject. In certain embodiments, the method comprises administering to the subject an effective amount of an multispecific antibody, an immunoconjugate, or a pharmaceutical composition disclosed herein.

The present disclosure further provides methods of lengthening survival of a subject having a neoplasm. In certain embodiments, the method comprises administering to the subject an effective amount of an multispecific antibody, an immunoconjugate, or a pharmaceutical composition disclosed herein.

In certain embodiments, the neoplasm is selected from the group consisting of mesothelioma, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, cholangiocarcinoma, head and neck cancer, blood cancer and a combination thereof.

The present disclosure further provides multispecific antibodies disclosed herein for use as a medicament. The present disclosure further provides multispecific antibodies disclosed herein for use in treating cancer. The present disclosure further provides pharmaceutical compositions disclosed herein for use as a medicament. The present disclosure further provides pharmaceutical compositions disclosed herein for use in treating cancer. In certain embodiments, the cancer is selected from the group consisting of mesothelioma, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, cholangiocarcinoma, head and neck cancer, blood cancer and a combination thereof.

The present disclosure further provides kits comprising an multispecific antibody, an immunoconjugate, a pharmaceutical composition, a nucleic acid, a vector or a host cell disclosed herein. In certain embodiments, the kit comprise a written instruction for treating and/or preventing a neoplasm.

BRIEF DESCRIPTION OF THE FIGURES

FIG. 1A shows one assay with comparison to a reference anti-human-TIGIT antibody (Reference Ab 1). FIG. 1B shows a different assay with additional VHH antibodies. Y axis represents Mean Fluorescence Intensity of AlexaFlour 488. X axis represents antibody concentrations in nanomolar. 2B7, 1G1, 1C12, 3G6, 2B10, 3G7, 3G10, 13H11, and 15A5 are VHH clones of anti-human TIGIT. EC50 values were obtained using non-liner regression method by Prism, and values are shown in the table as nanomolar. FIG. 1C is a schematic of the structure of a TIGIT VHH bivalent antibody.

FIG. 6A shows binding of heated samples of representative clones to h-TIGIT ECD in an ELISA assay with clone names labeled in the figure legends. Y axis represents OD450 obtained from the ELISA assay. X axis represents temperature for the treatment. FIG. 6B shows binding of heated samples of representative clones to h-TIGIT stably expressed in Jurkat cells determined by flowcytometry. Y axis represents percentage of binding to h-TIGIT. X axis represents temperature for the treatment.

FIG. 8A shows binding of 2A3-Fc to recombinant human TIGIT ECD. Reference Ab 2 is an anti-h-TIGIT reference antibody. Both 2A3-Fc and Reference Ab 2bind to h-TIGIT with similar affinity. Anti-PDL1 did not bind to h-TIGIT. FIG. 8B shows binding of 2A3-Fc to recombinant cyno-TIGIT. Both 2A3-Fc and Reference Ab 2bind to cyno-TIGIT with similar affinity. Anti-PDL1 did not bind to cyno-TIGIT. FIG. 8C shows binding of 2A3-Fc to recombinant mouse-TIGIT. Neither 2A3-Fc nor Reference Ab 2binds to mouse-TIGIT, however an anti-mouse TIGIT reference antibody (Biolegend #142101) bind to mouse-TIGIT with a high affinity. Y axis represents OD450, X axis represents antibody concentrations in μg/ml.

FIG. 10A shows the comparison of potency of hotspot corrected version 2A3-LT-Fc to Reference Ab 2 in whole cell binding. Y axis represents mean fluorescence intensity of AlexaFlour 488 determined by flowcytometry assay using CytoFlex. X axis represents antibody concentrations in nanomolar. Data shown is a representative result from three different experiments. 2A3-LT-Fc had slightly higher affinity to h-TIGIT than Reference Ab 2. FIG. 10B shows the comparison of potency of hotspot corrected version 2A3-LT-Fc to Reference Ab 2 in TIGIT blockade NFAT reporter assay. Y axis represents NFAT luciferase reporter activity in relative luminescence units. X axis represents antibody concentrations in nanomolar. 2A3-LT-Fc had similar potency to that of Reference Ab 2.

FIG. 13A depicts the effects of TIGIT mAbs 2A3-LT-Fc wt, and DLE mutant on blocking TIGIT activity determined using NFAT luciferase reporter assay. Human TIGIT and NFAT reporter gene stably transfected Jurkat cells were co-cultured with PVR stably transfected Raji cells. 2A3-LT-Fc wt and mutants were added and cultured for 5 hours. The TCR-mediated activity was measured by luciferase activity. Y axis represents NFAT luciferase activity in relative luminescence units. X axis represents antibody concentrations in nanomolar. FIG. 13B depicts the effects of TIGIT mAbs 2A3-LT-Fc wt, and DLE mutant on human FcγRIIIA-mediated activity determined by FcγRIIIA-mediated NFAT luciferase reporter activity. Human FcγRIIIA and NFAT stably transfected Jurkat cells were co-cultured with human TIGIT stably transfected 293T cells in the presence of different concentrations of 2A3-LT-Fc wt, and DLE mutant for 5 hours. Luciferase activity was measured and is presented in Y axis as relative luminescence units. X axis represents antibody concentrations in nanomolar.

FIG. 14A depicts tumor growth curves of tumor bearing mice treated with vehicle control, 2A3-Fc-wt, 2A3-Fc with DLE mutations and Reference Ab 2. The results of individual tumor volume are shown in FIG. 14B. FIG. 14C shows that body weight changes were not significant between the groups throughout the study.

FIG. 19B shows that in survival monitoring, BsAb HCN showed better survival benefit than treatment of Combo with complete remission seen in two mice. All treatment was well-tolerated with no significant change of body weights among different groups.

FIG. 22A shows that both PDL1 and PVR suppress TCR signal in CD8+ T cells through binding to corresponding receptors, whereas blocking both PDL1/PD1 and PVR/TIGIT interactions by the BsAb can reduce suppressive effects from both PDL1 and PVR double positive tumor cells or antigen presenting cell (APC). As PVR is expressed in PDL1 negative cells, the suppressive effect by PVR to TIGIT can also be blocked by the BsAb through binding to TIGIT. FIG. 22B shows that PVR expressed on tumor cells or antigen presenting cells (APC) can also bind to TIGIT on NK cells, induce inhibitory signal and suppress NK cells function, whereas blocking binding of PVR to TIGIT by the BsAb can reduce the suppressive effect, leading to enhanced NK cells function. PVR on tumor cells or APC can also bind to TIGIT on Treg cells, induces stimulatory signal and enhances Tregs function, leading to suppression of anti-tumor immune activity, whereas blocking TIGIT on Tregs can reduce Tregs function and enhance anti-tumor activity. FIG. 22C shows that the BsAb is also capable of binding to PDL1 on tumor cells with one arm and binding to TIGIT on T cells with another arm, where the bridging effect by BsAb brings tumor cells closely to CD8+ T cells, leading to enhanced activation of CD8+ T cells by increased interaction between HLA-I and TCR.

DETAILED DESCRIPTION

Figure 1A:
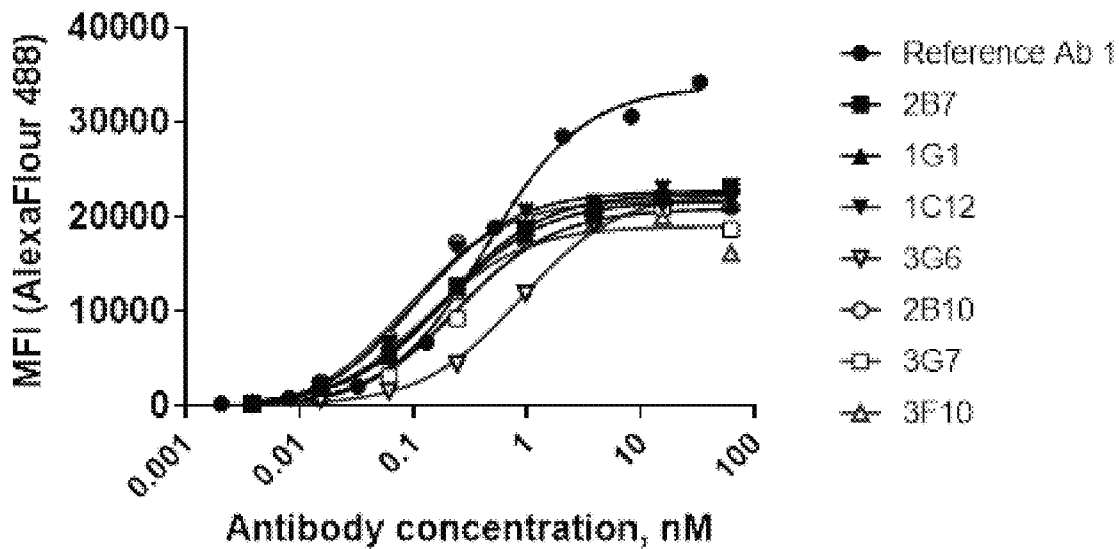
FIGS. 1A-1C depict whole cell binding of representative VHH bivalent antibodies to human TIGIT determined by flowcytometry assays.

The present disclosure provides isolated monoclonal antibodies that bind specifically to TIGIT with high affinity, including multispecific antibodies that binds to TIGIT and one or more additional target. In certain embodiments, the anti-TIGIT antibody comprises a single domain antibody that binds to TIGIT. In certain embodiments, the additional target is PDL1. This disclosure further provides methods of making and using the antibodies, immunoconjugates and pharmaceutical compositions comprising the antibodies, e.g., for treating diseases and disorders, e.g., cancer. The invention is based, in part, on the discovery of single domain anti-TIGIT antibodies that bind to TIGIT and multispecific antibodies that bind to both TIGIT and PDL1, which antibodies are capable of increasing an immune response in immune cells and provide improved anti-tumor efficacy.

For clarity and not by way of limitation the detailed description of the presently disclosed subject matter is divided into the following subsections:
  1. Definitions;
  2. Antibodies;
  3. Methods of use;
  4. Pharmaceutical formulations; and
  5. Articles of manufacture.

1. Definitions

The term "antibody" herein is used in the broadest sense and encompasses various antibody structures, including but not limited to monoclonal antibodies, polyclonal antibodies, multispecific antibodies (e.g., bispecific antibodies), single domain antibody and antibody fragments so long as they exhibit the desired antigen-binding activity.

An "antibody fragment" refers to a molecule that comprises an antigen binding portion of an intact full-length antibody that binds to the antigen to which the intact antibody binds. Examples of antibody fragments include but are not limited to Fv, Fab, Fab', Fab'-SH, F(ab')2, diabodies, linear antibodies, single-chain antibody molecules (e.g., scFv), multispecific antibodies formed from antibody fragments, a single domain antibody, a VHH, a nanobody, a domain antibody, a bivalent domain antibody, or any other fragment of an antibody that binds to an antigen. A "VHH" refers to a single domain antibody isolated from a camelid animal. In certain embodiments, a VHH comprises a variable region of a heavy chain of a camelid heavy chain antibody. In certain embodiments, a VHH has a size of no more than about 25 kDa. In certain embodiments, a VHH has a size of no more than about 20 kDa. In certain embodiments, a VHH has a size of no more than about 15 kDa.

A "full-length antibody" refers to an antibody comprising two heavy chains and two light chains. The variable regions of the light and heavy chains are responsible for antigen binding. The variable regions of a heavy chain and a light chain may be referred to as "VH" and "VL", respectively. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by well-known conventions, e.g., the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more conserved than the CDRs and form a scaffold to support the hypervariable loops. The constant regions of the heavy and light chains are not involved in antigen binding but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

An "antibody that cross-competes for binding" with a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is described in Antibodies, Harlow and Lane (Cold Spring Harbor Press, Cold Spring Harbor, NY).

"Fv" is a minimum antibody fragment which contains a complete antigen-recognition and -binding site. This fragment consists of a dimer of one heavy- and one light-chain variable region in tight, non-covalent association. From the folding of these two domains emanate six hypervariable loops (3 loops in each of the heavy and light chains) that contribute the amino acid residues to antigen binding and confer antigen binding specificity to the antibody. However, even a single variable domain (or half of an Fv comprising only three CDRs specific for an antigen) can recognize and bind to an antigen, although sometimes at a lower affinity than the entire binding site.

"Single-chain Fv," also abbreviated as "sFv" or "scFv," are antibody fragments that comprise the VH and VL antibody domains connected into a single polypeptide chain. In some embodiments, the scFv polypeptide further comprises a polypeptide linker between the VH and $V_L$ domains which enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994).

An "acceptor human framework" or "human framework" for the purposes herein is a framework comprising the amino acid sequence of a light chain variable domain (VL) framework or a heavy chain variable domain (VH) framework derived from a human immunoglobulin framework or a human consensus framework. An acceptor human framework "derived from" a human immunoglobulin framework or a human consensus framework may comprise the same amino acid sequence thereof, or it may contain amino acid sequence changes. In certain embodiments, the number of amino acid changes are 10 or less, 9 or less, 8 or less, 7 or less, 6 or less, 5 or less, 4 or less, 3 or less, or 2 or less. In certain embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more CDRs or hypervariable regions (HVRs), compared to a parent antibody which does not possess such alterations, which alterations provide improved affinity of the antibody for antigen.

"T cell immunoreceptor with Ig and ITIM domains" or "TIGIT" as used herein, refers to any native TIGIT polypeptide from any vertebrate source, including mammals such as primates (e.g., humans and cynomolgus monkeys), or any fragment thereof, and may optionally comprise up to one, up to two, up to three, up to four, up to five, up to six, up to seven, up to eight, up to nine or up to ten amino acid substitutions, additions and/or deletions. The term encompasses full-length, unprocessed TIGIT as well as any form of TIGIT that results from processing in the cell. The term also encompasses naturally occurring variants of TIGIT, e.g., splice variants or allelic variants. A non-limiting example of a human TIGIT amino acid sequence targeted by an anti-TIGIT antibody of the present disclosure is as follows:

```
                                                           [SEQ ID NO: 317]
  1    MRWCLLLIWA QGLRQAPLAS GMMTGTIETT GNISAEKGGS IILQCHLSST TAQVTQVNWE

61    QQDQLLAICN ADLGWHISPS FKDRVAPGPG LGLTLQSLTV NDTGEYFCIY HTYPDGTYTG

121    RIFLEVLESS VAEHGARFQI PLLGAMAATL VVICTAVIVV VALTRKKKAL RIHSVEGDLR

181    RKSAGQEEWS PSAPSPPGSC VQAEAAPAGL CGEQRGEDCA ELHDYFNVLS YRSLGNCSFF

241    TETG.
```

The term "ECD of TIGIT" refers to the extracellular domain of TIGIT. For example, the ECD of the exemplary TIGIT protein shown in SEQ ID NO: 317 comprises the following amino acid sequence:

```
                                           [SEQ ID NO: 318]
MRWCLLLIWA QGLRQAPLAS GMMTGTIETT GNISAEKGGS

IILQCHLSST TAQVTQVNWE QQDQLLAICN ADLGWHISPS

FKDRVAPGPG LGLTLQSLTV NDTGEYFCIY HTYPDGTYTG

RIFLEVLESS VAEHGARF.
```

The terms "anti-TIGIT antibody" and "an antibody that binds to TIGIT" refer to an antibody that is capable of binding to TIGIT with sufficient affinity such that the antibody is useful as a diagnostic and/or therapeutic agent for targeting TIGIT. In one embodiment, the extent of binding of an anti-TIGIT antibody to an unrelated, non-TIGIT protein is less than about 10% of the binding of the antibody to TIGIT as measured, e.g., by a BIACORE® surface plasmon resonance assay. In certain embodiments, an antibody that binds to TIGIT has a dissociation constant (Kd) of <about 1 µM, <about 100 nM, <about 10 nM, <about 1 nM, <about 0.1 nM, <about 0.01 nM, or <about 0.001 nM (e.g., $10^{-8}$ M or less, e.g., from $10^{-8}$ M to $10^{-12}$ M, e.g., from $10^{-9}$ M to $10^{-10}$ M). In certain embodiments, an anti-TIGIT antibody binds to an epitope of TIGIT that is conserved among TIGIT from different species. In certain embodiments, an anti-TIGIT antibody binds to an epitope on TIGIT that is in the ECD of the protein.

"Programmed cell death ligand 1" or "PDL1", as used herein, refers to any native PDL1 polypeptide from any vertebrate source, including mammals such as primates (e.g., humans and cynomolgus monkeys), or any fragment thereof, and may optionally comprise up to one or up to two or up to three amino acid substitutions, additions or deletions. The term encompasses "full-length", unprocessed PDL1 as well as any form of PDL1 that results from processing in the cell. The term also encompasses naturally occurring variants of PDL1, e.g., splice variants or allelic variants. Non-limiting examples of a human PDL1 amino acid sequence targeted by an anti-PDL1 antibody of the present disclosure include polypeptides having the NCBI Reference Nos: NP_001254635.1, NP_001300958.1, NP_054862.1, and any variants, modifications and descendants thereof.

The terms "anti-PDL1 antibody" and "an antibody that binds to PDL1" refer to an antibody that is capable of binding PDL1 with sufficient affinity such that the antibody is useful as a diagnostic and/or therapeutic agent in targeting PDL1. In certain embodiments, the antibody is any anti-PDL1 antibody disclosed in PCT/US2017/056689 (published as International Publication WO 2018/080812 A1), the content of which is incorporated herein by references in its entirety.

The term "chimeric" antibody refers to an antibody in which a portion of the heavy and/or light chain is derived from a particular source or species, while the remainder of the heavy and/or light chain is derived from a different source or species. In certain embodiments, a chimeric antibody disclosed herein comprises a camelid heavy chain variable region and a human Fc region.

As used herein, the term "CDR" or "complementarity determining region" is intended to mean the non-contiguous antigen combining sites within the variable region of a heavy chain and/or a light chain. These particular regions have been described by Kabat et al., J. Biol. Chem. 252: 6609-6616 (1977); Kabat et al., U.S. Dept. of Health and Human Services, "Sequences of proteins of immunological interest" (1991); Chothia et al., J. Mol. Biol. 196:901-917 (1987); Al-Lazikani B. et al., J. Mol. Biol., 273: 927-948 (1997); MacCallum et al., J. Mol. Biol. 262:732-745 (1996); Abhinandan and Martin, Mol. Immunol., 45: 3832-3839 (2008); Lefranc M. P. et al., Dev. Comp. Immunol., 27: 55-77 (2003); and Honegger and Pluckthun, J. Mol. Biol., 309:657-670 (2001), where the definitions include overlapping or subsets of amino acid residues when compared against each other. Nevertheless, application of any one of the definitions to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, Mol. Immunol., 45: 3832-3839 (2008); Ehrenmann F. et al., Nucleic Acids Res., 38: D301-D307 (2010); and Adolf-Bryfogle J. et al., Nucleic Acids Res., 43: D432-D438 (2015). The contents of the references cited in this paragraph are incorporated herein by reference in their entireties for use in the present application and for possible inclusion in one or more claims herein.

TABLE 1

CDR definitions

|  | Kabat[1] | Chothia[2] | MacCallum[3] | IMGT[4] | AHo[5] |
|---|---|---|---|---|---|
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra.
[2]Residue numbering follows the nomenclature of Chothia et al., supra.
[3]Residue numbering follows the nomenclature of MacCallum et al., supra.
[4]Residue numbering follows the nomenclature of Lefranc et al., supra.
[5]Residue numbering follows the nomenclature of Honegger and Plückthun, supra.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or CDR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

In certain embodiments, the amino acid residues which encompass the CDRs of a single domain antibody (e.g., a single domain anti-TIGIT antibody disclosed herein) is defined according to the IMGT nomenclature in Lefranc et al., supra. In certain embodiments, the amino acid residues which encompass the CDRs of a full-length antibody (e.g., an anti-PDL1 antibody disclosed herein) is defined according to the Kabat nomenclature in Kabat et al., supra. In certain embodiments, the numbering of the residues in an immunoglobulin heavy chain, e.g., in an Fc region, is that of the EU index as in Kabat et al., supra. The "EU index as in Kabat" refers to the residue numbering of the human IgG1 EU antibody.

"Framework" or "FR" refers to residues are those variable-domain residues other than the CDR residues as herein defined.

A "humanized" antibody refers to a chimeric antibody comprising amino acid residues from non-human CDRs/HVRs and amino acid residues from human FRs. In certain embodiments, a humanized antibody will comprise substantially all of at least one, and typically two, variable domains, in which all or substantially all of the HVRs/CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., Nucleic Acids Research 32(5):1792-1797, 2004; Edgar, R. C., BMC Bioinformatics 5(1):113, 2004).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "constant domain" refers to the portion of an immunoglobulin molecule having a more conserved amino acid sequence relative to the other portion of the immunoglobulin, the variable domain, which contains the antigen-binding site. The constant domain contains the CH1, CH2 and CH3 domains (collectively, CH) of the heavy chain and the CL domain of the light chain.

The "light chains" of antibodies (e.g., immunoglobulins) from any mammalian species can be assigned to one of two clearly distinct types, called kappa ("κ") and lambda ("λ"), based on the amino acid sequences of their constant domains.

The "CH1 domain" (also referred to as "C1" of "H1" domain) usually extends from about amino acid 118 to about amino acid 215 (EU numbering system).

"Hinge region" is generally defined as a region in IgG corresponding to Glu216 to Pro230 of human IgG1 (Burton, Molec. Immunol. 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec Immunol. 22:161-206 (1985).

The "CH3 domain" (also referred to as "C2" domain) comprises the residues between a CH2 domain and the C-terminal of an Fc region (i.e. from about amino acid residue 341 to the C-terminal end of an antibody sequence, typically at amino acid residue 446 or 447 of an IgG).

The term "Fc region" or "fragment crystallizable region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibitory receptor FcγRIIB contains an immunoreceptor tyrosine-based inhibition motif (ITIM) in its cytoplasmic domain. (See M. Daëron, Annu. Rev. Immunol. 15:203-234 (1997). FcRs are reviewed in Ravetch and Kinet, Annu. Rev. Immunol. 9: 457-92 (1991); Capel et al., Immunomethods 4: 25-34 (1994); and de Haas et al., J. Lab. Clin. Med. 126:

330-41 (1995). Other FcRs, including those to be identified in the future, are encompassed by the term "FcR" herein.

The term "epitope" as used herein refers to the specific group of atoms or amino acids on an antigen to which an antibody or antigen-binding moiety binds. Two antibodies or antigen-binding moieties may bind the same epitope within an antigen if they exhibit competitive binding for the antigen.

As use herein, the terms "specifically binds," "specifically recognizing," and "is specific for" refer to measurable and reproducible interactions, such as binding between a target and an antibody or antibody moiety, which is determinative of the presence of the target in the presence of a heterogeneous population of molecules, including biological molecules. For example, an antibody or antibody moiety that specifically recognizes a target (which can be an epitope) is an antibody or antibody moiety that binds this target with greater affinity, greater avidity, greater readiness, and/or greater duration than its bindings to other targets. In some embodiments, the extent of binding of an antibody to an unrelated target is less than about 10% of the binding of the antibody to the target as measured, e.g., by a radioimmunoassay (RIA). In some embodiments, an antibody that specifically binds a target has a dissociation constant ($K_D$) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, an antibody specifically binds an epitope on a protein that is conserved among the protein from different species. In some embodiments, specific binding can include, but does not require exclusive binding. Binding specificity of the antibody or antigen-binding domain can be determined experimentally by methods known in the art. Such methods comprise, but are not limited to Western blots, ELISA-, RIA-, ECL-, IRMA-, EIA-, BIACORE™-tests and peptide scans.

An "isolated" antibody (or construct) is one that has been identified, separated and/or recovered from a component of its production environment (e.g., natural or recombinant). In certain embodiments, the isolated polypeptide is free or substantially free from association with all other components from its production environment.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. In certain embodiments, the isolated nucleic acid is free or substantially free from association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid, which cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell and may contain mutations. Mutant progeny that have the same function or biological activity as screened or selected for in the originally transformed cell are included herein.

The terms "subject," "individual," and "patient" are used interchangeably herein to refer to a mammal, including, but not limited to, human, bovine, horse, feline, canine, rodent, or primate. In some embodiments, the subject is a human.

An "effective amount" of an agent refers to an amount effective, at dosages and for periods of time necessary, to achieve the desired therapeutic or prophylactic result. The specific dose may vary depending on one or more of the particular agent chosen, the dosing regimen to be followed, whether it is administered in combination with other compounds, timing of administration, the tissue to be imaged, and the physical delivery system in which it is carried.

A "therapeutically effective amount" of a substance/molecule of the application, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

As used herein, "treatment" or "treating" is an approach for obtaining beneficial or desired results, including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the application contemplate any one or more of these aspects of treatment. "Treatment" does not necessarily mean that the condition being treated will be cured.

It is understood that embodiments of the application described herein include "consisting" and/or "consisting essentially of" embodiments.

As used herein, the term "about" or "approximately" means within an acceptable error range for the particular value as determined by one of ordinary skill in the art, which will depend in part on how the value is measured or determined, i.e., the limitations of the measurement system. In certain embodiments, "about" can mean within 3 or more than 3 standard deviations, per the practice in the art. In certain embodiments, "about" can mean a range of up to 20%, e.g., up to 10%, up to 5%, or up to 1% of a given value. In certain embodiments, particularly with respect to biological systems or processes, the term can mean within an order of magnitude, e.g., within 5-fold or within 2-fold, of a value.

As used herein, the term "modulate" means positively or negatively alter. Exemplary modulations include a about 1%, about 2%, about 5%, about 10%, about 25%, about 50%, about 75%, or about 100% change.

As used herein, the term "increase" means alter positively by at least about 5%. An alteration may be by about 5%, about 10%, about 25%, about 30%, about 50%, about 75%, about 100% or more.

As used herein, the term "reduce" means alter negatively by at least about 5%. An alteration may be by about 5%, about 10%, about 25%, about 30%, about 50%, about 75%, or even by about 100%.

The term "about X-Y" used herein has the same meaning as "about X to about Y."

As used herein and in the appended claims, the singular forms "a," "or," and "the" include plural referents unless the context clearly dictates otherwise.

"Effector functions" refer to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), phagocytosis, down regulation of cell surface receptors (e.g., B cell receptor), and B cell activation.

An "immunoconjugate" refers to an antibody conjugated to one or more heterologous molecule(s), including but not limited to a cytotoxic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier," as used herein, refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "variable region" or "variable domain" refers to the domain of an antibody heavy or light chain that is involved in binding the antibody to antigen. In certain embodiments, the variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 61ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

2. Antibodies

In certain embodiments, the invention is based, in part, on the discovery of single domain antibodies that bind to TIGIT, which can be used in antitumor therapeutics where the antibodies selectively inhibit the TIGIT receptor and induce beneficial immune response of immune cells, e.g., T cells. Accordingly, the present disclosure provides anti-TIGIT antibodies. In certain embodiments, an anti-TIGIT antibody disclosed herein is an antagonist antibody, which inhibits TIGIT receptor functions. In certain embodiments, the anti-TIGIT antibody blocks an interaction between a TIGIT receptor and a ligand. In certain embodiments, the anti-TIGIT antibody blocks an immune inhibitory signal from a TIGIT receptor. In certain embodiments, the anti-TIGIT antibody comprises a single domain antibody, e.g., a camelid antibody or a VHH antibody. In certain embodiments, the anti-TIGIT antibody has an improved capability of tissue infiltration due to its smaller size compared to traditional antibodies in IgG, Fab and/or scFv forms.

The present disclosure further provides anti-PDL1 antibodies and multispecific antibodies that bind to both TIGIT and PDL1 (referred to herein as anti-TIGIT/anti-PDL1 antibodies. In certain embodiments, an antibody of the present disclosure can be or comprise a monoclonal antibody, including a chimeric, humanized or human antibody. In certain embodiments, the antibody disclosed herein comprises a humanized antibody. In certain embodiments, the antibody comprises an acceptor human framework, e.g., a human immunoglobulin framework or a human consensus framework.

In certain embodiments, an antibody of the present disclosure can be an antibody fragment, e.g., a Fv, Fab, Fab', scFv, diabody, or F(ab')2 fragment. In certain embodiments, the antibody is a full-length antibody, e.g., an intact IgG 1 antibody, or other antibody class or isotype as defined herein. In certain embodiments, an antibody of the present disclosure can incorporate any of the features, singly or in combination, as described in this application, e.g., Sections 2.1-2.13 detailed herein.

Antibodies of the present disclosure are useful, e.g., for the diagnosis or treatment of a neoplasm or a cancer. In certain embodiments, the neoplasia and cancers whose growth may be inhibited using the antibodies of this disclosure include neoplasia and cancers typically responsive to immunotherapy. In certain embodiments, the neoplasia and cancers include breast cancer (e.g., breast cell carcinoma), ovarian cancer (e.g., ovarian cell carcinoma) and renal cell carcinoma (RCC). Examples of other cancers that may be treated using the methods of this disclosure include melanoma (e.g., metastatic malignant melanoma), prostate cancer, colon cancer, lung cancer, bone cancer, pancreatic cancer, skin cancer, brain tumors, chronic or acute leukemias including acute myeloid leukemia, chronic myeloid leukemia, acute lymphoblastic leukemia, chronic lymphocytic leukemia, lymphomas (e.g., Hodgkin's and non-Hodgkin's lymphoma, lymphocytic lymphoma, primary CNS lymphoma, T-cell lymphoma) nasopharangeal carcinomas, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the breast gland, sarcoma of soft tissue, cancer of the urethra, cancer of the penis, solid tumors of childhood, cancer of the bladder, cancer of the kidney or ureter, carcinoma of the breast pelvis, neoplasm of the central nervous system (CNS), tumor angiogenesis, spinal axis tumor, brain stem glioma, pituitary adenoma, Kaposi's sarcoma, epidermoid cancer, squamous cell cancer, environmentally induced cancers including those induced by asbestos, e.g., mesothelioma and combinations of said cancers.

2.1. Exemplary Anti-TIGIT Antibodies

The present disclosure provides isolated antibodies that bind to a TIGIT protein. In certain embodiments, an anti-TIGIT antibody of the present disclosure binds to the ECD of TIGIT. In certain embodiments, the anti-TIGIT antibody binds to the ECD of TIGIT that comprises the amino acid sequence set forth in SEQ ID NO: 318. In certain embodiments, the anti-TIGIT antibody binds to the same epitope as an anti-TIGIT antibody, e.g., 2A3, described herein.

In certain embodiments, the anti-TIGIT antibody disclosed herein can function as an antagonist of a TIGIT receptor. In certain embodiments, the anti-TIGIT antibody can reduce the activity of the TIGIT receptor by at least about 10%, about 20%, about 30%, about 40%, about 50%, about 60%, about 70%, about 80%, about 90%, about 99% or about 99.9%. In certain embodiments, the anti-TIGIT antibody can block the downstream immune inhibitory signaling of the TIGIT receptor. In certain embodiments, the anti-TIGIT antibody increases an immune response and/or an antitumor effect of an immune cell, e.g., a T cell and/or a NK cell. In certain embodiments, treatment using the anti-TIGIT antibody exhibits antitumor efficacy in a subject, whereby reduces tumor growth and/or lengthen the survival of a subject. In certain embodiments, the anti-TIGIT antibody comprising a single domain antibody (e.g., a VHH) has a smaller molecule size compared to a full-length antibody due to the smaller size of a single domain antibody compared to a Fab domain of a full-length antibody, which can result in superior tissue infiltration, e.g., at a tumor site, compared to a full-length antibody. In certain embodiments, treatment using the anti-TIGIT antibody exhibits superior antitumor efficacy compared to treatment using a full-length anti-TIGIT antibody, e.g., Reference Ab 1having the same amino acid sequences of BMS 22G2 disclosed in U.S. 2016/0176963 A1 and Reference Ab 2 having the same amino acid sequences of Tiragolumab, which sequences are disclosed in U.S. 2017/0088613 A1.

In certain embodiments, the anti-TIGIT antibody comprises a single domain antibody that binds to TIGIT. In certain embodiments, the single domain antibody comprises a VHH. In certain embodiments, the single domain antibody comprises a heavy chain variable region (VH). In certain embodiments, the single domain antibody is linked to a Fc region. In certain embodiments, the single domain antibody is not linked to a Fc region.

In certain embodiments, the single domain antibody binds to TIGIT with a $K_D$ of about $1\times10^{-7}$ M or less. In certain embodiments, the single domain antibody binds to TIGIT with a KD of about $1\times10^{-8}$ M or less. In certain embodiments, the single domain antibody binds to TIGIT with a $K_D$ of about $5\times10^{-9}$ M or less. In certain embodiments, the single domain antibody binds to TIGIT with a $K_D$ of about $1\times10^{-9}$ M or less. In certain embodiments, the single domain antibody binds to TIGIT with a KD of between about $1\times10^{-9}$M and about $1\times10^{-7}$ M. In certain embodiments, the single domain antibody binds to TIGIT with a KD of between about $1\times10^{-9}$M and about $1\times10^{-8}$ M. In certain embodiments, the single domain antibody binds to TIGIT with a KD of between about $2\times10^{-9}$ M and about $1\times10^{-8}$ M. In certain embodiments, the single domain antibody binds to TIGIT with a KD of between about $2\times10^{-9}$ M and about $5\times10^{-8}$ M. In certain embodiments, the single domain antibody binds to TIGIT with a KD of between about $1\times10^{-9}$M and about $5\times10^{-9}$ M.

In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 94, a heavy chain variable region CDR2 comprising amino acids having the sequence set forth in SEQ ID NO: 95, and a heavy chain variable region CDR3 comprising amino acids having the sequence set forth in SEQ ID NO: 96. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 98, a heavy chain variable region CDR2 comprising amino acids having the sequence set forth in SEQ ID NO: 99, and a heavy chain variable region CDR3 comprising amino acids having the sequence set forth in SEQ ID NO: 100. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 102, a heavy chain variable region CDR2 comprising amino acids having the sequence set forth in SEQ ID NO: 103, and a heavy chain variable region CDR3 comprising amino acids having the sequence set forth in SEQ ID NO: 104. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 106, a heavy chain variable region CDR2 comprising amino acids having the sequence set forth in SEQ ID NO: 107, and a heavy chain variable region CDR3 comprising amino acids having the sequence set forth in SEQ ID NO: 108. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 110, a heavy chain variable region CDR2 comprising amino acids having the sequence set forth in SEQ ID NO: 111, and a heavy chain variable region CDR3 comprising amino acids having the sequence set forth in SEQ ID NO: 112. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 114, a heavy chain variable region CDR2 comprising amino acids having the sequence set forth in SEQ ID NO: 115, and a heavy chain variable region CDR3 comprising amino acids having the sequence set forth in SEQ ID NO: 116. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 118, a heavy chain variable region CDR2 comprising amino acids having the sequence set forth in SEQ ID NO: 119, and a heavy chain variable region CDR3 comprising amino acids having the sequence set forth in SEQ ID NO: 120. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 122, a heavy chain variable region CDR2 comprising amino acids having the sequence set forth in SEQ ID NO: 123, and a heavy chain variable region CDR3 comprising amino acids having the sequence set forth in SEQ ID NO: 124. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 126, a heavy chain variable region CDR2 comprising amino acids having the sequence set forth in SEQ ID NO: 127, and a heavy chain variable region CDR3 comprising amino acids having the sequence set forth in SEQ ID NO: 128. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 130, a heavy chain variable region CDR2 comprising amino acids having the sequence set forth in SEQ ID NO: 131, and a heavy chain variable region CDR3 comprising amino acids having the sequence set forth in SEQ ID NO: 132. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 134, a heavy chain variable region CDR2 comprising amino acids having the sequence set forth in SEQ ID NO: 135, and a heavy chain variable region CDR3 comprising amino acids having the sequence set forth in SEQ ID NO: 136. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 138, a heavy chain variable region CDR2 comprising amino acids having the sequence set forth in SEQ ID NO: 139, and a heavy chain variable region CDR3 comprising amino acids having the sequence set forth in SEQ ID NO: 140. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 142, a heavy chain variable region CDR2 comprising amino acids having the sequence set forth in SEQ ID NO: 143, and a heavy chain variable region CDR3 comprising amino acids having the sequence set forth in SEQ ID NO: 144. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 146, a heavy chain variable region CDR2 comprising amino acids having the sequence set forth in SEQ ID NO: 147, and a heavy chain variable region CDR3 comprising amino acids having the sequence set forth in SEQ ID NO: 148. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 150, a heavy chain variable region CDR2 comprising amino acids having the sequence set forth in SEQ ID NO: 151, and a heavy chain variable region CDR3 comprising amino acids having the sequence set forth in SEQ ID NO: 152. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 154, a heavy chain variable region CDR2 comprising amino acids having the sequence set forth in SEQ ID NO: 155, and a heavy chain variable region CDR3 comprising amino acids having the sequence set forth in SEQ ID NO: 156. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 158, a heavy chain variable region CDR2 comprising amino acids having the sequence set forth in SEQ ID NO: 159, and a heavy chain variable region CDR3 comprising amino acids having the sequence set forth in SEQ ID NO: 160. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 162, a heavy chain variable region CDR2 comprising amino acids having the sequence set forth in SEQ ID NO: 163, and a heavy chain variable region CDR3 comprising amino acids having the sequence set forth in SEQ ID NO: 164. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 166, a heavy chain variable region CDR2 comprising amino acids having the sequence set forth in SEQ ID NO: 167, and a heavy chain variable region CDR3 comprising amino acids having the sequence set forth in SEQ ID NO: 168. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 170, a heavy chain variable region CDR2 comprising amino acids having the sequence set forth in SEQ ID NO: 171, and a heavy chain variable region CDR3 comprising amino acids having the sequence set forth in SEQ ID NO: 172. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 174, a heavy chain variable region CDR2 comprising amino acids having the sequence set forth in SEQ ID NO: 175, and a heavy chain variable region CDR3 comprising amino acids having the sequence set forth in SEQ ID NO: 176. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 178, a heavy chain variable region CDR2 comprising amino acids having the sequence set forth in SEQ ID NO: 179, and a heavy chain variable region CDR3 comprising amino acids having the sequence set forth in SEQ ID NO: 180. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 182, a heavy chain variable region CDR2 comprising amino acids having the sequence set forth in SEQ ID NO: 183, and a heavy chain variable region CDR3 comprising amino acids having the sequence set forth in SEQ ID NO: 184. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 186, a heavy chain variable region CDR2 comprising amino acids having the sequence set forth in SEQ ID NO: 187, and a heavy chain variable region CDR3 comprising amino acids having the sequence set forth in SEQ ID NO: 188. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 190, a heavy chain variable region CDR2 comprising amino acids having the sequence set forth in SEQ ID NO: 191, and a heavy chain variable region CDR3 comprising amino acids having the sequence set forth in SEQ ID NO: 192.

In certain embodiments, the single domain antibody comprises a heavy chain variable region comprising: a) a heavy chain variable region CDR1 comprises an amino acid sequence of any one of SEQ ID NOs: 94, 98, 102, 106, 110, 114, 118, 122, 126, 130, 134, 138, 142, 146, 150, 154, 158, 162, 166, 170, 174, 178, 182, 186 and 190, or a variant thereof comprising up to about 3 amino acid substitutions; b) a heavy chain variable region CDR2 comprises an amino acid sequence of any one of SEQ ID NOs: 95, 99, 103, 107, 111, 115, 119, 123, 127, 131, 135, 139, 143, 147, 151, 155, 159, 163, 167, 171, 175, 179, 183, 187 and 191, or a variant thereof comprising up to about 3 amino acid substitutions; and c) a heavy chain variable region CDR3 comprises an amino acid sequence of any one of SEQ ID NOs: 96, 100, 104, 108, 112, 116, 120, 124, 128, 132, 136, 140, 144, 148, 152, 156, 160, 164, 168, 172, 176, 180, 184, 188 and 192, or a variant thereof comprising up to about 3 amino acid substitutions.

In certain embodiments, the single domain antibody comprises a heavy chain variable region that comprises a CDR1 domain, a CDR2 domain and a CDR3 domain, wherein the CDR1 domain, the CDR2 domain and the CDR3 domain respectively comprise a CDR1 domain, a CDR2 domain and a CDR3 domain comprised in a reference heavy chain variable region comprising the amino acid sequence selected from the group consisting of SEQ ID NOs: 97, 101, 105, 109, 113, 117, 121, 125, 129, 133, 137, 141, 145, 149, 153, 157, 161, 165, 169, 173, 177, 181, 185, 189 and 193.

In certain embodiments, the single domain antibody comprises a heavy chain variable region CDR1 comprising amino acids having the sequence set forth in SEQ ID NO: 94, a heavy chain variable region CDR2 comprising amino acids having the sequence set forth in SEQ ID NO: 95, and a heavy chain variable region CDR3 comprising amino acids having the sequence set forth in SEQ ID NO: 96. In certain embodiments, the single domain antibody comprises a heavy chain variable region CDR1 comprising amino acids having the sequence set forth in SEQ ID NO: 98, a heavy chain variable region CDR2 comprising amino acids having the sequence set forth in SEQ ID NO: 99, and a heavy chain variable region CDR3 comprising amino acids having the sequence set forth in SEQ ID NO: 100. In certain embodiments, the single domain antibody comprises a heavy chain variable region CDR1 comprising amino acids having the sequence set forth in SEQ ID NO: 102, a heavy chain variable region CDR2 comprising amino acids having the sequence set forth in SEQ ID NO: 103, and a heavy chain variable region CDR3 comprising amino acids having the sequence set forth in SEQ ID NO: 104. In certain embodiments, the single domain antibody comprises a heavy chain variable region CDR1 comprising amino acids having the sequence set forth in SEQ ID NO: 106, a heavy chain variable region CDR2 comprising amino acids having the sequence set forth in SEQ ID NO: 107, and a heavy chain variable region CDR3 comprising amino acids having the sequence set forth in SEQ ID NO: 108. In certain embodiments, the single domain antibody comprises a heavy chain variable region CDR1 comprising amino acids having the sequence set forth in SEQ ID NO: 110, a heavy chain variable region CDR2 comprising amino acids having the sequence set forth in SEQ ID NO: 111, and a heavy chain variable region CDR3 comprising amino acids having the sequence set forth in SEQ ID NO: 112. In certain embodiments, the single domain antibody comprises a heavy chain variable region CDR1 comprising amino acids having the sequence set forth in SEQ ID NO: 114, a heavy chain variable region CDR2 comprising amino acids having the sequence set forth in SEQ ID NO: 115, and a heavy chain variable region CDR3 comprising amino acids having the sequence set forth in SEQ ID NO: 116. In certain embodiments, the single domain antibody comprises a heavy chain variable region CDR1 comprising amino acids having the sequence set forth in SEQ ID NO: 118, a heavy chain variable region CDR2 comprising amino acids having the sequence set forth in SEQ ID NO: 119, and a heavy chain variable region CDR3 comprising amino acids having the sequence set forth in SEQ ID NO: 120. In certain embodiments, the single domain antibody comprises a heavy chain variable region CDR1 comprising amino acids having the sequence set forth in SEQ ID NO: 122, a heavy chain variable region CDR2 comprising amino acids having the sequence set forth in SEQ ID NO: 123, and a heavy chain variable region CDR3 comprising amino acids having the sequence set forth in SEQ ID NO: 124. In certain embodiments, the single domain antibody comprises a heavy chain variable region CDR1 comprising amino acids having the sequence set forth in SEQ ID NO: 126, a heavy chain variable region CDR2 comprising amino acids having the sequence set forth in SEQ ID NO: 127, and a heavy chain variable region CDR3 comprising amino acids having the sequence set forth in SEQ ID NO: 128. In certain embodiments, the single domain antibody comprises a heavy chain variable region CDR1 comprising amino acids having the sequence set forth in SEQ ID NO: 130, a heavy chain variable region CDR2 comprising amino acids having the sequence set forth in SEQ ID NO: 131, and a heavy chain variable region CDR3 comprising amino acids having the sequence set forth in SEQ ID NO: 132. In certain embodiments, the single domain antibody comprises a heavy chain variable region CDR1 comprising amino acids having the sequence set forth in SEQ ID NO: 134, a heavy chain variable region CDR2 comprising amino acids having the sequence set forth in SEQ ID NO: 135, and a heavy chain variable region CDR3 comprising amino acids having the sequence set forth in SEQ ID NO: 136. In certain embodiments, the single domain antibody comprises a heavy chain variable region CDR1 comprising amino acids having the sequence set forth in SEQ ID NO: 138, a heavy chain variable region CDR2 comprising amino acids having the sequence set forth in SEQ ID NO: 139, and a heavy chain variable region CDR3 comprising amino acids having the sequence set forth in SEQ ID NO: 140. In certain embodiments, the single domain antibody comprises a heavy chain variable region CDR1 comprising amino acids having the sequence set forth in SEQ ID NO: 142, a heavy chain variable region CDR2 comprising amino acids having the sequence set forth in SEQ ID NO: 143, and a heavy chain variable region CDR3 comprising amino acids having the sequence set forth in SEQ ID NO: 144. In certain embodiments, the single domain antibody comprises a heavy chain variable region CDR1 comprising amino acids having the sequence set forth in SEQ ID NO: 146, a heavy chain variable region CDR2 comprising amino acids having the sequence set forth in SEQ ID NO: 147, and a heavy chain variable region CDR3 comprising amino acids having the sequence set forth in SEQ ID NO: 148. In certain embodiments, the single domain antibody comprises a heavy chain variable region CDR1 comprising amino acids having the sequence set forth in SEQ ID NO: 150, a heavy chain variable region CDR2 comprising amino acids having the sequence set forth in SEQ ID NO: 151, and a heavy chain variable region CDR3 comprising amino acids having the sequence set forth in SEQ ID NO: 152. In certain embodiments, the single domain antibody comprises a heavy chain variable region CDR1 comprising amino acids having the sequence set forth in SEQ ID NO: 154, a heavy chain variable region CDR2 comprising amino acids having the sequence set forth in SEQ ID NO: 155, and a heavy chain variable region CDR3 comprising amino acids having the sequence set forth in SEQ ID NO: 156. In certain embodiments, the single domain antibody comprises a heavy chain variable region CDR1 comprising amino acids having the sequence set forth in SEQ ID NO: 158, a heavy chain variable region CDR2 comprising amino acids having the sequence set forth in SEQ ID NO: 159, and a heavy chain variable region CDR3 comprising amino acids having the sequence set forth in SEQ ID NO: 160. In certain embodiments, the single domain antibody comprises a heavy chain variable region CDR1 comprising amino acids having the sequence set forth in SEQ ID NO: 162, a heavy chain variable region CDR2 comprising amino acids having the sequence set forth in SEQ ID NO: 163, and a heavy chain variable region CDR3 comprising amino acids having the sequence set forth in SEQ ID NO: 164. In certain embodiments, the single domain antibody comprises a heavy chain variable region CDR1 comprising amino acids having the sequence set forth in SEQ ID NO: 166, a heavy chain variable region CDR2 comprising amino acids having the sequence set forth in SEQ ID NO: 167, and a heavy chain variable region CDR3 comprising amino acids having the sequence set forth in SEQ ID NO: 168. In certain embodiments, the single domain antibody comprises a heavy chain variable region CDR1 comprising amino acids having the sequence set forth in SEQ ID NO: 170, a heavy chain variable region CDR2 comprising amino acids having the sequence set forth in SEQ ID NO: 171, and a heavy chain variable region CDR3 comprising amino acids having the sequence set forth in SEQ ID NO: 172. In certain embodiments, the single domain antibody comprises a heavy chain variable region CDR1 comprising amino acids having the sequence set forth in SEQ ID NO: 174, a heavy chain variable region CDR2 comprising amino acids having the sequence set forth in SEQ ID NO: 175, and a heavy chain variable region CDR3 comprising amino acids having the sequence set forth in SEQ ID NO: 176. In certain embodiments, the single domain antibody comprises a heavy chain variable region CDR1 comprising amino acids having the sequence set forth in SEQ ID NO: 178, a heavy chain variable region CDR2 comprising amino acids having the sequence set forth in SEQ ID NO: 179, and a heavy chain variable region CDR3 comprising amino acids having the sequence set forth in SEQ ID NO: 180. In certain embodiments, the single domain antibody comprises a heavy chain variable region CDR1 comprising amino acids having the sequence set forth in SEQ ID NO: 182, a heavy chain variable region CDR2 comprising amino acids having the sequence set forth in SEQ ID NO: 183, and a heavy chain variable region CDR3 comprising amino acids having the sequence set forth in SEQ ID NO: 184. In certain embodiments, the single domain antibody comprises a heavy chain variable region CDR1 comprising amino acids having the sequence set forth in SEQ ID NO: 186, a heavy chain variable region CDR2 comprising amino acids having the sequence set forth in SEQ ID NO: 187, and a heavy chain variable region CDR3 comprising amino acids having the sequence set forth in SEQ ID NO: 188. In certain embodiments, the single domain antibody comprises a heavy chain variable region CDR1 comprising amino acids having the sequence set forth in SEQ ID NO: 190, a heavy chain variable region CDR2 comprising amino acids having the sequence set forth in SEQ ID NO: 191, and a heavy chain variable region CDR3 comprising amino acids having the sequence set forth in SEQ ID NO: 192.

In certain embodiments, the single domain antibody comprises a heavy chain variable region comprising an amino acid sequence having at least about 80%, 85%, 90%, 91%, 92%, 93%, 94%, 95%, 96%, 97%, 98%, 99%, or 100% sequence identity to the amino acid sequence selected from the group consisting of SEQ ID NOs: 97, 101, 105, 109, 113, 117, 121, 125, 129, 133, 137, 141, 145, 149, 153, 157, 161, 165, 169, 173, 177, 181, 185, 189 and 193. In certain embodiments, the single domain antibody comprises a heavy chain variable region comprising an amino acid sequence selected from the group consisting of SEQ ID NOs: 97, 101, 105, 109, 113, 117, 121, 125, 129, 133, 137, 141, 145, 149, 153, 157, 161, 165, 169, 173, 177, 181, 185, 189 and 193.

In certain embodiments, the single domain antibody comprises a heavy chain variable region comprising the amino acid sequence set forth in SEQ ID NO: 97. In certain embodiments, the single domain antibody comprises a heavy chain variable region comprising the amino acid sequence set forth in SEQ ID NO: 101. In certain embodiments, the single domain antibody comprises a heavy chain variable region comprising the amino acid sequence set forth in SEQ ID NO: 105. In certain embodiments, the single domain antibody comprises a heavy chain variable region comprising the amino acid sequence set forth in SEQ ID NO: 109. In certain embodiments, the single domain antibody comprises a heavy chain variable region comprising the amino acid sequence set forth in SEQ ID NO: 113. In certain embodiments, the single domain antibody comprises a heavy chain variable region comprising the amino acid sequence set forth in SEQ ID NO: 117. In certain embodiments, the single domain antibody comprises a heavy chain variable region comprising the amino acid sequence set forth in SEQ ID NO: 121. In certain embodiments, the single domain antibody comprises a heavy chain variable region comprising the amino acid sequence set forth in SEQ ID NO: 125. In certain embodiments, the single domain antibody comprises a heavy chain variable region comprising the amino acid sequence set forth in SEQ ID NO: 129. In certain embodiments, the single domain antibody comprises a heavy chain variable region comprising the amino acid sequence set forth in SEQ ID NO: 133. In certain embodiments, the single domain antibody comprises a heavy chain variable region comprising the amino acid sequence set forth in SEQ ID NO: 137. In certain embodiments, the single domain antibody comprises a heavy chain variable region comprising the amino acid sequence set forth in SEQ ID NO: 141. In certain embodiments, the single domain antibody comprises a heavy chain variable region comprising the amino acid sequence set forth in SEQ ID NO: 145. In certain embodiments, the single domain antibody comprises a heavy chain variable region comprising the amino acid sequence set forth in SEQ ID NO: 149. In certain embodiments, the single domain antibody comprises a heavy chain variable region comprising the amino acid sequence set forth in SEQ ID NO: 153. In certain embodiments, the single domain antibody comprises a heavy chain variable region comprising the amino acid sequence set forth in SEQ ID NO: 157. In certain embodiments, the single domain antibody comprises a heavy chain variable region comprising the amino acid sequence set forth in SEQ ID NO: 161. In certain embodiments, the single domain antibody comprises a heavy chain variable region comprising the amino acid sequence set forth in SEQ ID NO: 165. In certain embodiments, the single domain antibody comprises a heavy chain variable region comprising the amino acid sequence set forth in SEQ ID NO: 169. In certain embodiments, the single domain antibody comprises a heavy chain variable region comprising the amino acid sequence set forth in SEQ ID NO: 173. In certain embodiments, the single domain antibody comprises a heavy chain variable region comprising the amino acid sequence set forth in SEQ ID NO: 177. In certain embodiments, the single domain antibody comprises a heavy chain variable region comprising the amino acid sequence set forth in SEQ ID NO: 181. In certain embodiments, the single domain antibody comprises a heavy chain variable region comprising the amino acid sequence set forth in SEQ ID NO: 185. In certain embodiments, the single domain antibody comprises a heavy chain variable region comprising the amino acid sequence set forth in SEQ ID NO: 189. In certain embodiments, the single domain antibody comprises a heavy chain variable region comprising the amino acid sequence set forth in SEQ ID NO: 193.

In certain embodiments, any one of the amino acid sequences comprised in the heavy chain variable region can comprise up to about 1, about 2, about 3, about 4, about 5, about 6, about 7, about 8, about 9 or about 10 amino acid substitutions, deletions and/or additions. In certain embodiments, the amino acid substitution is a conservative substitution.

In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 1, a heavy chain variable region CDR2 comprising amino acids having the sequence set forth in SEQ ID NO: 2, and a heavy chain variable region CDR3 comprising amino acids having the sequence set forth in SEQ ID NO: 3. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 5, a heavy chain variable region CDR2 comprising amino acids having the sequence set forth in SEQ ID NO: 6, and a heavy chain variable region CDR3 comprising amino acids having the sequence set forth in SEQ ID NO: 7. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 9, a heavy chain variable region CDR2 comprising amino acids having the sequence set forth in SEQ ID NO: 10, and a heavy chain variable region CDR3 comprising amino acids having the sequence set forth in SEQ ID NO: 11. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 13, a heavy chain variable region CDR2 comprising amino acids having the sequence set forth in SEQ ID NO: 14, and a heavy chain variable region CDR3 comprising amino acids having the sequence set forth in SEQ ID NO: 15. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 17, a heavy chain variable region CDR2 comprising amino acids having the sequence set forth in SEQ ID NO: 18, and a heavy chain variable region CDR3 comprising amino acids having the sequence set forth in SEQ ID NO: 19. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 21, a heavy chain variable region CDR2 comprising amino acids having the sequence set forth in SEQ ID NO: 22, and a heavy chain variable region CDR3 comprising amino acids having the sequence set forth in SEQ ID NO: 23. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 25, a heavy chain variable region CDR2 comprising amino acids having the sequence set forth in SEQ ID NO: 26, and a heavy chain variable region CDR3 comprising amino acids having the sequence set forth in SEQ ID NO: 27. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 29, a heavy chain variable region CDR2 comprising amino acids having the sequence set forth in SEQ ID NO: 30, and a heavy chain variable region CDR3 comprising amino acids having the sequence set forth in SEQ ID NO: 31. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 33, a heavy chain variable region CDR2 comprising amino acids having the sequence set forth in SEQ ID NO: 34, and a heavy chain variable region CDR3 comprising amino acids having the sequence set forth in SEQ ID NO: 35. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 37, a heavy chain variable region CDR2 comprising amino acids having the sequence set forth in SEQ ID NO: 38, and a heavy chain variable region CDR3 comprising amino acids having the sequence set forth in SEQ ID NO: 39. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 41, a heavy chain variable region CDR2 comprising amino acids having the sequence set forth in SEQ ID NO: 42, and a heavy chain variable region CDR3 comprising amino acids having the sequence set forth in SEQ ID NO: 43. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 45, a heavy chain variable region CDR2 comprising amino acids having the sequence set forth in SEQ ID NO: 46, and a heavy chain variable region CDR3 comprising amino acids having the sequence set forth in SEQ ID NO: 47. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 49, a heavy chain variable region CDR2 comprising amino acids having the sequence set forth in SEQ ID NO: 50, and a heavy chain variable region CDR3 comprising amino acids having the sequence set forth in SEQ ID NO: 51. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 53, a heavy chain variable region CDR2 comprising amino acids having the sequence set forth in SEQ ID NO: 54, and a heavy chain variable region CDR3 comprising amino acids having the sequence set forth in SEQ ID NO: 55. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 57, a heavy chain variable region CDR2 comprising amino acids having the sequence set forth in SEQ ID NO: 58, and a heavy chain variable region CDR3 comprising amino acids having the sequence set forth in SEQ ID NO: 59. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 61, a heavy chain variable region CDR2 comprising amino acids having the sequence set forth in SEQ ID NO: 62, and a heavy chain variable region CDR3 comprising amino acids having the sequence set forth in SEQ ID NO: 63. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 65, a heavy chain variable region CDR2 comprising amino acids having the sequence set forth in SEQ ID NO: 66, and a heavy chain variable region CDR3 comprising amino acids having the sequence set forth in SEQ ID NO: 67. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 69, a heavy chain variable region CDR2 comprising amino acids having the sequence set forth in SEQ ID NO: 70, and a heavy chain variable region CDR3 comprising amino acids having the sequence set forth in SEQ ID NO: 71. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 73, a heavy chain variable region CDR2 comprising amino acids having the sequence set forth in SEQ ID NO: 74, and a heavy chain variable region CDR3 comprising amino acids having the sequence set forth in SEQ ID NO: 75. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 77, a heavy chain variable region CDR2 comprising amino acids having the sequence set forth in SEQ ID NO: 78, and a heavy chain variable region CDR3 comprising amino acids having the sequence set forth in SEQ ID NO: 79. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 81, a heavy chain variable region CDR2 comprising amino acids having the sequence set forth in SEQ ID NO: 82, and a heavy chain variable region CDR3 comprising amino acids having the sequence set forth in SEQ ID NO: 83.

In certain embodiments, the single domain antibody comprises a heavy chain variable region comprising a heavy chain variable region CDR1 comprising amino acids having the sequence set forth in SEQ ID NO: 1, a heavy chain variable region CDR2 comprising amino acids having the sequence set forth in SEQ ID NO: 2, and a heavy chain variable region CDR3 comprising amino acids having the sequence set forth in SEQ ID NO: 3. In certain embodiments, the single domain antibody comprises a heavy chain variable region comprising a heavy chain variable region CDR1 comprising amino acids having the sequence set forth in SEQ ID NO: 5, a heavy chain variable region CDR2 comprising amino acids having the sequence set forth in SEQ ID NO: 6, and a heavy chain variable region CDR3 comprising amino acids having the sequence set forth in SEQ ID NO: 7. In certain embodiments, the single domain antibody comprises a heavy chain variable region comprising a heavy chain variable region CDR1 comprising amino acids having the sequence set forth in SEQ ID NO: 9, a heavy chain variable region CDR2 comprising amino acids having the sequence set forth in SEQ ID NO: 10, and a heavy chain variable region CDR3 comprising amino acids having the sequence set forth in SEQ ID NO: 11. In certain embodiments, the single domain antibody comprises a heavy chain variable region comprising a heavy chain variable region CDR1 comprising amino acids having the sequence set forth in SEQ ID NO: 13, a heavy chain variable region CDR2 comprising amino acids having the sequence set forth in SEQ ID NO: 14, and a heavy chain variable region CDR3 comprising amino acids having the sequence set forth in SEQ ID NO: 15. In certain embodiments, the single domain antibody comprises a heavy chain variable region comprising a heavy chain variable region CDR1 comprising amino acids having the sequence set forth in SEQ ID NO: 17, a heavy chain variable region CDR2 comprising amino acids having the sequence set forth in SEQ ID NO: 18, and a heavy chain variable region CDR3 comprising amino acids having the sequence set forth in SEQ ID NO: 19. In certain embodiments, the single domain antibody comprises a heavy chain variable region comprising a heavy chain variable region CDR1 comprising amino acids having the sequence set forth in SEQ ID NO: 21, a heavy chain variable region CDR2 comprising amino acids having the sequence set forth in SEQ ID NO: 22, and a heavy chain variable region CDR3 comprising amino acids having the sequence set forth in SEQ ID NO: 23. In certain embodiments, the single domain antibody comprises a heavy chain variable region comprising a heavy chain variable region CDR1 comprising amino acids having the sequence set forth in SEQ ID NO: 25, a heavy chain variable region CDR2 comprising amino acids having the sequence set forth in SEQ ID NO: 26, and a heavy chain variable region CDR3 comprising amino acids having the sequence set forth in SEQ ID NO: 27. In certain embodiments, the single domain antibody comprises a heavy chain variable region comprising a heavy chain variable region CDR1 comprising amino acids having the sequence set forth in SEQ ID NO: 29, a heavy chain variable region CDR2 comprising amino acids having the sequence set forth in SEQ ID NO: 30, and a heavy chain variable region CDR3 comprising amino acids having the sequence set forth in SEQ ID NO: 31. In certain embodiments, the single domain antibody comprises a heavy chain variable region comprising a heavy chain variable region CDR1 comprising amino acids having the sequence set forth in SEQ ID NO: 33, a heavy chain variable region CDR2 comprising amino acids having the sequence set forth in SEQ ID NO: 34, and a heavy chain variable region CDR3 comprising amino acids having the sequence set forth in SEQ ID NO: 35. In certain embodiments, the single domain antibody comprises a heavy chain variable region comprising a heavy chain variable region CDR1 comprising amino acids having the sequence set forth in SEQ ID NO: 37, a heavy chain variable region CDR2 comprising amino acids having the sequence set forth in SEQ ID NO: 38, and a heavy chain variable region CDR3 comprising amino acids having the sequence set forth in SEQ ID NO: 39. In certain embodiments, the single domain antibody comprises a heavy chain variable region comprising a heavy chain variable region CDR1 comprising amino acids having the sequence set forth in SEQ ID NO: 41, a heavy chain variable region CDR2 comprising amino acids having the sequence set forth in SEQ ID NO: 42, and a heavy chain variable region CDR3 comprising amino acids having the sequence set forth in SEQ ID NO: 43. In certain embodiments, the single domain antibody comprises a heavy chain variable region comprising a heavy chain variable region CDR1 comprising amino acids having the sequence set forth in SEQ ID NO: 45, a heavy chain variable region CDR2 comprising amino acids having the sequence set forth in SEQ ID NO: 46, and a heavy chain variable region CDR3 comprising amino acids having the sequence set forth in SEQ ID NO: 47. In certain embodiments, the single domain antibody comprises a heavy chain variable region comprising a heavy chain variable region CDR1 comprising amino acids having the sequence set forth in SEQ ID NO: 49, a heavy chain variable region CDR2 comprising amino acids having the sequence set forth in SEQ ID NO: 50, and a heavy chain variable region CDR3 comprising amino acids having the sequence set forth in SEQ ID NO: 51. In certain embodiments, the single domain antibody comprises a heavy chain variable region comprising a heavy chain variable region CDR1 comprising amino acids having the sequence set forth in SEQ ID NO: 53, a heavy chain variable region CDR2 comprising amino acids having the sequence set forth in SEQ ID NO: 54, and a heavy chain variable region CDR3 comprising amino acids having the sequence set forth in SEQ ID NO: 55. In certain embodiments, the single domain antibody comprises a heavy chain variable region comprising a heavy chain variable region CDR1 comprising amino acids having the sequence set forth in SEQ ID NO: 57, a heavy chain variable region CDR2 comprising amino acids having the sequence set forth in SEQ ID NO: 58, and a heavy chain variable region CDR3 comprising amino acids having the sequence set forth in SEQ ID NO: 59. In certain embodiments, the single domain antibody comprises a heavy chain variable region comprising a heavy chain variable region CDR1 comprising amino acids having the sequence set forth in SEQ ID NO: 61, a heavy chain variable region CDR2 comprising amino acids having the sequence set forth in SEQ ID NO: 62, and a heavy chain variable region CDR3 comprising amino acids having the sequence set forth in SEQ ID NO: 63. In certain embodiments, the single domain antibody comprises a heavy chain variable region comprising a heavy chain variable region CDR1 comprising amino acids having the sequence set forth in SEQ ID NO: 65, a heavy chain variable region CDR2 comprising amino acids having the sequence set forth in SEQ ID NO: 66, and a heavy chain variable region CDR3 comprising amino acids having the sequence set forth in SEQ ID NO: 67. In certain embodiments, the single domain antibody comprises a heavy chain variable region comprising a heavy chain variable region CDR1 comprising amino acids having the sequence set forth in SEQ ID NO: 69, a heavy chain variable region CDR2 comprising amino acids having the sequence set forth in SEQ ID NO: 70, and a heavy chain variable region CDR3 comprising amino acids having the sequence set forth in SEQ ID NO: 71. In certain embodiments, the single domain antibody comprises a heavy chain variable region comprising a heavy chain variable region CDR1 comprising amino acids having the sequence set forth in SEQ ID NO: 73, a heavy chain variable region CDR2 comprising amino acids having the sequence set forth in SEQ ID NO: 74, and a heavy chain variable region CDR3 comprising amino acids having the sequence set forth in SEQ ID NO: 75. In certain embodiments, the single domain antibody comprises a heavy chain variable region comprising a heavy chain variable region CDR1 comprising amino acids having the sequence set forth in SEQ ID NO: 77, a heavy chain variable region CDR2 comprising amino acids having the sequence set forth in SEQ ID NO: 78, and a heavy chain variable region CDR3 comprising amino acids having the sequence set forth in SEQ ID NO: 79. In certain embodiments, the single domain antibody comprises a heavy chain variable region comprising a heavy chain variable region CDR1 comprising amino acids having the sequence set forth in SEQ ID NO: 81, a heavy chain variable region CDR2 comprising amino acids having the sequence set forth in SEQ ID NO: 82, and a heavy chain variable region CDR3 comprising amino acids having the sequence set forth in SEQ ID NO: 83.

In certain embodiments, the single domain antibody comprises a heavy chain variable region comprising an amino acid sequence having at least about 80%, 85%, 90%, 91%, 92%, 93%, 94%, 95%, 96%, 97%, 98%, 99%, or 100% sequence identity to the amino acid sequence selected from the group consisting of SEQ ID NOs: 4, 8, 12, 16, 20, 24, 28, 32, 36, 40, 44, 48, 52, 56, 60, 64, 68, 72, 76, 80 and 84. In certain embodiments, the single domain antibody comprises a heavy chain variable region comprising an amino acid sequence selected from the group consisting of SEQ ID NOs: 4, 8, 12, 16, 20, 24, 28, 32, 36, 40, 44, 48, 52, 56, 60, 64, 68, 72, 76, 80 and 84.

In certain embodiments, any one of the amino acid sequences comprised in the heavy chain variable region can comprise up to about 1, about 2, about 3, about 4, about 5, about 6, about 7, about 8, about 9 or about 10 amino acid substitutions, deletions and/or additions. In certain embodiments, the amino acid substitution is a conservative substitution.

In certain embodiments, the single domain antibody comprises a heavy chain variable region comprising the amino acid sequence set forth in SEQ ID NO: 4. In certain embodiments, the single domain antibody comprises a heavy chain variable region comprising the amino acid sequence set forth in SEQ ID NO: 8. In certain embodiments, the single domain antibody comprises a heavy chain variable region comprising the amino acid sequence set forth in SEQ ID NO: 12. In certain embodiments, the single domain antibody comprises a heavy chain variable region comprising the amino acid sequence set forth in SEQ ID NO: 16. In certain embodiments, the single domain antibody comprises a heavy chain variable region comprising the amino acid sequence set forth in SEQ ID NO: 20. In certain embodiments, the single domain antibody comprises a heavy chain variable region comprising the amino acid sequence set forth in SEQ ID NO: 24. In certain embodiments, the single domain antibody comprises a heavy chain variable region comprising the amino acid sequence set forth in SEQ ID NO: 28. In certain embodiments, the single domain antibody comprises a heavy chain variable region comprising the amino acid sequence set forth in SEQ ID NO: 32. In certain embodiments, the single domain antibody comprises a heavy chain variable region comprising the amino acid sequence set forth in SEQ ID NO: 36. In certain embodiments, the single domain antibody comprises a heavy chain variable region comprising the amino acid sequence set forth in SEQ ID NO: 40. In certain embodiments, the single domain antibody comprises a heavy chain variable region comprising the amino acid sequence set forth in SEQ ID NO: 44. In certain embodiments, the single domain antibody comprises a heavy chain variable region comprising the amino acid sequence set forth in SEQ ID NO: 48. In certain embodiments, the single domain antibody comprises a heavy chain variable region comprising the amino acid sequence set forth in SEQ ID NO: 52. In certain embodiments, the single domain antibody comprises a heavy chain variable region comprising the amino acid sequence set forth in SEQ ID NO: 56. In certain embodiments, the single domain antibody comprises a heavy chain variable region comprising the amino acid sequence set forth in SEQ ID NO: 60. In certain embodiments, the single domain antibody comprises a heavy chain variable region comprising the amino acid sequence set forth in SEQ ID NO: 64. In certain embodiments, the single domain antibody comprises a heavy chain variable region comprising the amino acid sequence set forth in SEQ ID NO: 68. In certain embodiments, the single domain antibody comprises a heavy chain variable region comprising the amino acid sequence set forth in SEQ ID NO: 72. In certain embodiments, the single domain antibody comprises a heavy chain variable region comprising the amino acid sequence set forth in SEQ ID NO: 76. In certain embodiments, the single domain antibody comprises a heavy chain variable region comprising the amino acid sequence set forth in SEQ ID NO: 80. In certain embodiments, the single domain antibody comprises a heavy chain variable region comprising the amino acid sequence set forth in SEQ ID NO: 84.

In certain embodiments, the single domain antibody comprises a humanized framework. In certain embodiments, the humanized framework comprises a framework sequence of the heavy chain variable region sequences selected from the group consisting of SEQ ID NOs: 85-93. In certain embodiments, the humanized framework comprises a FR2 sequence of the heavy chain variable region sequences selected from the group consisting of SEQ ID NOs: 85-93.

In certain embodiments, the anti-TIGIT antibody does not comprise a Fc region. In certain embodiments, the anti-TIGIT antibody further comprises a Fc region. In certain embodiments, the Fc region comprises a human Fc region. In certain embodiments, the Fc region comprises a Fc region selected from the group consisting of the Fc regions of IgG, IgA, IgD, IgE and IgM. In certain embodiments, the Fc region comprises a Fc region selected from the group consisting of the Fc regions of IgG1, IgG2, IgG3 and IgG4. In certain embodiments, the Fc region comprises an IgG1 Fc region. In certain embodiments, the IgG1 Fc region comprising one or more mutation that enhances an antibody-dependent cell-mediated cytotoxicity (ADCC). In certain embodiments, the IgG1 Fc region comprises the mutations of L235V, F243L, R292P, Y300L and P396L. In certain embodiments, the IgG1 Fc region comprises the mutations of S239D, A330L and I332E. In certain embodiments, the anti-TIGIT antibody comprises the amino acid sequence set forth in SEQ ID NO: 194

In certain embodiments, the heavy chain variable region is linked to a Fc region via a linker. In certain embodiments, the linker is a peptide linker. In certain embodiments, the peptide linker comprises about four to about thirty amino acids. In certain embodiments, the peptide linker comprises about four to about fifteen amino acids. In certain embodiments, the peptide linker comprise an amino acid sequence selected from the group consisting of SEQ ID NOs: 195-220.

In certain embodiments, the Fc region is capable of dimerization. In certain embodiments, the Fc region can dimerize through one or more disulfide bond. In certain embodiments, the anti-TIGIT antibody comprises two dimerized heavy chains, each of the heavy chain comprising a heavy chain variable region and a Fc region capable of dimerization. In certain embodiments, the anti-TIGIT antibody comprises two disulfide bonds. In certain embodiments, the anti-TIGIT antibody comprises three disulfide bonds. In certain embodiments, the anti-TIGIT antibody does not comprise a light chain.

In certain embodiments, the anti-TIGIT antibody can be a multivalent antibody. In certain embodiments, the anti-TIGIT antibody can be monovalent, bivalent, trivalent, tetravalent, pentavalent, hexavalent, heptavalent or octavalent. In certain embodiments, the anti-TIGIT antibody is monovalent. In certain embodiments, the anti-TIGIT antibody is bivalent. In certain embodiments, the anti-TIGIT antibody is tetravalent.

In certain embodiments, the anti-TIGIT antibody comprises a multispecific antibody, e.g., a bispecific antibody, a full-length immunoglobulin, a single-chain Fv (scFv) fragment, a Fab fragment, a Fab' fragment, a F(ab')2, an Fv fragment, a disulfide stabilized Fv fragment (dsFv), a (dsFv) 2, a VHH, a Fv-Fc fusion, a scFv-Fc fusion, a scFv-Fv fusion, a diabody, a tribody, a tetrabody or any combination thereof. In certain embodiments, the antibody comprises a multispecific antibody, e.g., a bispecific antibody, which comprises a second antibody moiety that specifically binds to a second antigen.

In certain embodiments, the second antigen is a tumor associated antigen. In certain embodiments, the tumor associated antigen is selected from the group consisting of Her-2, EGFR, PD-L1, c-Met, B Cell Maturation Antigen (BCMA), carbonic anhydrase IX (CA1X), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, CD276 (B7H3), epithelial glycoprotein (EGP2), trophoblast cell-surface antigen 2 (TROP-2), epithelial glycoprotein-40 (EGP-40), epithelial cell adhesion molecule (EpCAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human telomerase reverse transcriptase (hTERT), kinase insert domain receptor (KDR), Lewis A (CA 1.9.9), Lewis Y (LeY), Glypican-3 (GPC3), L1 cell adhesion molecule (L1CAM), Mucin 16 (Muc-16), Mucin 1 (Muc-1), NG2D ligands, oncofetal antigen (h5T4), prostate stem cell antigen (PSCA), prostate-specific membrane antigen (PSMA), tumor-associated glycoprotein 72 (TAG-72), Claudin18.2 (CLDN18.2), vascular endothelial growth factor R2 (VEGF-R2), Wilms tumor protein (WT-1), type 1 tyrosine-protein kinase transmembrane receptor (ROR1) and any combination thereof.

In certain embodiments, the anti-TIGIT antibody is conjugated to a therapeutic agent or a label. In certain embodiments, the label is selected from the group consisting of a radioisotope, a fluorescent dye and an enzyme.

2.2. Exemplary Anti-PDL1 Antibodies

The present disclosure further provides anti-PDL1 antibodies. In certain embodiments, an anti-PDL1 antibody disclosed herein binds to a PDL1 protein with high affinity. In certain embodiments, the anti-PDL1 antibody blocks the interaction between PDL1 and PD1. In certain embodiments, the antibody is any anti-PDL1 antibody disclosed in PCT/US2017/056689 (published as International Publication WO 2018/080812 A1), the content of which is incorporated herein by references in its entirety.

In certain embodiments, the anti-PDL1 antibody cross-competes with a reference anti-PDL1 antibody that comprises: a) a heavy chain variable domain (VH) sequence comprising (1) a CDR-H1 comprising the amino acid sequence set forth in SEQ ID NO: 221, (2) a CDR-H2 comprising the amino acid sequence set forth in SEQ ID NO: 222, and (3) a CDR-H3 comprising the amino acid sequence set forth in SEQ ID NO: 223; and a light chain variable domain (VL) sequence comprising (1) a CDR-L1 comprising the amino acid sequence set forth in SEQ ID NO: 224, (2) a CDR-L2 comprising the amino acid sequence set forth in SEQ ID NO: 225, and (3) a CDR-L3 comprising the amino acid sequence set forth in SEQ ID NO: 226; b) a heavy chain variable domain (VH) sequence comprising (1) a CDR-H1 comprising the amino acid sequence set forth in SEQ ID NO: 229, (2) a CDR-H2 comprising the amino acid sequence set forth in SEQ ID NO: 230, and (3) a CDR-H3 comprising the amino acid sequence set forth in SEQ ID NO: 231; and a light chain variable domain (VL) sequence comprising (1) a CDR-L1 comprising the amino acid sequence set forth in SEQ ID NO: 232, (2) a CDR-L2 comprising the amino acid sequence set forth in SEQ ID NO: 233, and (3) a CDR-L3 comprising the amino acid sequence set forth in SEQ ID NO: 234; c) a heavy chain variable domain (VH) sequence comprising (1) a CDR-H1 comprising the amino acid sequence set forth in SEQ ID NO: 237, (2) a CDR-H2 comprising the amino acid sequence set forth in SEQ ID NO: 238, and (3) a CDR-H3 comprising the amino acid sequence set forth in SEQ ID NO: 239; and a light chain variable domain (VL) sequence comprising (1) a CDR-L1 comprising the amino acid sequence set forth in SEQ ID NO: 240, (2) a CDR-L2 comprising the amino acid sequence set forth in SEQ ID NO: 241, and (3) a CDR-L3 comprising the amino acid sequence set forth in SEQ ID NO: 242; d) a heavy chain variable domain (VH) sequence comprising (1) a CDR-H1 comprising the amino acid sequence set forth in SEQ ID NO: 245, (2) a CDR-H2 comprising the amino acid sequence set forth in SEQ ID NO: 246, and (3) a CDR-H3 comprising the amino acid sequence set forth in SEQ ID NO: 247; and a light chain variable domain (VL) sequence comprising (1) a CDR-L1 comprising the amino acid sequence set forth in SEQ ID NO: 248, (2) a CDR-L2 comprising the amino acid sequence set forth in SEQ ID NO: 249, and (3) a CDR-L3 comprising the amino acid sequence set forth in SEQ ID NO: 250; e) a heavy chain variable domain (VH) sequence comprising (1) a CDR-H1 comprising the amino acid sequence set forth in SEQ ID NO: 253, (2) a CDR-H2 comprising the amino acid sequence set forth in SEQ ID NO: 254, and (3) a CDR-H3 comprising the amino acid sequence set forth in SEQ ID NO: 255; and a light chain variable domain (VL) sequence comprising (1) a CDR-L1 comprising the amino acid sequence set forth in SEQ ID NO: 256, (2) a CDR-L2 comprising the amino acid sequence set forth in SEQ ID NO: 257, and (3) a CDR-L3 comprising the amino acid sequence set forth in SEQ ID NO: 258; f) a heavy chain variable domain (VH) sequence comprising (1) a CDR-H1 comprising the amino acid sequence set forth in SEQ ID NO: 261, (2) a CDR-H2 comprising the amino acid sequence set forth in SEQ ID NO: 262, and (3) a CDR-H3 comprising the amino acid sequence set forth in SEQ ID NO: 263; and a light chain variable domain (VL) sequence comprising (1) a CDR-L1 comprising the amino acid sequence set forth in SEQ ID NO: 264, (2) a CDR-L2 comprising the amino acid sequence set forth in SEQ ID NO: 265, and (3) a CDR-L3 comprising the amino acid sequence set forth in SEQ ID NO: 266; g) a heavy chain variable domain (VH) sequence comprising (1) a CDR-H1 comprising the amino acid sequence set forth in SEQ ID NO: 269, (2) a CDR-H2 comprising the amino acid sequence set forth in SEQ ID NO: 270, and (3) a CDR-H3 comprising the amino acid sequence set forth in SEQ ID NO: 271; and a light chain variable domain (VL) sequence comprising (1) a CDR-L1 comprising the amino acid sequence set forth in SEQ ID NO: 272, (2) a CDR-L2 comprising the amino acid sequence set forth in SEQ ID NO: 273, and (3) a CDR-L3 comprising the amino acid sequence set forth in SEQ ID NO: 274; h) a heavy chain variable domain (VH) sequence comprising (1) a CDR-H1 comprising the amino acid sequence set forth in SEQ ID NO: 277, (2) a CDR-H2 comprising the amino acid sequence set forth in SEQ ID NO: 278, and (3) a CDR-H3 comprising the amino acid sequence set forth in SEQ ID NO: 279; and a light chain variable domain (VL) sequence comprising (1) a CDR-L1 comprising the amino acid sequence set forth in SEQ ID NO: 280, (2) a CDR-L2 comprising the amino acid sequence set forth in SEQ ID NO: 281, and (3) a CDR-L3 comprising the amino acid sequence set forth in SEQ ID NO: 282; i) a heavy chain variable domain (VH) sequence comprising (1) a CDR-H1 comprising the amino acid sequence set forth in SEQ ID NO: 285, (2) a CDR-H2 comprising the amino acid sequence set forth in SEQ ID NO: 286, and (3) a CDR-H3 comprising the amino acid sequence set forth in SEQ ID NO: 287; and a light chain variable domain (VL) sequence comprising (1) a CDR-L1 comprising the amino acid sequence set forth in SEQ ID NO: 288, (2) a CDR-L2 comprising the amino acid sequence set forth in SEQ ID NO: 289, and (3) a CDR-L3 comprising the amino acid sequence set forth in SEQ ID NO: 290; or j) a heavy chain variable domain (VH) sequence comprising (1) a CDR-H1 comprising the amino acid sequence set forth in SEQ ID NO: 293, (2) a CDR-H2 comprising the amino acid sequence set forth in SEQ ID NO: 294, and (3) a CDR-H3 comprising the amino acid sequence set forth in SEQ ID NO: 295; and a light chain variable domain (VL) sequence comprising (1) a CDR-L1 comprising the amino acid sequence set forth in SEQ ID NO: 296, (2) a CDR-L2 comprising the amino acid sequence set forth in SEQ ID NO: 297, and (3) a CDR-L3 comprising the amino acid sequence set forth in SEQ ID NO: 298.

In certain embodiments, the anti-PDL1 antibody comprises a heavy chain variable domain (VH) sequence comprising (1) a CDR-H1 comprising the amino acid sequence set forth in SEQ ID NO: 221, (2) a CDR-H2 comprising the amino acid sequence set forth in SEQ ID NO: 222, and (3) a CDR-H3 comprising the amino acid sequence set forth in SEQ ID NO: 223; and a light chain variable domain (VL) sequence comprising (1) a CDR-L1 comprising the amino acid sequence set forth in SEQ ID NO: 224, (2) a CDR-L2 comprising the amino acid sequence set forth in SEQ ID NO: 225, and (3) a CDR-L3 comprising the amino acid sequence set forth in SEQ ID NO: 226. In certain embodiments, the anti-PDL1 antibody comprises a heavy chain variable domain (VH) sequence comprising (1) a CDR-H1 comprising the amino acid sequence set forth in SEQ ID NO: 229, (2) a CDR-H2 comprising the amino acid sequence set forth in SEQ ID NO: 230, and (3) a CDR-H3 comprising the amino acid sequence set forth in SEQ ID NO: 231; and a light chain variable domain (VL) sequence comprising (1) a CDR-L1 comprising the amino acid sequence set forth in SEQ ID NO: 232, (2) a CDR-L2 comprising the amino acid sequence set forth in SEQ ID NO: 233, and (3) a CDR-L3 comprising the amino acid sequence set forth in SEQ ID NO: 234. In certain embodiments, the anti-PDL1 antibody comprises a heavy chain variable domain (VH) sequence comprising (1) a CDR-H1 comprising the amino acid sequence set forth in SEQ ID NO: 237, (2) a CDR-H2 comprising the amino acid sequence set forth in SEQ ID NO: 238, and (3) a CDR-H3 comprising the amino acid sequence set forth in SEQ ID NO: 239; and a light chain variable domain (VL) sequence comprising (1) a CDR-L1 comprising the amino acid sequence set forth in SEQ ID NO: 240, (2) a CDR-L2 comprising the amino acid sequence set forth in SEQ ID NO: 241, and (3) a CDR-L3 comprising the amino acid sequence set forth in SEQ ID NO: 242. In certain embodiments, the anti-PDL1 antibody comprises a heavy chain variable domain (VH) sequence comprising (1) a CDR-H1 comprising the amino acid sequence set forth in SEQ ID NO: 245, (2) a CDR-H2 comprising the amino acid sequence set forth in SEQ ID NO: 246, and (3) a CDR-H3 comprising the amino acid sequence set forth in SEQ ID NO: 247; and a light chain variable domain (VL) sequence comprising (1) a CDR-L1 comprising the amino acid sequence set forth in SEQ ID NO: 248, (2) a CDR-L2 comprising the amino acid sequence set forth in SEQ ID NO: 249, and (3) a CDR-L3 comprising the amino acid sequence set forth in SEQ ID NO: 250. In certain embodiments, the anti-PDL1 antibody comprises a heavy chain variable domain (VH) sequence comprising (1) a CDR-H1 comprising the amino acid sequence set forth in SEQ ID NO: 253, (2) a CDR-H2 comprising the amino acid sequence set forth in SEQ ID NO: 254, and (3) a CDR-H3 comprising the amino acid sequence set forth in SEQ ID NO: 255; and a light chain variable domain (VL) sequence comprising (1) a CDR-L1 comprising the amino acid sequence set forth in SEQ ID NO: 256, (2) a CDR-L2 comprising the amino acid sequence set forth in SEQ ID NO: 257, and (3) a CDR-L3 comprising the amino acid sequence set forth in SEQ ID NO: 258. In certain embodiments, the anti-PDL1 antibody comprises a heavy chain variable domain (VH) sequence comprising (1) a CDR-H1 comprising the amino acid sequence set forth in SEQ ID NO: 261, (2) a CDR-H2 comprising the amino acid sequence set forth in SEQ ID NO: 262, and (3) a CDR-H3 comprising the amino acid sequence set forth in SEQ ID NO: 263; and a light chain variable domain (VL) sequence comprising (1) a CDR-L1 comprising the amino acid sequence set forth in SEQ ID NO: 264, (2) a CDR-L2 comprising the amino acid sequence set forth in SEQ ID NO: 265, and (3) a CDR-L3 comprising the amino acid sequence set forth in SEQ ID NO: 266. In certain embodiments, the anti-PDL1 antibody comprises a heavy chain variable domain (VH) sequence comprising (1) a CDR-H1 comprising the amino acid sequence set forth in SEQ ID NO: 269, (2) a CDR-H2 comprising the amino acid sequence set forth in SEQ ID NO: 270, and (3) a CDR-H3 comprising the amino acid sequence set forth in SEQ ID NO: 271; and a light chain variable domain (VL) sequence comprising (1) a CDR-L1 comprising the amino acid sequence set forth in SEQ ID NO: 272, (2) a CDR-L2 comprising the amino acid sequence set forth in SEQ ID NO: 273, and (3) a CDR-L3 comprising the amino acid sequence set forth in SEQ ID NO: 274. In certain embodiments, the anti-PDL1 antibody comprises a heavy chain variable domain (VH) sequence comprising (1) a CDR-H1 comprising the amino acid sequence set forth in SEQ ID NO: 277, (2) a CDR-H2 comprising the amino acid sequence set forth in SEQ ID NO: 278, and (3) a CDR-H3 comprising the amino acid sequence set forth in SEQ ID NO: 279; and a light chain variable domain (VL) sequence comprising (1) a CDR-L1 comprising the amino acid sequence set forth in SEQ ID NO: 280, (2) a CDR-L2 comprising the amino acid sequence set forth in SEQ ID NO: 281, and (3) a CDR-L3 comprising the amino acid sequence set forth in SEQ ID NO: 282. In certain embodiments, the anti-PDL1 antibody comprises a heavy chain variable domain (VH) sequence comprising (1) a CDR-H1 comprising the amino acid sequence set forth in SEQ ID NO: 285, (2) a CDR-H2 comprising the amino acid sequence set forth in SEQ ID NO: 286, and (3) a CDR-H3 comprising the amino acid sequence set forth in SEQ ID NO: 287; and a light chain variable domain (VL) sequence comprising (1) a CDR-L1 comprising the amino acid sequence set forth in SEQ ID NO: 288, (2) a CDR-L2 comprising the amino acid sequence set forth in SEQ ID NO: 289, and (3) a CDR-L3 comprising the amino acid sequence set forth in SEQ ID NO: 290. In certain embodiments, the anti-PDL1 antibody comprises a heavy chain variable domain (VH) sequence comprising (1) a CDR-H1 comprising the amino acid sequence set forth in SEQ ID NO: 293, (2) a CDR-H2 comprising the amino acid sequence set forth in SEQ ID NO: 294, and (3) a CDR-H3 comprising the amino acid sequence set forth in SEQ ID NO: 295; and a light chain variable domain (VL) sequence comprising (1) a CDR-L1 comprising the amino acid sequence set forth in SEQ ID NO: 296, (2) a CDR-L2 comprising the amino acid sequence set forth in SEQ ID NO: 297, and (3) a CDR-L3 comprising the amino acid sequence set forth in SEQ ID NO: 298. In certain embodiments, the anti-PDL1 antibody comprises a heavy chain variable domain (VH) sequence comprising (1) a CDR-H1 comprising the amino acid sequence set forth in SEQ ID NO: 301, (2) a CDR-H2 comprising the amino acid sequence set forth in SEQ ID NO: 302, and (3) a CDR-H3 comprising the amino acid sequence set forth in SEQ ID NO: 303; and a light chain variable domain (VL) sequence comprising (1) a CDR-L1 comprising the amino acid sequence set forth in SEQ ID NO: 304, (2) a CDR-L2 comprising the amino acid sequence set forth in SEQ ID NO: 305, and (3) a CDR-L3 comprising the amino acid sequence set forth in SEQ ID NO: 306.

In certain embodiments, the anti-PDL1 antibody comprises a heavy chain variable region comprising an amino acid sequence having at least about 80%, 85%, 90%, 91%, 92%, 93%, 94%, 95%, 96%, 97%, 98%, 99%, or 100% sequence identity to the amino acid sequence selected from the group consisting of SEQ ID NOs: 227, 235, 243, 251, 259, 267, 275, 283, 291, 299 and 307, and a light chain variable region comprising an amino acid sequence having at least about 80%, 85%, 90%, 91%, 92%, 93%, 94%, 95%, 96%, 97%, 98%, 99%, or 100% sequence identity to the amino acid sequence selected from the group consisting of SEQ ID NOs: 228, 236, 244, 252, 260, 268, 276, 284, 292, 300 and 308. In certain embodiments, the anti-PDL1 antibody comprises a heavy chain variable region comprising an amino acid sequence selected from the group consisting of SEQ ID NOs: 227, 235, 243, 251, 259, 267, 275, 283, 291, 299 and 307, and a light chain variable region comprising an amino acid sequence selected from the group consisting of SEQ ID NOs: 228, 236, 244, 252, 260, 268, 276, 284, 292, 300 and 308.

In certain embodiments, the anti-PDL1 antibody comprises a heavy chain variable region comprising the amino acid sequence set forth in SEQ ID NO: 227, and a light chain variable region comprising the amino acid sequence set forth in SEQ ID NO: 228. In certain embodiments, the anti-PDL1 antibody comprises a heavy chain variable region comprising the amino acid sequence set forth in SEQ ID NO: 235, and a light chain variable region comprising the amino acid sequence set forth in SEQ ID NO: 236. In certain embodiments, the anti-PDL1 antibody comprises a heavy chain variable region comprising the amino acid sequence set forth in SEQ ID NO: 243, and a light chain variable region comprising the amino acid sequence set forth in SEQ ID NO: 244. In certain embodiments, the anti-PDL1 antibody comprises a heavy chain variable region comprising the amino acid sequence set forth in SEQ ID NO: 251, and a light chain variable region comprising the amino acid sequence set forth in SEQ ID NO: 252. In certain embodiments, the anti-PDL1 antibody comprises a heavy chain variable region comprising the amino acid sequence set forth in SEQ ID NO: 259, and a light chain variable region comprising the amino acid sequence set forth in SEQ ID NO: 260. In certain embodiments, the anti-PDL1 antibody comprises a heavy chain variable region comprising the amino acid sequence set forth in SEQ ID NO: 267, and a light chain variable region comprising the amino acid sequence set forth in SEQ ID NO: 268. In certain embodiments, the anti-PDL1 antibody comprises a heavy chain variable region comprising the amino acid sequence set forth in SEQ ID NO: 275, and a light chain variable region comprising the amino acid sequence set forth in SEQ ID NO: 276. In certain embodiments, the anti-PDL1 antibody comprises a heavy chain variable region comprising the amino acid sequence set forth in SEQ ID NO: 283, and a light chain variable region comprising the amino acid sequence set forth in SEQ ID NO: 284. In certain embodiments, the anti-PDL1 antibody comprises a heavy chain variable region comprising the amino acid sequence set forth in SEQ ID NO: 291, and a light chain variable region comprising the amino acid sequence set forth in SEQ ID NO: 292. In certain embodiments, the anti-PDL1 antibody comprises a heavy chain variable region comprising the amino acid sequence set forth in SEQ ID NO: 300, and a light chain variable region comprising the amino acid sequence set forth in SEQ ID NO: 301. In certain embodiments, the anti-PDL1 antibody comprises a heavy chain variable region comprising the amino acid sequence set forth in SEQ ID NO: 307, and a light chain variable region comprising the amino acid sequence set forth in SEQ ID NO: 308.

In certain embodiments, any one of the amino acid sequences comprised in the heavy chain variable region and/or the light chain variable region can comprise up to about 1, about 2, about 3, about 4, about 5, about 6, about 7, about 8, about 9 or about 10 amino acid substitutions, deletions and/or additions. In certain embodiments, the amino acid substitution is a conservative substitution.

In certain embodiments, the anti-PDL1 antibody comprises a Fc region. In certain embodiments, the Fc region is selected from the group consisting of the Fc regions of IgG, IgA, IgD, IgE and IgM. In certain embodiments, the Fc region is selected from the group consisting of the Fc regions of IgG1, IgG2, IgG3 and IgG4. In certain embodiments, the Fc region comprises a human Fc region. In certain embodiments, the Fc region comprises an IgG1 Fc region. In certain embodiments, the IgG1 Fc region comprising one or more mutation that modifies an antibody-dependent cell-mediated cytotoxicity (ADCC). In certain embodiments, the IgG1 Fc region comprising one or more mutation that enhances an antibody-dependent cell-mediated cytotoxicity (ADCC). In certain embodiments, the IgG1 Fc region comprising one or more mutation that reduces an antibody-dependent cell-mediated cytotoxicity (ADCC). In certain embodiments, the Fc region comprises an IgG4 Fc region. In certain embodiments, the IgG4 Fc region comprises an S228P mutation.

In certain embodiments, the anti-PDL1 antibody comprises a human antibody. In certain embodiments, the anti-PDL1 antibody is identified by screening of a human phage display library with a polypeptide comprising the ECD of a human PDL1 protein.

2.3. Multispecific Antibodies

The present disclosure further provides multispecific antibodies, e.g., a bispecific antibody. Multispecific antibodies are monoclonal antibodies that have binding specificities for at least two different epitopes. In certain embodiments, one of the binding specificities is for an epitope present on TIGIT and the other is for any other antigen. In certain embodiments, one of the binding specificities is for an epitope present on PDL1 and the other is for any other antigen. In certain embodiments, a multispecific antibody of the present disclosure can bind to an epitope on TIGIT and can bind to an epitope on PDL1. In certain embodiments, a multispecific antibody of the present disclosure can comprise a full-length antibody, an antibody fragment and/or any combination thereof.

In certain embodiments, the multispecific antibody binds to TIGIT and PDL1. In certain embodiments, the multispecific antibody is a bispecific, anti-TIGIT/anti-PDL1 antibodies. In certain embodiments, the multispecific antibody has at least two different binding specificities, see, e.g., U.S. Pat. Nos. 5,922,845 and 5,837,243; Zeilder (1999) J. Immunol. 163: 1246-1 252; Somasundaram (1999) Hum. Antibodies 9:47-54; Keler (1997) Cancer Res. 57:4008-401 4. For example, and not by way of limitation, the presently disclosed subject matter provides multispecific antibodies comprising one antigen-binding moiety for a first epitope present on TIGIT and a second antigen-binding moiety for a second epitope present on PDL1. In certain embodiments, the multispecific antibody comprises a first antigen-binding moiety comprising an anti-TIGIT antibody disclosed herein; and a second antigen-binding moiety comprising an anti-PDL1 antibody disclosed herein.

In certain embodiments, the anti-TIGIT/anti-PDL1 antibody disclosed herein can function as an antagonist of both a TIGIT receptor and PD1/PDL1 signaling. In certain embodiments, the anti-TIGIT/anti-PDL1 antibody blocks immune checkpoint inhibition of an immune cell, e.g., a T cell or a NK cell. In certain embodiments, without bound by any theory, the anti-PDL1 moiety of the anti-TIGIT/anti-PDL1 antibody can guide and/or concentrate the antibody at a tumor site, whereby enhances the antitumor functions of an immune cell at the vicinity of the tumor site and/or reduces the toxicity and side effects of a peripheral immune cells. In certain embodiments, without bound by any theory, the anti-TIGIT/anti-PDL1 antibody can ligate a tumor cells expressing PDL1 and an immune cell, e.g., a T cell or a NK cell, that expresses TIGIT, whereby brings the immune cell to the vicinity of a tumor site and facilitates tumor eradication. In certain embodiments, treatment using the anti-TIGIT/anti-PDL1 antibody exhibits superior antitumor efficacy compared to treatment using a monospecific anti-TIGIT antibody and/or a monospecific anti-PDL1 antibody. In certain embodiments, treatment using the anti-TIGIT/anti-PDL1 antibody exhibits superior antitumor efficacy compared to treatment using a combination of a monospecific anti-TIGIT antibody and a monospecific anti-PDL1 antibody.

In certain embodiments, the anti-TIGIT/anti-PDL1 antibody comprises a first antigen-binding moiety comprising an anti-TIGIT antibody comprising a single domain antibody that binds to TIGIT, and a second antigen-binding moiety comprising an anti-PDL1 antibody that binds to PDL1.

2.3.1 First Antigen-Binding Moiety

In certain embodiments, the first antigen-binding moiety of a multispecific anti-TIGIT/anti-PDL1 antibody disclosed herein comprises an anti-TIGIT antibody disclosed herein. In certain embodiments, an anti-TIGIT antibody of the present disclosure binds to the ECD of TIGIT. In certain embodiments, the anti-TIGIT antibody binds to the ECD of TIGIT that comprises the amino acid sequence set forth in SEQ ID NO: 318. In certain embodiments, the anti-TIGIT antibody binds to the same epitope as an anti-TIGIT antibody, e.g., 2A3, described herein.

In certain embodiments, the anti-TIGIT antibody disclosed herein can function as an antagonist of a TIGIT receptor. In certain embodiments, the anti-TIGIT antibody can reduce the activity of the TIGIT receptor by at least about 10%, about 20%, about 30%, about 40%, about 50%, about 60%, about 70%, about 80%, about 90%, about 99% or about 99.9%. In certain embodiments, the anti-TIGIT antibody can block the downstream immune inhibitory signaling of the TIGIT receptor. In certain embodiments, the anti-TIGIT antibody increases an immune response and/or an antitumor effect of an immune cell, e.g., a T cell and/or a NK cell. In certain embodiments, treatment using the anti-TIGIT antibody exhibits antitumor efficacy in a subject, whereby reduces tumor growth and/or lengthen the survival of a subject. In certain embodiments, the anti-TIGIT antibody comprising a single domain antibody (e.g., a VHH) has a smaller molecule size compared to a full-length antibody due to the smaller size of a single domain antibody compared to a Fab domain of a full-length antibody, which can result in superior tissue infiltration, e.g., at a tumor site, compared to a full-length antibody. In certain embodiments, treatment using the anti-TIGIT antibody exhibits superior antitumor efficacy compared to treatment using a full-length anti-TIGIT antibody, e.g., Reference Ab lhaving the same amino acid sequences of BMS 22G2 disclosed in U.S. 2016/0176963 A1 and Reference Ab 2 having the same amino acid sequences of Tiragolumab, which sequences are disclosed in U.S. 2017/0088613 A1.

In certain embodiments, the anti-TIGIT antibody comprises a single domain antibody that binds to TIGIT. In certain embodiments, the single domain antibody comprises a VHH. In certain embodiments, the single domain antibody comprises a heavy chain variable region (VH). In certain embodiments, the single domain antibody is linked to a Fc region. In certain embodiments, the single domain antibody is not linked to a Fc region.

In certain embodiments, the single domain antibody binds to TIGIT with a $K_D$ of about $1 \times 10^{-7}$ M or less. In certain embodiments, the single domain antibody binds to TIGIT with a KD of about $1 \times 10^{-8}$ M or less. In certain embodiments, the single domain antibody binds to TIGIT with a $K_D$ of about $5 \times 10^{-9}$ M or less. In certain embodiments, the single domain antibody binds to TIGIT with a $K_D$ of about $1 \times 10^{-9}$ M or less. In certain embodiments, the single domain antibody binds to TIGIT with a KD of between about $1 \times 10^{-9}$ M and about $1 \times 10^{-7}$ M. In certain embodiments, the single domain antibody binds to TIGIT with a KD of between about $1 \times 10^{-9}$M and about $1 \times 10^{-8}$ M. In certain embodiments, the single domain antibody binds to TIGIT with a KD of between about $2 \times 10^{-9}$ M and about $1 \times 10^{-8}$ M. In certain embodiments, the single domain antibody binds to TIGIT with a KD of between about $2 \times 10^{-9}$ M and about $5 \times 10^{-8}$ M.

In certain embodiments, the single domain antibody binds to TIGIT with a KD of between about $1\times10^{-9}$ M and about $5\times10^{-9}$ M.

In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 94, a heavy chain variable region CDR2 comprising amino acids having the sequence set forth in SEQ ID NO: 95, and a heavy chain variable region CDR3 comprising amino acids having the sequence set forth in SEQ ID NO: 96. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 98, a heavy chain variable region CDR2 comprising amino acids having the sequence set forth in SEQ ID NO: 99, and a heavy chain variable region CDR3 comprising amino acids having the sequence set forth in SEQ ID NO: 100. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 102, a heavy chain variable region CDR2 comprising amino acids having the sequence set forth in SEQ ID NO: 103, and a heavy chain variable region CDR3 comprising amino acids having the sequence set forth in SEQ ID NO: 104. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 106, a heavy chain variable region CDR2 comprising amino acids having the sequence set forth in SEQ ID NO: 107, and a heavy chain variable region CDR3 comprising amino acids having the sequence set forth in SEQ ID NO: 108. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 110, a heavy chain variable region CDR2 comprising amino acids having the sequence set forth in SEQ ID NO: 111, and a heavy chain variable region CDR3 comprising amino acids having the sequence set forth in SEQ ID NO: 112. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 114, a heavy chain variable region CDR2 comprising amino acids having the sequence set forth in SEQ ID NO: 115, and a heavy chain variable region CDR3 comprising amino acids having the sequence set forth in SEQ ID NO: 116. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 118, a heavy chain variable region CDR2 comprising amino acids having the sequence set forth in SEQ ID NO: 119, and a heavy chain variable region CDR3 comprising amino acids having the sequence set forth in SEQ ID NO: 120. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 122, a heavy chain variable region CDR2 comprising amino acids having the sequence set forth in SEQ ID NO: 123, and a heavy chain variable region CDR3 comprising amino acids having the sequence set forth in SEQ ID NO: 124. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 126, a heavy chain variable region CDR2 comprising amino acids having the sequence set forth in SEQ ID NO: 127, and a heavy chain variable region CDR3 comprising amino acids having the sequence set forth in SEQ ID NO: 128. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 130, a heavy chain variable region CDR2 comprising amino acids having the sequence set forth in SEQ ID NO: 131, and a heavy chain variable region CDR3 comprising amino acids having the sequence set forth in SEQ ID NO: 132. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 134, a heavy chain variable region CDR2 comprising amino acids having the sequence set forth in SEQ ID NO: 135, and a heavy chain variable region CDR3 comprising amino acids having the sequence set forth in SEQ ID NO: 136. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 138, a heavy chain variable region CDR2 comprising amino acids having the sequence set forth in SEQ ID NO: 139, and a heavy chain variable region CDR3 comprising amino acids having the sequence set forth in SEQ ID NO: 140. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 142, a heavy chain variable region CDR2 comprising amino acids having the sequence set forth in SEQ ID NO: 143, and a heavy chain variable region CDR3 comprising amino acids having the sequence set forth in SEQ ID NO: 144. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 146, a heavy chain variable region CDR2 comprising amino acids having the sequence set forth in SEQ ID NO: 147, and a heavy chain variable region CDR3 comprising amino acids having the sequence set forth in SEQ ID NO: 148. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 150, a heavy chain variable region CDR2 comprising amino acids having the sequence set forth in SEQ ID NO: 151, and a heavy chain variable region CDR3 comprising amino acids having the sequence set forth in SEQ ID NO: 152. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 154, a heavy chain variable region CDR2 comprising amino acids having the sequence set forth in SEQ ID NO: 155, and a heavy chain variable region CDR3 comprising amino acids having the sequence set forth in SEQ ID NO: 156. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 158, a heavy chain variable region CDR2 comprising amino acids having the sequence set forth in SEQ ID NO: 159, and a heavy chain variable region CDR3 comprising amino acids having the sequence set forth in SEQ ID NO: 160. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 162, a heavy chain variable region CDR2 comprising amino acids having the sequence set forth in SEQ ID NO: 163, and a heavy chain variable region CDR3 comprising amino acids having the sequence set forth in SEQ ID NO: 164. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 166, a heavy chain variable region CDR2 comprising amino acids having the sequence set forth in SEQ ID NO: 167, and a heavy chain variable region CDR3 comprising amino acids having the sequence set forth in SEQ ID NO: 168. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 170, a heavy chain variable region CDR2 comprising amino acids having the sequence set forth in SEQ ID NO: 171, and a heavy chain variable region CDR3 comprising amino acids having the sequence set forth in SEQ ID NO: 172. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 174, a heavy chain variable region CDR2 comprising amino acids having the sequence set forth in SEQ ID NO: 175, and a heavy chain variable region CDR3 comprising amino acids having the sequence set forth in SEQ ID NO: 176. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 178, a heavy chain variable region CDR2 comprising amino acids having the sequence set forth in SEQ ID NO: 179, and a heavy chain variable region CDR3 comprising amino acids having the sequence set forth in SEQ ID NO: 180. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 182, a heavy chain variable region CDR2 comprising amino acids having the sequence set forth in SEQ ID NO: 183, and a heavy chain variable region CDR3 comprising amino acids having the sequence set forth in SEQ ID NO: 184. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 186, a heavy chain variable region CDR2 comprising amino acids having the sequence set forth in SEQ ID NO: 187, and a heavy chain variable region CDR3 comprising amino acids having the sequence set forth in SEQ ID NO: 188. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 190, a heavy chain variable region CDR2 comprising amino acids having the sequence set forth in SEQ ID NO: 191, and a heavy chain variable region CDR3 comprising amino acids having the sequence set forth in SEQ ID NO: 192.

In certain embodiments, the single domain antibody comprises a heavy chain variable region comprising: a) a heavy chain variable region CDR1 comprises an amino acid sequence of any one of SEQ ID NOs: 94, 98, 102, 106, 110, 114, 118, 122, 126, 130, 134, 138, 142, 146, 150, 154, 158, 162, 166, 170, 174, 178, 182, 186 and 190, or a variant thereof comprising up to about 3 amino acid substitutions; b) a heavy chain variable region CDR2 comprises an amino acid sequence of any one of SEQ ID NOs: 95, 99, 103, 107, 111, 115, 119, 123, 127, 131, 135, 139, 143, 147, 151, 155, 159, 163, 167, 171, 175, 179, 183, 187 and 191, or a variant thereof comprising up to about 3 amino acid substitutions; and c) a heavy chain variable region CDR3 comprises an amino acid sequence of any one of SEQ ID NOs: 96, 100, 104, 108, 112, 116, 120, 124, 128, 132, 136, 140, 144, 148, 152, 156, 160, 164, 168, 172, 176, 180, 184, 188 and 192, or a variant thereof comprising up to about 3 amino acid substitutions.

In certain embodiments, the single domain antibody comprises a heavy chain variable region that comprises a CDR1 domain, a CDR2 domain and a CDR3 domain, wherein the CDR1 domain, the CDR2 domain and the CDR3 domain respectively comprise a CDR1 domain, a CDR2 domain and a CDR3 domain comprised in a reference heavy chain variable region comprising the amino acid sequence selected from the group consisting of SEQ ID NOs: 97, 101, 105, 109, 113, 117, 121, 125, 129, 133, 137, 141, 145, 149, 153, 157, 161, 165, 169, 173, 177, 181, 185, 189 and 193.

In certain embodiments, the single domain antibody comprises a heavy chain variable region CDR1 comprising amino acids having the sequence set forth in SEQ ID NO: 94, a heavy chain variable region CDR2 comprising amino acids having the sequence set forth in SEQ ID NO: 95, and a heavy chain variable region CDR3 comprising amino acids having the sequence set forth in SEQ ID NO: 96. In certain embodiments, the single domain antibody comprises a heavy chain variable region CDR1 comprising amino acids having the sequence set forth in SEQ ID NO: 98, a heavy chain variable region CDR2 comprising amino acids having the sequence set forth in SEQ ID NO: 99, and a heavy chain variable region CDR3 comprising amino acids having the sequence set forth in SEQ ID NO: 100. In certain embodiments, the single domain antibody comprises a heavy chain variable region CDR1 comprising amino acids having the sequence set forth in SEQ ID NO: 102, a heavy chain variable region CDR2 comprising amino acids having the sequence set forth in SEQ ID NO: 103, and a heavy chain variable region CDR3 comprising amino acids having the sequence set forth in SEQ ID NO: 104. In certain embodiments, the single domain antibody comprises a heavy chain variable region CDR1 comprising amino acids having the sequence set forth in SEQ ID NO: 106, a heavy chain variable region CDR2 comprising amino acids having the sequence set forth in SEQ ID NO: 107, and a heavy chain variable region CDR3 comprising amino acids having the sequence set forth in SEQ ID NO: 108. In certain embodiments, the single domain antibody comprises a heavy chain variable region CDR1 comprising amino acids having the sequence set forth in SEQ ID NO: 110, a heavy chain variable region CDR2 comprising amino acids having the sequence set forth in SEQ ID NO: 111, and a heavy chain variable region CDR3 comprising amino acids having the sequence set forth in SEQ ID NO: 112. In certain embodiments, the single domain antibody comprises a heavy chain variable region CDR1 comprising amino acids having the sequence set forth in SEQ ID NO: 114, a heavy chain variable region CDR2 comprising amino acids having the sequence set forth in SEQ ID NO: 115, and a heavy chain variable region CDR3 comprising amino acids having the sequence set forth in SEQ ID NO: 116. In certain embodiments, the single domain antibody comprises a heavy chain variable region CDR1 comprising amino acids having the sequence set forth in SEQ ID NO: 118, a heavy chain variable region CDR2 comprising amino acids having the sequence set forth in SEQ ID NO: 119, and a heavy chain variable region CDR3 comprising amino acids having the sequence set forth in SEQ ID NO: 120. In certain embodiments, the single domain antibody comprises a heavy chain variable region CDR1 comprising amino acids having the sequence set forth in SEQ ID NO: 122, a heavy chain variable region CDR2 comprising amino acids having the sequence set forth in SEQ ID NO: 123, and a heavy chain variable region CDR3 comprising amino acids having the sequence set forth in SEQ ID NO: 124. In certain embodiments, the single domain antibody comprises a heavy chain variable region CDR1 comprising amino acids having the sequence set forth in SEQ ID NO: 126, a heavy chain variable region CDR2 comprising amino acids having the sequence set forth in SEQ ID NO: 127, and a heavy chain variable region CDR3 comprising amino acids having the sequence set forth in SEQ ID NO: 128. In certain embodiments, the single domain antibody comprises a heavy chain variable region CDR1 comprising amino acids having the sequence set forth in SEQ ID NO: 130, a heavy chain variable region CDR2 comprising amino acids having the sequence set forth in SEQ ID NO: 131, and a heavy chain variable region CDR3 comprising amino acids having the sequence set forth in SEQ ID NO: 132. In certain embodiments, the single domain antibody comprises a heavy chain variable region CDR1 comprising amino acids having the sequence set forth in SEQ ID NO: 134, a heavy chain variable region CDR2 comprising amino acids having the sequence set forth in SEQ ID NO: 135, and a heavy chain variable region CDR3 comprising amino acids having the sequence set forth in SEQ ID NO: 136. In certain embodiments, the single domain antibody comprises a heavy chain variable region CDR1 comprising amino acids having the sequence set forth in SEQ ID NO: 138, a heavy chain variable region CDR2 comprising amino acids having the sequence set forth in SEQ ID NO: 139, and a heavy chain variable region CDR3 comprising amino acids having the sequence set forth in SEQ ID NO: 140. In certain embodiments, the single domain antibody comprises a heavy chain variable region CDR1 comprising amino acids having the sequence set forth in SEQ ID NO: 142, a heavy chain variable region CDR2 comprising amino acids having the sequence set forth in SEQ ID NO: 143, and a heavy chain variable region CDR3 comprising amino acids having the sequence set forth in SEQ ID NO: 144. In certain embodiments, the single domain antibody comprises a heavy chain variable region CDR1 comprising amino acids having the sequence set forth in SEQ ID NO: 146, a heavy chain variable region CDR2 comprising amino acids having the sequence set forth in SEQ ID NO: 147, and a heavy chain variable region CDR3 comprising amino acids having the sequence set forth in SEQ ID NO: 148. In certain embodiments, the single domain antibody comprises a heavy chain variable region CDR1 comprising amino acids having the sequence set forth in SEQ ID NO: 150, a heavy chain variable region CDR2 comprising amino acids having the sequence set forth in SEQ ID NO: 151, and a heavy chain variable region CDR3 comprising amino acids having the sequence set forth in SEQ ID NO: 152. In certain embodiments, the single domain antibody comprises a heavy chain variable region CDR1 comprising amino acids having the sequence set forth in SEQ ID NO: 154, a heavy chain variable region CDR2 comprising amino acids having the sequence set forth in SEQ ID NO: 155, and a heavy chain variable region CDR3 comprising amino acids having the sequence set forth in SEQ ID NO: 156. In certain embodiments, the single domain antibody comprises a heavy chain variable region CDR1 comprising amino acids having the sequence set forth in SEQ ID NO: 158, a heavy chain variable region CDR2 comprising amino acids having the sequence set forth in SEQ ID NO: 159, and a heavy chain variable region CDR3 comprising amino acids having the sequence set forth in SEQ ID NO: 160. In certain embodiments, the single domain antibody comprises a heavy chain variable region CDR1 comprising amino acids having the sequence set forth in SEQ ID NO: 162, a heavy chain variable region CDR2 comprising amino acids having the sequence set forth in SEQ ID NO: 163, and a heavy chain variable region CDR3 comprising amino acids having the sequence set forth in SEQ ID NO: 164. In certain embodiments, the single domain antibody comprises a heavy chain variable region CDR1 comprising amino acids having the sequence set forth in SEQ ID NO: 166, a heavy chain variable region CDR2 comprising amino acids having the sequence set forth in SEQ ID NO: 167, and a heavy chain variable region CDR3 comprising amino acids having the sequence set forth in SEQ ID NO: 168. In certain embodiments, the single domain antibody comprises a heavy chain variable region CDR1 comprising amino acids having the sequence set forth in SEQ ID NO: 170, a heavy chain variable region CDR2 comprising amino acids having the sequence set forth in SEQ ID NO: 171, and a heavy chain variable region CDR3 comprising amino acids having the sequence set forth in SEQ ID NO: 172. In certain embodiments, the single domain antibody comprises a heavy chain variable region CDR1 comprising amino acids having the sequence set forth in SEQ ID NO: 174, a heavy chain variable region CDR2 comprising amino acids having the sequence set forth in SEQ ID NO: 175, and a heavy chain variable region CDR3 comprising amino acids having the sequence set forth in SEQ ID NO: 176. In certain embodiments, the single domain antibody comprises a heavy chain variable region CDR1 comprising amino acids having the sequence set forth in SEQ ID NO: 178, a heavy chain variable region CDR2 comprising amino acids having the sequence set forth in SEQ ID NO: 179, and a heavy chain variable region CDR3 comprising amino acids having the sequence set forth in SEQ ID NO: 180. In certain embodiments, the single domain antibody comprises a heavy chain variable region CDR1 comprising amino acids having the sequence set forth in SEQ ID NO: 182, a heavy chain variable region CDR2 comprising amino acids having the sequence set forth in SEQ ID NO: 183, and a heavy chain variable region CDR3 comprising amino acids having the sequence set forth in SEQ ID NO: 184. In certain embodiments, the single domain antibody comprises a heavy chain variable region CDR1 comprising amino acids having the sequence set forth in SEQ ID NO: 186, a heavy chain variable region CDR2 comprising amino acids having the sequence set forth in SEQ ID NO: 187, and a heavy chain variable region CDR3 comprising amino acids having the sequence set forth in SEQ ID NO: 188. In certain embodiments, the single domain antibody comprises a heavy chain variable region CDR1 comprising amino acids having the sequence set forth in SEQ ID NO: 190, a heavy chain variable region CDR2 comprising amino acids having the sequence set forth in SEQ ID NO: 191, and a heavy chain variable region CDR3 comprising amino acids having the sequence set forth in SEQ ID NO: 192.

In certain embodiments, the single domain antibody comprises a heavy chain variable region comprising an amino acid sequence having at least about 80%, 85%, 90%, 91%, 92%, 93%, 94%, 95%, 96%, 97%, 98%, 99%, or 100% sequence identity to the amino acid sequence selected from the group consisting of SEQ ID NOs: 97, 101, 105, 109, 113, 117, 121, 125, 129, 133, 137, 141, 145, 149, 153, 157, 161, 165, 169, 173, 177, 181, 185, 189 and 193. In certain embodiments, the single domain antibody comprises a heavy chain variable region comprising an amino acid sequence selected from the group consisting of SEQ ID NOs: 97, 101, 105, 109, 113, 117, 121, 125, 129, 133, 137, 141, 145, 149, 153, 157, 161, 165, 169, 173, 177, 181, 185, 189 and 193.

In certain embodiments, the single domain antibody comprises a heavy chain variable region comprising the amino acid sequence set forth in SEQ ID NO: 97. In certain embodiments, the single domain antibody comprises a heavy chain variable region comprising the amino acid sequence set forth in SEQ ID NO: 101. In certain embodiments, the single domain antibody comprises a heavy chain variable region comprising the amino acid sequence set forth in SEQ ID NO: 105. In certain embodiments, the single domain antibody comprises a heavy chain variable region comprising the amino acid sequence set forth in SEQ ID NO: 109. In certain embodiments, the single domain antibody comprises a heavy chain variable region comprising the amino acid sequence set forth in SEQ ID NO: 113. In certain embodiments, the single domain antibody comprises a heavy chain variable region comprising the amino acid sequence set forth in SEQ ID NO: 117. In certain embodiments, the single domain antibody comprises a heavy chain variable region comprising the amino acid sequence set forth in SEQ ID NO: 121. In certain embodiments, the single domain antibody comprises a heavy chain variable region comprising the amino acid sequence set forth in SEQ ID NO: 125. In certain embodiments, the single domain antibody comprises a heavy chain variable region comprising the amino acid sequence set forth in SEQ ID NO: 129. In certain embodiments, the single domain antibody comprises a heavy chain variable region comprising the amino acid sequence set forth in SEQ ID NO: 133. In certain embodiments, the single domain antibody comprises a heavy chain variable region comprising the amino acid sequence set forth in SEQ ID NO: 137. In certain embodiments, the single domain antibody comprises a heavy chain variable region comprising the amino acid sequence set forth in SEQ ID NO: 141. In certain embodiments, the single domain antibody comprises a heavy chain variable region comprising the amino acid sequence set forth in SEQ ID NO: 145. In certain embodiments, the single domain antibody comprises a heavy chain variable region comprising the amino acid sequence set forth in SEQ ID NO: 149. In certain embodiments, the single domain antibody comprises a heavy chain variable region comprising the amino acid sequence set forth in SEQ ID NO: 153. In certain embodiments, the single domain antibody comprises a heavy chain variable region comprising the amino acid sequence set forth in SEQ ID NO: 157. In certain embodiments, the single domain antibody comprises a heavy chain variable region comprising the amino acid sequence set forth in SEQ ID NO: 161. In certain embodiments, the single domain antibody comprises a heavy chain variable region comprising the amino acid sequence set forth in SEQ ID NO: 165. In certain embodiments, the single domain antibody comprises a heavy chain variable region comprising the amino acid sequence set forth in SEQ ID NO: 169. In certain embodiments, the single domain antibody comprises a heavy chain variable region comprising the amino acid sequence set forth in SEQ ID NO: 173. In certain embodiments, the single domain antibody comprises a heavy chain variable region comprising the amino acid sequence set forth in SEQ ID NO: 177. In certain embodiments, the single domain antibody comprises a heavy chain variable region comprising the amino acid sequence set forth in SEQ ID NO: 181. In certain embodiments, the single domain antibody comprises a heavy chain variable region comprising the amino acid sequence set forth in SEQ ID NO: 185. In certain embodiments, the single domain antibody comprises a heavy chain variable region comprising the amino acid sequence set forth in SEQ ID NO: 189. In certain embodiments, the single domain antibody comprises a heavy chain variable region comprising the amino acid sequence set forth in SEQ ID NO: 193.

In certain embodiments, any one of the amino acid sequences comprised in the heavy chain variable region can comprise up to about 1, about 2, about 3, about 4, about 5, about 6, about 7, about 8, about 9 or about 10 amino acid substitutions, deletions and/or additions. In certain embodiments, the amino acid substitution is a conservative substitution.

In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 1, a heavy chain variable region CDR2 comprising amino acids having the sequence set forth in SEQ ID NO: 2, and a heavy chain variable region CDR3 comprising amino acids having the sequence set forth in SEQ ID NO: 3. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 5, a heavy chain variable region CDR2 comprising amino acids having the sequence set forth in SEQ ID NO: 6, and a heavy chain variable region CDR3 comprising amino acids having the sequence set forth in SEQ ID NO: 7. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 9, a heavy chain variable region CDR2 comprising amino acids having the sequence set forth in SEQ ID NO: 10, and a heavy chain variable region CDR3 comprising amino acids having the sequence set forth in SEQ ID NO: 11. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 13, a heavy chain variable region CDR2 comprising amino acids having the sequence set forth in SEQ ID NO: 14, and a heavy chain variable region CDR3 comprising amino acids having the sequence set forth in SEQ ID NO: 15. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 17, a heavy chain variable region CDR2 comprising amino acids having the sequence set forth in SEQ ID NO: 18, and a heavy chain variable region CDR3 comprising amino acids having the sequence set forth in SEQ ID NO: 19. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 21, a heavy chain variable region CDR2 comprising amino acids having the sequence set forth in SEQ ID NO: 22, and a heavy chain variable region CDR3 comprising amino acids having the sequence set forth in SEQ ID NO: 23. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 25, a heavy chain variable region CDR2 comprising amino acids having the sequence set forth in SEQ ID NO: 26, and a heavy chain variable region CDR3 comprising amino acids having the sequence set forth in SEQ ID NO: 27. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 29, a heavy chain variable region CDR2 comprising amino acids having the sequence set forth in SEQ ID NO: 30, and a heavy chain variable region CDR3 comprising amino acids having the sequence set forth in SEQ ID NO: 31. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 33, a heavy chain variable region CDR2 comprising amino acids having the sequence set forth in SEQ ID NO: 34, and a heavy chain variable region CDR3 comprising amino acids having the sequence set forth in SEQ ID NO: 35. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 37, a heavy chain variable region CDR2 comprising amino acids having the sequence set forth in SEQ ID NO: 38, and a heavy chain variable region CDR3 comprising amino acids having the sequence set forth in SEQ ID NO: 39. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 41, a heavy chain variable region CDR2 comprising amino acids having the sequence set forth in SEQ ID NO: 42, and a heavy chain variable region CDR3 comprising amino acids having the sequence set forth in SEQ ID NO: 43. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 45, a heavy chain variable region CDR2 comprising amino acids having the sequence set forth in SEQ ID NO: 46, and a heavy chain variable region CDR3 comprising amino acids having the sequence set forth in SEQ ID NO: 47. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 49, a heavy chain variable region CDR2 comprising amino acids having the sequence set forth in SEQ ID NO: 50, and a heavy chain variable region CDR3 comprising amino acids having the sequence set forth in SEQ ID NO: 51. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 53, a heavy chain variable region CDR2 comprising amino acids having the sequence set forth in SEQ ID NO: 54, and a heavy chain variable region CDR3 comprising amino acids having the sequence set forth in SEQ ID NO: 55. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 57, a heavy chain variable region CDR2 comprising amino acids having the sequence set forth in SEQ ID NO: 58, and a heavy chain variable region CDR3 comprising amino acids having the sequence set forth in SEQ ID NO: 59. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 61, a heavy chain variable region CDR2 comprising amino acids having the sequence set forth in SEQ ID NO: 62, and a heavy chain variable region CDR3 comprising amino acids having the sequence set forth in SEQ ID NO: 63. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 65, a heavy chain variable region CDR2 comprising amino acids having the sequence set forth in SEQ ID NO: 66, and a heavy chain variable region CDR3 comprising amino acids having the sequence set forth in SEQ ID NO: 67. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 69, a heavy chain variable region CDR2 comprising amino acids having the sequence set forth in SEQ ID NO: 70, and a heavy chain variable region CDR3 comprising amino acids having the sequence set forth in SEQ ID NO: 71. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 73, a heavy chain variable region CDR2 comprising amino acids having the sequence set forth in SEQ ID NO: 74, and a heavy chain variable region CDR3 comprising amino acids having the sequence set forth in SEQ ID NO: 75. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 77, a heavy chain variable region CDR2 comprising amino acids having the sequence set forth in SEQ ID NO: 78, and a heavy chain variable region CDR3 comprising amino acids having the sequence set forth in SEQ ID NO: 79. In certain embodiments, the single domain antibody cross-competes for binding to TIGIT with a reference anti-TIGIT single domain antibody comprising a heavy chain variable region CDR1 comprising amino acids having the sequence set forth in SEQ ID NO: 81, a heavy chain variable region CDR2 comprising amino acids having the sequence set forth in SEQ ID NO: 82, and a heavy chain variable region CDR3 comprising amino acids having the sequence set forth in SEQ ID NO: 83.

In certain embodiments, the single domain antibody comprises a heavy chain variable region comprising a heavy chain variable region CDR1 comprising amino acids having the sequence set forth in SEQ ID NO: 1, a heavy chain variable region CDR2 comprising amino acids having the sequence set forth in SEQ ID NO: 2, and a heavy chain variable region CDR3 comprising amino acids having the sequence set forth in SEQ ID NO: 3. In certain embodiments, the single domain antibody comprises a heavy chain variable region comprising a heavy chain variable region CDR1 comprising amino acids having the sequence set forth in SEQ ID NO: 5, a heavy chain variable region CDR2 comprising amino acids having the sequence set forth in SEQ ID NO: 6, and a heavy chain variable region CDR3 comprising amino acids having the sequence set forth in SEQ ID NO: 7. In certain embodiments, the single domain antibody comprises a heavy chain variable region comprising a heavy chain variable region CDR1 comprising amino acids having the sequence set forth in SEQ ID NO: 9, a heavy chain variable region CDR2 comprising amino acids having the sequence set forth in SEQ ID NO: 10, and a heavy chain variable region CDR3 comprising amino acids having the sequence set forth in SEQ ID NO: 11. In certain embodiments, the single domain antibody comprises a heavy chain variable region comprising a heavy chain variable region CDR1 comprising amino acids having the sequence set forth in SEQ ID NO: 13, a heavy chain variable region CDR2 comprising amino acids having the sequence set forth in SEQ ID NO: 14, and a heavy chain variable region CDR3 comprising amino acids having the sequence set forth in SEQ ID NO: 15. In certain embodiments, the single domain antibody comprises a heavy chain variable region comprising a heavy chain variable region CDR1 comprising amino acids having the sequence set forth in SEQ ID NO: 17, a heavy chain variable region CDR2 comprising amino acids having the sequence set forth in SEQ ID NO: 18, and a heavy chain variable region CDR3 comprising amino acids having the sequence set forth in SEQ ID NO: 19. In certain embodiments, the single domain antibody comprises a heavy chain variable region comprising a heavy chain variable region CDR1 comprising amino acids having the sequence set forth in SEQ ID NO: 21, a heavy chain variable region CDR2 comprising amino acids having the sequence set forth in SEQ ID NO: 22, and a heavy chain variable region CDR3 comprising amino acids having the sequence set forth in SEQ ID NO: 23. In certain embodiments, the single domain antibody comprises a heavy chain variable region comprising a heavy chain variable region CDR1 comprising amino acids having the sequence set forth in SEQ ID NO: 25, a heavy chain variable region CDR2 comprising amino acids having the sequence set forth in SEQ ID NO: 26, and a heavy chain variable region CDR3 comprising amino acids having the sequence set forth in SEQ ID NO: 27. In certain embodiments, the single domain antibody comprises a heavy chain variable region comprising a heavy chain variable region CDR1 comprising amino acids having the sequence set forth in SEQ ID NO: 29, a heavy chain variable region CDR2 comprising amino acids having the sequence set forth in SEQ ID NO: 30, and a heavy chain variable region CDR3 comprising amino acids having the sequence set forth in SEQ ID NO: 31. In certain embodiments, the single domain antibody comprises a heavy chain variable region comprising a heavy chain variable region CDR1 comprising amino acids having the sequence set forth in SEQ ID NO: 33, a heavy chain variable region CDR2 comprising amino acids having the sequence set forth in SEQ ID NO: 34, and a heavy chain variable region CDR3 comprising amino acids having the sequence set forth in SEQ ID NO: 35. In certain embodiments, the single domain antibody comprises a heavy chain variable region comprising a heavy chain variable region CDR1 comprising amino acids having the sequence set forth in SEQ ID NO: 37, a heavy chain variable region CDR2 comprising amino acids having the sequence set forth in SEQ ID NO: 38, and a heavy chain variable region CDR3 comprising amino acids having the sequence set forth in SEQ ID NO: 39. In certain embodiments, the single domain antibody comprises a heavy chain variable region comprising a heavy chain variable region CDR1 comprising amino acids having the sequence set forth in SEQ ID NO: 41, a heavy chain variable region CDR2 comprising amino acids having the sequence set forth in SEQ ID NO: 42, and a heavy chain variable region CDR3 comprising amino acids having the sequence set forth in SEQ ID NO: 43. In certain embodiments, the single domain antibody comprises a heavy chain variable region comprising a heavy chain variable region CDR1 comprising amino acids having the sequence set forth in SEQ ID NO: 45, a heavy chain variable region CDR2 comprising amino acids having the sequence set forth in SEQ ID NO: 46, and a heavy chain variable region CDR3 comprising amino acids having the sequence set forth in SEQ ID NO: 47. In certain embodiments, the single domain antibody comprises a heavy chain variable region comprising a heavy chain variable region CDR1 comprising amino acids having the sequence set forth in SEQ ID NO: 49, a heavy chain variable region CDR2 comprising amino acids having the sequence set forth in SEQ ID NO: 50, and a heavy chain variable region CDR3 comprising amino acids having the sequence set forth in SEQ ID NO: 51. In certain embodiments, the single domain antibody comprises a heavy chain variable region comprising a heavy chain variable region CDR1 comprising amino acids having the sequence set forth in SEQ ID NO: 53, a heavy chain variable region CDR2 comprising amino acids having the sequence set forth in SEQ ID NO: 54, and a heavy chain variable region CDR3 comprising amino acids having the sequence set forth in SEQ ID NO: 55. In certain embodiments, the single domain antibody comprises a heavy chain variable region comprising a heavy chain variable region CDR1 comprising amino acids having the sequence set forth in SEQ ID NO: 57, a heavy chain variable region CDR2 comprising amino acids having the sequence set forth in SEQ ID NO: 58, and a heavy chain variable region CDR3 comprising amino acids having the sequence set forth in SEQ ID NO: 59. In certain embodiments, the single domain antibody comprises a heavy chain variable region comprising a heavy chain variable region CDR1 comprising amino acids having the sequence set forth in SEQ ID NO: 61, a heavy chain variable region CDR2 comprising amino acids having the sequence set forth in SEQ ID NO: 62, and a heavy chain variable region CDR3 comprising amino acids having the sequence set forth in SEQ ID NO: 63. In certain embodiments, the single domain antibody comprises a heavy chain variable region comprising a heavy chain variable region CDR1 comprising amino acids having the sequence set forth in SEQ ID NO: 65, a heavy chain variable region CDR2 comprising amino acids having the sequence set forth in SEQ ID NO: 66, and a heavy chain variable region CDR3 comprising amino acids having the sequence set forth in SEQ ID NO: 67. In certain embodiments, the single domain antibody comprises a heavy chain variable region comprising a heavy chain variable region CDR1 comprising amino acids having the sequence set forth in SEQ ID NO: 69, a heavy chain variable region CDR2 comprising amino acids having the sequence set forth in SEQ ID NO: 70, and a heavy chain variable region CDR3 comprising amino acids having the sequence set forth in SEQ ID NO: 71. In certain embodiments, the single domain antibody comprises a heavy chain variable region comprising a heavy chain variable region CDR1 comprising amino acids having the sequence set forth in SEQ ID NO: 73, a heavy chain variable region CDR2 comprising amino acids having the sequence set forth in SEQ ID NO: 74, and a heavy chain variable region CDR3 comprising amino acids having the sequence set forth in SEQ ID NO: 75. In certain embodiments, the single domain antibody comprises a heavy chain variable region comprising a heavy chain variable region CDR1 comprising amino acids having the sequence set forth in SEQ ID NO: 77, a heavy chain variable region CDR2 comprising amino acids having the sequence set forth in SEQ ID NO: 78, and a heavy chain variable region CDR3 comprising amino acids having the sequence set forth in SEQ ID NO: 79. In certain embodiments, the single domain antibody comprises a heavy chain variable region comprising a heavy chain variable region CDR1 comprising amino acids having the sequence set forth in SEQ ID NO: 81, a heavy chain variable region CDR2 comprising amino acids having the sequence set forth in SEQ ID NO: 82, and a heavy chain variable region CDR3 comprising amino acids having the sequence set forth in SEQ ID NO: 83.

In certain embodiments, the single domain antibody comprises a heavy chain variable region comprising an amino acid sequence having at least about 80%, 85%, 90%, 91%, 92%, 93%, 94%, 95%, 96%, 97%, 98%, 99%, or 100% sequence identity to the amino acid sequence selected from the group consisting of SEQ ID NOs: 4, 8, 12, 16, 20, 24, 28, 32, 36, 40, 44, 48, 52, 56, 60, 64, 68, 72, 76, 80 and 84. In certain embodiments, the single domain antibody comprises a heavy chain variable region comprising an amino acid sequence selected from the group consisting of SEQ ID NOs: 4, 8, 12, 16, 20, 24, 28, 32, 36, 40, 44, 48, 52, 56, 60, 64, 68, 72, 76, 80 and 84.

In certain embodiments, any one of the amino acid sequences comprised in the heavy chain variable region can comprise up to about 1, about 2, about 3, about 4, about 5, about 6, about 7, about 8, about 9 or about 10 amino acid substitutions, deletions and/or additions. In certain embodiments, the amino acid substitution is a conservative substitution.

In certain embodiments, the single domain antibody comprises a heavy chain variable region comprising the amino acid sequence set forth in SEQ ID NO: 4. In certain embodiments, the single domain antibody comprises a heavy chain variable region comprising the amino acid sequence set forth in SEQ ID NO: 8. In certain embodiments, the single domain antibody comprises a heavy chain variable region comprising the amino acid sequence set forth in SEQ ID NO: 12. In certain embodiments, the single domain antibody comprises a heavy chain variable region comprising the amino acid sequence set forth in SEQ ID NO: 16. In certain embodiments, the single domain antibody comprises a heavy chain variable region comprising the amino acid sequence set forth in SEQ ID NO: 20. In certain embodiments, the single domain antibody comprises a heavy chain variable region comprising the amino acid sequence set forth in SEQ ID NO: 24. In certain embodiments, the single domain antibody comprises a heavy chain variable region comprising the amino acid sequence set forth in SEQ ID NO: 28. In certain embodiments, the single domain antibody comprises a heavy chain variable region comprising the amino acid sequence set forth in SEQ ID NO: 32. In certain embodiments, the single domain antibody comprises a heavy chain variable region comprising the amino acid sequence set forth in SEQ ID NO: 36. In certain embodiments, the single domain antibody comprises a heavy chain variable region comprising the amino acid sequence set forth in SEQ ID NO: 40. In certain embodiments, the single domain antibody comprises a heavy chain variable region comprising the amino acid sequence set forth in SEQ ID NO: 44. In certain embodiments, the single domain antibody comprises a heavy chain variable region comprising the amino acid sequence set forth in SEQ ID NO: 48. In certain embodiments, the single domain antibody comprises a heavy chain variable region comprising the amino acid sequence set forth in SEQ ID NO: 52. In certain embodiments, the single domain antibody comprises a heavy chain variable region comprising the amino acid sequence set forth in SEQ ID NO: 56. In certain embodiments, the single domain antibody comprises a heavy chain variable region comprising the amino acid sequence set forth in SEQ ID NO: 60. In certain embodiments, the single domain antibody comprises a heavy chain variable region comprising the amino acid sequence set forth in SEQ ID NO: 64. In certain embodiments, the single domain antibody comprises a heavy chain variable region comprising the amino acid sequence set forth in SEQ ID NO: 68. In certain embodiments, the single domain antibody comprises a heavy chain variable region comprising the amino acid sequence set forth in SEQ ID NO: 72. In certain embodiments, the single domain antibody comprises a heavy chain variable region comprising the amino acid sequence set forth in SEQ ID NO: 76. In certain embodiments, the single domain antibody comprises a heavy chain variable region comprising the amino acid sequence set forth in SEQ ID NO: 80. In certain embodiments, the single domain antibody comprises a heavy chain variable region comprising the amino acid sequence set forth in SEQ ID NO: 84.

In certain embodiments, the single domain antibody comprises a humanized framework. In certain embodiments, the humanized framework comprises a framework sequence of the heavy chain variable region sequences selected from the group consisting of SEQ ID NOs: 85-93. In certain embodiments, the humanized framework comprises a FR2 sequence of the heavy chain variable region sequences selected from the group consisting of SEQ ID NOs: 85-93.

2.3.2 Second Antigen-Binding Moiety

In certain embodiments, the second antigen-binding moiety of a multispecific anti-TIGIT/anti-PDL1 antibody disclosed herein comprises an anti-PDL1 antibody that binds to PDL1. In certain embodiments, the anti-PDL1 antibody blocks the interaction between PDL1 and PD1. In certain embodiments, the antibody is any anti-PDL1 antibody disclosed in PCT/US2017/056689 (published as International Publication WO 2018/080812 A1), the content of which is incorporated herein by references in its entirety.

In certain embodiments, the anti-PDL1 antibody cross-competes with a reference anti-PDL1 antibody that comprises: a) a heavy chain variable domain (VH) sequence comprising (1) a CDR-H1 comprising the amino acid sequence set forth in SEQ ID NO: 221, (2) a CDR-H2 comprising the amino acid sequence set forth in SEQ ID NO: 222, and (3) a CDR-H3 comprising the amino acid sequence set forth in SEQ ID NO: 223; and a light chain variable domain (VL) sequence comprising (1) a CDR-L1 comprising the amino acid sequence set forth in SEQ ID NO: 224, (2) a CDR-L2 comprising the amino acid sequence set forth in SEQ ID NO: 225, and (3) a CDR-L3 comprising the amino acid sequence set forth in SEQ ID NO: 226; b) a heavy chain variable domain (VH) sequence comprising (1) a CDR-H1 comprising the amino acid sequence set forth in SEQ ID NO: 229, (2) a CDR-H2 comprising the amino acid sequence set forth in SEQ ID NO: 230, and (3) a CDR-H3 comprising the amino acid sequence set forth in SEQ ID NO: 231; and a light chain variable domain (VL) sequence comprising (1) a CDR-L1 comprising the amino acid sequence set forth in SEQ ID NO: 232, (2) a CDR-L2 comprising the amino acid sequence set forth in SEQ ID NO: 233, and (3) a CDR-L3 comprising the amino acid sequence set forth in SEQ ID NO: 234; c) a heavy chain variable domain (VH) sequence comprising (1) a CDR-H1 comprising the amino acid sequence set forth in SEQ ID NO: 237, (2) a CDR-H2 comprising the amino acid sequence set forth in SEQ ID NO: 238, and (3) a CDR-H3 comprising the amino acid sequence set forth in SEQ ID NO: 239; and a light chain variable domain (VL) sequence comprising (1) a CDR-L1 comprising the amino acid sequence set forth in SEQ ID NO: 240, (2) a CDR-L2 comprising the amino acid sequence set forth in SEQ ID NO: 241, and (3) a CDR-L3 comprising the amino acid sequence set forth in SEQ ID NO: 242; d) a heavy chain variable domain (VH) sequence comprising (1) a CDR-H1 comprising the amino acid sequence set forth in SEQ ID NO: 245, (2) a CDR-H2 comprising the amino acid sequence set forth in SEQ ID NO: 246, and (3) a CDR-H3 comprising the amino acid sequence set forth in SEQ ID NO: 247; and a light chain variable domain (VL) sequence comprising (1) a CDR-L1 comprising the amino acid sequence set forth in SEQ ID NO: 248, (2) a CDR-L2 comprising the amino acid sequence set forth in SEQ ID NO: 249, and (3) a CDR-L3 comprising the amino acid sequence set forth in SEQ ID NO: 250; e) a heavy chain variable domain (VH) sequence comprising (1) a CDR-H1 comprising the amino acid sequence set forth in SEQ ID NO: 253, (2) a CDR-H2 comprising the amino acid sequence set forth in SEQ ID NO: 254, and (3) a CDR-H3 comprising the amino acid sequence set forth in SEQ ID NO: 255; and a light chain variable domain (VL) sequence comprising (1) a CDR-L1 comprising the amino acid sequence set forth in SEQ ID NO: 256, (2) a CDR-L2 comprising the amino acid sequence set forth in SEQ ID NO: 257, and (3) a CDR-L3 comprising the amino acid sequence set forth in SEQ ID NO: 258; f) a heavy chain variable domain (VH) sequence comprising (1) a CDR-H1 comprising the amino acid sequence set forth in SEQ ID NO: 261, (2) a CDR-H2 comprising the amino acid sequence set forth in SEQ ID NO: 262, and (3) a CDR-H3 comprising the amino acid sequence set forth in SEQ ID NO: 263; and a light chain variable domain (VL) sequence comprising (1) a CDR-L1 comprising the amino acid sequence set forth in SEQ ID NO: 264, (2) a CDR-L2 comprising the amino acid sequence set forth in SEQ ID NO: 265, and (3) a CDR-L3 comprising the amino acid sequence set forth in SEQ ID NO: 266; g) a heavy chain variable domain (VH) sequence comprising (1) a CDR-H1 comprising the amino acid sequence set forth in SEQ ID NO: 269, (2) a CDR-H2 comprising the amino acid sequence set forth in SEQ ID NO: 270, and (3) a CDR-H3 comprising the amino acid sequence set forth in SEQ ID NO: 271; and a light chain variable domain (VL) sequence comprising (1) a CDR-L1 comprising the amino acid sequence set forth in SEQ ID NO: 272, (2) a CDR-L2 comprising the amino acid sequence set forth in SEQ ID NO: 273, and (3) a CDR-L3 comprising the amino acid sequence set forth in SEQ ID NO: 274; h) a heavy chain variable domain (VH) sequence comprising (1) a CDR-H1 comprising the amino acid sequence set forth in SEQ ID NO: 277, (2) a CDR-H2 comprising the amino acid sequence set forth in SEQ ID NO: 278, and (3) a CDR-H3 comprising the amino acid sequence set forth in SEQ ID NO: 279; and a light chain variable domain (VL) sequence comprising (1) a CDR-L1 comprising the amino acid sequence set forth in SEQ ID NO: 280, (2) a CDR-L2 comprising the amino acid sequence set forth in SEQ ID NO: 281, and (3) a CDR-L3 comprising the amino acid sequence set forth in SEQ ID NO: 282; i) a heavy chain variable domain (VH) sequence comprising (1) a CDR-H1 comprising the amino acid sequence set forth in SEQ ID NO: 285, (2) a CDR-H2 comprising the amino acid sequence set forth in SEQ ID NO: 286, and (3) a CDR-H3 comprising the amino acid sequence set forth in SEQ ID NO: 287; and a light chain variable domain (VL) sequence comprising (1) a CDR-L1 comprising the amino acid sequence set forth in SEQ ID NO: 288, (2) a CDR-L2 comprising the amino acid sequence set forth in SEQ ID NO: 289, and (3) a CDR-L3 comprising the amino acid sequence set forth in SEQ ID NO: 290; or j) a heavy chain variable domain (VH) sequence comprising (1) a CDR-H1 comprising the amino acid sequence set forth in SEQ ID NO: 293, (2) a CDR-H2 comprising the amino acid sequence set forth in SEQ ID NO: 294, and (3) a CDR-H3 comprising the amino acid sequence set forth in SEQ ID NO: 295; and a light chain variable domain (VL) sequence comprising (1) a CDR-L1 comprising the amino acid sequence set forth in SEQ ID NO: 296, (2) a CDR-L2 comprising the amino acid sequence set forth in SEQ ID NO: 297, and (3) a CDR-L3 comprising the amino acid sequence set forth in SEQ ID NO: 298.

In certain embodiments, the anti-PDL1 antibody comprises a heavy chain variable domain (VH) sequence comprising (1) a CDR-H1 comprising the amino acid sequence set forth in SEQ ID NO: 221, (2) a CDR-H2 comprising the amino acid sequence set forth in SEQ ID NO: 222, and (3) a CDR-H3 comprising the amino acid sequence set forth in SEQ ID NO: 223; and a light chain variable domain (VL) sequence comprising (1) a CDR-L1 comprising the amino acid sequence set forth in SEQ ID NO: 224, (2) a CDR-L2 comprising the amino acid sequence set forth in SEQ ID NO: 225, and (3) a CDR-L3 comprising the amino acid sequence set forth in SEQ ID NO: 226. In certain embodiments, the anti-PDL1 antibody comprises a heavy chain variable domain (VH) sequence comprising (1) a CDR-H1 comprising the amino acid sequence set forth in SEQ ID NO: 229, (2) a CDR-H2 comprising the amino acid sequence set forth in SEQ ID NO: 230, and (3) a CDR-H3 comprising the amino acid sequence set forth in SEQ ID NO: 231; and a light chain variable domain (VL) sequence comprising (1) a CDR-L1 comprising the amino acid sequence set forth in SEQ ID NO: 232, (2) a CDR-L2 comprising the amino acid sequence set forth in SEQ ID NO: 233, and (3) a CDR-L3 comprising the amino acid sequence set forth in SEQ ID NO: 234. In certain embodiments, the anti-PDL1 antibody comprises a heavy chain variable domain (VH) sequence comprising (1) a CDR-H1 comprising the amino acid sequence set forth in SEQ ID NO: 237, (2) a CDR-H2 comprising the amino acid sequence set forth in SEQ ID NO: 238, and (3) a CDR-H3 comprising the amino acid sequence set forth in SEQ ID NO: 239; and a light chain variable domain (VL) sequence comprising (1) a CDR-L1 comprising the amino acid sequence set forth in SEQ ID NO: 240, (2) a CDR-L2 comprising the amino acid sequence set forth in SEQ ID NO: 241, and (3) a CDR-L3 comprising the amino acid sequence set forth in SEQ ID NO: 242. In certain embodiments, the anti-PDL1 antibody comprises a heavy chain variable domain (VH) sequence comprising (1) a CDR-H1 comprising the amino acid sequence set forth in SEQ ID NO: 245, (2) a CDR-H2 comprising the amino acid sequence set forth in SEQ ID NO: 246, and (3) a CDR-H3 comprising the amino acid sequence set forth in SEQ ID NO: 247; and a light chain variable domain (VL) sequence comprising (1) a CDR-L1 comprising the amino acid sequence set forth in SEQ ID NO: 248, (2) a CDR-L2 comprising the amino acid sequence set forth in SEQ ID NO: 249, and (3) a CDR-L3 comprising the amino acid sequence set forth in SEQ ID NO: 250. In certain embodiments, the anti-PDL1 antibody comprises a heavy chain variable domain (VH) sequence comprising (1) a CDR-H1 comprising the amino acid sequence set forth in SEQ ID NO: 253, (2) a CDR-H2 comprising the amino acid sequence set forth in SEQ ID NO: 254, and (3) a CDR-H3 comprising the amino acid sequence set forth in SEQ ID NO: 255; and a light chain variable domain (VL) sequence comprising (1) a CDR-L1 comprising the amino acid sequence set forth in SEQ ID NO: 256, (2) a CDR-L2 comprising the amino acid sequence set forth in SEQ ID NO: 257, and (3) a CDR-L3 comprising the amino acid sequence set forth in SEQ ID NO: 258. In certain embodiments, the anti-PDL1 antibody comprises a heavy chain variable domain (VH) sequence comprising (1) a CDR-H1 comprising the amino acid sequence set forth in SEQ ID NO: 261, (2) a CDR-H2 comprising the amino acid sequence set forth in SEQ ID NO: 262, and (3) a CDR-H3 comprising the amino acid sequence set forth in SEQ ID NO: 263; and a light chain variable domain (VL) sequence comprising (1) a CDR-L1 comprising the amino acid sequence set forth in SEQ ID NO: 264, (2) a CDR-L2 comprising the amino acid sequence set forth in SEQ ID NO: 265, and (3) a CDR-L3 comprising the amino acid sequence set forth in SEQ ID NO: 266. In certain embodiments, the anti-PDL1 antibody comprises a heavy chain variable domain (VH) sequence comprising (1) a CDR-H1 comprising the amino acid sequence set forth in SEQ ID NO: 269, (2) a CDR-H2 comprising the amino acid sequence set forth in SEQ ID NO: 270, and (3) a CDR-H3 comprising the amino acid sequence set forth in SEQ ID NO: 271; and a light chain variable domain (VL) sequence comprising (1) a CDR-L1 comprising the amino acid sequence set forth in SEQ ID NO: 272, (2) a CDR-L2 comprising the amino acid sequence set forth in SEQ ID NO: 273, and (3) a CDR-L3 comprising the amino acid sequence set forth in SEQ ID NO: 274. In certain embodiments, the anti-PDL1 antibody comprises a heavy chain variable domain (VH) sequence comprising (1) a CDR-H1 comprising the amino acid sequence set forth in SEQ ID NO: 277, (2) a CDR-H2 comprising the amino acid sequence set forth in SEQ ID NO: 278, and (3) a CDR-H3 comprising the amino acid sequence set forth in SEQ ID NO: 279; and a light chain variable domain (VL) sequence comprising (1) a CDR-L1 comprising the amino acid sequence set forth in SEQ ID NO: 280, (2) a CDR-L2 comprising the amino acid sequence set forth in SEQ ID NO: 281, and (3) a CDR-L3 comprising the amino acid sequence set forth in SEQ ID NO: 282. In certain embodiments, the anti-PDL1 antibody comprises a heavy chain variable domain (VH) sequence comprising (1) a CDR-H1 comprising the amino acid sequence set forth in SEQ ID NO: 285, (2) a CDR-H2 comprising the amino acid sequence set forth in SEQ ID NO: 286, and (3) a CDR-H3 comprising the amino acid sequence set forth in SEQ ID NO: 287; and a light chain variable domain (VL) sequence comprising (1) a CDR-L1 comprising the amino acid sequence set forth in SEQ ID NO: 288, (2) a CDR-L2 comprising the amino acid sequence set forth in SEQ ID NO: 289, and (3) a CDR-L3 comprising the amino acid sequence set forth in SEQ ID NO: 290. In certain embodiments, the anti-PDL1 antibody comprises a heavy chain variable domain (VH) sequence comprising (1) a CDR-H1 comprising the amino acid sequence set forth in SEQ ID NO: 293, (2) a CDR-H2 comprising the amino acid sequence set forth in SEQ ID NO: 294, and (3) a CDR-H3 comprising the amino acid sequence set forth in SEQ ID NO: 295; and a light chain variable domain (VL) sequence comprising (1) a CDR-L1 comprising the amino acid sequence set forth in SEQ ID NO: 296, (2) a CDR-L2 comprising the amino acid sequence set forth in SEQ ID NO: 297, and (3) a CDR-L3 comprising the amino acid sequence set forth in SEQ ID NO: 298. In certain embodiments, the anti-PDL1 antibody comprises a heavy chain variable domain (VH) sequence comprising (1) a CDR-H1 comprising the amino acid sequence set forth in SEQ ID NO: 301, (2) a CDR-H2 comprising the amino acid sequence set forth in SEQ ID NO: 302, and (3) a CDR-H3 comprising the amino acid sequence set forth in SEQ ID NO: 303; and a light chain variable domain (VL) sequence comprising (1) a CDR-L1 comprising the amino acid sequence set forth in SEQ ID NO: 304, (2) a CDR-L2 comprising the amino acid sequence set forth in SEQ ID NO: 305, and (3) a CDR-L3 comprising the amino acid sequence set forth in SEQ ID NO: 306.

In certain embodiments, the anti-PDL1 antibody comprises a heavy chain variable region comprising an amino acid sequence having at least about 80%, 85%, 90%, 91%, 92%, 93%, 94%, 95%, 96%, 97%, 98%, 99%, or 100% sequence identity to the amino acid sequence selected from the group consisting of SEQ ID NOs: 227, 235, 243, 251, 259, 267, 275, 283, 291, 299 and 307, and a light chain variable region comprising an amino acid sequence having at least about 80%, 85%, 90%, 91%, 92%, 93%, 94%, 95%, 96%, 97%, 98%, 99%, or 100% sequence identity to the amino acid sequence selected from the group consisting of SEQ ID NOs: 228, 236, 244, 252, 260, 268, 276, 284, 292, 300 and 308. In certain embodiments, the anti-PDL1 antibody comprises a heavy chain variable region comprising an amino acid sequence selected from the group consisting of SEQ ID NOs: 227, 235, 243, 251, 259, 267, 275, 283, 291, 299 and 307, and a light chain variable region comprising an amino acid sequence selected from the group consisting of SEQ ID NOs: 228, 236, 244, 252, 260, 268, 276, 284, 292, 300 and 308.

In certain embodiments, the anti-PDL1 antibody comprises a heavy chain variable region comprising the amino acid sequence set forth in SEQ ID NO: 227, and a light chain variable region comprising the amino acid sequence set forth in SEQ ID NO: 228. In certain embodiments, the anti-PDL1 antibody comprises a heavy chain variable region comprising the amino acid sequence set forth in SEQ ID NO: 235, and a light chain variable region comprising the amino acid sequence set forth in SEQ ID NO: 236. In certain embodiments, the anti-PDL1 antibody comprises a heavy chain variable region comprising the amino acid sequence set forth in SEQ ID NO: 243, and a light chain variable region comprising the amino acid sequence set forth in SEQ ID NO: 244. In certain embodiments, the anti-PDL1 antibody comprises a heavy chain variable region comprising the amino acid sequence set forth in SEQ ID NO: 251, and a light chain variable region comprising the amino acid sequence set forth in SEQ ID NO: 252. In certain embodiments, the anti-PDL1 antibody comprises a heavy chain variable region comprising the amino acid sequence set forth in SEQ ID NO: 259, and a light chain variable region comprising the amino acid sequence set forth in SEQ ID NO: 260. In certain embodiments, the anti-PDL1 antibody comprises a heavy chain variable region comprising the amino acid sequence set forth in SEQ ID NO: 267, and a light chain variable region comprising the amino acid sequence set forth in SEQ ID NO: 268. In certain embodiments, the anti-PDL1 antibody comprises a heavy chain variable region comprising the amino acid sequence set forth in SEQ ID NO: 275, and a light chain variable region comprising the amino acid sequence set forth in SEQ ID NO: 276. In certain embodiments, the anti-PDL1 antibody comprises a heavy chain variable region comprising the amino acid sequence set forth in SEQ ID NO: 283, and a light chain variable region comprising the amino acid sequence set forth in SEQ ID NO: 284. In certain embodiments, the anti-PDL1 antibody comprises a heavy chain variable region comprising the amino acid sequence set forth in SEQ ID NO: 291, and a light chain variable region comprising the amino acid sequence set forth in SEQ ID NO: 292. In certain embodiments, the anti-PDL1 antibody comprises a heavy chain variable region comprising the amino acid sequence set forth in SEQ ID NO: 300, and a light chain variable region comprising the amino acid sequence set forth in SEQ ID NO: 301. In certain embodiments, the anti-PDL1 antibody comprises a heavy chain variable region comprising the amino acid sequence set forth in SEQ ID NO: 307, and a light chain variable region comprising the amino acid sequence set forth in SEQ ID NO: 308.

In certain embodiments, any one of the amino acid sequences comprised in the heavy chain variable region and/or the light chain variable region can comprise up to about 1, about 2, about 3, about 4, about 5, about 6, about 7, about 8, about 9 or about 10 amino acid substitutions, deletions and/or additions. In certain embodiments, the amino acid substitution is a conservative substitution.

In certain embodiments, the anti-PDL1 antibody comprises a Fc region. In certain embodiments, the Fc region is selected from the group consisting of the Fc regions of IgG, IgA, IgD, IgE and IgM. In certain embodiments, the Fc region is selected from the group consisting of the Fc regions of IgG1, IgG2, IgG3 and IgG4. In certain embodiments, the Fc region comprises a human Fc region. In certain embodiments, the Fc region comprises an IgG1 Fc region. In certain embodiments, the IgG1 Fc region comprising one or more mutation that modifies an antibody-dependent cell-mediated cytotoxicity (ADCC). In certain embodiments, the IgG1 Fc region comprising one or more mutation that enhances an antibody-dependent cell-mediated cytotoxicity (ADCC). In certain embodiments, the IgG1 Fc region comprising one or more mutation that reduces an antibody-dependent cell-mediated cytotoxicity (ADCC). In certain embodiments, the Fc region comprises an IgG4 Fc region. In certain embodiments, the IgG4 Fc region comprises an S228P mutation.

In certain embodiments, the anti-PDL1 antibody comprises a human antibody. In certain embodiments, the anti-PDL1 antibody is identified by screening of a human phage display library with a polypeptide comprising the ECD of a human PDL1 protein.

2.3.3 Features of Multispecific Antibodies

In certain embodiments, the anti-TIGIT/anti-PDL1 multispecific antibody can be a multivalent antibody. In certain embodiments, the anti-TIGIT/anti-PDL1 antibody can be bivalent, trivalent, tetravalent, pentavalent, hexavalent, heptavalent or octavalent. In certain embodiments, each of the first and the second antigen-binding moieties of the anti-TIGIT/anti-PDL1 antibody can be monovalent, bivalent, trivalent, tetravalent, pentavalent, hexavalent, heptavalent or octavalent. In certain embodiments, each of the first and the second antigen-binding moieties is monovalent. In certain embodiments, each of the first and the second antigen-binding moieties is bivalent. In certain embodiments, the anti-TIGIT/anti-PDL1 multispecific antibody is bivalent. In certain embodiments, the anti-TIGIT/anti-PDL1 multispecific antibody is tetravalent.

In certain embodiments, the second antigen binding moiety comprises an anti-PDL1 antibody comprising two antibody heavy chains and two antibody light chains. In certain embodiments, the first antigen-binding moiety comprises two or more anti-TIGIT antibodies. In certain embodiments, the first antigen-binding moiety comprises two anti-TIGIT antibodies. In certain embodiments, the C-terminus of at least one of the two anti-PDL1 light chains is linked to an anti-TIGIT antibody of the first antigen binding moiety. In certain embodiments, the C-terminus of each of the two anti-PDL1 light chains is linked to an anti-TIGIT antibody of the first antigen binding moiety. In certain embodiments, the N-terminus of at least one of the two anti-PDL1 light chains is linked to an anti-TIGIT antibody of the first antigen binding moiety. In certain embodiments, the N-terminus of each of the two anti-PDL1 light chains is linked to an anti-TIGIT antibody of the first antigen binding moiety. In certain embodiments, the C-terminus of at least one of the two anti-PDL1 heavy chains is linked to an anti-TIGIT antibody of the first antigen binding moiety. In certain embodiments, the C-terminus of each of the two anti-PDL1 heavy chains is linked to an anti-TIGIT antibody of the first antigen binding moiety. In certain embodiments, the N-terminus of at least one of the two anti-PDL1 heavy chains is linked to an anti-TIGIT antibody of the first antigen binding moiety. In certain embodiments, the N-terminus of each of the two anti-PDL1 heavy chains is linked to an anti-TIGIT antibody of the first antigen binding moiety.

In certain embodiments, the multispecific antibody comprises i) a first antigen-binding moiety comprising a single domain anti-TIGIT antibody that comprises a heavy chain variable region CDR1 comprising amino acids having the sequence set forth in SEQ ID NO: 186, a heavy chain variable region CDR2 comprising amino acids having the sequence set forth in SEQ ID NO: 187, and a heavy chain variable region CDR3 comprising amino acids having the sequence set forth in SEQ ID NO: 188; and ii) a second antigen-binding moiety comprising an anti-PDL1 antibody comprising a heavy chain variable domain (VH) sequence that comprises (1) a CDR-H1 comprising the amino acid sequence set forth in SEQ ID NO: 237, (2) a CDR-H2 comprising the amino acid sequence set forth in SEQ ID NO: 238, and (3) a CDR-H3 comprising the amino acid sequence set forth in SEQ ID NO: 239; and a light chain variable domain (VL) sequence comprising (1) a CDR-L1 comprising the amino acid sequence set forth in SEQ ID NO: 240, (2) a CDR-L2 comprising the amino acid sequence set forth in SEQ ID NO: 241, and (3) a CDR-L3 comprising the amino acid sequence set forth in SEQ ID NO: 242.

In certain embodiments, the multispecific antibody comprises i) a first antigen-binding moiety comprising a single domain anti-TIGIT antibody that comprises a heavy chain variable region CDR1 comprising amino acids having the sequence set forth in SEQ ID NO: 178, a heavy chain variable region CDR2 comprising amino acids having the sequence set forth in SEQ ID NO: 179, and a heavy chain variable region CDR3 comprising amino acids having the sequence set forth in SEQ ID NO: 180; and ii) a second antigen-binding moiety comprising an anti-PDL1 antibody comprising a heavy chain variable domain (VH) sequence that comprises (1) a CDR-H1 comprising the amino acid sequence set forth in SEQ ID NO: 253, (2) a CDR-H2 comprising the amino acid sequence set forth in SEQ ID NO: 254, and (3) a CDR-H3 comprising the amino acid sequence set forth in SEQ ID NO: 255; and a light chain variable domain (VL) sequence comprising (1) a CDR-L1 comprising the amino acid sequence set forth in SEQ ID NO: 256, (2) a CDR-L2 comprising the amino acid sequence set forth in SEQ ID NO: 257, and (3) a CDR-L3 comprising the amino acid sequence set forth in SEQ ID NO: 258.

In certain embodiments, the multispecific antibody comprises i) a first antigen-binding moiety comprising a single domain anti-TIGIT antibody that comprises a heavy chain variable region CDR1 comprising amino acids having the sequence set forth in SEQ ID NO: 182, a heavy chain variable region CDR2 comprising amino acids having the sequence set forth in SEQ ID NO: 183, and a heavy chain variable region CDR3 comprising amino acids having the sequence set forth in SEQ ID NO: 184; and ii) a second antigen-binding moiety comprising an anti-PDL1 antibody comprising a heavy chain variable domain (VH) sequence that comprises (1) a CDR-H1 comprising the amino acid sequence set forth in SEQ ID NO: 245, (2) a CDR-H2 comprising the amino acid sequence set forth in SEQ ID NO: 246, and (3) a CDR-H3 comprising the amino acid sequence set forth in SEQ ID NO: 247; and a light chain variable domain (VL) sequence comprising (1) a CDR-L1 comprising the amino acid sequence set forth in SEQ ID NO: 248, (2) a CDR-L2 comprising the amino acid sequence set forth in SEQ ID NO: 249, and (3) a CDR-L3 comprising the amino acid sequence set forth in SEQ ID NO: 250.

In certain embodiments, the multispecific antibody comprises i) a first antigen-binding moiety comprising a single domain anti-TIGIT antibody that comprises a heavy chain variable region CDR1 comprising amino acids having the sequence set forth in SEQ ID NO: 94, a heavy chain variable region CDR2 comprising amino acids having the sequence set forth in SEQ ID NO: 95, and a heavy chain variable region CDR3 comprising amino acids having the sequence set forth in SEQ ID NO: 96; and ii) a second antigen-binding moiety comprising an anti-PDL1 antibody comprising a heavy chain variable domain (VH) sequence that comprises (1) a CDR-H1 comprising the amino acid sequence set forth in SEQ ID NO: 293, (2) a CDR-H2 comprising the amino acid sequence set forth in SEQ ID NO: 294, and (3) a CDR-H3 comprising the amino acid sequence set forth in SEQ ID NO: 295; and a light chain variable domain (VL) sequence comprising (1) a CDR-L1 comprising the amino acid sequence set forth in SEQ ID NO: 296, (2) a CDR-L2 comprising the amino acid sequence set forth in SEQ ID NO: 297, and (3) a CDR-L3 comprising the amino acid sequence set forth in SEQ ID NO: 298.

In certain embodiments, the multispecific antibody comprises i) a first antigen-binding moiety comprising a single domain anti-TIGIT antibody that comprises a heavy chain variable region CDR1 comprising amino acids having the sequence set forth in SEQ ID NO: 190, a heavy chain variable region CDR2 comprising amino acids having the sequence set forth in SEQ ID NO: 191, and a heavy chain variable region CDR3 comprising amino acids having the sequence set forth in SEQ ID NO: 192; and ii) a second antigen-binding moiety comprising an anti-PDL1 antibody comprising a heavy chain variable domain (VH) sequence that comprises (1) a CDR-H1 comprising the amino acid sequence set forth in SEQ ID NO: 221, (2) a CDR-H2 comprising the amino acid sequence set forth in SEQ ID NO: 222, and (3) a CDR-H3 comprising the amino acid sequence set forth in SEQ ID NO: 223; and a light chain variable domain (VL) sequence comprising (1) a CDR-L1 comprising the amino acid sequence set forth in SEQ ID NO: 224, (2) a CDR-L2 comprising the amino acid sequence set forth in SEQ ID NO: 225, and (3) a CDR-L3 comprising the amino acid sequence set forth in SEQ ID NO: 226.

In certain embodiments, the multispecific antibody comprises an anti-PDL1 antibody heavy chain linked to an anti-TIGIT antibody comprising the amino acid sequence set forth in SEQ ID NO: 309, and an anti-PDL1 antibody light chain comprising the amino acid sequence set forth in SEQ ID NO: 310. In certain embodiments, the multispecific antibody comprises an anti-PDL1 antibody heavy chain comprising the amino acid sequence set forth in SEQ ID NO: 311, and an anti-PDL1 antibody light chain linked to an anti-TIGIT antibody comprising the amino acid sequence set forth in SEQ ID NO: 312. In certain embodiments, the multispecific antibody comprises an anti-PDL1 antibody heavy chain linked to an anti-TIGIT antibody comprising the amino acid sequence set forth in SEQ ID NO: 313, and an anti-PDL1 antibody light chain comprising the amino acid sequence set forth in SEQ ID NO: 314. In certain embodiments, the multispecific antibody comprises an anti-PDL1 antibody heavy chain comprising the amino acid sequence set forth in SEQ ID NO: 315, and an anti-PDL1 antibody light chain linked to an anti-TIGIT antibody comprising the amino acid sequence set forth in SEQ ID NO: 316.

In certain embodiments, the first antigen binding moiety is linked to the second antigen binding moiety via a linker. In certain embodiments, the linker is a peptide linker. In certain embodiments, the peptide linker comprises about four to about thirty amino acids. In certain embodiments, the peptide linker comprises about four to about fifteen amino acids. In certain embodiments, the peptide linker comprises an amino acid sequence selected from the group consisting of SEQ ID NOs: 195-220.

In certain embodiments, the anti-PDL1 antibody of the second antigen-binding moiety comprises an Fc region selected from the group consisting of the Fc regions of IgG, IgA, IgD, IgE and IgM. In certain embodiments, the anti-PDL1 antibody of the second antigen-binding moiety comprises an Fc region selected from the group consisting of the Fc regions of IgG1, IgG2, IgG3 and IgG4. In certain embodiments, the Fc region comprises a human Fc region. In certain embodiments, the Fc region comprises an IgG1 Fc region. In certain embodiments, the IgG1 Fc region comprising one or more mutation that modifies an antibody-dependent cell-mediated cytotoxicity (ADCC). In certain embodiments, the IgG1 Fc region comprising one or more mutation that enhances an antibody-dependent cell-mediated cytotoxicity (ADCC). In certain embodiments, the IgG1 Fc region comprising one or more mutation that reduces an antibody-dependent cell-mediated cytotoxicity (ADCC). In certain embodiments, the Fc region comprises an IgG4 Fc region. In certain embodiments, the IgG4 Fc region comprises an S228P mutation.

2.4 Antibody Affinity

In certain embodiments, an antibody or an antigen-binding moiety of a multispecific antibody disclosed herein has a high binding affinity to its target antigen. In certain embodiments, the antibody or antigen-binding moiety binds to the target with a $K_D$ of about $1 \times 10^{-7}$ M or less. In certain embodiments, the antibody or antigen-binding moiety binds to the target with a $K_D$ of about $1 \times 10^{-8}$ M or less. In certain embodiments, the antibody or antigen-binding moiety binds to the target with a $K_D$ of about $5 \times 10^{-9}$ M or less. In certain embodiments, the antibody or antigen-binding moiety binds to the target with a $K_D$ of about $1 \times 10^{-9}$ M or less. In certain embodiments, the antibody or antigen-binding moiety binds to the target with a KD of between about $1 \times 10^{-9}$ M and about $1 \times 10^{-7}$ M. In certain embodiments, the antibody or antigen-binding moiety binds to the target with a KD of between about $1 \times 10^{-9}$ M and about $1 \times 10^{-8}$ M. In certain embodiments, the antibody or antigen-binding moiety binds to the target with a KD of between about $2 \times 10^{-9}$ M and about $1 \times 10^{-8}$ M. In certain embodiments, the antibody or antigen-binding moiety binds to the target with a KD of between about $2 \times 10^{-9}$ M and about $5 \times 10^{-8}$ M. In certain embodiments, the antibody or antigen-binding moiety binds to the target with a KD of between about $1 \times 10^{-9}$ M and about $5 \times 10^{-9}$ M.

The KD of the antibody or antigen-binding moiety can be determined by methods known in the art. Such methods comprise, but are not limited to Western blots, ELISA-, RIA-, ECL-, IRMA-, EIA-, Octet-BIACORE®-tests and peptide scans.

In certain embodiments, KD can be measured using a BIACORE® surface plasmon resonance assay. For example, and not by way of limitation, an assay using a BIACORE®-2000 or a BIACORE® 3000 (Biacore, Inc., Piscataway, NJ) is performed at 25° C. with immobilized antigen CM5 chips at about 10 response units (RU). In certain embodiments, carboxymethylated dextran biosensor chips (CM5, Biacore, Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 μg/ml (about 0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) can be calculated as the ratio koff/kon. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2.5 Antibody Fragments

In certain embodiments, an antibody of the present disclosure comprises an antigen-binding fragment or antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9: 129-134 (2003). For a review of scFv fragments, see, e.g., Pluckthtin, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab)2 fragments comprising salvage receptor binding epitope residues and having increased in vivo half-life, see U.S. Pat. No. 5,869,046.

In certain embodiments, an antibody of the present disclosure can be a diabody. Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9: 129-134 (2003).

In certain embodiments, an antibody of the present disclosure can comprise a single domain antibody. Single domain antibodies are antibody fragments that comprise all or a portion of the heavy chain variable domain or all or a portion of the light chain variable domain of an antibody. In certain embodiments, the single domain antibody is a human single-domain antibody (Domantis, Inc., Waltham, MA; see, e.g., U.S. Pat. No. 6,248,516 B1). In certain embodiments, the single domain antibody is camelid single-domain antibody. In certain embodiments, the single domain antibody is a VHH. In certain embodiments, the single domain antibody is humanized.

Antibody fragments can be made by various techniques including, but not limited to, proteolytic digestion of an intact antibody as well as production by recombinant host cells (e.g., E. coli or phage), as described herein.

2.6 Chimeric and Humanized Antibodies

In certain embodiments, an antibody, including an antigen-binding moiety of a multispecific antibody, of the present disclosure is a chimeric antibody. Certain chimeric antibodies are described, e.g., in U.S. Pat. No. 4,816,567; and Morrison et al., Proc. Natl. Acad. Sci. USA, 81:6851-6855 (1984)). In certain embodiments, a chimeric antibody comprises a non-human variable region (e.g., a variable region derived from mouse) and a human constant region. In certain embodiments, a chimeric antibody is a "class switched" antibody in which the class or subclass has been changed from that of the parent antibody. Chimeric antibodies include antigen-binding fragments thereof.

In certain embodiments, an antibody, including an antigen-binding moiety of a multispecific antibody, of the present disclosure can be a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or any portion thereof) are derived from human antibody sequences. A humanized antibody optionally can also comprise at least a portion of a human constant region. In certain embodiments, certain FR residues in a humanized antibody are substituted with corresponding residues from a non-human antibody (e.g., the antibody from which the HVR residues are derived), e.g., to restore or improve antibody specificity or affinity.

Humanized antibodies and methods of making them are described, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); Framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

2.7 Human Antibodies

In certain embodiments, an antibody of the present disclosure can be a human antibody (e.g., human domain antibody, or human DAb). Human antibodies can be produced using various techniques known in the art. Human antibodies are described generally in van Dijk and van de Winkel, Curr. Opin. Pharmacol. 5: 368-74 (2001), Lonberg, Curr. Opin. Immunol. 20:450-459 (2008), and Chen, Mol. Immunol. 47(4):912-21 (2010). Transgenic mice or rats capable of producing fully human single-domain antibodies (or DAb) are known in the art. See, e.g., US20090307787A1, U.S. Pat. No. 8,754,287, US20150289489A1, US20100122358A1, and WO2004049794.

Human antibodies (e.g., human DAbs) may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies (e.g., human DAbs) can also be made by hybridoma-based methods. Human myeloma and mouse-human heteromyeloma cell lines for the production of human monoclonal antibodies have been described (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991)). Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4): 265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies (e.g., human DAbs) may also be generated by isolating Fv clone variable domain sequences selected from human-derived phage display libraries. Such variable domain sequences may then be combined with a desired human constant domain. Techniques for selecting human antibodies from antibody libraries are described below.

2.8 Library-Derived Antibodies

The antibody moieties may be isolated by screening combinatorial libraries for antibodies with the desired activity or activities. For example, a variety of methods are known in the art for generating phage display libraries and screening such libraries for antibodies possessing the desired binding characteristics. Such methods are described, e.g., in Hoogenboom et al. in Methods in Molecular Biology 178: 1-37 (O'Brien et al., ed., Human Press, Totowa, NJ, 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004). Methods for constructing single-domain antibody libraries have been described, for example, see U.S. Pat. No. 7,371,849.

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically displays antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

2.9 Antibody Variants

The presently disclosed subject matter further provides amino acid sequence variants of the disclosed antibodies. For example, it may be desirable to improve the binding affinity and/or other biological properties of the antibody. Amino acid sequence variants of an antibody can be prepared by introducing appropriate modifications into the nucleotide sequence encoding the antibody, or by peptide synthesis. Such modifications include, but are not limited to, deletions from, and/or insertions into and/or substitutions of residues within the amino acid sequences of the antibody. Any combination of deletion, insertion, and substitution can be made to arrive at the final construct, provided that the final antibody, i.e., modified, possesses the desired characteristics, e.g., antigen-binding.

2.9.1 Substitution, Insertion, and Deletion Variants

In certain embodiments, antibody variants having one or more amino acid substitutions are provided. Sites of interest for substitutional mutagenesis include the HVRs (or CDRs) and FRs. Conservative substitutions are shown in Table 2 under the heading of "Preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

Amino acid substitutions

| Original | Exemplary Substitutions | Preferred |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; | Leu |
| Leu (L) | Norleucine; Ile; Val; Met; | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |

TABLE 2-continued

Amino acid substitutions

| Original | Exemplary Substitutions | Preferred |
| --- | --- | --- |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe. In certain embodiments, non-conservative substitutions will entail exchanging a member of one of these classes for another class.

In certain embodiments, a type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR (or CDR) residues are mutated and the variant antibodies displayed on phage and screened for a particular biological activity (e.g. binding affinity).

Alterations (e.g., substitutions) may be made in HVRs (or CDRs), e.g., to improve antibody affinity. Such alterations may be made in HVR (or CDRs) "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, NJ, (2001)). In certain embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR (or CDRs)-directed approaches, in which several HVR (or CDRs) residues (e.g., 4-6 residues at a time) are randomized. HVR (or CDRs) residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs (or CDRs) so long as such alterations do not substantially reduce the ability of the antibody to bind antigen. For example, conservative alterations (e.g., conservative substitutions as provided herein) that do not substantially reduce binding affinity may be made in HVRs (or CDRs). Such alterations may be outside of HVR (or CDR) "hotspots" or CDRs. In certain embodiments of the variant VHH sequences provided above, each HVR (or CDR) either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

2.9.2 Glycosylation Variants

In certain embodiments, the antibody moiety is altered to increase or decrease the extent to which the construct is glycosylated. Addition or deletion of glycosylation sites to an antibody may be conveniently accomplished by altering the amino acid sequence such that one or more glycosylation sites is created or removed.

Where the antibody moiety comprises an Fc region (e.g., scFv-Fc), the carbohydrate attached thereto may be altered. Native antibodies produced by mammalian cells typically comprise a branched, biantennary oligosaccharide that is generally attached by an N-linkage to Asn297 of the $C_H2$ domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In certain embodiments, modifications of the oligosaccharide in the antibody moiety may be made in order to create antibody variants with certain improved properties.

In certain embodiments, the antibody moiety has a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Patent Application No. US 2003/0157108 A1, Presta, L; and WO 2004/056312 A1, Adams et al.), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

In certain embodiments, the antibody moiety has bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

2.9.3 Fc Region Variants

In certain embodiments, one or more amino acid modifications may be introduced into the Fc region of the antibody moiety (e.g., scFv-Fc), thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the Fc fragment possesses some but not all effector functions, which make it a desirable candidate for applications in which the half-life of the antibody moiety in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity) but retains FcRn binding ability. The primary cells for mediating ADCC, NK cells, express FcγRIII only, whereas monocytes express FcγRI, FcγRII and FcγRIII. FcR expression on hematopoietic cells is summarized in Table 2 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). Clq binding assays may also be carried out to confirm that the antibody is unable to bind Clq and hence lacks CDC activity. See, e.g., Clq and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, the Fc fragment is an IgG1 Fc fragment. In certain embodiments, the IgG1 Fc fragment comprises a L234A mutation and/or a L235A mutation. In certain embodiments, the Fc fragment is an IgG2 or IgG4 Fc fragment. In certain embodiments, the Fc fragment is an IgG4 Fc fragment comprising a S228P, F234A, and/or a L235A mutation.

In certain embodiments, the antibody moiety comprises an Fc region with one or more amino acid substitutions which improve ADCC, e.g., substitutions at positions 298, 333, and/or 334 of the Fc region (EU numbering of residues).

In certain embodiments, alterations are made in the Fc region that result in altered (i.e., either improved or diminished) Clq binding and/or Complement Dependent Cytotoxicity (CDC), e.g., as described in U.S. Pat. No. 6,194,551, WO 99/51642, and Idusogie et al. J. Immunol. 164: 4178-4184 (2000).

In certain embodiments, the antibody moiety (e.g., scFv-Fc) variant comprising a variant Fc region comprising one or more amino acid substitutions which alters half-life and/or changes binding to the neonatal Fc receptor (FcRn). Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which alters binding of the Fc region to FcRn. Such Fc variants include those with substitutions at one or more of Fc region residues, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

2.9.4 Cysteine Engineered Antibody Variants

In certain embodiments, it may be desirable to create cysteine engineered antibody moieties, e.g., "thioMAbs," in which one or more residues of an antibody are substituted with cysteine residues. In certain embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: A118 (EU numbering) of the heavy chain; and S400 (EU numbering) of the heavy chain Fc region. Cysteine engineered antibody moieties may be generated as described, e.g., in U.S. Pat. No. 7,521,541.

2.10 Antibody Derivatives

In certain embodiments, the antibody moiety described herein may be further modified to comprise additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in diagnosis under defined conditions, etc.

In certain embodiments, the antibody moiety may be further modified to comprise one or more biologically active protein, polypeptides or fragments thereof. "Bioactive" or "biologically active", as used herein interchangeably, means showing biological activity in the body to carry out a specific function. For example, it may mean the combination with a particular biomolecule such as protein, DNA, etc., and then promotion or inhibition of the activity of such biomolecule. In certain embodiments, the bioactive protein or fragments thereof include proteins and polypeptides that are administered to patients as the active drug substance for prevention of or treatment of a disease or condition, as well as proteins and polypeptides that are used for diagnostic purposes, such as enzymes used in diagnostic tests or in vitro assays, as well as proteins and polypeptides that are administered to a patient to prevent a disease such as a vaccine.

2.11 Methods of Antibody Production

The antibodies disclosed herein can be produced using any available or known technique in the art. For example, but not by way of limitation, antibodies can be produced using recombinant methods and compositions, e.g., as described in U.S. Pat. No. 4,816,567. Detailed procedures to generate antibodies are described in the Examples below.

The presently disclosed subject matter further provides an isolated nucleic acid encoding an antibody disclosed herein. For example, the isolated nucleic acid can encode an amino acid sequence comprising the VL and/or an amino acid sequence comprising the VH of the antibody, e.g., the light and/or heavy chains of the antibody.

In certain embodiments, the nucleic acid can be present in one or more vectors, e.g., expression vectors. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, where additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the disclosed subject matter is intended to include such other forms of expression vectors, such as viral vectors (e.g., replication defective retroviruses, adenoviruses and adeno-associated viruses) that serve equivalent functions.

Different parts of the antibodies disclosed herein can be constructed in a single, multicistronic expression cassette, in multiple expression cassettes of a single vector, or in multiple vectors. Examples of elements that create polycistronic expression cassette include, but are not limited to, various viral and non-viral Internal Ribosome Entry Sites (IRES, e.g., FGF-1 IRES, FGF-2 IRES, VEGF IRES, IGF-II IRES, NF-kB IRES, RUNX1 IRES, p53 IRES, hepatitis A IRES, hepatitis C IRES, pestivirus IRES, aphthovirus IRES, picornavirus IRES, poliovirus IRES and encephalomyocarditis virus IRES) and cleavable linkers (e.g., 2A peptides, e.g., P2A, T2A, E2A and F2A peptides). Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) Mol. Cell. Biol. 5:431-437); PA317 (Miller, et al. (1986) Mol. Cell. Biol. 6:2895-2902); and CRIP (Danos, et al. (1988) Proc. Natl. Acad. Sci. USA 85:6460-6464). Non-amphotropic particles are suitable too, e.g., particles pseudotyped with VSVG, RD114 or GALV envelope and any other known in the art.

In certain embodiments, the nucleic acid encoding an antibody of the present disclosure and/or the one or more vectors including the nucleic acid can be introduced into a host cell. In certain embodiments, the introduction of a nucleic acid into a cell can be carried out by any method known in the art including, but not limited to, transfection, electroporation, microinjection, infection with a viral or bacteriophage vector containing the nucleic acid sequences, cell fusion, chromosome-mediated gene transfer, microcell-mediated gene transfer, spheroplast fusion, etc. In certain embodiments, a host cell can include, e.g., has been transformed with: a vector comprising a nucleic acid that encodes an amino acid sequence comprising a single domain antibody and/or the VH of a single domain antibody. In certain embodiments, a host cell can include, e.g., has been transformed with: (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In certain embodiments, the host cell is eukaryotic, e.g., a Chinese Hamster Ovary (CHO) cell or lymphoid cell (e.g., YO, NSO, Sp20 cell).

In certain embodiments, the methods of making an antibody disclosed herein can include culturing a host cell, in which a nucleic acid encoding the antibody has been introduced, under conditions suitable for expression of the antibody, and optionally recovering the antibody from the host cell and/or host cell culture medium. In certain embodiments, the antibody is recovered from the host cell through chromatography techniques.

For recombinant production of an antibody of the present disclosure, a nucleic acid encoding an antibody, e.g., as described above, can be isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody). Suitable host cells for cloning or expression of antibody-encoding vectors include prokaryotic or eukaryotic cells described herein. For example, antibodies can be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, Nat. Biotech. 22:1409-1414 (2004), and Li et al., Nat. Biotech. 24:210-215 (2006). Suitable host cells for the expression of glycosylated antibody can also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. In certain embodiments, plant cell cultures can be utilized as host cells. See, e.g., U.S. Pat. Nos. 5,959,177, 6,040,498, 6,420,548, 7,125,978, and 6,417,429 (describing PLANTIBODIES™ technology for producing antibodies in transgenic plants).

In certain embodiments, vertebrate cells can also be used as hosts. For example, and not by way of limitation, mammalian cell lines that are adapted to grow in suspension can be useful. Non-limiting examples of useful mammalian host cell lines are monkey kidney CV1 line transformed by SY40 (COS-7); human embryonic kidney line (293 or 293 cells as described, e.g., in Graham et al., J Gen Viral. 36:59 (1977)); baby hamster kidney cells (BHK); mouse sertoli cells (TM4 cells as described, e.g., in Mather, Biol. Reprod. 23:243-251 (1980)); monkey kidney cells (CV 1); African green monkey kidney cells (VERO-76); human cervical carcinoma cells (HELA); canine kidney cells (MDCK; buffalo rat liver cells (BRL 3A); human lung cells (W138); human liver cells (Hep 02); mouse mammary tumor (MMT 060562); TRI cells, as described, e.g., in Mather et al., Annals N. Y. Acad. Sci. 383:44-68 (1982); MRC 5 cells; and FS4 cells. Other useful mammalian host cell lines include Chinese hamster ovary (CHO) cells, including DHFK CHO cells (Urlaub et al., Proc. Natl. Acad. Sci. USA 77:42 16 (1980)); and myeloma cell lines such as YO, NSO and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

In certain embodiments, techniques for making bispecific and/or multispecific antibodies include, but are not limited to, recombinant expression of two immunoglobulin heavy chain-light chain pairs having the same specificity, where one or two of the heavy chains or the light chains are fuse to an antigen binding moiety (e.g., a single domain antibody, e.g., a VHH) having a different specificity, recombinant coexpression of two immunoglobulin heavy chain-light chain pairs having different specificities (see Milstei n and Cuello, Nature 305: 537 (1983)), PCT Patent Application No. WO 93/08829, and Traunecker et al., EMBO J 10: 3655 (1991)), and "knob-in-hole" engineering (see, e.g., U.S. Pat. No. 5,731,168). Bispecific antibodies can also be made by engineering electrostatic steering effects for making antibody Fc-heterodimeric molecules (WO 2009/089004A 1); cross-linking two or more antibodies or fragments (see, e.g., U.S. Pat. No. 4,676,980, and Brennan et al., Science, 229: 81 (1985)); using leucine zippers to produce bi specific antibodies (see, e.g., Kostelny et al., J Immunol; 148(5): 1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g., Gruber et al., J. Immunol., 152:5368 (1994)); and preparing trispecific antibodies as described, e.g., in Tutt et al. J Immunol. 147: 60 (1991).

Bispecific and multispecific molecules of the present disclosure can also be made using chemical techniques (see, e.g., Kranz (1981) Proc. Natl. Acad. Sci. USA 78:5807), "polydoma" techniques (see, e.g., U.S. Pat. No. 4,474,893), or recombinant DNA techniques. Bispecific and multispecific molecules of the presently disclosed subject matter can also be prepared by conjugating the constituent binding specificities, e.g., a first epitope and a second epitope binding specificities, using methods known in the art and as described herein. For example, and not by way of limitation, each binding specificity of the bispecific and multispecific molecule can be generated together by recombinant fusion protein techniques, or can be generated separately and then conjugated to one another. When the binding specificities are proteins or peptides, a variety of coupling or cross-linking agents can be used for covalent conjugation. Non-limiting examples of cross-linking agents include protein A, carbodiimide, N-succinimidyl-S-acetyl-thioacetate (SATA), N-succinimidyl-3-(2-pyridyldithio)propionate (SPDP), and sulfosuccinimidyl 4-(N-maleimidomethyl) cyclohaxane-1-carboxylate (sulfo-SMCC) (see, e.g., Karpovsky (1984) J. Exp. Med. 160:1686; Liu (1985) Proc. Natl. Acad. Sci. USA 82:8648). Other methods include those described by Paulus (Behring Ins. Mitt. (1985) No. 78, 118-132; Brennan (1985) Science 229:81-83), Glennie (1987) J Immunol. 139: 2367-2375). When the binding specificities are antibodies (e.g., two humanized antibodies), they can be conjugated via sulfhydryl bonding of the C-terminus hinge regions of the two heavy chains. In certain embodiments, the hinge region can be modified to contain an odd number of sulfhydryl residues, e.g., one, prior to conjugation.

In certain embodiments, both binding specificities of a bispecific antibody can be encoded in the same vector and expressed and assembled in the same host cell. This method is particularly useful where the bispecific and multispecific molecule is a MAb×MAb, MAb×Fab, Fab×F(ab')2 or ligand×Fab fusion protein. In certain embodiments, a bispecific antibody of the present disclosure can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or can comprise at least two single chain molecules. Methods for preparing bi- and multispecific molecules are described, for example, in U.S. Pat. Nos. 5,260,203; 5,455,030; 4,881,175; 5,132,405; 5,091,513; 5,476,786; 5,013,653; 5,258,498; and 5,482,858. Engineered antibodies with three or more functional antigen binding sites (e.g., epitope binding sites) including "Octopus antibodies," are also included herein (see, e.g., US 2006/0025576A1).

In certain embodiments, an animal system can be used to produce an antibody of the present disclosure. One animal system for preparing hybridomas is the murine system.

Hybridoma production in the mouse is a very well-established procedure. Immunization protocols and techniques for isolation of immunized splenocytes for fusion are known in the art. Fusion partners (e.g., murine myeloma cells) and fusion procedures are also known (see, e.g., Harlow and Lane (1988), Antibodies, A Laboratory Manual, Cold Spring Harbor Laboratory Press, Cold Spring Harbor New York).

2.12 Assays

The antibodies of the present disclosure provided herein can be identified, screened for, or characterized for their physical/chemical properties and/or biological activities by various assays known in the art and provided herein.

In certain embodiments, an antibody of the present disclosure can be tested for its antigen binding activity by known methods, such enzyme-linked immunosorbent assay (ELISA), a radioimmunoassay (RIA), or a Western Blot Assay. Each of these assays generally detects the presence of protein-antibody complexes of particular interest by employing a labeled reagent (e.g., an antibody) specific for the complex of interest. For example, the antibody can be detected using, e.g., an enzyme-linked antibody or antibody fragment which recognizes and specifically binds to the antibody. Alternatively, the antibody can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March 1986, which is incorporated by reference herein). The radioactive isotope can be detected by such means as the use of a Geiger counter or a scintillation counter or by autoradiography.

In certain embodiments, competition assays can be used to identify an antibody that competes with an antibody of the present disclosure, e.g., 1C12, 2A3 or 1G1, for binding to TIGIT. In certain embodiments, such a competing antibody binds to the same epitope (e.g., a linear or a conformational epitope) that is bound by 1C12, 2A3 or 1G1. Detailed exemplary methods for mapping an epitope to which an antibody binds are provided in Morris (1996) "Epitope Mapping Protocols," in Methods in Molecular Biology vol. 66 (Humana Press, Totowa, NJ).

In a non-limiting example of a competition assay, immobilized TIGIT can be incubated in a solution comprising a first labeled antibody that binds to TIGIT (e.g., 1C12, 2A3 or 1G1) and a second unlabeled antibody that is being tested for its ability to compete with the first antibody for binding to TIGIT. The second antibody may be present in a hybridoma supernatant. As a control, immobilized TIGIT is incubated in a solution comprising the first labeled antibody but not the second unlabeled antibody. After incubation under conditions permissive for binding of the first antibody to TIGIT, excess unbound antibody is removed, and the amount of label associated with immobilized TIGIT is measured. If the amount of label associated with immobilized TIGIT is substantially reduced in the test sample relative to the control sample, then that indicates that the second antibody is competing with the first antibody for binding to TIGIT. See Harlow and Lane (1988) Antibodies: A Laboratory Manual ch.14 (Cold Spring Harbor Laboratory, Cold Spring Harbor, NY).

The present disclosure provides assays for identifying anti-TIGIT antibodies thereof having biological activity. Biological activity may include, e.g., activating an immune cell or an immune activation reporter, e.g., a NFAT reporter. Antibodies having such biological activity in vivo and/or in vitro are also provided.

2.13 Immunoconjugates

The presently disclosed subject matter further provides immunoconjugates comprising an antibody, disclosed herein, conjugated to one or more detection probe and/or cytotoxic agents, such as chemotherapeutic agents or drugs, growth inhibitory agents, toxins (e.g; protein toxins, enzymatically active toxins of bacterial, fungal, plant, or animal origin, or fragments thereof), or radioactive isotopes. For example, an antibody or antigen-binding portion of the disclosed subject matter can be functionally linked (e.g., by chemical coupling, genetic fusion, noncovalent association or otherwise) to one or more other binding molecules, such as another antibody, antibody fragment, peptide or binding mimetic.

In certain embodiments, an immunoconjugate is an antibody drug conjugate (ADC) in which an antibody is conjugated to one or more drugs, including but not limited to a maytansinoid (see U.S. Pat. Nos. 5,208,020, 5,416,064 and European Patent EP 0 425 235); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In certain embodiments, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In certain embodiments, an immunoconjugate comprises an antibody as described herein conjugated to a radioactive atom to form a radioconjugate. A variety of radioactive isotopes are available for the production of radioconjugates. Non-limiting examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it can include a radioactive atom for scintigraphic studies, for example tc99m or 1123, or a spin label for nuclear magnetic resonance (NMR) imaging (also known as magnetic resonance imaging, MRI), such as iodine-123, iodine-131, indium-11, fluorine-19, carbon-13, nitrogen-15, oxygen-17, gadolinium, manganese or iron.

Conjugates of an antibody and cytotoxic agent can be made using a variety of bi functional protein coupling agents such as N-succinimid yl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-4-labeled 1-isothiocyanatobenzyl-3-methyldiethylene triaminepentaacetic acid (MX-DTPA) is an exemplary chelating agent for conjugation of radionucleotide to the antibody. See WO94/11026. The linker can be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) can be used.

The immunuoconjugates or ADCs herein expressly contemplate, but are not limited to, such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

3. Methods of Use

The presently disclosed subject matter further provides methods for using the disclosed antibodies, e.g., an anti-TIGIT antibody and an anti-TIGIT/anti-PDL1 multi specific antibody. In certain embodiments, the methods are directed to therapeutic uses of the presently disclosed antibodies. In certain embodiments, the methods are directed to diagnostic use of the presently disclosed antibodies.

3.1 Treatment Methods

The present disclosure provides methods and use of any antibodies disclosed herein (e.g., the anti-TIGIT antibody and/or the anti-TIGIT/anti-PDL1 multispecific antibody) for treatment of diseases and disorders or for increasing an immune response. In certain embodiments, the antibody and/or pharmaceutical compositions comprising the same disclosed herein can be administered to subjects (e.g., mammals such as humans) to treat diseases and disorders or to increases an immune response. In certain embodiments, the diseases and disorders involve immune checkpoint inhibitions and/or abnormal TIGIT and/or PDL1 activity. In certain embodiments, the diseases and disorders that can be treated by the antibodies disclosed herein include, but are not limited to, neoplasia, e.g., cancer.

In certain embodiments, the present disclosure provides anti-TIGIT and/or anti-TIGIT/anti-PDL1 antibodies described herein (or fragments thereof) for use in the manufacture of a medicament. In certain embodiments, the present disclosure provides anti-TIGIT and/or anti-TIGIT/anti-PDL1 antibodies described herein (or fragments thereof) for use in the manufacture of a medicament for treating of cancer. In certain embodiments, the present disclosure provides anti-TIGIT and/or anti-TIGIT/anti-PDL1 antibodies described herein (or fragments thereof) for use in treating cancer in a subject. In certain embodiments, the present disclosure provides pharmaceutical compositions comprising an anti-TIGIT and/or anti-TIGIT/anti-PDL1 antibody provided herein (or fragments thereof) for use in treating cancer in a subject. In certain embodiments, the cancer can be blood cancers (e.g. leukemias, lymphomas, and myelomas), ovarian cancer, breast cancer, bladder cancer, brain cancer, colon cancer, intestinal cancer, liver cancer, lung cancer, pancreatic cancer, prostate cancer, skin cancer, stomach cancer, glioblastoma, throat cancer, melanoma, neuroblastoma, adenocarcinoma, glioma, soft tissue sarcoma, and various carcinomas (including prostate and small cell lung cancer). Suitable carcinomas further include any known carcinoma in the field of oncology, including, but not limited to, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolarcarcinoma, epithelial adenocarcinoma, and liver metastases thereof, lymphangiosarcoma, lymphangioendotheliosarcoma, hepatoma, cholangiocarcinoma, synovioma, mesothelioma, Ewing's tumor, rhabdomyosarcoma, colon carcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bile duct carcinoma, choriocarcinoma, seminoma, embryonal carcinoma, Wilms' tumor, testicular tumor, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas.

In certain embodiments, the cancer can be melanoma, NSCLC, head and neck cancer, urothelial cancer, breast cancer (e.g., triple-negative breast cancer, TNBC), gastric cancer, cholangiocarcinoma, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer or thyroid cancer.

In certain embodiments, the subject to be treated is a mammal (e.g., human, non-human primate, rat, mouse, cow, horse, pig, sheep, goat, dog, cat, etc.). In certain embodiments, the subject is a human. In certain embodiments, the subject is suspected of having or at risk of having a cancer or be diagnosed with a cancer or any other disease having abnormal TIGIT and/or PDL1 expression or activity.

Many diagnostic methods for cancer or any other disease exhibiting abnormal TIGIT and/or PDL1 activity and the clinical delineation of those diseases are known in the art. Such methods include, but are not limited to, e.g., immunohistochemistry, PCR, fluorescent in situ hybridization (FISH). Additional details regarding diagnostic methods for abnormal TIGIT and/or PDL1 activity or expression are described in, e.g., Gupta et al. (2009) Mod Pathol. 22(1): 128-133; Lopez-Rios et al. (2013) J Clin Pathol. 66(5): 381-385; Ellison et al. (2013) J Clin Pathol 66(2): 79-89; and Guha et al. (2013) PLoS ONE 8(6): e67782.

Administration can be by any suitable route including, e.g., intravenous, intramuscular, or subcutaneous. In some embodiments, the anti-TIGIT and/or anti-TIGIT/anti-PDL-lantibodies (or fragments thereof) and/or compositions provided herein are administered in combination with a second, third, or fourth agent (including, e.g., an antineoplastic agent, a growth inhibitory agent, a cytotoxic agent, or a chemotherapeutic agent) to treat the diseases or disorders involving abnormal TIGIT/PDL1 activity. Such agents include, e.g., docetaxel, gefitinib, FOLFIRI (irinotecan, 5-fluorouracil, and leucovorin), irinotecan, cisplatin, carboplatin, paclitaxel, bevacizumab (anti-VEGF antibody), FOLFOX-4, infusional fluorouracil, leucovorin, and oxaliplatin, afatinib, gemcitabine, capecitabine, pemetrexed, tivantinib, everolimus, CpG-ODN, rapamycin, lenalidomide, vemurafenib, endostatin, lapatinib, PX-866, Imprime PGG, and irlotinibm. In some embodiments, the anti-TIGIT and/or anti-TIGIT/anti-PDL1 antibodies (or fragments thereof) are conjugated to the additional agent.

In certain embodiments, the anti-TIGIT and/or anti-TIGIT/anti-PDL1 antibodies (or fragments thereof) and/or compositions provided herein are administered in combination with one or more additional therapies, such as radiation therapy, surgery, chemotherapy, and/or targeted therapy. In certain embodiments, the anti-TIGIT and/or anti-TIGIT/anti-PDL1 antibodies (or fragments thereof) and/or compositions provided herein are administered in combination with radiation therapy. In certain embodiments, the combination of an anti-TIGIT and/or anti-TIGIT/anti-PDL1 antibody (or fragment thereof) and/or composition provided herein and radiation therapy is used for treating a neoplasm or cancer disclosed herein.

Depending on the indication to be treated and factors relevant to the dosing that a physician of skill in the field would be familiar with, the anti-TIGIT and/or anti-TIGIT/anti-PDL1 antibodies or fragments thereof, provided herein will be administered at a dosage that is efficacious for the treatment of that indication while minimizing toxicity and side effects. For the treatment of a cancer, a typical dose can be, for example, in the rage of 0.001 to 1000 μg; however, doses below or above this exemplary range are within the scope of the invention. The daily dose can be about 0.1 µg/kg to about 100 mg/kg of total body weight, about 0.1 µg/kg to about 100 µg/kg of total body weight or about 1 µg/kg to about 100 µg/kg of total body weight. As noted above, therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

A pharmaceutical composition comprising the anti-TIGIT and/or anti-TIGIT/anti-PDL1 antibody or a fragment thereof can be administered one, two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection.

The antibody (or a fragment thereof) may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The antibody (or a fragment thereof) may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgically implanted in various locations.

Cancer treatments can be evaluated by, e.g., but not limited to, tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In certain embodiments, the efficacy of treatment is measured by the percentage tumor growth inhibition (% TGI), calculated using the equation 100−(T/C×100), where T is the mean relative tumor volume of the treated tumor, and C is the mean relative tumor volume of a non-treated tumor. In certain embodiments, the % TGI is about 10%, about 20%, about 30%, about 40%, about 50%, about 60%, about 70%, about 80%, about 90%, about 91%, about 92%, about 93%, about 94%, about 95%, or more than 95%.

3.2 Methods of Diagnosis and Imaging

Labeled anti-TIGIT and/or anti-TIGIT/anti-PDL1 antibodies, fragments thereof, and derivatives and analogs thereof can be used for diagnostic purposes to detect, diagnose, or monitor diseases and/or disorders associated with the expression, aberrant expression and/or activity of TIGIT and/or PDL1. For example, the anti-TIGIT and/or anti-TIGIT/anti-PDL1 antibodies (or fragments thereof) provided herein can be used in in situ, in vivo, ex vivo, and in vitro diagnostic assays or imaging assays. Methods for detecting expression of a TIGIT polypeptide, comprising (a) assaying the expression of the polypeptide in cells (e.g., tissue) or body fluid of an individual using one or more antibodies of this invention and (b) comparing the level of gene expression with a standard gene expression level, whereby an increase or decrease in the assayed gene expression level compared to the standard expression level is indicative of aberrant expression.

Additional embodiments provided herein include methods of diagnosing a disease or disorder associated with expression or aberrant expression of TIGIT and/or PD1 in an animal (e.g., a mammal such as a human). The methods comprise detecting TIGIT and/or PDL1 molecules in the mammal. In certain embodiments, diagnosis comprises: (a) administering an effective amount of a labeled anti-TIGIT and/or anti-TIGIT/anti-PDL1 antibody (or fragment thereof) to a mammal (b) waiting for a time interval following the administering for permitting the labeled anti-TIGIT and/or anti-TIGIT/anti-PDL1 antibody (or fragment thereof) to preferentially concentrate at sites in the subject where the TIGIT and/or PDL1 molecule is expressed (and for unbound labeled molecule to be cleared to background level); (c) determining background level; and (d) detecting the labeled molecule in the subject, such that detection of labeled molecule above the background level indicates that the subject has a particular disease or disorder associated with expression or aberrant expression of TIGIT/PDL1. Background level can be determined by various methods including, comparing the amount of labeled molecule detected to a standard value previously determined for a particular system.

Anti-TIGIT and/or anti-TIGIT/anti-PDL1 antibodies (or fragments thereof) provided herein can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc) thallium ($^{201}$Ti), gallium ($^{68}$Ga, $^{67}$Ga), palladium ($^{103}$Pd) molybdenum ($^{99}$Mo), xenon ($^{133}$Xe), fluorine ($^{18}$F) $^{153}$Sm, $^{177}$Lu, $^{159}$Gd, $^{149}$P, $^{140}$La, $^{175}$Yb $^{166}$Ho, $^{90}$Y, $^{47}$Sc, $^{186}$Re, $^{188}$Re, $^{142}$Pr, $^{105}$Rh, $^{97}$Ru; luminol; and fluorescent labels, such as fluorescein and rhodamine, and biotin.

Techniques known in the art may be applied to labeled antibodies (or fragments thereof) provided herein. Such techniques include, but are not limited to, the use of bifunctional conjugating agents (see e.g., U.S. Pat. Nos. 5,756,065;

5,714,631; 5,696,239; 5,652,361; 5,505,931; 5,489,425; 5,435,990; 5,428,139; 5,342,604; 5,274,119; 4,994,560; and 5,808,003).

Alternatively, or additionally, one can measure levels of a TIGIT and/or PDL1 polypeptide-encoding nucleic acid or mRNA in the cell, e.g., via fluorescent in situ hybridization using a nucleic acid based probe corresponding to an EGFR-encoding nucleic acid or the complement thereof; (FISH; see WO98/45479 published October, 1998), Southern blotting, Northern blotting, or polymerase chain reaction (PCR) techniques, such as real time quantitative PCR (RT-PCR). One can also study TIGIT and/or PDL1 overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., J. Immunol. Methods 132:73-80 (1990)). Aside from the above assays, various in vivo and ex vivo assays are available to the skilled practitioner. For example, one can expose cells within the body of the mammal to an antibody which is optionally labeled with a detectable label, e.g., a radioactive isotope, and binding of the antibody to the body cells can be evaluated, e.g., by external scanning for radioactivity or by analyzing a sample (e.g., a biopsy or other biological sample) taken from a mammal previously exposed to the antibody.

4. Pharmaceutical Formulations

The presently disclosed subject matter further provides pharmaceutical formulations containing one or more antibodies disclosed herein, with a pharmaceutically acceptable carrier. In certain embodiments, the pharmaceutical compositions can include a combination of multiple (e.g., two or more) antibodies and/or antigen-binding portions thereof of the presently disclosed subject matter. In certain embodiments, a pharmaceutical composition of the present disclosure can include one or more anti-TIGIT antibodies or one or more of anti-TIGIT/anti-PDL1 multispecific antibodies.

In certain embodiments, the disclosed pharmaceutical formulations can be prepared by combining an antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. For example, but not by way of limitation, lyophilized antibody formulations are described in U.S. Pat. No. 6,267,958. In certain embodiments, aqueous antibody formulations can include those described in U.S. Pat. No. 6,171,586 and WO2006/044908, the latter formulations including a histidine-acetate buffer. In certain embodiments, the antibody can be of a purity greater than about 80%, greater than about 90%, greater than about 91%, greater than about 92%, greater than about 93%, greater than about 94%, greater than about 95%, greater than about 96%, greater than about 97%, greater than about 98%, greater than about 99%, greater than about 99.1%, greater than about 99.2%, greater than about 99.3%, greater than about 99.4%, greater than about 99.5%, greater than about 99.6%, greater than about 99.7%, greater than about 99.8% or greater than about 99.9%.

Pharmaceutically acceptable carriers are generally non-toxic to recipients at the dosages and concentrations employed, and include, but are not limited to: buffers such as phosphate, citrate, and other organic acids, antioxidants including ascorbic acid and methionine, preservatives (such as octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol), low molecular weight (less than about 10 residues) polypeptides, proteins, such as serum albumin, gelatin, or immunoglobulins, hydrophilic polymers such as polyvinylpyrrolidone, amino acids such as glycine, glutamine, asparagine, histidine, arginine, or lysine, monosaccharides, disaccharides, and other carbohydrates including glucose, mannose, or dextrins, chelating agents such as EDTA, sugars such as sucrose, mannitol, trehalose or sorbitol, salt-forming counter-ions such as sodium, metal complexes (e.g., Zn-protein complexes), and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In certain embodiments, a sHASEGP is combined with one or more additional glycosaminoglycanases such as chondroitinases.

The carrier can be suitable for intravenous, intramuscular, subcutaneous, parenteral, spinal or epidermal administration (e.g., by injection or infusion). Depending on the route of administration, the active compound, i.e., an anti-TIGIT/anti-PDL1 antibody or an anti-TIGIT antibody, can be coated in a material to protect the compound from the action of acids and other natural conditions that may inactivate the compound.

Pharmaceutical compositions of the present disclosure also can be administered in combination therapy, i.e., combined with other agents. In certain embodiments, pharmaceutical compositions disclosed herein can also contain more than one active ingredients as necessary for the particular indication being treated, for example, those with complementary activities that do not adversely affect each other. In certain embodiments, the pharmaceutical formulation can include a second active ingredient for treating the same disease treated by the first therapeutic. Such active ingredients are suitably present in combination in amounts that are effective for the purpose intended. For example, and not by way of limitation, the formulation of the present disclosure can also contain more than one active ingredients as necessary for the particular indication being treated, preferably those with complementary activities that do not adversely affect each other. For example, it may be desirable to further provide a second therapeutic useful for treatment of the same disease. Such active ingredients are suitably present in combination in amounts that are effective for the purpose intended.

A composition of the present disclosure can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J. R. Robinson, ed., Marcel Dekker, Inc., New York, 1978. In certain embodiments, the pharmaceutical compositions are manufactured under Good Manufacturing Practice (GMP) conditions of the U.S. Food and Drug Administration.

Sustained-release preparations containing a disclosed antibody can also be prepared. Suitable examples of sustained-release preparations include semipermeable matrices of solid hydrophobic polymers containing the antibody, which matrices are in the form of shaped articles, e.g. films, or microcapsules. In certain embodiments, active ingredients can be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

To administer an antibody of the present disclosure by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) J Neuroimmunol. 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art.

Except insofar as any conventional media or agent is incompatible with the active compound, use thereof in the pharmaceutical compositions of the present disclosure is contemplated. Supplementary active compounds can also be incorporated into the compositions.

Therapeutic compositions typically must be sterile, substantially isotonic, and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it is preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating one or more disclosed antibodies in the required amount in an appropriate solvent with one or a combination of ingredients enumerated above, as required, followed by sterilization microfiltration, e.g., by filtration through sterile filtration membranes. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Therapeutic compositions can also be administered with medical devices known in the art.

For example, a therapeutic composition of the present disclosure can be administered with a needleless hypodermic injection device, such as the devices disclosed in, e.g., U.S. Pat. Nos. 5,399,163, 5,383,851, 5,312,335, 5,064,413, 4,941,880, 4,790,824 or 4,596,556. Examples of implants and modules useful in the present disclosure include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known.

For the therapeutic compositions, formulations of the present disclosure include those suitable for oral, nasal, topical (including buccal and sublingual), rectal, vaginal and/or parenteral administration. The formulations can conveniently be presented in unit dosage form and may be prepared by any methods known in the art of pharmacy. The amount of antibody, which can be combined with a carrier material to produce a single dosage form, vary depending upon the subject being treated, and the particular mode of administration. The amount of the antibody which can be combined with a carrier material to produce a single dosage form generally be that amount of the composition which produces a therapeutic effect. Generally, out of one hundred percent, this amount range from about 0.01 percent to about ninety-nine percent of active ingredient, from about 0.1 percent to about 70 percent, or from about 1 percent to about 30 percent.

Dosage forms for the topical or transdermal administration of compositions of the present disclosure include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, sub arachnoid, intraspinal, epidural and intrasternal injection and infusion.

These pharmaceutical compositions can also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

In certain embodiments, when the antibodies of the present disclosure are administered as pharmaceuticals, to humans and animals, they can be given alone or as a pharmaceutical composition containing, for example, from about 0.01% to about 99.5% (or about 0.1% to about 90%) of an antibody, described herein, in combination with a pharmaceutically acceptable carrier.

5. Articles of Manufacture

The presently disclosed subject matter further provides articles of manufacture containing materials useful for the treatment, prevention and/or diagnosis of the disorders described above.

In certain embodiments, the article of manufacture includes a container and a label or package insert on or associated with the container. Non limiting examples of suitable containers include bottles, vials, syringes, IV solution bags, etc. The containers can be formed from a variety of materials such as glass or plastic. The container can hold a composition which is by itself or combined with another composition effective for treating, preventing and/or diagnosing the condition and may have a sterile access port (for example, the container may be an intravenous solution bag or a vial having a stopper pierceable by a hypodermic injection needle).

In certain embodiments, at least one active agent in the composition is an antibody of the presently disclosed subject matter. The label or package insert can indicate that the composition is used for treating the condition of choice.

In certain embodiments, the article of manufacture can comprise (a) a first container with a composition contained therein, wherein the composition comprises an antibody of the present disclosure; and (b) a second container with a composition contained therein, wherein the composition comprises a further cytotoxic or otherwise therapeutic agent. In certain embodiments, the article of manufacture can further comprise a package insert indicating that the compositions can be used to treat a particular condition.

Alternatively, or additionally, the article of manufacture can further an additional container, e.g., a second or third container, including a pharmaceutically acceptable buffer, such as, but not limited to, bacteriostatic water for injection (BWFI), phosphate-buffered saline, Ringer's solution and dextrose solution. The article of manufacture can include other materials desirable from a commercial and user standpoint, including other buffers, diluents, filters, needles, and syringes.

SEQUENCE TABLE

| SEQ ID NO | Gene Name | Sequence |
|---|---|---|
| 1. | 4A11 CDR1 | GRPFSNYT |
| 2. | 4A11 CDR2 | AWPSPST |
| 3. | 4A11 CDR3 | AADYKSLTQSWLNAALDY |
| 4. | 4A11 VHH | QVKLEESGGGEAQPGGSLRLSCTASGRPFSNYTMGWFRR APGKEREFVGLAWPSPSTYVVDSVKGRFTISRDNAKNTIY LQMNSLKPEDTAIYYCAADYKSLTQSWLNAALDYWGQG TQVTVSS |
| 5. | 4B5 CDR1 | PRTFSTFH |
| 6. | 4B5 CDR2 | FNWSGGRT |
| 7. | 4B5 CDR3 | AAARDRGLHDGTTSDSYLEGSHEYEY |
| 8. | 4B5 VHH | QVKLEESGGRSVLAGGSLRLRCAGTPRTFSTFHIGWFRQA PGKEREFVAAFNWSGGRTYYADSVKGRFTISRNNGKNM VYLQMTSLTPEDTGLYYCAAARDRGLHDGTTSDSYLEGS HEYEYWGQGTQVTVSS |
| 9. | 4C5 CDR1 | GRSVSTYF |
| 10. | 4C5 CDR2 | IDRGSTVT |
| 11. | 4C5 CDR3 | AAKAITRNFIATNDYDY |
| 12. | 4C5 VHH | QVQLVDSGGGLVQAGGSLRLSCAVSGRSVSTYFVGWFR QAPGKEREFVAAIDRGSTVTRYDDSVKGRFTISRDNAKD TVYLQMNSLKPEDTAVYYCAAKAITRNFIATNDYDYWG QGTQVTVSS |
| 13. | 4D5 CDR1 | GRAFNEYA |
| 14. | 4D5 CDR2 | ISSDGRFT |
| 15. | 4D5 CDR3 | AARDSGSGYYSRAQWYDY |
| 16. | 4D5 VHH | VDSGGGAVKAGDSLRLVCSAPGRTHGRAFNEYAMAWF RQGPGKERESVAAISSDGRFTYYAASVKGRFTISKDNAKS AAFLQMNSLKPEDTAVYYCAARDSGSGYYSRAQWYDY WGQGTQVTVSS |

-continued

| SEQ ID NO | Gene Name | Sequence |
|---|---|---|
| 17. | 4D11 CDR1 | GSISSINA |
| 18. | 4D11 CDR2 | ITNSGST |
| 19. | 4D11 CDR3 | TARRSTWYIS |
| 20. | 4D11 VHH | QVQLQESGGGLVQPGGSLRLSCAASGSISSINAMGWYRL APGKHREFVADITNSGSTNYAASVKGRFNISRDNAKDTV YLQMNSLKFEDTAVYYCTARRSTWYISSGRGTQVTVSS |
| 21. | 4E5 CDR1 | GLTSSDIA |
| 22. | 4E5 CDR2 | ISSDGRFT |
| 23. | 4E5 CDR3 | AARDSGSGYYSRAQWYDY |
| 24. | 4E5 VHH | QVQLVDSGGGVVEVGASLTLSCETSGLTSSDIAVGWFRQ GPGKERESVAAISSDGRFTYYAASVKGRFTISKDNAKSAA FLQMNSLKPEDTAVYYCAARDSGSGYYSRAQWYDYWG QGTQVTVSS |
| 25. | 4H6 CDR1 | GTIFRLNR |
| 26. | 4H6 CDR2 | TIWSGRRT |
| 27. | 4H6 CDR3 | NYRRITPWEASGNY |
| 28. | 4H6 VHH | QVQLVESGGGLATAGASLILSCAASGTIFRLNRMGWFRQ APGKERERVAATIWSGRRTHYADSVKGRFTISTDNAKKT VYLRMSSLKPEDTAVYYCNYRRITPWEASGNYWGQTQ VTVSS |
| 29. | 4H9 CDR1 | GPIARSRS |
| 30. | 4H9 CDR2 | AAISSDGRFT |
| 31. | 4H9 CDR3 | AARDSGSGYYSRAQWYDY |
| 32. | 4H9 VHH | QVQLVESGGGAVQAGGSLRLSCTASGPIARSRSTGMGWF RQGPGKERESVAAISSDGRFTYYAASVKGRFTISKDNAKS AAFLQMNSLKPEDTAVYYCAARDSGSGYYSRAQWYDY WGQGTQVTVSS |
| 33. | 10H5 CDR1 | ETTFKSMA |
| 34. | 10H5 CDR2 | TNYNGGRT |
| 35. | 10H5 CDR3 | AAKATEGTTFPSRTYEF |
| 36. | 10H5 VHH | GGGLVQAGGSLRLACTASDPPFANYETTFKSMAMGWVR HIPGKERELVAATNYNGGRTWYSNSAKARSTISRDNAKN TVYLQMSSLKPEDTAVYYCAAKATEGTTFPSRTYEFWGQ GIQVTVSS |
| 37. | 12H7 CDR1 | GNFLSVSD |
| 38. | 12H7 CDR2 | VTEHGRT |
| 39. | 12H7 CDR3 | KASDVFTDAGAHEAVLIRDY |
| 40. | 12H7 VHH | QVQLVDSGGGLVQAGGSLRLSCKVSGNFLSVSDMSWYR QAPGMERDVVATVTEHGRTTYTDSVKGRFTISRDNAEHT TYLEMNNLKPEDTAVYFCKASDVFTDAGAHEAVLIRDY WGQGTQVTVSS |
| 41. | 13H11 CDR1 | GLTFSMYA |
| 42. | 13H11 CDR2 | ISSDGRFT |
| 43. | 13H11 CDR3 | AARDSGSGYYSRAQWYDY |

SEQUENCE TABLE

| SEQ ID NO | Gene Name | Sequence |
|---|---|---|
| 44. | 13H11 VHH | QVQLVESGGGLVQAGGSLRLSCAASGLTFSMYAMGWFRQGPGKERESVAAISSDGRFTYYAASVKGRFTISKDNAKSAAFLQMNSLKPEDTAVYYCAARDSGSGYYSRAQWYDYWGQGTQVTVSS |
| 45. | 15A5 CDR1 | ERTFSSFA |
| 46. | 15A5 CDR2 | IDPSGRYI |
| 47. | 15A5 CDR3 | AARIRGEGYYTRSSFYHY |
| 48. | 15A5 VHH | QVQLVESGGGLVQAGGSLRLSCAASERTFSSFAMGWFRQAPGKEREVVAAIDPSGRYIYYKDSVKGRFTMSRDNAKSTVYLQMNSLKPDDTARYYCAARIRGEGYYTRSSFYHYWGQGTQVTVSS |
| 49. | 2B7 CDR1 | GRTFSSYP |
| 50. | 2B7 CDR2 | ISSDGRFT |
| 51. | 2B7 CDR3 | AARDSGSGYYSRAQWYDY |
| 52. | 2B7 VHH | QVQLVESGGGLVQAGGSLRLACAASGRTFSSYPMGWFRQGPGKERESVAAISSDGRFTYYAASVKGRFTISKDNAKSAAFLQMNSLKPEDTAVYYCAARDSGSGYYSRAQWYDYWGQGTQVTVSS |
| 53. | 2B10 CDR1 | SRIFRRYA |
| 54. | 2B10 CDR2 | ITWSGAST |
| 55. | 2B10 CDR3 | AADPWGSVIVGTAEYEY |
| 56. | 2B10 VHH | QVKLEESGGGLVQTGDSLRLSCAASSRIFRRYAMGWFRQAPGKEREFVAAITWSGASTTYTDSVKGRFTISRDSAENTTYLQMTSLRPEDTAVYYCAADPWGSVIVGTAEYEYWGQGTLVTVSS |
| 57. | 3F10 CDR1 | EHTFSNFP |
| 58. | 3F10 CDR2 | IDSSGRLT |
| 59. | 3F10 CDR3 | AARTGGVGYYSRSSFYNY |
| 60. | 3F10 VHH | QVQLVESGGGLVQAGGSLRLSCASSEHTFSNFPMGWFRQAPGKERNVVAAIDSSGRLTYYADSVKGRFTISKDNAKSTVYLQMNSLKSEDTARYYCAARTGGVGYYSRSSFYNYWGQGTLVTVSS |
| 61. | 3G6 CDR1 | GSIFGISV |
| 62. | 3G6 CDR2 | LTRAGLT |
| 63. | 3G6 CDR3 | HANIMESAASTFGRY |
| 64. | 3G6 VHH | QVQLVESGGGLVQAGGSLSLSCAASGSIFGISVMGWYRQAPGEQRDLVATLTRAGLTTYGDSVKGRFSISRDSAKNTVYLQMNNLKPEDTAVYYCHANIMESAASTFGRYWGQGTQVTVSS |
| 65. | 3G7 CDR1 | GRTLSTYT |
| 66. | 3G7 CDR2 | AWPSPST |
| 67. | 3G7 CDR3 | AADYKSLTQSWLNAALDY |
| 68. | 3G7 VHH | QVQLVESGGGLVQAGDSLRLSCEASGRTLSTYTMGWFRRAPGKEREFVGLAWPSPSTYVVDSVKGRFTISRDNAKNTIYLQMNSLKPEDTAIYYCAADYKSLTQSWLNAALDYWGQGTQVTVSS |
| 69. | 3H7 CDR1 | GSILSAGV |

| SEQ ID NO | Gene Name | Sequence |
|---|---|---|
| 70. | 3H7 CDR2 | IALDGSTG |
| 71. | 3H7 CDR3 | NANIRTDMRSAPFDH |
| 72. | 3H7 VHH | QVKLEESGGGLVQAGGSLRLSCAASGSILSAGVMRWYRQAPGKQRELVASIALDGSTGYYIDSVKGRFTISRDNAKNIVYLDMRSLEPADTAVYLCNANIRTDMRSAPFDHWGHGTQVTVSS |
| 73. | 4C6 CDR1 | GRTFSSYP |
| 74. | 4C6 CDR2 | ISSDGRFT |
| 75. | 4C6 CDR3 | AVDPTGWGTIEADFRS |
| 76. | 4C6 VHH | QVQLVESGGGLVQAGGSLRLACAASGRTFSSYPMGWFRQGPGKERESVAAISSDGRFTYYAASVKGRFTISKDNAKSAAFLQMNSLKPEDTAVYRCAVDPTGWGTIEADFRSWGQGTQVTVSS |
| 77. | 1C12 CDR1 | SRIFSRYG |
| 78. | 1C12 CDR2 | ISWNGAST |
| 79. | 1C12 CDR3 | AADPWGAVKLGTAEYEY |
| 80. | 1C12 VHH | QVQLVESGGGLVQTGDSLRLSCAASSRIFSRYGMGWFRQAPGKEREFVAAISWNGASTTYTDSVKGRFTISRDSAENTTYLQINSLRPEDTAVYYCAADPWGAVKLGTAEYEYWGQGTQVTVSS |
| 81. | 1G1 CDR1 | GPSFSSYP |
| 82. | 1G1 CDR2 | ISSDGRFT |
| 83. | 1G1 CDR3 | AARDSGSGYYSRAQWYDY |
| 84. | 1G1 VHH | QVQLVESGGGLVQAGDSLRLSCVASGPSFSSYPMGWFRQGPGKERESVAAISSDGRFTYYAASVKGRFTISKDNAKSAAFLQMNSLKPEDTAVYYCAARDSGSGYYSRAQWYDYWGQGTLVTVSS |
| 85. | 1G1-F-G-ERES VHH | QVQLVESGGGVVQPGRSLRLSCAASGPSFSSYPMGWFRQGPGKERESVAAISSDGRFTYYADSVKGRFTISRDNSKNTLYLQMNSLRAEDTAVYYCAARDSGSGYYSRAQWYDYWGQGTLVTVSS |
| 86. | 1G1-F-A-ERES VHH | QVQLVESGGGVVQPGRSLRLSCAASGPSFSSYPMGWFRQAPGKERESVAAISSDGRFTYYADSVKGRFTISRDNSKNTLYLQMNSLRAEDTAVYYCAARDSGSGYYSRAQWYDYWGQGTLVTVSS |
| 87. | 1G1-F-A-EREW VHH | QVQLVESGGGVVQPGRSLRLSCAASGPSFSSYPMGWFRQAPGKEREWVAAISSDGRFTYYADSVKGRFTISRDNSKNTLYLQMNSLRAEDTAVYYCAARDSGSGYYSRAQWYDYWGQGTLVTVSS |
| 88. | 1G1-F-A-GLEW VHH | QVQLVESGGGVVQPGRSLRLSCAASGPSFSSYPMGWFRQAPGKGLEWVAAISSDGRFTYYADSVKGRFTISRDNSKNTLYLQMNSLRAEDTAVYYCAARDSGSGYYSRAQWYDYWGQGTLVTVSS |
| 89. | 1G1-F-A-GREL VHH | QVQLVESGGGVVQPGRSLRLSCAASGPSFSSYPMGWFRQAPGKGRELVAAISSDGRFTYYADSVKGRFTISRDNSKNTLYLQMNSLRAEDTAVYYCAARDSGSGYYSRAQWYDYWGQGTLVTVSS |
| 90. | 1G1-F-A-GRES VHH | QVQLVESGGGVVQPGRSLRLSCAASGPSFSSYPMGWFRQAPGKGRESVAAISSDGRFTYYADSVKGRFTISRDNSKNTLYLQMNSLRAEDTAVYYCAARDSGSGYYSRAQWYDYWGQGTLVTVSS |

SEQUENCE TABLE

| SEQ ID NO | Gene Name | Sequence |
|---|---|---|
| 91. | 1C12-EREF VHH | QVQLVESGGGVVQPGRSLRLSCAASSRIFSRYGMGWFRQAPGKEREFVAAISWNGASTTYTDSVKGRFTISRDNSKNTLYLQMNSLRAEDTAVYYCAADPWGAVKLGTAEYEYWGQGTQVTVSS |
| 92. | 1C12-EREW VHH | QVQLVESGGGVVQPGRSLRLSCAASSRIFSRYGMGWFRQAPGKEREWVAAISWNGASTTYTDSVKGRFTISRDNSKNTLYLQMNSLRAEDTAVYYCAADPWGAVKLGTAEYEYWGQGTQVTVSS |
| 93. | 1C12_GLEW VHH | QVQLVESGGGVVQPGRSLRLSCAASSRIFSRYGMGWFRQAPGKGLEWVAAISWNGASTTYTDSVKGRFTISRDNSKNTLYLQMNSLRAEDTAVYYCAADPWGAVKLGTAEYEYWGQGTQVTVSS |
| 94. | 2A3 CDR1 | GGSFSSYP |
| 95. | 2A3 CDR2 | ISSDMRFT |
| 96. | 2A3 CDR3 | AARDSGVGYYSRAQWYDY |
| 97. | 2A3 VHH | QVQLVESGGGVVQPGRSLRLSCAASGGSFSSYPMGWFRQAPGKERESVAAISSDMRFTYYADSVKGRFTISRDNSKNTLYLQMNSLRAEDTAVYYCAARDSGVGYYSRAQWYDYWGQGTLVTVSS |
| 98. | 1A8 CDR1 | GPSFSSYP |
| 99. | 1A8 CDR2 | ISSRGRFT |
| 100. | 1A8 CDR3 | AARDSGSGYYSRAQWYDY |
| 101. | 1A8 VHH | QVQLVESGGGVVQPGRSLRLSCAASGPSFSSYPMGWFRQAPGKERESVAAISSRGRFTYYADSVKGRFTISRDNSKNTLYLQMNSLRAEDTAVYYCAARDSGSGYYSRAQWYDYWGQGTLVTVSS |
| 102. | 1D11 CDR1 | GPSFSSSP |
| 103. | 1D11 CDR2 | ISSMGRFT |
| 104. | 1D11 CDR3 | AARDSGSGYYSRAQWYDY |
| 105. | 1D11 VHH | QVQLVESGGGVVQPGRSLRLSCAASGPSFSSSPMGWFRQAPGKERESVAAISSMGRFTYYADSVKGRFTISRDNSKNTLYLQMNSLRAEDTAVYYCAARDSGSGYYSRAQWYDYWGQGTLVTVSS |
| 106. | 5E8 CDR1 | GPSFSSYP |
| 107. | 5E8 CDR2 | QSSDGRFT |
| 108. | 5E8 CDR3 | AARDSGSGYYSRAQWYDY |
| 109. | 5E8 VHH | QVQLVESGGGVVQPGRSLRLSCAASGPSFSSYPMGWFRQAPGKERESVAAQSSDGRFTYYADSVKGRFTISRDNSKNTLYLQMNSLRAEDTAVYYCAARDSGSGYYSRAQWYDYWGQGTLVTVSS |
| 110. | 2A5 CDR1 | GPSFSSYP |
| 111. | 2A5 CDR2 | ISSVGRFT |
| 112. | 2A5 CDR3 | AARDSGSGYYSRWQWYDY |
| 113. | 2A5 VHH | QVQLVESGGGVVQPGRSLRLSCAASGPSFSSYPMGWFRQAPGKERESVAAISSVGRFTYYADSVKGRFTISRDNSKNTLYLQMNSLRAEDTAVYYCAARDSGSGYYSRWQWYDYWGQGTLVTVSS |
| 114. | 5G10 CDR1 | GPRFSSYP |
| 115. | 5G10 CDR2 | ISSDGRFT |

| SEQ ID NO | Gene Name | Sequence |
|---|---|---|
| 116. | 5G10 CDR3 | AARDSGSGYYSRAQWYDG |
| 117. | 5G10 VHH | QVQLVESGGGVVQPGRSLRLSCAASGPRFSSYPMGWFRQ APGKERESVAAISSDGRFTYYADSVKGRFTISRDNSKNTL YLQMNSLRAEDTAVYYCAARDSGSGYYSRAQWYDGWG QGTLVTVSS |
| 118. | 2A6 CDR1 | GPSFSLYP |
| 119. | 2A6 CDR2 | ISSDRRFT |
| 120. | 2A6 CDR3 | AARDSGSGYYSRAQWYDY |
| 121. | 2A6 VHH | QVQLVESGGGVVQPGRSLRLSCAASGPSFSLYPMGWFRQ APGKERESVAAISSDRRFTYYADSVKGRFTISRDNSKNTL YLQMNSLRAEDTAVYYCAARDSGSGYYSRAQWYDYWG QGTLVTVSS |
| 122. | 1G1-1C12 CDR1 | GPSFSSYP |
| 123. | 1G1-1C12 CDR2 | ISSDLRFT |
| 124. | 1G1-1C12 CDR3 | AARDSGSGYYSRKQWYDY |
| 125. | 1G1-1C12 VHH | QVQLVESGGGVVQPGRSLRLSCAASGPSFSSYPMGWFRQ APGKERESVAAISSDLRFTYYADSVKGRFTISRDNSKNTL YLQMNSLRAEDTAVYYCAARDSGSGYYSRKQWYDYWG QGTLVTVSS |
| 126. | 5B5 CDR1 | GPSFSSYP |
| 127. | 5B5 CDR2 | ISSDTRFT |
| 128. | 5B5 CDR3 | AARDSGSGYYSRAQWYDR |
| 129. | 5B5 VHH | QVQLVESGGGVVQPGRSLRLSCAASGPSFSSYPMGWFRQ APGKERESVAAISSDTRFTYYADSVKGRFTISRDNSKNTL YLQMNSLRAEDTAVYYCAARDSGSGYYSRAQWYDRWG QGTLVTVSS |
| 130. | 6F12 CDR1 | GPSFTSYP |
| 131. | 6F12 CDR2 | ISSDGRFK |
| 132. | 6F12 CDR3 | AAEDSGSGYYSRAQWYDY |
| 133. | 6F12 VHH | QVQLVESGGGVVQPGRSLRLSCAASGPSFTSYPMGWFRQ APGKERESVAAISSDGRFKYYADSVKGRFTISRDNSKNTL YLQMNSLRAEDTAVYYCAAEDSGSGYYSRAQWYDYWG QGTLVTVSS |
| 134. | 1C7 CDR1 | GPSFSSYP |
| 135. | 1C7 CDR2 | ISSRGRFT |
| 136. | 1C7 CDR3 | AARGSGSGYYSRAQWYDY |
| 137. | 1C7 VHH | QVQLVESGGGVVQPGRSLRLSCAASGPSFSSYPMGWFRQ APGKERESVAAISSRGRFTYYADSVKGRFTISRDNSKNTL YLQMNSLRAEDTAVYYCAARGSGSGYYSRAQWYDYWG QGTLVTVSS |
| 138. | 6E9 CDR1 | GPSRSSYP |
| 139. | 6E9 CDR2 | ISSDGKFT |
| 140. | 6E9 CDR3 | AARDSGSGYYSRANWYDY |

SEQUENCE TABLE

| SEQ ID NO | Gene Name | Sequence |
|---|---|---|
| 141. | 6E9 VHH | QVQLVESGGGVVQPGRSLRLSCAASGPSRSSYPMGWFRQ APGKERESVAAISSDGKFTYYADSVKGRFTISRDNSKNTL YLQMNSLRAEDTAVYYCAARDSGSGYYSRANWYDYWG QGTLVTVSS |
| 142. | 1A10 CDR1 | GNSFSSYP |
| 143. | 1A10 CDR2 | ISSDGRFS |
| 144. | 1A10 CDR3 | ACRDSGSGYYSRAQWYDY |
| 145. | 1A10 VHH | QVQLVESGGGVVQPGRSLRLSCAASGNSFSSYPMGWFRQ APGKERESVAAISSDGRFSYYADSVKGRFTISRDNSKNTL YLQMNSLRAEDTAVYYCACRDSGSGYYSRAQWYDYWG QGTLVTVSS |
| 146. | 6B11 CDR1 | GPSFPSYP |
| 147. | 6B11 CDR2 | ISSRGRFT |
| 148. | 6B11 CDR3 | AARDSGSGYYSRLQWYDY |
| 149. | 6B11 VHH | QVQLVESGGGVVQPGRSLRLSCAASGPSFPSYPMGWFRQ APGKERESVAAISSRGRFTYYADSVKGRFTISRDNSKNTL YLQMNSLRAEDTAVYYCAARDSGSGYYSRLQWYDYWG QGTLVTVSS |
| 150. | 6D8 CDR1 | GPSFSSKP |
| 151. | 6D8 CDR2 | RSSDGRFT |
| 152. | 6D8 CDR3 | AARDSGSGRYSRAQWYDY |
| 153. | 6D8 VHH | QVQLVESGGGVVQPGRSLRLSCAASGPSFSSKPMGWFRQ APGKERESVAARSSDGRFTYYADSVKGRFTISRDNSKNTL YLQMNSLRAEDTAVYYCAARDSGSGRYSRAQWYDYWG QGTLVTVSS |
| 154. | 6D12 CDR1 | GPSFSTYP |
| 155. | 6D12 CDR2 | ISSDGVFT |
| 156. | 6D12 CDR3 | AARDSGSGYYSREQWYDY |
| 157. | 6D12 VHH | QVQLVESGGGVVQPGRSLRLSCAASGPSFSTYPMGWFRQ APGKERESVAAISSDGVFTYYADSVKGRFTISRDNSKNTL YLQMNSLRAEDTAVYYCAARDSGSGYYSREQWYDYWG QGTLVTVSS |
| 158. | 2C5 CDR1 | GPSFSTYP |
| 159. | 2C5 CDR2 | ISSQGRFT |
| 160. | 2C5 CDR3 | AARDSGSGYYSRAQWYDY |
| 161. | 2C5 VHH | QVQLVESGGGVVQPGRSLRLSCAASGPSFSTYPMGWFRQ APGKERESVAAISSQGRFTYYADSVKGRFTISRDNSKNTL YLQMNSLRAEDTAVYYCAARDSGSGYYSRAQWYDYWG QGTLVTVSS |
| 162. | 7F6 CDR1 | GPMFSSYP |
| 163. | 7F6 CDR2 | ISSDPRFT |
| 164. | 7F6 CDR3 | AARDSGSGYYSRAQWYDY |
| 165. | 7F6 VHH | QVQLVESGGGVVQPGRSLRLSCAASGPMFSSYPMGWFR QAPGKERESVAAISSDPRFTYYADSVKGRFTISRDNSKNT LYLQMNSLRAEDTAVYYCAARDSGSGYYSRAQWYDYW GQGTLVTVSS |
| 166. | 2D5 CDR1 | GPSFSSSP |

SEQUENCE TABLE

| SEQ ID NO | Gene Name | Sequence |
|---|---|---|
| 167. | 2D5 CDR2 | ISWDGRFT |
| 168. | 2D5 CDR3 | AARDSGSGYYSRAQWYVY |
| 169. | 2D5 VHH | QVQLVESGGGVVQPGRSLRLSCAASGPSFSSSPMGWFRQAPGKERESVAAISWDGRFTYYADSVKGRFTISRDNSKNTLYLQMNSLRAEDTAVYYCAARDSGSGYYSRAQWYVYWGQGTLVTVSS |
| 170. | 7B11 CDR1 | GPSFLIYP |
| 171. | 7B11 CDR2 | ISSDGRFW |
| 172. | 7B11 CDR3 | AARDSGSGYYSRVQWYDY |
| 173. | 7B11 VHH | QVQLVESGGGVVQPGRSLRLSCAASGPSFLIYPMGWFRQAPGKERESVAAISSDGRFWYYADSVKGRFTISRDNSKNTLYLQMNSLRAEDTAVYYCAARDSGSGYYSRVQWYDYWGQGTLVTVSS |
| 174. | 7D12 CDR1 | GPSFLSYP |
| 175. | 7D12 CDR2 | ISSDGRFS |
| 176. | 7D12 CDR3 | AARDWGSGYYSRAQWYDY |
| 177. | 7D12 VHH | QVQLVESGGGVVQPGRSLRLSCAASGPSFLSYPMGWFRQAPGKERESVAAISSDGRFSYYADSVKGRFTISRDNSKNTLYLQMNSLRAEDTAVYYCAARDWGSGYYSRAQWYDYWGQGTLVTVSS |
| 178. | 2A3 ML CDR1 | GGSFSSYP |
| 179. | 2A3 ML CDR2 | ISSDLRFT |
| 180. | 2A3 ML CDR3 | AARDSGVGYYSRAQWYDY |
| 181. | 2A3 ML VHH | QVQLVESGGGVVQPGRSLRLSCAASGGSFSSYPMGWFRQAPGKERESVAAISSDLRFTYYADSVKGRFTISRDNSKNTLYLQMNSLRAEDTAVYYCAARDSGVGYYSRAQWYDYWGQGTLVTVSS |
| 182. | 2A3 MI CDR1 | GGSFSSYP |
| 183. | 2A3 MI CDR2 | ISSDIRFT |
| 184. | 2A3 MI CDR3 | AARDSGVGYYSRAQWYDY |
| 185. | 2A3 MI VHH | QVQLVESGGGVVQPGRSLRLSCAASGGSFSSYPMGWFRQAPGKERESVAAISSDIRFTYYADSVKGRFTISRDNSKNTLYLQMNSLRAEDTAVYYCAARDSGVGYYSRAQWYDYWGQGTLVTVSS |
| 186. | 2A3 ML DT CDR1 | GGSFSSYP |
| 187. | 2A3 ML DT CDR2 | ISSDLRFT |
| 188. | 2A3 ML DT CDR3 | AARTSGVGYYSRAQWYDY |
| 189. | 2A3 ML DT VHH | QVQLVESGGGVVQPGRSLRLSCAASGGSFSSYPMGWFRQAPGKERESVAAISSDLRFTYYADSVKGRFTISRDNSKNTLYLQMNSLRAEDTAVYYCAARTSGVGYYSRAQWYDYWGQGTLVTVSS |
| 190. | 2A3 ML DE CDR1 | GGSFSSYP |
| 191. | 2A3 ML DE CDR2 | ISSDLRFT |

SEQUENCE TABLE

| SEQ ID NO | Gene Name | Sequence |
|---|---|---|
| 192. | 2A3 ML DE CDR3 | AARESGVGYYSRAQWYDY |
| 193. | 2A3 ML DE VHH | QVQLVESGGGVVQPGRSLRLSCAASGGSFSSYPMGWFRQAPGKERESVAAISSDLRFTYYADSVKGRFTISRDNSKNTLYLQMNSLRAEDTAVYYCAARESGVGYYSRAQWYDYWGQGTLVTVSS |
| 194. | 2A3 LT Fc | QVQLVESGGGVVQPGRSLRLSCAASGGSFSSYPMGWFRQAPGKERESVAAISSDLRFTYYADSVKGRFTISRDNSKNTLYLQMNSLRAEDTAVYYCAARTSGVGYYSRAQWYDYWGQGTLVTVSSEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 195. | Exemplary linker | GSGGSGGSGGSG |
| 196. | Exemplary linker | GGGGSGGGGSGGGGS |
| 197. | Exemplary linker | GGGSG |
| 198. | Exemplary linker | GGGSGGGGSG |
| 199. | Exemplary linker | GGSGGGSG |
| 200. | Exemplary linker | GGSGGGSGGGSG |
| 201. | Exemplary linker | GSGGSG |
| 202. | Exemplary linker | GSGGSGGSG |
| 203. | Exemplary linker | GSGSGSG |
| 204. | Exemplary linker | GGGGSGGGGSGGGGSGGG |
| 205. | Exemplary linker | PAPAP |
| 206. | Exemplary linker | PAPAPPAPAPPAPAP |
| 207. | Exemplary linker | IKRTVAA |
| 208. | Exemplary linker | VSSASTK |
| 209. | Exemplary linker | AEAAAKA |
| 210. | Exemplary linker | AEAAAKEAAAKA |
| 211. | Exemplary linker | GRPGS GRPGS |
| 212. | Exemplary linker | GRPGS GRPGS GRPGS GRPGS |

SEQUENCE TABLE

| SEQ ID NO | Gene Name | Sequence |
|---|---|---|
| 213. | Exemplary linker | GRGGS GRGGS |
| 214. | Exemplary linker | GRGGS GRGGS GRGGS GRGGS |
| 215. | Exemplary linker | GKPGS GKPGS |
| 216. | Exemplary linker | GKPGS GKPGS GKPGS GKPGS |
| 217. | Exemplary linker | GEPGS GEPGS |
| 218. | Exemplary linker | GEGGS GEGGS GEGGS GEGGS |
| 219. | Exemplary linker | GDPGS GDPGS |
| 220. | Exemplary linker | GDPGS GDPGS GDPGS GDPGS |
| 221. | PL2#3 CDR-H1 | SYTMN |
| 222. | PL2#3 CDR-H2 | SISSGSDYLYYADSVKG |
| 223. | PL2#3 CDR-H3 | NELRWYPQAGAFDR |
| 224. | PL2#3 CDR-L1 | SGSSSYIESSYVG |
| 225. | PL2#3 CDR-L2 | DDDMRPS |
| 226. | PL2#3 CDR-L3 | EIWRSGLGGV |
| 227. | PL2#3 VH | EVQLVQSGGGLVKPGGSLRLSCAASGFTFSSYTMNWVRQAPGKGLEWVSSISSGSDYLYYADSVKGRFTISRDNAKNSLYLQMNSLRAEDTAVYYCARNELRWYPQAGAFDRWGQGTMVTVSS |
| 228. | PL2#3 VL | QSVVTQPPSMSAAPGQRVTISCSGSSSYIESSYVGWYQQLPGTAPRLLIYDDDMRPSGIPDRFSGSKSGTSATLAITGLQTGDEADYYCEIWRSGLGGVFGGGTKLTVL |
| 229. | PL3#7 CDR-H1 | SYPIS |
| 230. | PL3#7 CDR-H2 | RIIPILGIANYAQKFQG |
| 231. | PL3#7 CDR-H3 | SRDGYAFGAFDI |
| 232. | PL3#7 CDR-L1 | TGSSSNIGAGYDVH |
| 233. | PL3#7 CDR-L2 | GNSNRPS |
| 234. | PL3#7 CDR-L3 | QTYDSSLSARVV |
| 235. | PL3#7 VH | QVQLVQSGAEVKKPGSSVKVSCKASGGTFSSYPISWVRQAPGQGLEWIGRIIPILGIANYAQKFQGRVTITADKSTSTAYMELSSLRSEDTAVYYCARSRDGYAFGAFDIWGQGTLVTVSS |
| 236. | PL3#7 VL | QSVVTQPPPVSGAPGQRVTISCTGSSSNIGAGYDVHWYQQLPGTAPKLLIYGNSNRPSGVPDRFSGSKSGTSASLAITGLQAEDEADYYCQTYDSSLSARVVFGGGTKLTVL |
| 237. | PL3#7-19 CDR-H1 | SYPIS |
| 238. | PL3#7-19 CDR-H2 | RIIPILGIANYAQKFQG |

SEQUENCE TABLE

| SEQ ID NO | Gene Name | Sequence |
|---|---|---|
| 239. | PL3#7-19 CDR-H3 | SRDGYAFGAFDV |
| 240. | PL3#7-19 CDR-L1 | TGSSSNIGGGYDVH |
| 241. | PL3#7-19 CDR-L2 | GNSTRPS |
| 242. | PL3#7-19 CDR-L3 | QTYDSSLSATVV |
| 243. | PL3#7-19 VH | QVQLVQSGAEVKKPGSSVKVSCKASGGTFSSYPISWVRQAPGQGLEWMGRIIPILGIANYAQKFQGRVTITADKSTSTAYMELSSLRSEDTAVYYCARSRDGYAFGAFDVWGQGTLVTVSS |
| 244. | PL3#7-19 VL | QSVVTQPPPVSGAPGQRVTISCTGSSSNIGGGYDVHWYQQLPGTAPKLLIYGNSTRPSGVPDRFSGSKSGTSASLAITGLQAEDEADYYCQTYDSSLSATVVFGGGTKLTVL |
| 245. | PL3#7-43 CDR-H1 | SYPIS |
| 246. | PL3#7-43 CDR-H2 | RIIPILGIANYAQKFQG |
| 247. | PL3#7-43 CDR-H3 | SRPGYAFGAFDI |
| 248. | PL3#7-43 CDR-L1 | TGSSSNVGAGYDVH |
| 249. | PL3#7-43 CDR-L2 | GNSNRSS |
| 250. | PL3#7-43 CDR-L3 | QTYDSSGSARVV |
| 251. | PL3#7-43 VH | QVQLVQSGAEVKKPGSSVKVSCKASGGTFSSYPISWVRQAPGQGLEWMGRIIPILGIANYAQKFQGRVTITADKSTSTAYMELSSLRSEDTAVYYCARSRPGYAFGAFDIWGQGTLVTVSS |
| 252. | PL3#7-43 VL | QSVVTQPPPVSGAPGQRVTISCTGSSSNVGAGYDVHWYQQLPGTAPKLLIYGNSNRSSGVPDRFSGSKSGTSASLAITGLQAEDEADYYCQTYDSSGSARVVFGGGTKLTVL |
| 253. | PL3#7-54 CDR-H1 | SYPIS |
| 254. | PL3#7-54 CDR-H2 | RIIPILGIADYAQKFQG |
| 255. | PL3#7-54 CDR-H3 | SRPGYAFGAFDI |
| 256. | PL3#7-54 CDR-L1 | TGSSSNIGQGYDVH |
| 257. | PL3#7-54 CDR-L2 | ANSNRPS |
| 258. | PL3#7-54 CDR-L3 | QTYDSSLSARVV |
| 259. | PL3#7-54 VH | QVQLVQSGAEVKKPGSSVKVSCKASGGTFSSYPISWVRQAPGQGLEWMGRIIPILGIADYAQKFQGRVTITADKSTSTAYMELSSLRSEDTAVYYCARSRPGYAFGAFDIWGQGTLVTVSS |

SEQUENCE TABLE

| SEQ ID NO | Gene Name | Sequence |
|---|---|---|
| 260. | PL3#7-54 VL | QSVVTQPPPVSGAPGQRVTISCTGSSSNIGQGYDVHWYQQLPGTAPKLLIYANSNRPSGVPDRFSGSKSGTSASLAITGLQAEDEADYYCQTYDSSLSARVVFGGGTKLTVL |
| 261. | PL2#4 CDR-H1 | SYTMN |
| 262. | PL2#4 CDR-H2 | SISSGSDYLYYADSVKG |
| 263. | PL2#4 CDR-H3 | NELRWYPLAGAFDI |
| 264. | PL2#4 CDR-L1 | SGVSSYIESSYVS |
| 265. | PL2#4 CDR-L2 | DDDMRPS |
| 266. | PL2#4 CDR-L3 | KIWDSGLGGV |
| 267. | PL2#4 VH | EVQLVQSGGGLVKPGGSLRLSCAASGFTFSSYTMNWVRQAPGKGLEWVSSISSGSDYLYYADSVKGRFTISRDNAKNSLYLQMNSLRAEDTAVYYCARNELRWYPLAGAFDIWGQGTMVTVSS |
| 268. | PL2#4 VL | QSVVTQPPSMSAAPGQRVTISCSGVSSYIESSYVSWYQQLPGTAPRLLIYDDDMRPSGIPDRFSGSKSGTSATLAITGLQTGDEADYYCKIWDSGLGGVFGGGTKLTVL |
| 269. | PL2#5 CDR-H1 | SYTMN |
| 270. | PL2#5 CDR-H2 | SISSGSDYLYYADSVKG |
| 271. | PL2#5 CDR-H3 | NELRWYPFAGAFDI |
| 272. | PL2#5 CDR-L1 | SGSSSYIESSYVS |
| 273. | PL2#5 CDR-L2 | DDDMRPS |
| 274. | PL2#5 CDR-L3 | EIWDSRLGGV |
| 275. | PL2#5 VH | EVQLVQSGGGLVKPGGSLRLSCAASGFTFSSYTMNWVRQAPGKGLEWVSSISSGSDYLYYADSVKGRFTISRDNAKNSLYLQMNSLRAEDTAVYYCARNELRWYPFAGAFDIWGQGTMVTVSS |
| 276. | PL2#5 VL | QSVVTQPPSMSAAPGQRVTISCSGSSSYIESSYVSWYQQLPGTAPRLLIYDDDMRPSGIPDRFSGSKSGTSATLAITGLQTGDEADYYCEIWDSRLGGVFGGGTKLTVL |
| 277. | PL2#39 CDR-H1 | SYTMN |
| 278. | PL2#39 CDR-H2 | SISSGSDYLYYADSVKG |
| 279. | PL2#39 CDR-H3 | NELRWYPKAGAFDI |
| 280. | PL2#39 CDR-L1 | SGSSSYITSSYVS |
| 281. | PL2#39 CDR-L2 | DDDMRPS |
| 282. | PL2#39 CDR-L3 | KIWDSGLGGV |
| 283. | PL2#39 VH | EVQLVQSGGGLVKPGGSLRLSCAASGFTFSSYTMNWVRQAPGKGLEWVSSISSGSDYLYYADSVKGRFTISRDNAKNSLYLQMNSLRAEDTAVYYCARNELRWYPKAGAFDIWGQGTMVTVSS |
| 284. | PL2#39 VL | QSVVTQPPSMSAAPGQRVTISCSGSSSYITSSYVSWYQQLPGTAPRLLIYDDDMRPSGIPDRFSGSKSGTSATLAITGLQTGDEADYYCKIWDSGLGGVFGGGTKLTVL |

SEQUENCE TABLE

| SEQ ID NO | Gene Name | Sequence |
|---|---|---|
| 285. | PL3#1 CDR-H1 | SYRIS |
| 286. | PL3#1 CDR-H2 | RIIPILGIANYAQKFQG |
| 287. | PL3#1 CDR-H3 | SRDGYSVGAFDS |
| 288. | PL3#1 CDR-L1 | TGSSSNIGAGYDVH |
| 289. | PL3#1 CDR-L2 | GNSRRPS |
| 290. | PL3#1 CDR-L3 | QTYDSSLSRPVV |
| 291. | PL3#1 VH | QVQLVQSGAEVKKPGSSVKVSCKASGGTFSSYRISWVRQAPGQGLEWMGRIIPILGIANYAQKFQGRVTITADKSTSTAYMELSSLRSEDTAVYYCARSRDGYSVGAFDSWGQGTLVTVSS |
| 292. | PL3#1 VL | QSVVTQPPPVSGAPGQRVTISCTGSSSNIGAGYDVHWYQQLPGTAPKLLIYGNSRRPSGVPDRFSGSKSGTSASLAITGLQAEDEADYYCQTYDSSLSRPVVFGGGTKLTVL |
| 293. | PL3#7-43 D2 CDR-H1 | SYPIS |
| 294. | PL3#7-43 D2 CDR-H2 | RIIPILGIANYAQKFQG |
| 295. | PL3#7-43 D2 CDR-H3 | SRPGYAFGAFDI |
| 296. | PL3#7-43 D2 CDR-L1 | TGSSSNVGAGYDVH |
| 297. | PL3#7-43 D2 CDR-L2 | GNSQRSS |
| 298. | PL3#7-43 D2 CDR-L3 | QTYDSSGSARVV |
| 299. | PL3#7-43 D2 VH | QVQLVQSGAEVKKPGSSVKVSCKASGGTFSSYPISWVRQAPGQGLEWMGRIIPILGIANYAQKFQGRVTITADKSTSTAYMELSSLRSEDTAVYYCARSRPGYAFGAFDIWGQGTLVTVSS |
| 300. | PL3#7-43 D2 VL | QSVVTQPPPVSGAPGQRVTISCTGSSSNVGAGYDVHWYQQLPGTAPKLLIYGNSQRSSGVPDRFSGSKSGTSASLAITGLQAEDEADYYCQTYDSSGSARVVFGGGTKLTVL |
| 301. | PL3#7-43 D1 CDR-H1 | SYPIS |
| 302. | PL3#7-43 D1 CDR-H2 | RIIPILGIANYAQKFQG |
| 303. | PL3#7-43 D1 CDR-H3 | SRPGYAFGAFDI |
| 304. | PL3#7-43 D1 CDR-L1 | TGSSSNVGAGYDVH |
| 305. | PL3#7-43 D1 CDR-L2 | GNSNRPS |
| 306. | PL3#7-43 D1 CDR-L3 | QTYDSSGSARVV |
| 307. | PL3#7-43 D1 VH | QVQLVQSGAEVKKPGSSVKVSCKASGGTFSSYPISWVRQAPGQGLEWMGRIIPILGIANYAQKFQGRVTITADKSTSTAYMELSSLRSEDTAVYYCARSRPGYAFGAFDIWGQGTLVTVSS |

SEQUENCE TABLE

| SEQ ID NO | Gene Name | Sequence |
|---|---|---|
| 308. | PL3#7-43 D1 VL | QSVVTQPPPVSGAPGQRVTISCTGSSSNVGAGYDVHWY QQLPGTAPKLLIYGNSNRPSGVPDRFSGSKSGTSASLAIT GLQAEDEADYYCQTYDSSGSARVVFGGGTKLTVL |
| 309. | anti-PDL1 HC-Linker-2A3 (HCC heavy chain) | QVQLVQSGAEVKKPGSSVKVSCKASGGTFSSYPISWVRQ APGQGLEWMGRIIPILGIANYAQKFQGRVTITADKSTSTA YMELSSLRSEDTAVYYCARSRPGYAFGAFDIWGQGTLVT VSSASTKGPSVFPLAPSSKSTSGGTAALGCLVKDYFPEPV TVSWNSGALTSGVHTFPAVLQSSGLYSLSSVVTVPSSSLG TQTYICNVNHKPSNTKVDKKVEPKSCDKTHTCPPCPAPEL LGGPSVFLFPPKPKDTLMISRTPEVTCVVVDVSHEDPEVK FNWYVDGVEVHNAKTKPREEQYNSTYRVVSVLTVLHQD WLNGKEYKCKVSNKALPAPIEKTISKAKGQPREPQVYTL PPSREEMTKNQVSLTCLVKGFYPSDIAVEWESNGQPENN YKTTPPVLDSDGSFFLYSKLTVDKSRWQQGNVFSCSVMH EALHNHYTQKSLSLSPGKGSGGSGGSGGSGGSGQVQLVESGG GVVQPGRSLRLSCAASGGSFSSYPMGWFRQAPGKERESV AAISSDMRFTYYADSVKGRFTISRDNSKNTLYLQMNSLR AEDTAVYYCAARDSGVGYYSRAQWYDYWGQGTLVTVS S |
| 310. | anti-PDL1 LC1 (HCC light chain) | QSVVTQPPPVSGAPGQRVTISCTGSSSNVGAGYDVHWYQ QLPGTAPKLLIYGNSQRSSGVPDRFSGSKSGTSASLAITGL QAEDEADYYCQTYDSSGSARVVFGGGTKLTVLGQPKAA PSVTLFPPSSEELQANKATLVCLISDFYPGAVTVAWKADS SPVKAGVETTTPSKQSNNKYAASSYLSLTPEQWKSHKSY SCQVTHEGSTVEKTVAPTECS |
| 311. | anti-PDL1 HC1 (LCC heavy chain) | QVQLVQSGAEVKKPGSSVKVSCKASGGTFSSYPISWVRQ APGQGLEWMGRIIPILGIANYAQKFQGRVTITADKSTSTA YMELSSLRSEDTAVYYCARSRPGYAFGAFDIWGQGTLVT VSSASTKGPSVFPLAPSSKSTSGGTAALGCLVKDYFPEPV TVSWNSGALTSGVHTFPAVLQSSGLYSLSSVVTVPSSSLG TQTYICNVNHKPSNTKVDKKVEPKSCDKTHTCPPCPAPEL LGGPSVFLFPPKPKDTLMISRTPEVTCVVVDVSHEDPEVK FNWYVDGVEVHNAKTKPREEQYNSTYRVVSVLTVLHQD WLNGKEYKCKVSNKALPAPIEKTISKAKGQPREPQVYTL PPSREEMTKNQVSLTCLVKGFYPSDIAVEWESNGQPENN YKTTPPVLDSDGSFFLYSKLTVDKSRWQQGNVFSCSVMH EALHNHYTQKSLSLSPGK |
| 312. | anti-PDL1 LC-Linker-2A3 (LCC light chain) | QSVVTQPPPVSGAPGQRVTISCTGSSSNVGAGYDVHWYQ QLPGTAPKLLIYGNSQRSSGVPDRFSGSKSGTSASLAITGL QAEDEADYYCQTYDSSGSARVVFGGGTKLTVLGQPKAA PSVTLFPPSSEELQANKATLVCLISDFYPGAVTVAWKADS SPVKAGVETTTPSKQSNNKYAASSYLSLTPEQWKSHKSY SCQVTHEGSTVEKTVAPTECSGSGGSGGSGGSGQVQLVE SGGGVVQPGRSLRLSCAASGGSFSSYPMGWFRQAPGKER ESVAAISSDMRFTYYADSVKGRFTISRDNSKNTLYLQMN SLRAEDTAVYYCAARDSGVGYYSRAQWYDYWGQGTLV TVSS |
| 313. | 2A3-Linker-anti-PDL1 HC (HCN heavy chain) | QVQLVESGGGVVQPGRSLRLSCAASGGSFSSYPMGWFRQ APGKERESVAAISSDMRFTYYADSVKGRFTISRDNSKNTL YLQMNSLRAEDTAVYYCAARDSGVGYYSRAQWYDYW GQGTLVTVSSGSGGSGGSGGSGQVQLVQSGAEVKKPGSS VKVSCKASGGTFSSYPISWVRQAPGQGLEWMGRIIPILGI ANYAQKFQGRVTITADKSTSTAYMELSSLRSEDTAVYYC ARSRPGYAFGAFDIWGQGTLVTVSSASTKGPSVFPLAPSS KSTSGGTAALGCLVKDYFPEPVTVSWNSGALTSGVHTFP AVLQSSGLYSLSSVVTVPSSSLGTQTYICNVNHKPSNTKV DKKVEPKSCDKTHTCPPCPAPELLGGPSVFLFPPKPKDTL MISRTPEVTCVVVDVSHEDPEVKFNWYVDGVEVHNAKT KPREEQYNSTYRVVSVLTVLHQDWLNGKEYKCKVSNKA LPAPIEKTISKAKGQPREPQVYTLPPSREEMTKNQVSLTCL VKGFYPSDIAVEWESNGQPENNYKTTPPVLDSDGSFFLYS KLTVDKSRWQQGNVFSCSVMHEALHNHYTQKSLSLSPG K |

SEQUENCE TABLE

| SEQ ID NO | Gene Name | Sequence |
|---|---|---|
| 314. | anti-PDL1 LC2 (HCN light chain) | QSVVTQPPPVSGAPGQRVTISCTGSSSNVGAGYDVHWYQ QLPGTAPKLLIYGNSQRSSGVPDRFSGSKSGTSASLAITGL QAEDEADYYCQTYDSSGSARVVFGGGTKLTVLGQPKAA PSVTLFPPSSEELQANKATLVCLISDFYPGAVTVAWKADS SPVKAGVETTTPSKQSNNKYAASSYLSLTPEQWKSHKSY SCQVTHEGSTVEKTVAPTECS |
| 315. | anti-PDL1 HC2 (LCN heavy chain) | QVQLVQSGAEVKKPGSSVKVSCKASGGTFSSYPISWVRQ APGQGLEWMGRIIPILGIANYAQKFQGRVTITADKSTSTA YMELSSLRSEDTAVYYCARSRPGYAFGAFDIWGQGTLVT VSSASTKGPSVFPLAPSSKSTSGGTAALGCLVKDYFPEPV TVSWNSGALTSGVHTFPAVLQSSGLYSLSSVVTVPSSSLG TQTYICNVNHKPSNTKVDKKVEPKSCDKTHTCPPCPAPEL LGGPSVFLFPPKPKDTLMISRTPEVTCVVVDVSHEDPEVK FNWYVDGVEVHNAKTKPREEQYNSTYRVVSVLTVLHQD WLNGKEYKCKVSNKALPAPIEKTISKAKGQPREPQVYTL PPSREEMTKNQVSLTCLVKGFYPSDIAVEWESNGQPENN YKTTPPVLDSDGSFFLYSKLTVDKSRWQQGNVFSCSVMH EALHNHYTQKSLSLSPGK |
| 316. | 2A3-Linker-anti-PDL1 LC (LCN light chain) | QVQLVESGGGVVQPGRSLRLSCAASGGSFSSYPMGWFRQ APGKERESVAAISSDMRFTYYADSVKGRFTISRDNSKNTL YLQMNSLRAEDTAVYYCAARDSGVGYYSRAQWYDYW GQGTLVTVSSGSGGSGGSGGSGQSVVTQPPPVSGAPGQR VTISCTGSSSNVGAGYDVHWYQQLPGTAPKLLIYGNSQR SSGVPDRFSGSKSGTSASLAITGLQAEDEADYYCQTYDSS GSARVVFGGGTKLTVLGQPKAAPSVTLFPPSSEELQANK ATLVCLISDFYPGAVTVAWKADSSPVKAGVETTTPSKQS NNKYAASSYLSLTPEQWKSHKSYSCQVTHEGSTVEKTVA PTECS |
| 317. | Human TIGIT polypeptide | MRWCLLLIWA QGLRQAPLAS GMMTGTIETT GNISAEKGGS IILQCHLSST TAQVTQVNWEQQDQLLAICN ADLGWHISPS FKDRVAPGPG LGLTLQSLTV NDTGEYFCIY HTYPDGTYTGRIFLEVLESS VAEHGARFQI PLLGAMAATL VVICTAVIVV VALTRKKKAL RIHSVEGDLRRKSAGQEEWS PSAPSPPGSC VQAEAAPAGL CGEQRGEDCA ELHDYFNVLS YRSLGNCSFFTETG |
| 318. | ECD of Human TIGIT polypeptide | MRWCLLLIWA QGLRQAPLAS GMMTGTIETT GNISAEKGGS IILQCHLSST TAQVTQVNWEQQDQLLAICN ADLGWHISPS FKDRVAPGPG LGLTLQSLTV NDTGEYFCIY HTYPDGTYTGRIFLEVLESS VAEHGARF |

The following examples are merely illustrative of the presently disclosed subject matter and should not be considered as limitations in any way.

EXAMPLES

Example 1. Immunization, Generation of Anti-Human TIGIT VHH Antibodies & Hits Identification Antigen of recombinant human TIGIT extra cellular domain (ECD) protein was purchased from Arco Bio. Immunization of TIGIT was performed using llama under protocols known in the art. The titer of serum antibodies was measured by ELISA assays. After 3 rounds of immunization, a high titer (1:100,000) was observed. Whole blood was then collected, and PBMCs were isolated. RNA was then isolated from the PBMCs.

The VHH antibody genes were amplified by PCR under protocols know in the art, purified by DNA agarose gel, constructed into a phagemid vector pADL-23c (Antibody Design Labs) and transformed to TG1 electrocompetent cells (from Lucigen). Transformed TG1 cells were cultured in Y2T medium. Phages with target VHH displayed were produced by adding helper phages and co-culturing overnight. Phages in supernatants of culture were harvested by centrifugation, and panning of binders to human-TIGIT (h-TIGIT) or cynomolgus-TIGIT (cyno-TIGIT) antigen was performed using streptavidin-coupled Dynabeads coated with biotinylated h-TIGIT or cyno-TIGIT ECD. After 3 rounds of panning, binders of h-TIGIT or cyno-TIGIT were eluted, which were used to infect SS320 cells. Colonies of SS320 cells were picked and cultured in Y2T medium, and IPTG was added for secretion of VHH antibodies. Supernatants with VHH antibodies were screened by ELISA assays using h-TIGIT ECD coated plates. Positive h-TIGIT binders were picked for sequencing. 29 clones with different sequences were selected. Binding ability of VHH antibodies on cyno-TIGIT was also examined by ELISA. The top 21 binders and their CDRs and VHs are shown in the Sequence Table (SEQ ID NOS: 1-84).

The effects of VHH antibody clones on blocking Poliovirus Receptor (PVR, a.k.a. CD155) binding to TIGIT were also determined using blocking ELISA assay. 9 clones with over 90% inhibition of PVR binding to h-TIGIT were further selected (clone name: 2B7, 1G1, 1C12, 3G6, 2B10, 3G7, 3F10, 13H11 and 15A5).

Example 2—Characterization and Selection of TIGIT VHH Antibodies

Figure 1B:
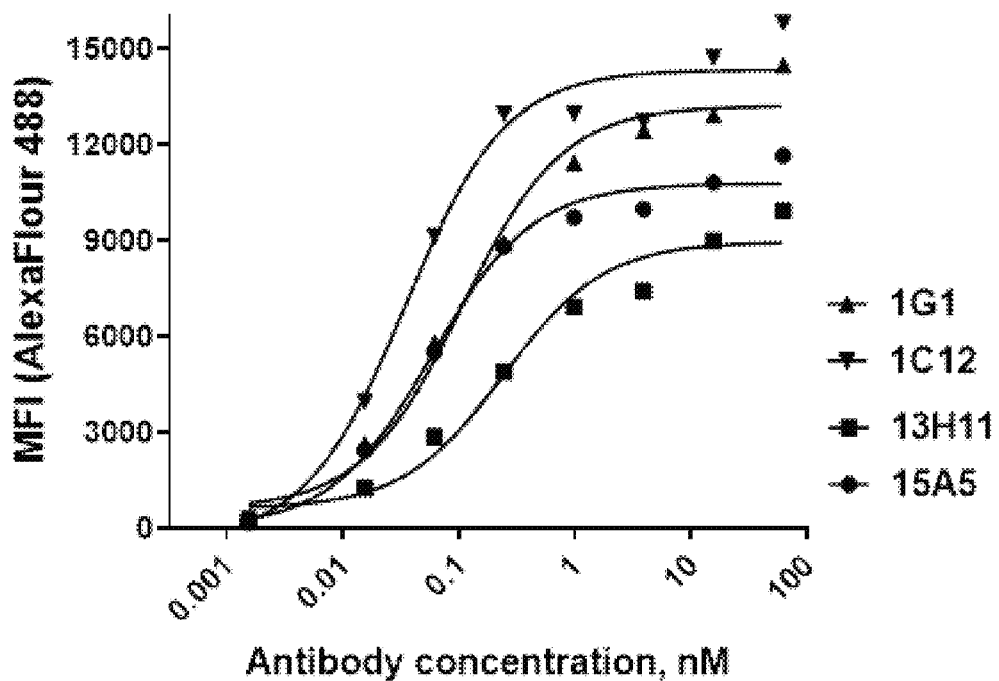
Figure 1C:
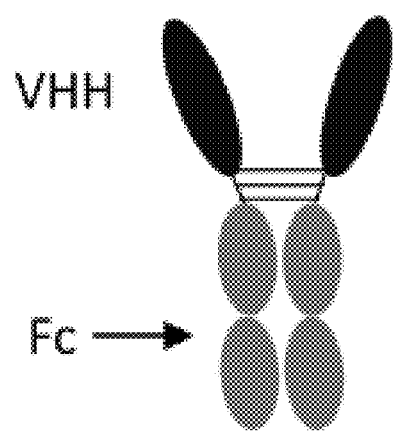

Antibody clones identified from Example 1 were constructed to make bivalent antibody by adding human constant heavy chain2 (CH2) and constant heavy chain 3 (CH3) domains shown in FIG. 1C. Constructed bivalent VHH antibodies were expressed in ExpiCHO cells, and proteins in supernatants were harvested and purified by Protein A.

Binding affinities of the bivalent clones to human TIGIT transfected Jurkat cells were confirmed by flowcytometry assays. Jurkat cells stably expressing human TIGIT and NFAT reporter gene were established. Specifically, Jurkat cells were transfected with human TIGIT expression vector by electroporation, and cells stably expressing human TIGIT were selected by 1 µg/ml puromycin during cell culture. Representative antibody clones were incubated at different concentrations with h-TIGIT stably expressing Jurkat cells (0.2×10$^6$/ml) in 100 µl/well in 96-well plate in FACS buffer (PBS with 1.5% FBS) for 30 min. After washing, Alexaflour 488 conjugated anti-human IgG Fc secondary antibody (Alexa Fluor® 488 AffiniPure Goat Anti-Human IgG, Fcγ fragment specific, Jackson labs, 1:500 dilution) was added and incubated for 30 min. After washing, mean fluorescence intensity was measured using CytoFlex (Beckman Coulter) by gating live cell population. Binding affinity was calculated using GraphPad Prism. Representative results are shown in FIGS. 1A and 1B. All tested antibodies showed high binding affinity to cells expressing human TIGIT compared to Reference Ab 1, a reference anti-human-TIGIT antibody disclosed in U.S. 2016/0176963 A1 as BMS 22G2, which was synthesized in-house based on the disclosed sequences.

Figure 2A:
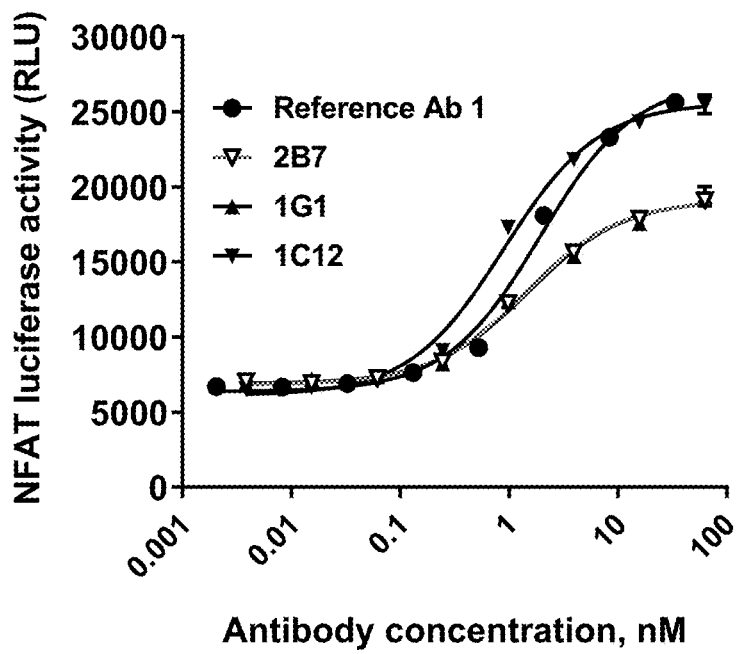
FIG. 2A-2B depict the potency of representative bivalent antibodies in blocking TIGIT activity determined by luciferase reporter assays. Human TIGIT and NFAT reporter gene stably transfected Jurkat cells were co-cultured with PVR (CD155) stably transfected Raji cells in the presence of representative anti-TIGIT bivalent antibodies and a low concentration of staphylococcal enterotoxin. Y axis represents NFAT luciferase activity in relative luminescence units. X axis represents antibody concentration in nanomolar. Reference Ab 1 is a reference anti-h-TIGIT antibody. 2B7, 1G1, 1C12, 3G6, 2B10, 3G7 and 3F10 are representative clones of anti-h-TIGIT. EC50 values were obtained using non-liner regression method by Prism, and values are shown in the table as nanomolar.
Figure 2B:
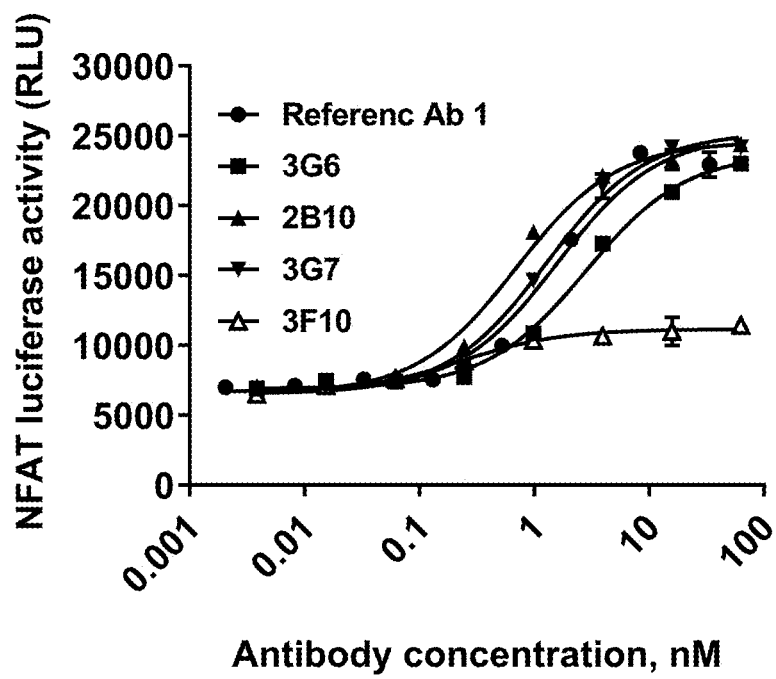

Furthermore, Jurkat cells stably expressing human TIGIT were transfected with NFAT reporter gene using electroporation. NFAT reporter expressing cells were selected by 300 µg/ml hygromycin in culture medium. Moreover, Raji cells were stably transfected with human PVR, and transfected cells were selected by hygromycin at 125 µg/ml in culture medium. The antibodies' effects on PVR-mediated suppression of TCR-induced NFAT reporter activity were then determined by co-incubation of Raji cells expressing human PVR and Jurkat cells expressing human TIGIT and NFAT reporter gene in the presence of staphylococcal enterotoxin (SEE, 0.01 ng/ml) for 5 hours. Bright-Glo luciferase assay buffer with substrate (Promega) was added, and luciferase activity was measured by chemiluminescence activity using a plate reader. Potency of antibody in blocking TIGIT activity was calculated using non-linear regression method by GraphPad Prims. Representative results are shown in FIG. 2. All tested clones except 3F10 showed similar TIGIT blocking effects compared to Reference Ab1.

Example 3—Humanization of Anti-TIGIT Antibodies

Two representative clones 1G1 and 1C12 were selected for humanization of their framework. Briefly, Igblast was performed using the sequences of the two clones to search database of human germline genes. Ideal germline sequences were selected, and mutations of framework sequences were made to change the framework sequences from llama to human. For 1C12 clone, human germline IGHV-3-30*10 was used, and three version of humanized 1C12 were made (1C12-EREF, 1C12-EREW and 1C12-GLEW). For 1G1, human germline IGHV-3-30*01 was used, and six versions of humanized 1G1 were made (1G1-F-G-ERES, 1G1-F-A-ERES, 1G1-F-A-EREW, 1G1-F-A-GLEW, 1G1-F-A-GREL and 1G1-F-A-GRES). The constructs were cloned into expression vectors, and antibody proteins were produced by transient transfection of ExpiCHO and purified by protein A.

Figure 3A:
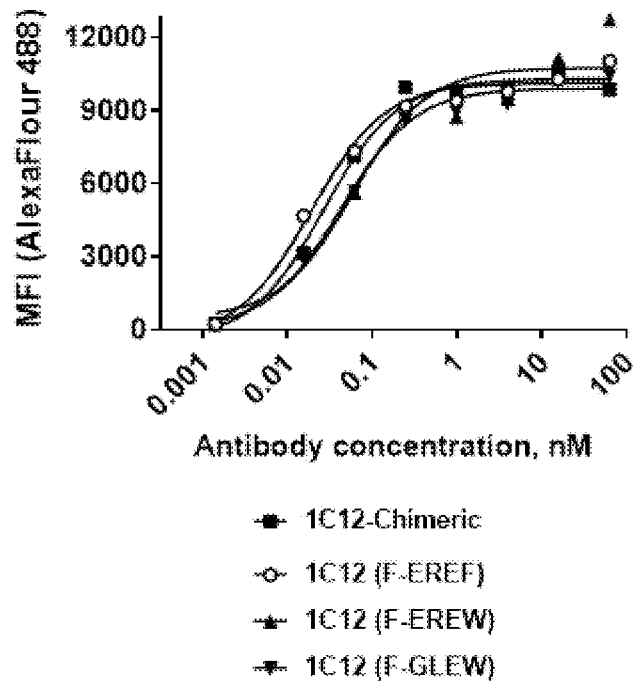
FIGS. 3A and 3B depict whole cell binding of humanized 1C12 and 1G1 clones to human TIGIT determined by flowcytometry assays. A representative result of 1C12 humanized versions is shown in FIG. 3A. 1C12-chimeric is an antibody with Llama VHH sequence of 1C12 clone and human IgG1 CH2 and CH3 domains, 1C12 (F-EREF), 1C12 (F-EREW) and 1C12(F-GLEW) are humanized versions of 1C12 clone with difference of mutations in Framework 2. A representative result of 1G1 humanized versions is shown in FIG. 3B. 1G1-chimeric is an antibody with Llama VHH sequence of 1G1 clone and human IgG1 CH2 and CH3 domains. 1G1 (F-G-ERES), 1G1 (F-A-ERES), 1G1 (F-A-EREW) and 1G1 (F-A-GLEW) are four different versions of humanized 1G1 clones with different mutations in framework 2. Y axis is values of Mean Fluorescence Intensity of AlexaFlour 488. X axis is values of antibody concentrations in nanomolar.
Figure 3B:
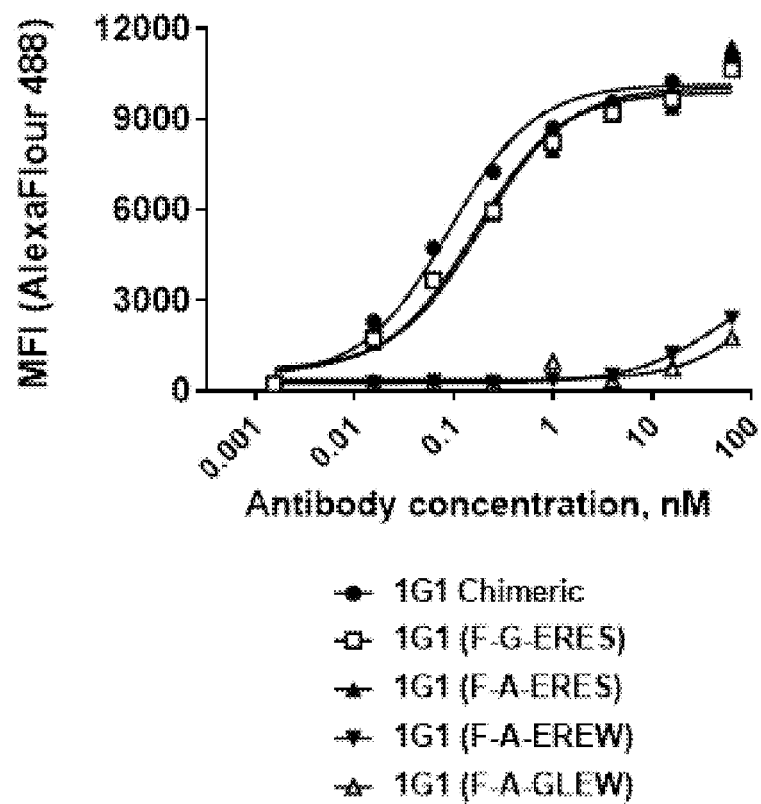

The binding affinities of the humanized bivalent antibodies to human TIGIT were determined by whole cell binding to h-TIGIT stably expressed on Jurkat cells. Briefly, antibodies were incubated with h-TIGIT transfected Jurkat cells (0.2×10$^6$/well in 100 µl) for 30 min in FACS buffer. The cells were washed once, then incubated with anti-human IgG Fc AlexaFluor488 (1:500). Mean fluorescence intensity was determined by CytoFlex, and binding affinities of antibodies to h-TIGIT were calculated using non-liner regression by GraphPad Prism 8.0 as shown in FIG. 3A. Similar binding affinities were observed for all three versions of 1C12 clones compared to the chimeric parental clone. For 1G1 clone, two humanized versions, F-G-ERES and F-A-ERES, exhibited similar affinity to h-TIGIT compared to chimeric clone, whereas two versions (F-A-EREW and F-A-GLEW) lost binding affinity to h-TIGIT as shown in FIG. 3B.

Figure 4A:
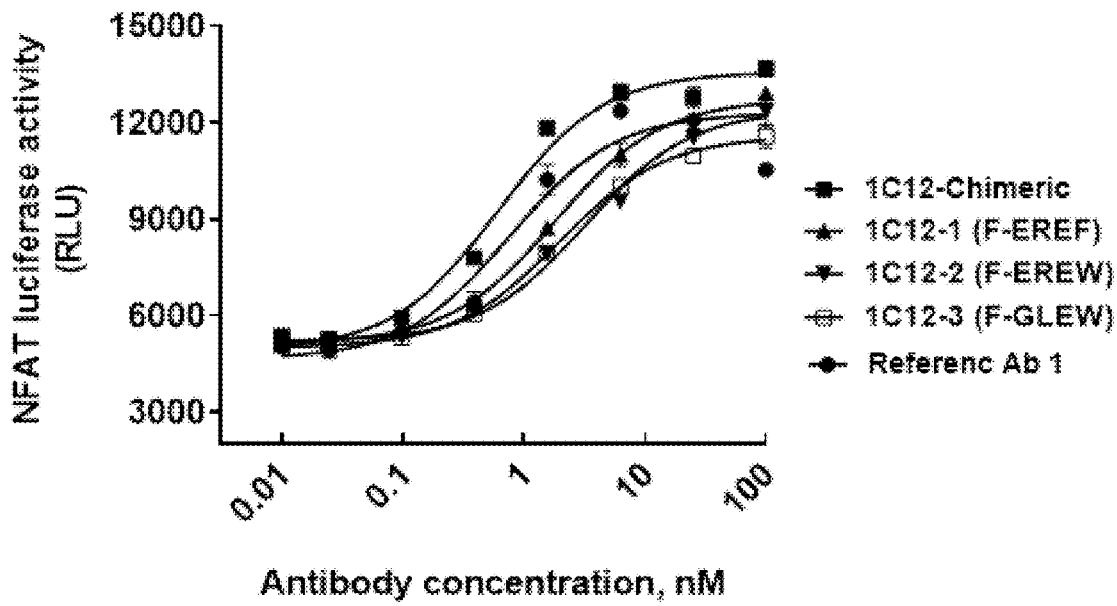
FIGS. 4A and 4B depict the potency of humanized 1C12 and 1G1 clones in blocking TIGIT activity determined by luciferase reporter assays. Representative results of 1C12 humanized versions in TIGIT blockade luciferase reporter assay is shown in FIG. 4A. All clones are more potent compared to Reference Ab 1, a reference anti-h-TIGIT antibody. Representative results of 1G1 humanized versions are shown in FIG. 4B. Y axis represents NFAT luciferase activity (RLU, relative luminescence unite). X axis represents antibody concentrations in nanomolar.
Figure 4B:
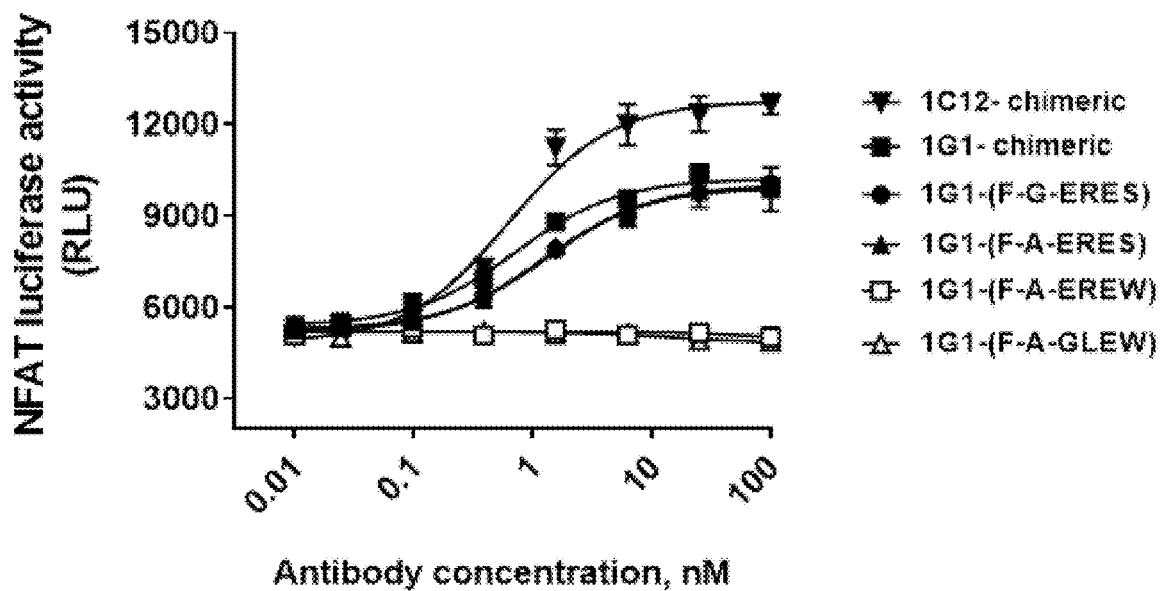

The activity of humanized antibodies in blocking PVR-mediated suppressive effects on TCR-mediated NFAT reporter activity was determined using a method descripted previously. Briefly, human TIGIT and NFAT reporter transfected Jurkat cells were incubated with antibodies in different concentrations, in the presence of PVR transfected Raji cells and a low concentration of staphylococcal enterotoxin (SEE, 0.01 ng/ml) for 5 hours. Bright-Glo luciferase assay buffer with substrate (Promega) was added, and luciferase activity was measured. Representative results are shown in FIGS. 4A and 4B. All humanized versions of 1C12 clone had similar potency in blocking TIGIT compared to the chimeric parental clone and Reference Ab 1, a reference anti-h-TIGIT antibody. All humanized versions of 1G1 had similar potency compared to the chimeric parental clone in blocking TIGIT, except two versions 1G1-(F-A-EREW) and 1G1-(F-A-GLEW) lost the blocking effect.

Example 4—Affinity Maturation, Selection & Modification

Affinity maturation was performed for the 1G1-F-A-ERES clone. Primers for making single mutation of amino acid for each CDR region were designed. A library of mutations was prepared using assembly PCR and cloned into phagemil vectors. Library quality was measured by transformation of TG1 cells and DNA sequencing of clones. Phage production was carried out using helper phages, and phage panning was performed using streptavidin-coupled Dynabeads coated with biotinylated h-TIGIT ECD or cyno-TIGIT ECD. After two round of panning, elution of panning products was used to infect SS320 cells, and colonies were picked and cultured in Y2T medium with IPTG. VHH antibodies in supernatants were examined by ELISA assays. Positive clones against h- & cyno-TIGIT were selected for whole cell binding to h- & cyno-TIGIT in stable cells. PVR blocking ELISA and human TIGIT blockade NFAT reporter assays were also performed for selected clones. EC50 or IC50 values were calculated using GraphPad Prism. The top 25 binders and their CDRs and VHHs are shown in the Sequence Table (SEQ ID NOS: 94-177).

Figure 5:
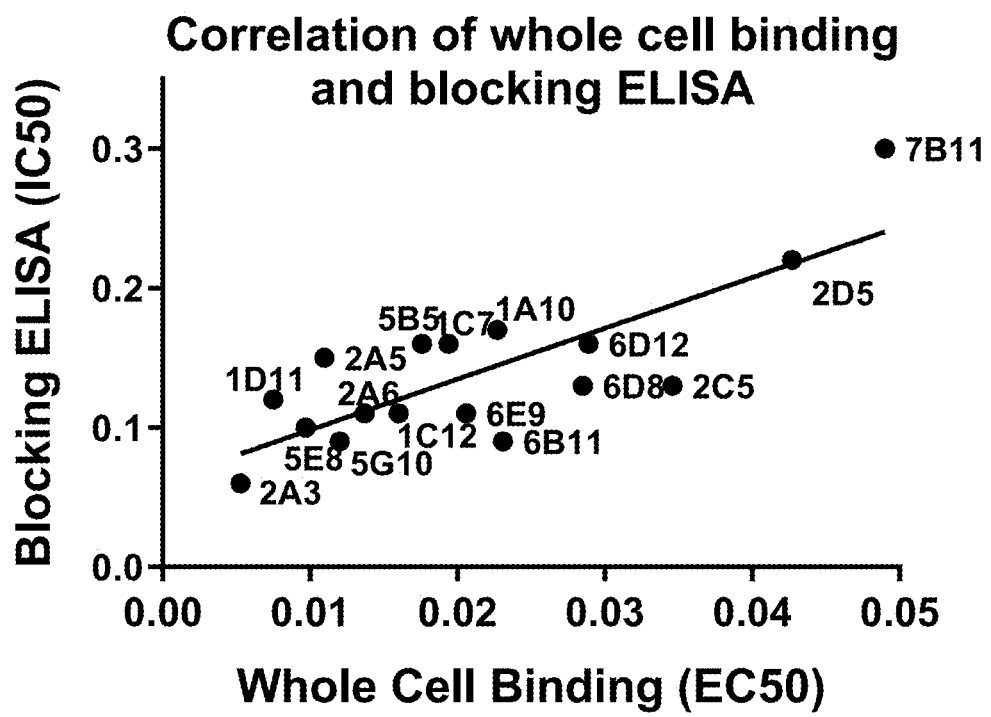
FIG. 5 depicts correlations betweenIC50 values (in nanomolar) of blocking ELISA and EC50 values (in nanomolar) of whole cell binding for representative clones. The clone names are labeled in the figures. Correlations were analyzed using GraphPad Prism.

Correlations between EC50/IC50 in whole cell binding and blocking ELISA were graphed using GraphPad Prism, and representative data are shown in FIG. 5. 2A3 was identified with the highest affinity and potency.

Figure 6A:
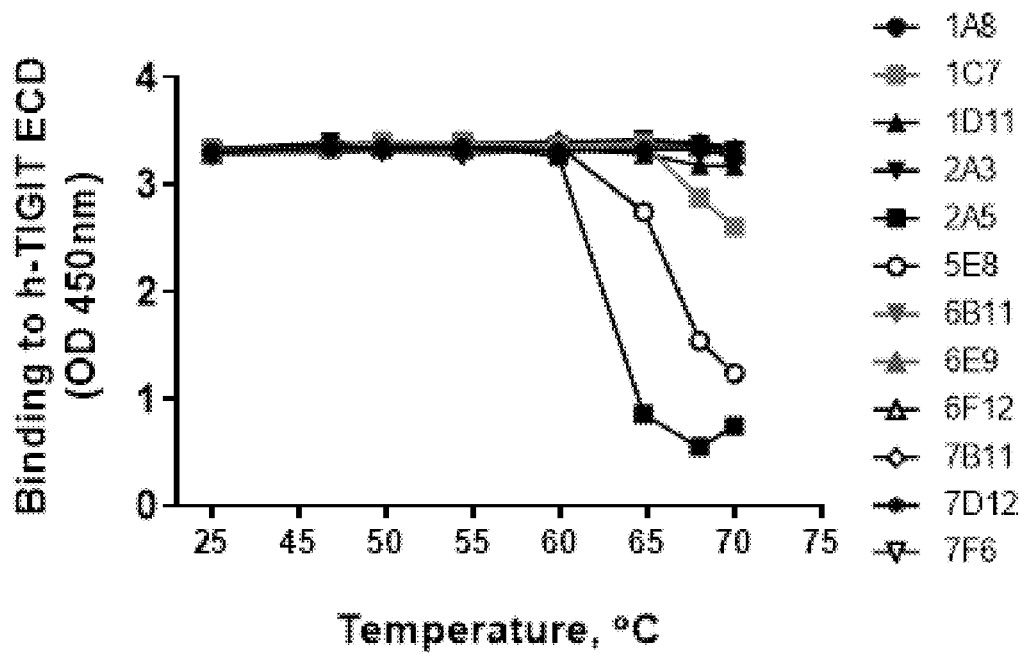
FIGS. 6A and 6B depict thermostability tested for representative clones. The VHH antibody samples were heated from 25 to 70° C. for 60 min. Binding of heated samples to human TIGIT was examined using ELISA or whole cell binding.
Figure 6B:
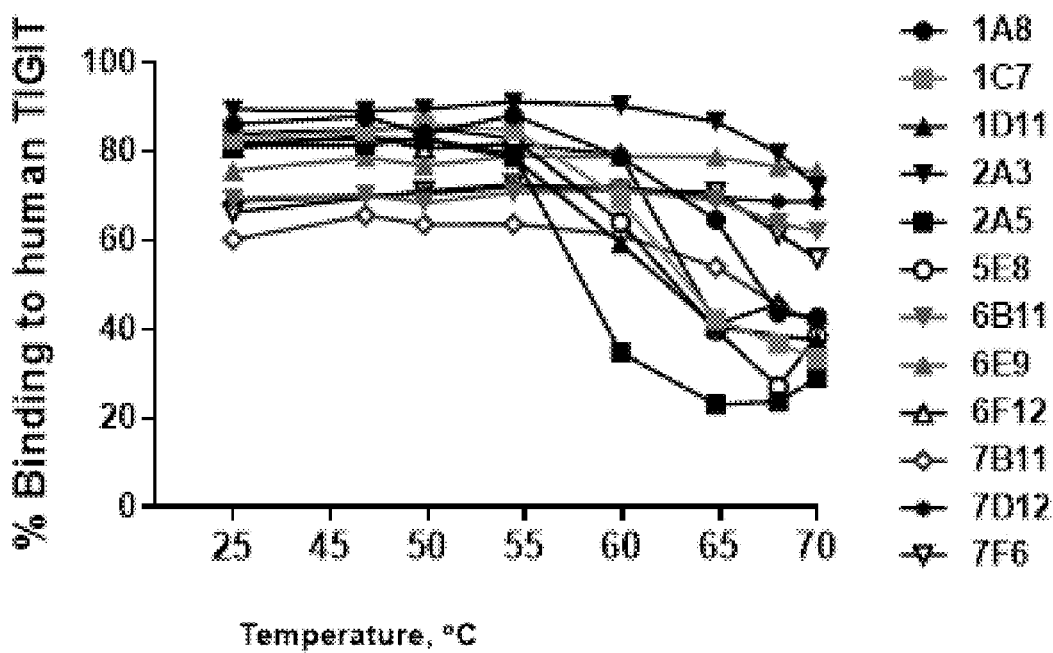
Figure 7A:
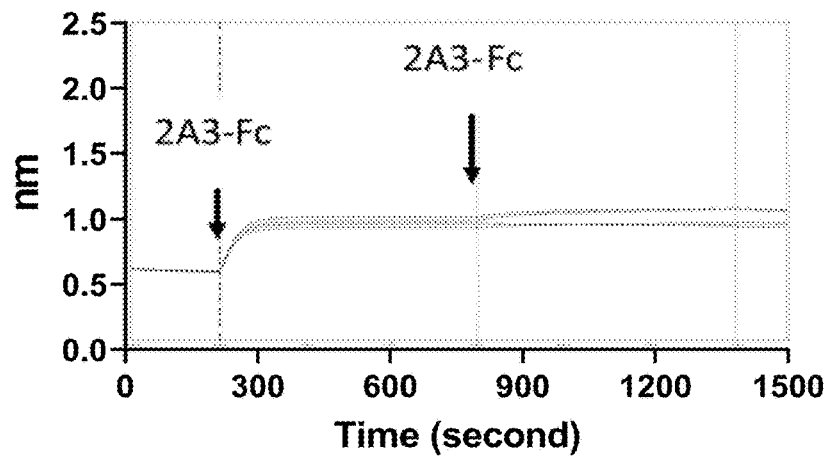
FIGS. 7A-7C depict the epitope at which 2A3-Fc binds to human TIGIT determined by Octet binding assay using ForteBio. Recombinant protein of his-tagged human TIGIT ECD (200 nM) was loaded on sensor. Binding was detected by injection of 2A3-Fc at three different concentrations. No additional binding was detected by second injection of 2A3-Fc shown in FIG. 7A, however strong binding was detected by injection of three different concentrations of either Reference Ab 2, a reference anti-human-TIGIT antibody, shown in FIG. 7B, or Reference Ab 1 shown in FIG. 7C. The results indicate that 2A3 clone has a different binding epitope compared to Reference Ab 2 and Reference Ab 1.
Figure 7B:
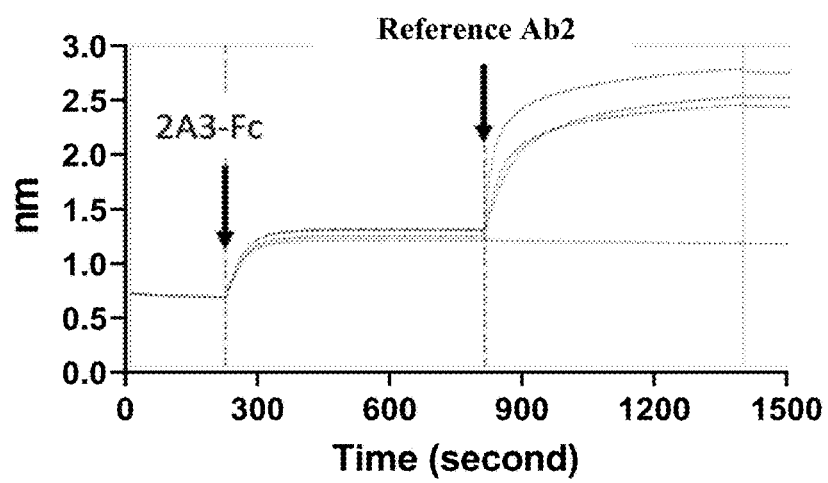
Figure 7C:
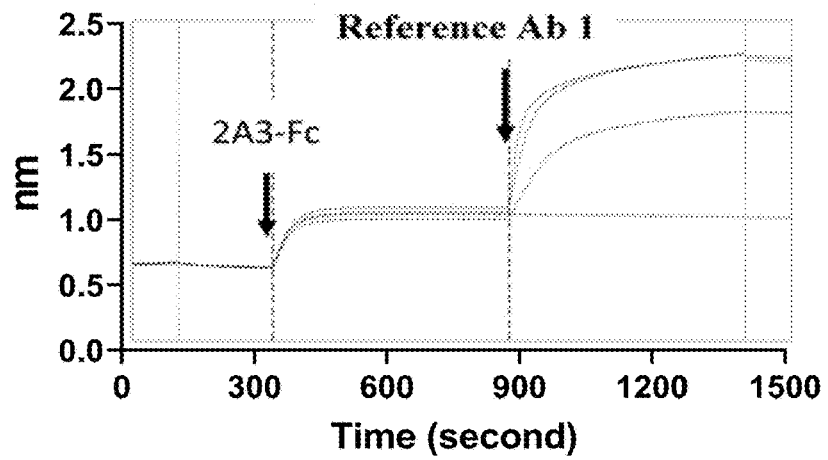

The thermostability of 12 representative clones was tested by heat treatment at 25 to 70° C. for 60 min, then the binding of the treated samples to human TIGIT was examined using ELISA and whole cell binding flow cytometry assays, the results of which are shown in FIGS. 6A and 6B. Clone 2A3 exhibited superior thermostability compared to other clones.

Bivalent 2A3 antibody (2A3-Fc) was constructed using human IgG1 CH2 and CH3 domains. The antibody was expressed in ExpiCHO cells and purified by protein A column. Epitope of 2A3-Fc binding to human TIGIT was studied using Octet binding assay in comparison with anti-TIGIT reference antibodies Reference Ab 1 and References Ab 2 (a reference anti-human-TIGIT antibody having the same amino acid sequences of Tiragolumab, which was synthesized in-house based on the disclosed sequences in U.S. 2017/0088613 A1). As shown in FIGS. 7A-7C, 2A3 clone bound to a different epitope compared to Reference Ab 1 and Reference Ab 2.

Figure 8A:
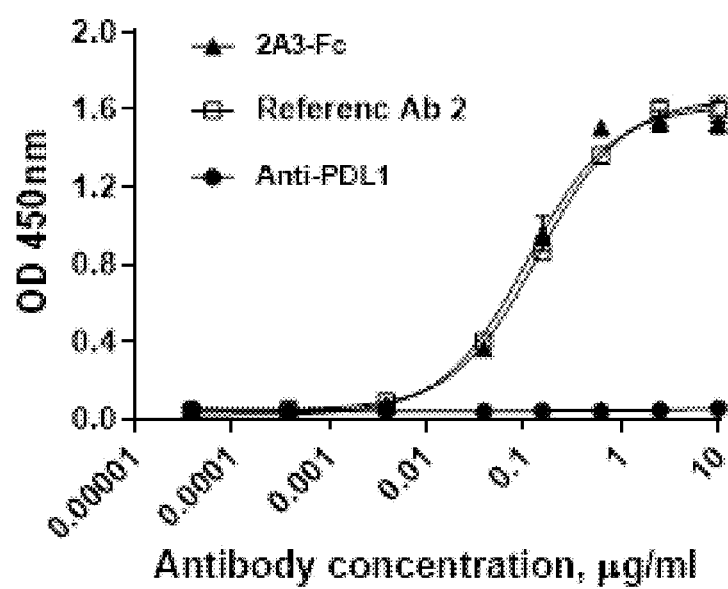
FIGS. 8A-8C depict cross-binding activity of 2A3-Fc to human-, cyno- and mouse-TIGIT determined by ELISA assays.
Figure 8B:
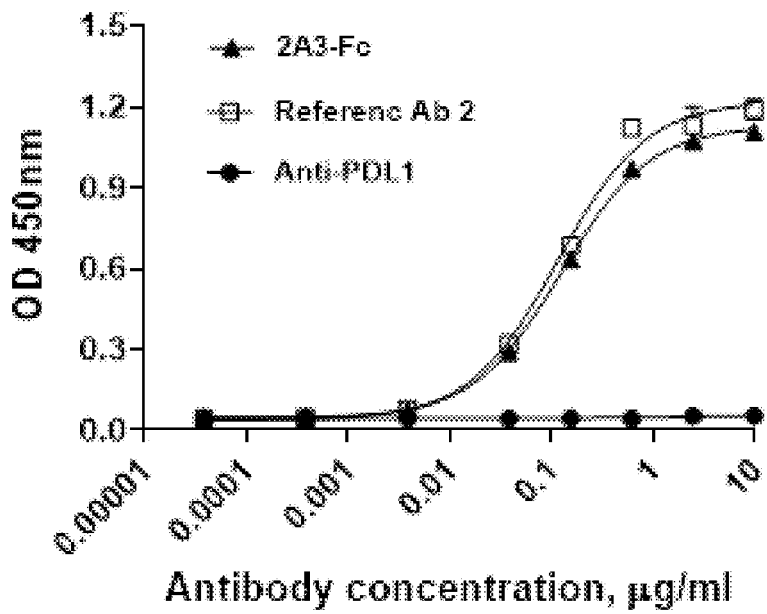
Figure 8C:
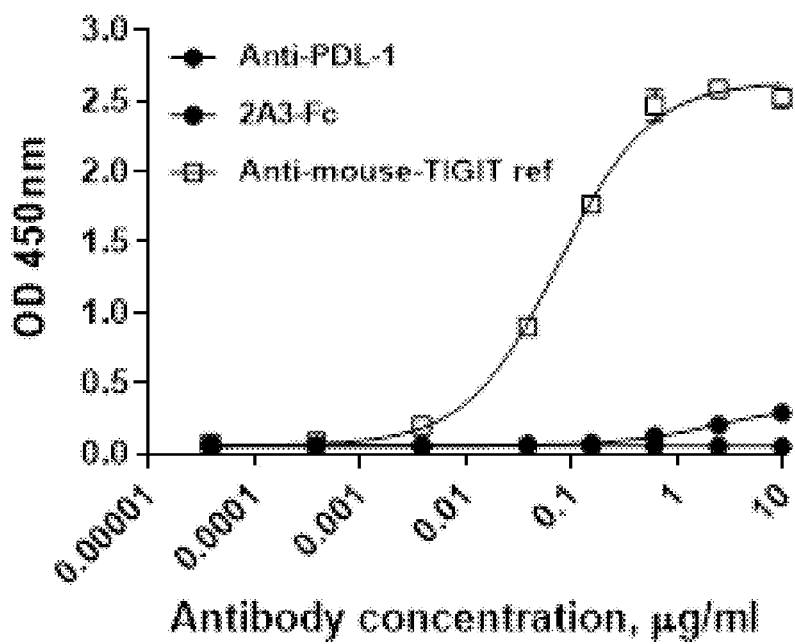

Cross-species binding activity of 2A3-Fc to human, cynomolgus and mouse TIGIT was determined by ELISA assays, results of which are shown in FIGS. 8A-8C. 2A3-Fc bound to human, cynomolgus monkey but not mouse TIGIT.

Figure 9:
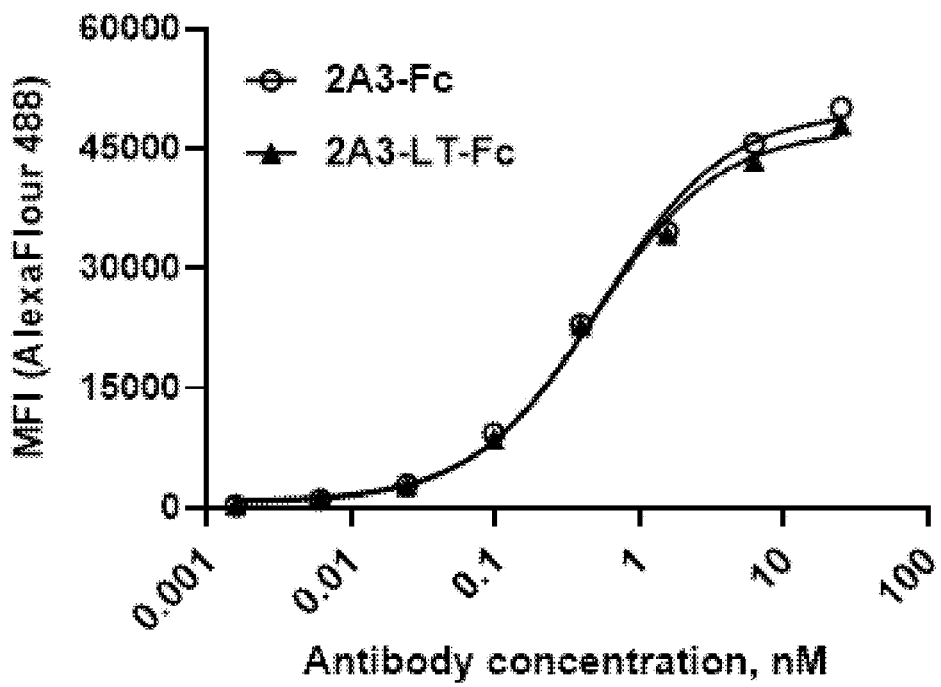
FIG. 9 depicts comparison of potency of representative clone 2A3-Fc and hotspot corrected version of 2A3-LT-Fc in whole cell binding assay and human TIGIT blockade reporter assay. Y axis represents mean fluorescent intensity (MFI) in the upper panel and NFAT luciferase reporter activity in relative luminescence unite in the lower panel. X axis represents antibody concentrations in nanomolar. Hotspot corrected version 2A3-LT-Fc had similar potency compared to the parental clone 2A3-Fc.
Figure 9:
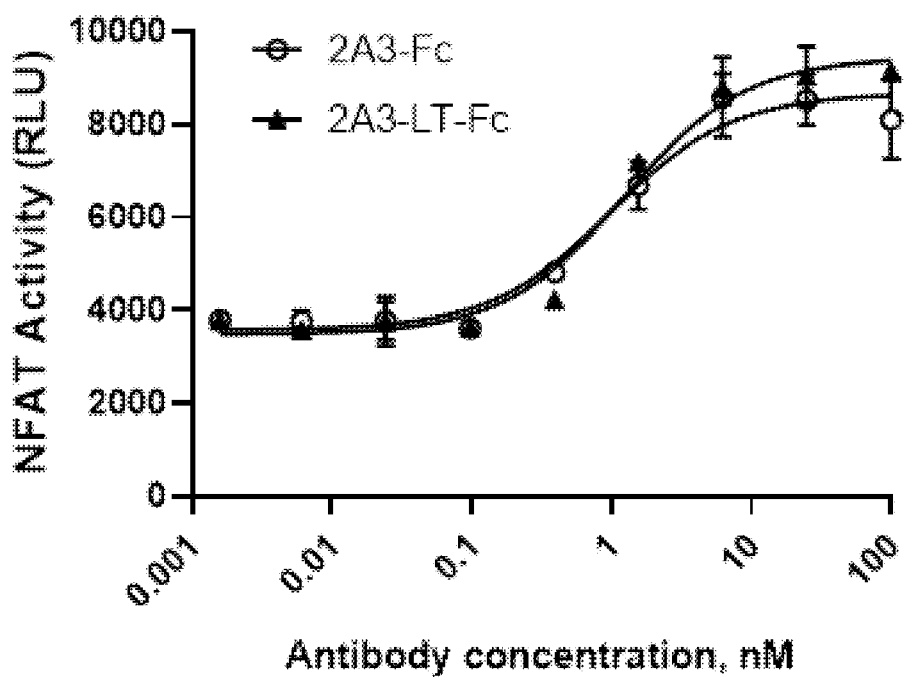

Analysis of CDR regions of 2A3 identified two hotspots, a methionine in CDR2 and an aspartic acid in CDR3 followed by serine. Mutations of methionine to leucine and isoleucine, and mutations of aspartic acid to threonine and glutamic acid were carried out. CDRs and VHHs of the modified antibodies (2A3 ML, 2A3 MI, 2A3 ML_DT (a.k.a 2A3 LT) and 2A3 ML_DE) are shown in the Sequence Table (SEQ ID NOs:178-193). The modified versions were tested in whole cell binding and NFAT luciferase reporter assays, all of which exhibited similar properties compared to the parental 2A3 clone. The representative data of 2A3-LT-Fc with changes of M to L and D to T (2A3 ML_DT) are shown in FIG. 9, where similar human TIGIT binding affinity in whole cell binding assay and similar potency in NFAT reporter assay were observed compared to parental 2A3-Fc.

Figure 10A:
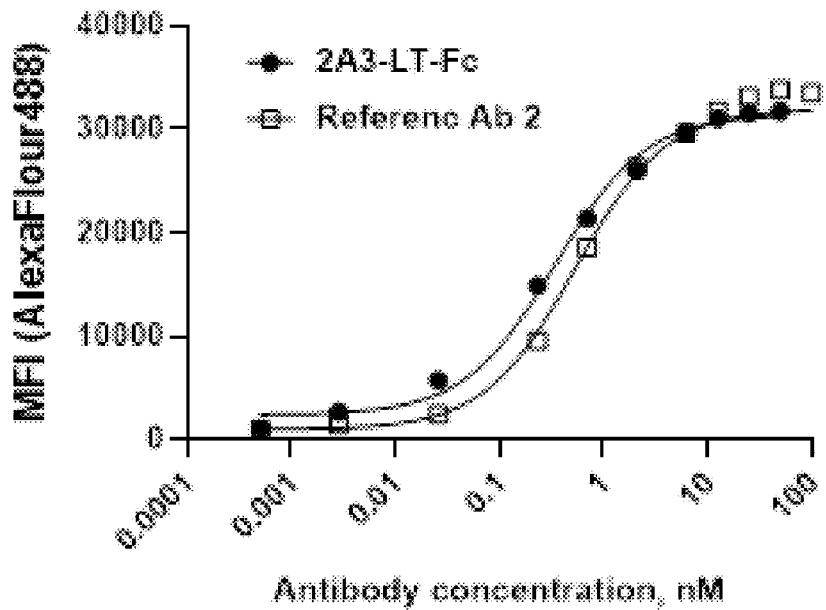
FIGS. 10A and 10B depict comparison of affinity of hotspot corrected version 2A3-LT-Fc to a reference anti-h-TIGIT antibody, Reference Ab 2.
Figure 10B:
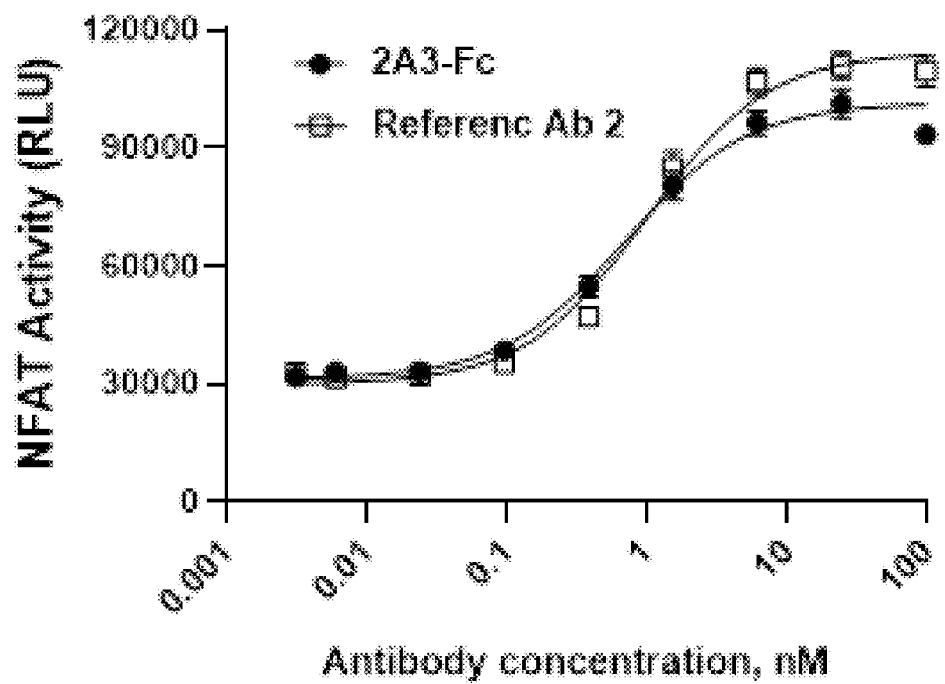

The affinity and potency of 2A3-Fc were compared to a reference anti-TIGIT antibody Reference Ab 2. 2A3-Fc exhibited significantly higher affinity than Reference Ab 2. The EC50 value of 2A3-Fc was 0.32±0.06 nM compared to 0.61±10.13 nM of Reference Ab 2 (n=3) in whole cell binding assays (FIG. 10A). 2A3-Fc also exhibited similar potency of blocking TIGIT in NFAT luciferase reporter assays compared to Tiragolumab. The EC50 value of 2A3-Fc was 0.48±1 0.18 nM compared to 0.72±0.42 nM of Reference Ab 2 (n=3) (FIG. 10B).

Example 5—In Vitro Antitumor Efficacy Study

The anti-TIGIT antibody's antitumor effects were further examined in vitro. In the tumor microenvironment, when TIGIT+ T cells are in contact with PVR+dendritic cells (DCs), PVR expressed on the DCs can bind to TIGIT expressed on the T cells and thereby suppresses the T cells' antitumor activity, e.g., antitumor cytokine secretion. Treatment using an effective anti-TIGIT antibody can block the interaction between TIGIT and PVR and thereby enhance the antitumor activity of T cells.

Mixed lymphocyte reaction assay (MLR) was used to model this phenomenon in the tumor microenvironment. CD14+ monocytes isolated from PBMCs of one healthy donor were cultured with 50 ng/ml IL-4 and 50 ng/ml GM-CSF in RPMI for 7 days (medium was changed on Day 4) to differentiate into DCs. Mature DCs were obtained by further culturing the DCs with 100 ng/ml LPS in RPMI for 1 day on Day 7. The natured DCs stably expressed CD11c (mature DC biomarker), MHC class II, CD80 (CD28 ligand), and PVR (TIGIT ligand). CD3+ T cells were isolated from PBMCs of another healthy donor using ThermoFisher T cell isolation kit and cultured overnight. Next, the CD3+ T cells (200,000) were mixed with the mature DCs (10,000) in RPMI 1640 culture medium with 10% FBS-HI, and anti-TIGIT antibody or control antibodies were added at various concentrations. After incubation for 48 hours at 37° C. and 5.0% CO2, IL-2 secretion from the T cells were measured in culture supernatant by PerkinElmer (AlphaLisa human IL-2 kit: Cat#AL221C). An anti-PD1 antibody was used as a positive control. An anti-HER2 antibody was used as a negative control.

Figure 11:
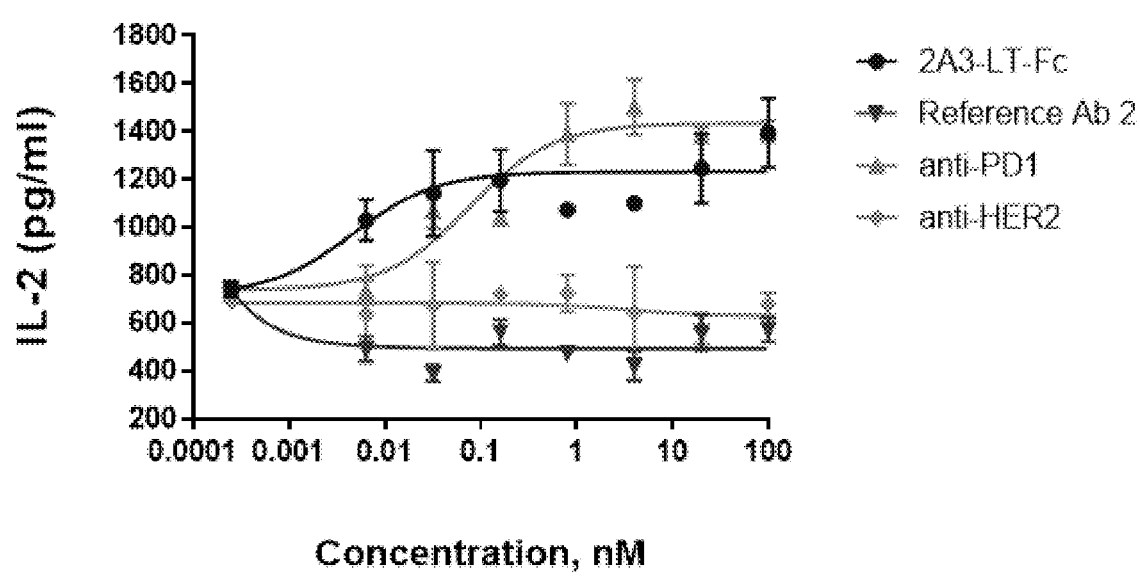
FIG. 11 depicts in vitro antitumor efficacy of 2A3-LT-Fc. Mixed lymphocyte reaction assay (MLR) was performed using TIGIT+ T cells and PVR+ dendritic cells (DCs). IL-2 secretion from the T cells were measured in culture supernatant after 48 hours of coculture. An anti-PD1 antibody was used as a positive control. An anti-HER2 antibody was used as a negative control.

As shown in FIG. 11, 2A3-LT-Fc enhanced the IL-2 secretion from T cells in a dose dependent manner comparable to the anti-PD1 antibody. In contrast, Reference Ab 2, a Tiragolumab analog, did not enhance the IL-2 secretion. As IL-2 is an important antitumor cytokine, the results indicate that the anti-TIGIT antibody 2A3-LT-Fc can significantly enhance T cell antitumor activity in the tumor microenvironment, and it exhibited superior antitumor effects compared to the Tiragolumab analog.

Example 6—Fc Engineering

Figure 12:
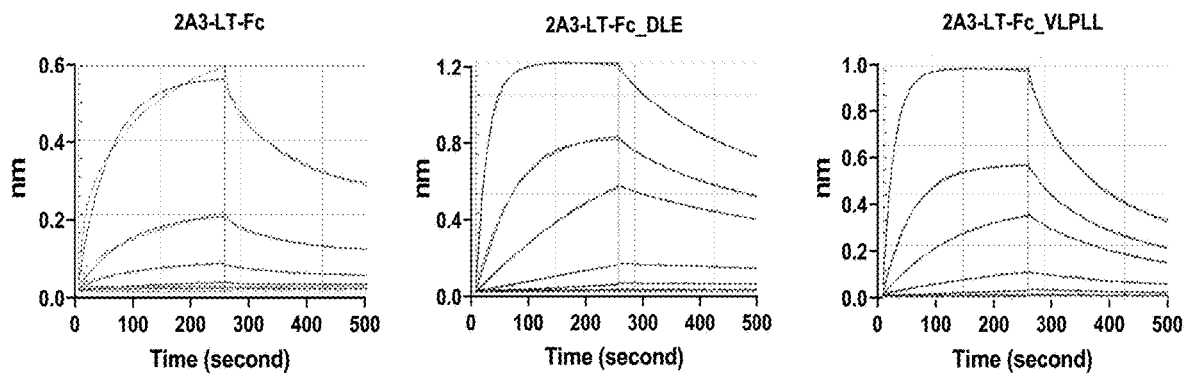
FIG. 12 depicts binding of 2A3-LT-Fc wild type (wt) and Fc mutations (DLE and VLPLL) to human FcγRIIIA, human FcγRIIB and mouse FcγRIV determined using Octet binding assay. Sensors were loaded with recombinant proteins of ECDs of FcγRIIIA, human FcγRIIB and mouse FcγRIV, association and dissociation of 2A3-LT-Fc wt, DLE or VLPLL mutants at 5 different concentrations were detected using ForteBio. Y axis represents association, dissociation & Rmax. X axis represents time in second. Both DLE and VLPLL mutants had enhanced binding affinity to human FcγRIIIA compared to that of wild type, DLE mutant also had enhanced binding affinity to human FcγRIIB, however VLPLL mutant reduced binding affinity to human FcγRIIB All versions had similar affinity to mouse FcγRIV.
Figure 12:
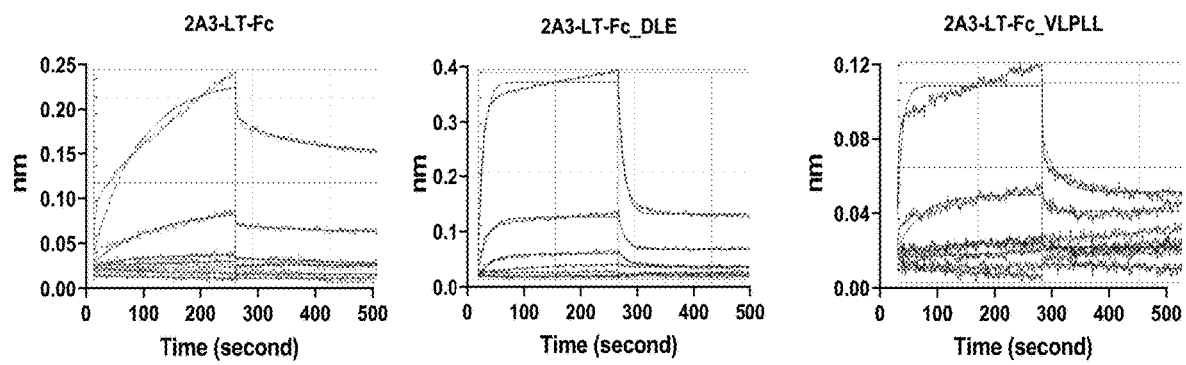
Figure 12:
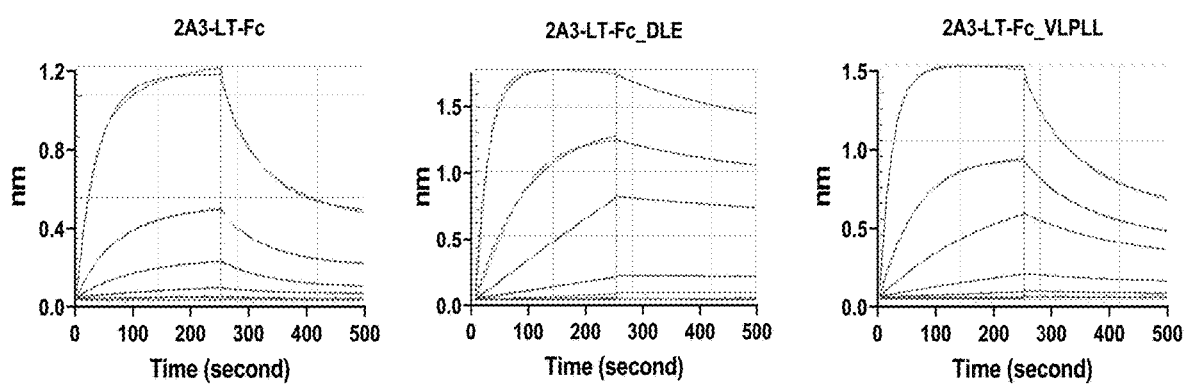

The mechanism of action of anti-TIGIT antibodies in enhancing immune function & anti-tumor activity can involve not only blockade effect on TIGIT but also bridging effect between antigen presenting cells (APC) and effective T cells (CD8+ T cells) through the binding of the antibody Fc region by FcγRIIIA on APC and the binding of the VHH domain to TIGIT on effective T cells. To take advantage of this mechanism, two different Fc-enhanced versions were made, one with mutations of DLE (S239D, A330L and I332E), one with mutations of VLPLL (L235V, F243L, R292P, Y300L and P396L). The binding of the Fc-mutants to human FcγRIIIA and FcγRIIB was examined by Octet binding assay using recombinant proteins of the ECD of FcγRIIIA and FcγRIIB, the results of which are shown in FIG. 12. Both DLE and VLPLL mutants had enhanced binding affinity to human FcγRIIIA DLE mutant also had enhanced binding affinity to human FcγRIIB, whereas VPVLL mutant had reduced binding affinity to human FcγRIIB The TIGIT blockade activity of a Fc-mutant was also examined, where the DLE mutant showed reduced TIGIT blockade function as shown in FIG. 13A.

Moreover, when antibody variable region binds to its specific antigen, its Fc region can cross-link the FcγRIIIA and triggers down-stream signaling. Using this mode of action, the effect of Fc-mutants on FcγRIIIA-mediated activity was examined using a human-FcγRIIIA and NFAT reporter transfected Jurkat cells and 293T cells overexpressing TIGIT. In this assay system, the DLE mutant significantly increased human-FcγRIIIA-mediated NFAT reporter activity compared to the wild type Fc version as shown in FIG. 13B.

TABLE 3

Figure 13A:
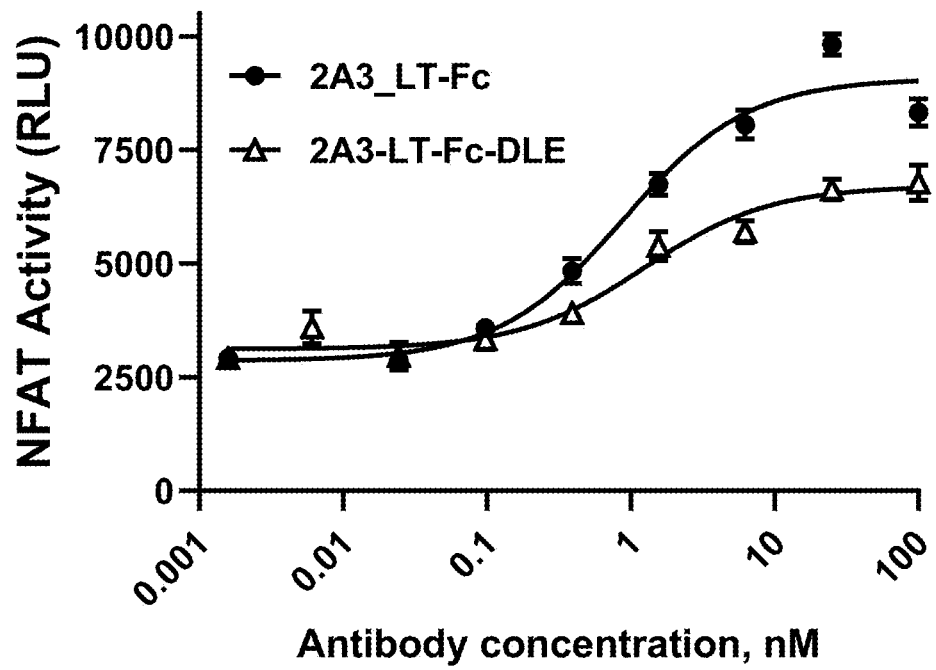
FIGS. 13A and 13B depict effects of TIGIT mAbs 2A3-LT-Fc wt, and DLE mutant on blocking TIGIT activity and human FcγRIIIA-mediated activity, respectively.
Figure 13B:
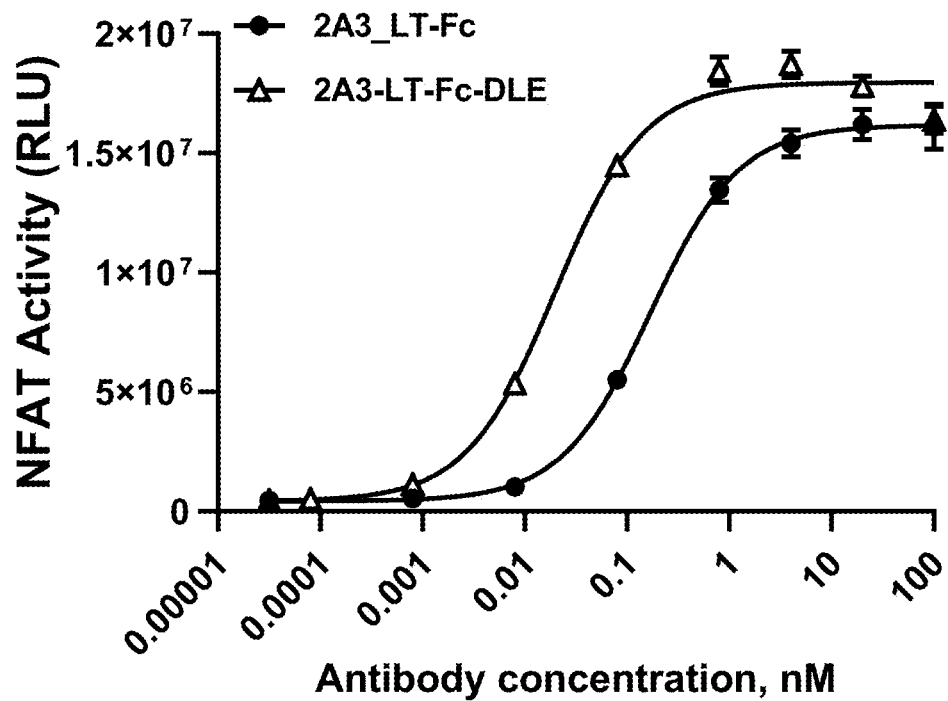

Test results shown in FIG. 13A

| EC50 (nM) | 2A3 LT-Fc | DLE |
|---|---|---|
| Exp 1 | 0.58 | 0.67 |
| Exp 2 | 0.687 | 0.92 |
| Exp 3 | 0.45 | 1.32 |
| Average | 0.57 | 0.97 |
| SD | 0.12 | 0.3279 |

TABLE 4

Test results shown in FIG. 13B

| EC50 (nM) | 2A3 LT-Fc | DLE |
|---|---|---|
| Exp 1 | 0.226 | 0.027 |
| Exp 2 | 0.175 | 0.0295 |
| Exp 3 | 0.144 | 0.018 |
| Exp 4 | 0.18 | 0.02 |
| Average | 0.18 | 0.024 |
| SD | 0.03 | 0.005 |

Example 7—In Vivo Efficacy Study

Figure 14A:
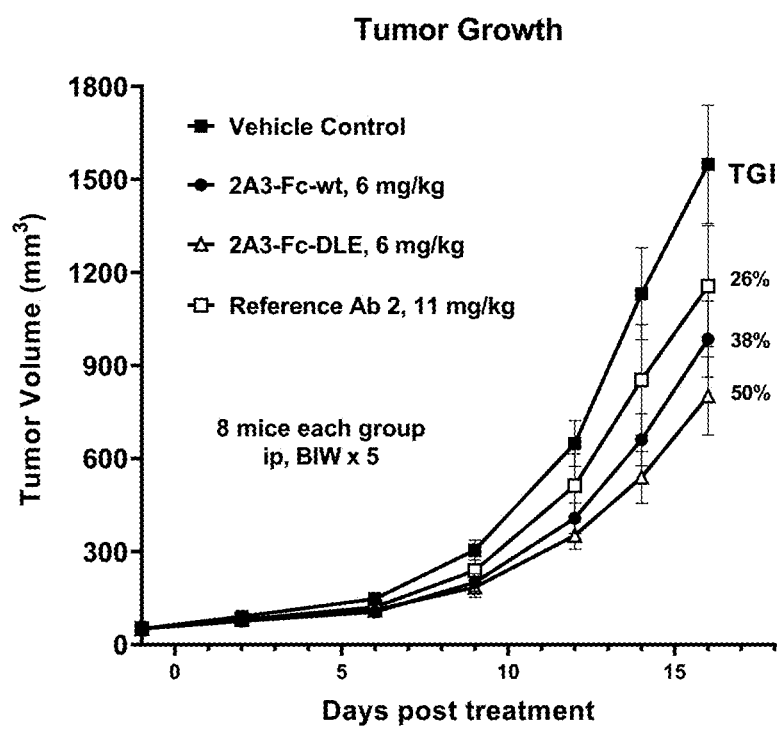
FIGS. 14A-14C depict in vivo efficacy analyses of the anti-TIGIT antibodies. H-TIGIT Knock-In C57BL/6 mice and MC38 murine colon cancer model were used. MC38 tumor cells were implanted one week before treatment. Treatment started when avarage tumor volume reached about 51 mm$^3$, when drugs were dosed intraperitoneally twice a week for 2.5 weeks at 6 mg/kg for 2A3-LT-Fc antibodies, or 11 mg/kg for Reference Ab 2 (equal to 6 mg/kg of 2A3-LT-Fc in mole/kg dosage).
Figure 14B:
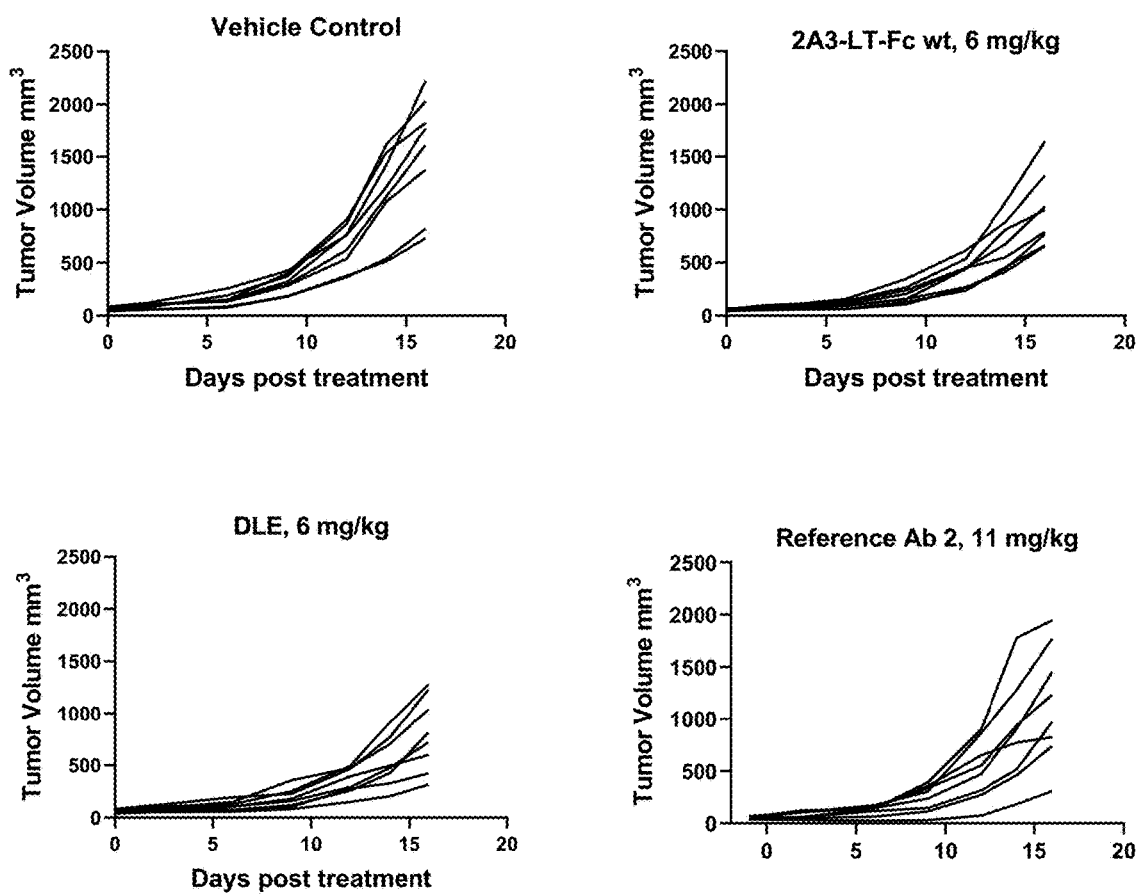
Figure 14C:
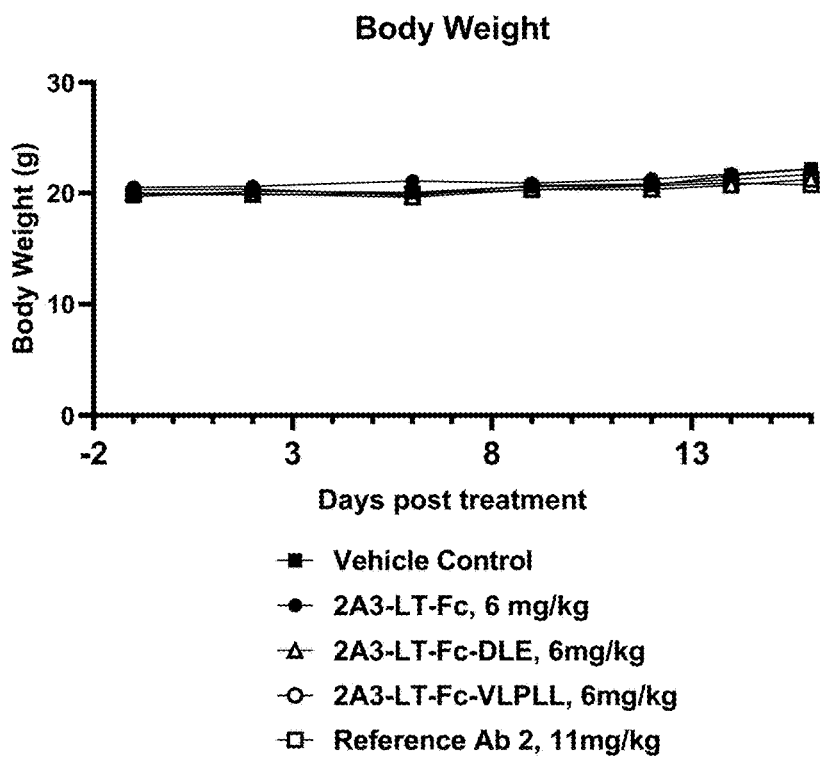

Using h-TIGIT Knock-In C57BL/6 mice and MC38 murine colon cancer model, efficacies of 2A3-LT-Fc wt and 2A3-LT-Fc-DLE were studied and compared to Reference Ab 2. MC38 tumor cells were implanted one week before treatment. Treatment started when tumor volume reached about 51 mm$^3$, when drugs were dosed intraperitoneally twice a week for 2.5 weeks at 6 mg/kg for 2A3-LT-Fc antibodies, or 11 mg/kg for reference antibody (equal to 6 mg/kg of 2A3-LT-Fc in mole/kg dosage). On day 16 post-treatment, tumor volumes in multiple mice of the control group reached tumor size limits (2000 mm$^3$). Therefore, day 16 post-treatment was the data end point for the analyses. Average tumor volume in the control group was 1548.76±191 mm$^3$ (mean±SEM) on day 16. The treatment with 2A3-LT-Fc wt and 2A3-LT-Fc-DLE significantly reduced tumor growth compared to vehicle control, resulting in respectively 38% and 50% of TGI (tumor growth inhibition) and tumor volume of 985.05±123 mm$^3$ and 802.20±126 mm$^3$ (P=0.037 and P=0.007 compared to Control by Mann-Whitney test), respectively. The treatment with the reference antibody also reduced tumor growth, but the reduction caused by the antibody was not statistically significant compared to the control group with the TGI of 26%, and tumor volume of 1156.16±195 mm$^3$ (FIG. 14A, Table 5). The results of individual tumor volume are shown in FIG. 14B. These results indicated that both 2A3-LT-Fc and 2A3-LT-Fc-DLE were more efficacious than Reference Ab 2. Body weight changes were not significant between the groups throughout the study (FIG. 14C), indicating the treatments were well tolerated.

TABLE 5

Mean Tumor Volumes on Day 16 in MC38 Syngeneic h-TIGIT Mouse Model

| Groups | Treatment | N | TV (mm$^3$)$^a$ | P$^b$ | % TGI (Day 16) |
|---|---|---|---|---|---|
| 1 | Vehicle | 8 | 1548.76 ± 191 | | |
| 2 | 2A3-LT-Fc-wt 6 mg/kg | 8 | 985.05 ± 123 | 0.037 | 38 |
| 3 | 2A3-LT-FC-DLE 6 mg/kg | 8 | 802.20 ± 126 | 0.007 | 50 |
| 4 | Reference Ab 2, 11 mg/kg | 8 | 1156.16 ± 195 | 0.234 | 26 |

Figure 15:
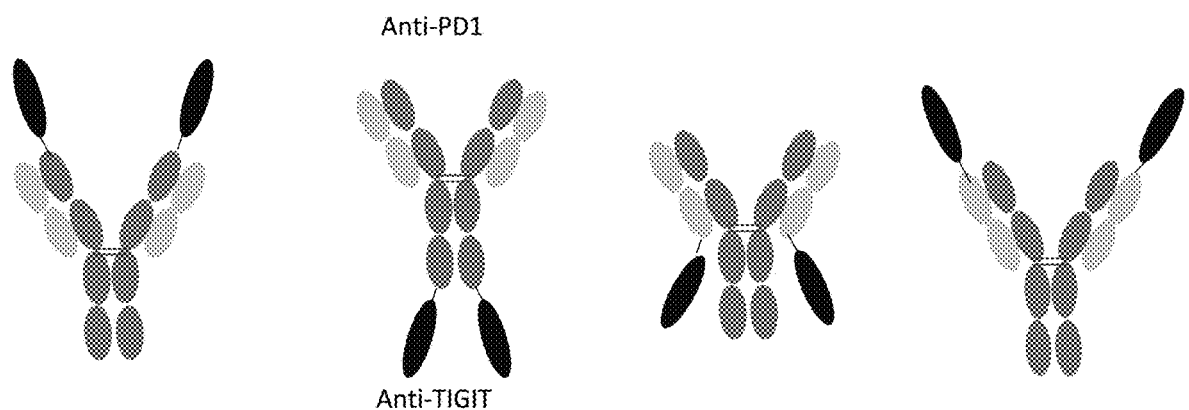
FIG. 15 depict various structures of anti-TIGIT/anti-PDL1 multispecific antibodies.

$^a$Mean ± SEM
$^b$Compared to vehicle control by Mann-Whitney test on day 16 post-treatment Example 8—Anti-TIGITxanti-PDL1 Bispecific Antibody Construction and Evaluation Bispecific antibodies (BsAbs) were constructed using humanized, affinity matured anti-TIGIT clone 2A3 and affinity matured human anti-PDL1 antibody disclosed in PCT/US2017/056689 (published as International Publication WO 2018/080812 A1). Four different versions were made, where VHH 2A3 was fused to N- or C-terminal of the heavy chain of the anti-PDL1 antibody, or N- or C-terminal of the light chain of the anti-PDL1 antibody (named as HCN, HCC, LCN, LCC, respectively). The structures of the BsAbs are shown in FIG. 15, and the sequences are shown in SEQ ID NOs: 309-316 in the Sequence Table. Production of the BsAbs were made from transient transfection of ExpiCHO and purified by Protein A column.

Figure 16A:
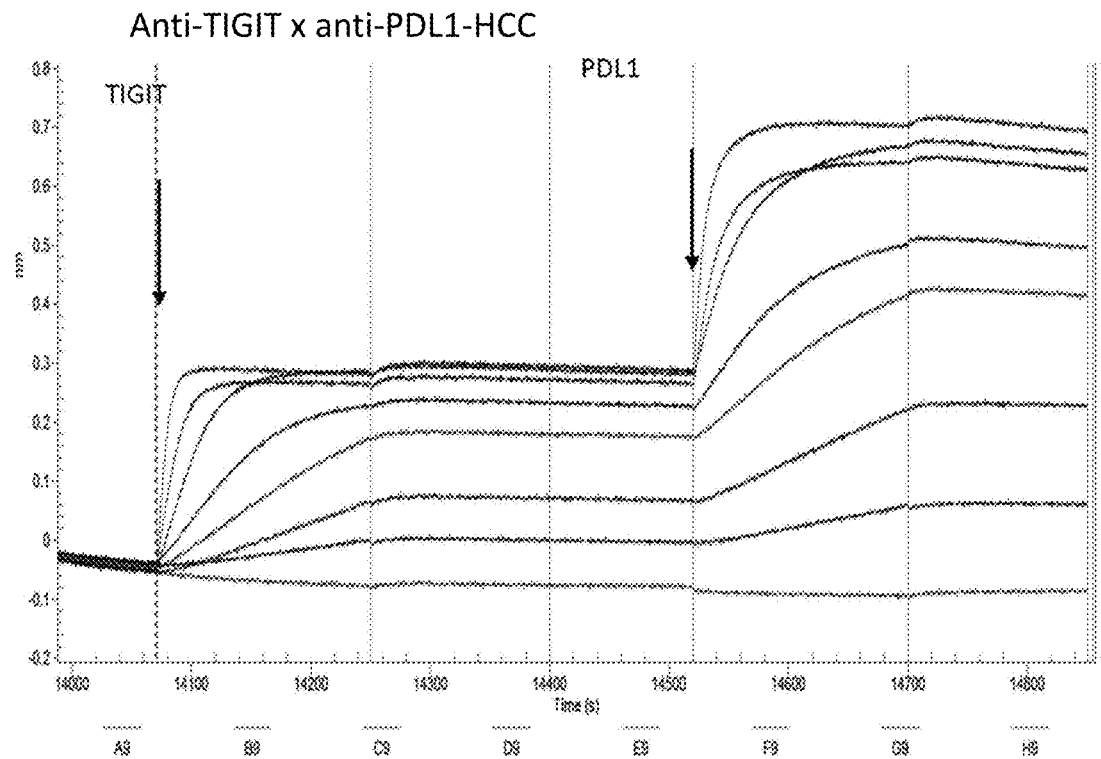
FIGS. 16A-16D depict double binding ability of bispecific antibodies (BsAbs) to h-TIGIT and h-PDL1 determined by Octet binding assay. The sensors were loaded with BsAbs and then injected with different concentrations of recombinant protein of h-TIGIT ECD (his-tagged). After association of BsAbs with h-TIGIT, the sensors were injected again with different concentrations of recombinant protein of h-PDL1 ECD (his-tagged). Binding curves of anti-TIGITxanti-PDL1 (aTIGITxaPDL1)-HCC, HCN, LCC & LCN are shown in FIG. 16A, FIG. 16B, FIG. 16C and FIG. 16D, respectively. Y axis represents association/disassociation and Rmax, X axis represents time in second.
Figure 16B:
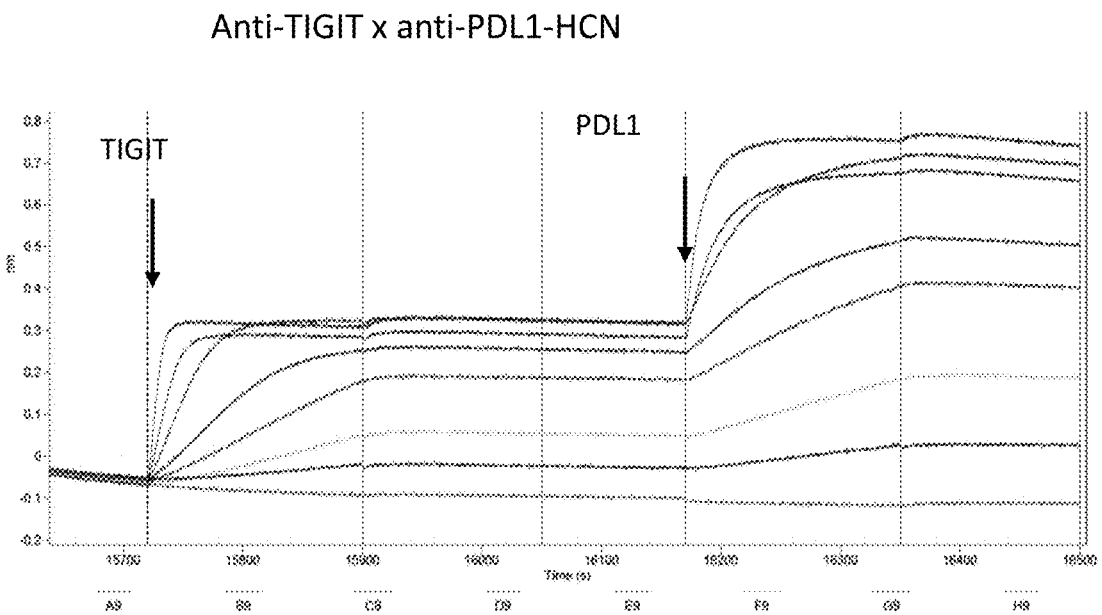
Figure 16C:
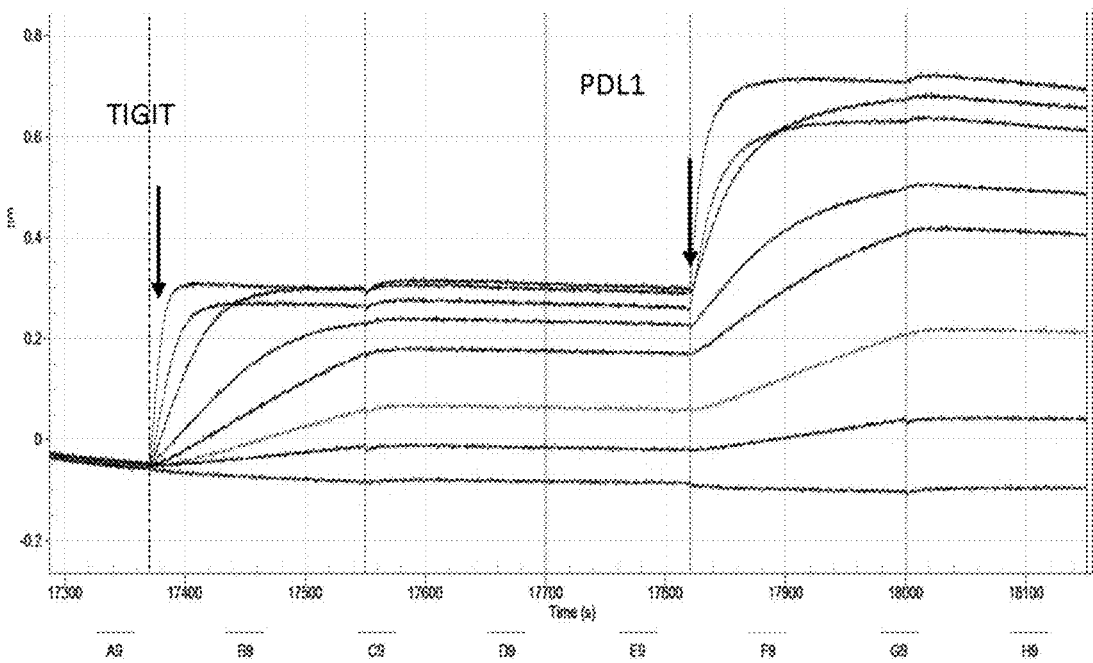
Figure 16D:
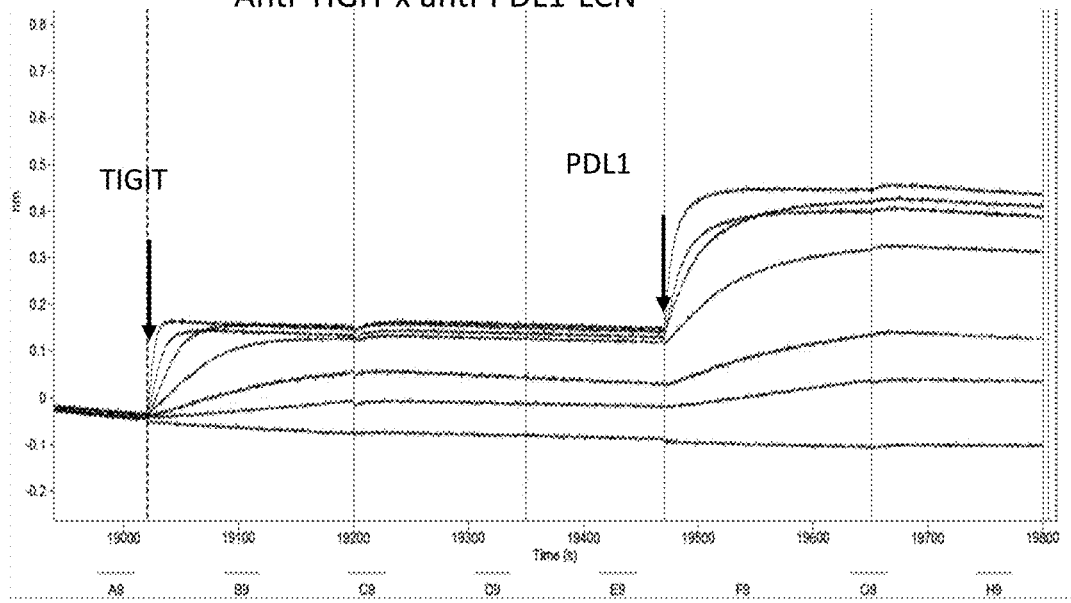

The binding affinity of the BsAbs to h-TIGIT and h-PDL1 was examined using Octet binding assays, where all BsAb formats bound to both h-TIGIT and h-PDL1 without reduction of affinity compared to parental mAbs as shown in FIGS. 16A-16C.

Figure 17A:
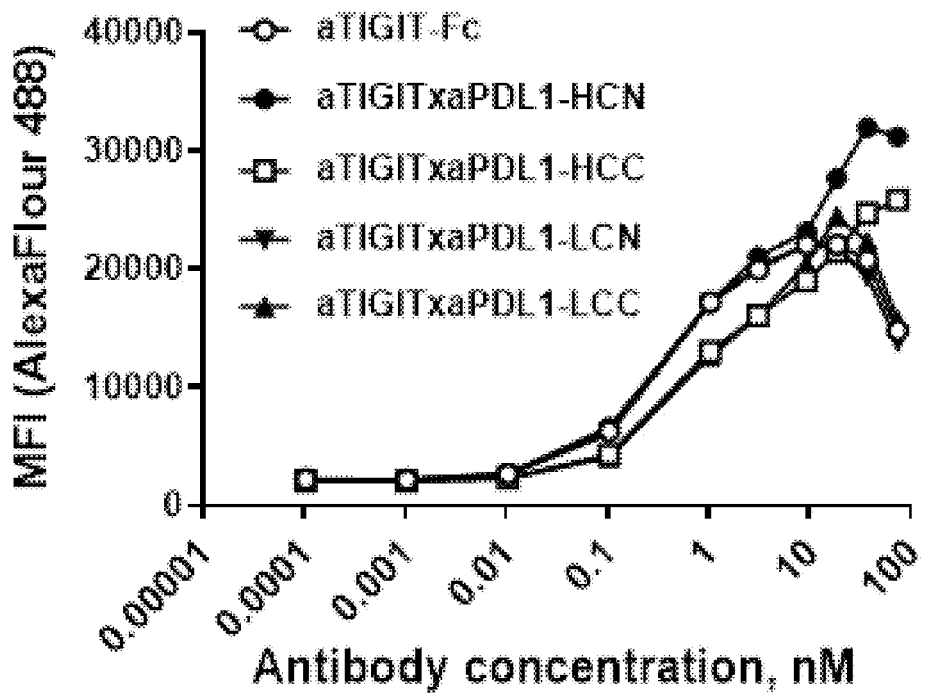
FIGS. 17A-17D depict affinity and potency of BsAbs to h-TIGIT and h-PDL1. (A) Concentration curves of BsAbs bind to h-TIGIT. Antibodies were incubated with h-TIGIT stably transfected Jurkat cells, and binding of antibodies to h-TIGIT was determined using a secondary anti-h-IgG Fc AlexaFluor488 conjugated antibody and detected by flowcytometry. Y axis represents mean fluorescent intensity (MFI). X axis represents concentrations of antibodies. (B) Concentration curves of BsAbs in blocking h-TIGIT activity determined by NFAT luciferase reporter assay. Antibodies were cultured with Jurkat cells transfected with h-TIGIT and NFAT reporter gene in the presence of PVR stably transfected Raji cells and a low concentration of staphylococcal enterotoxin. TCR-mediated NFAT luciferase reporter activity was measured by a chemiluminescent plate reader and is shown in Y axis. Blocking h-TIGIT induced higher TCR-mediated luciferase reporter activity. (C) Concentration curves of BsAbs bind to h-PDL1. The assay condition was similar to (A) except that h-PDL1 stably transfected CHO cells used. (D) Concentration curves of BsAbs in blocking PD1/PDL1 activity determined by NFAT luciferase reporter assay. Antibodies were cultured Jurkat cells transfected with h-PD1 and NFAT reporter gene in the presence of PDL1 and CD3 transfected CHO cells. TCR-mediated NFAT luciferase activity was measured by a chemiluminescent plate reader and is shown in Y axis.
Figure 17B:
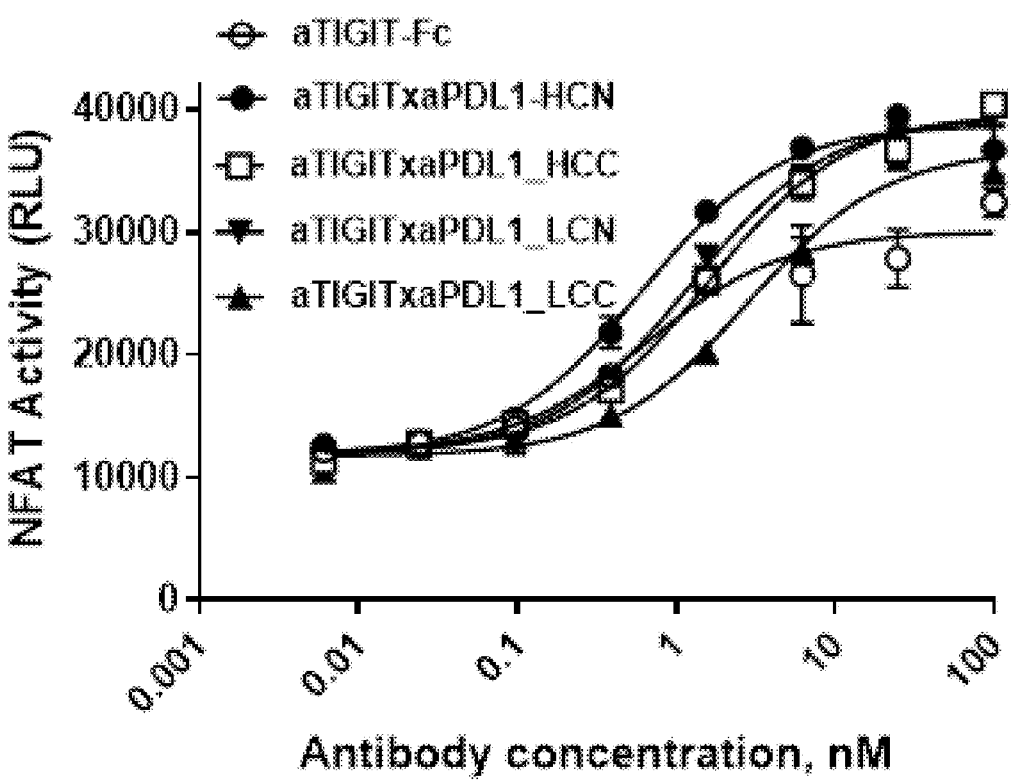
Figure 17C:
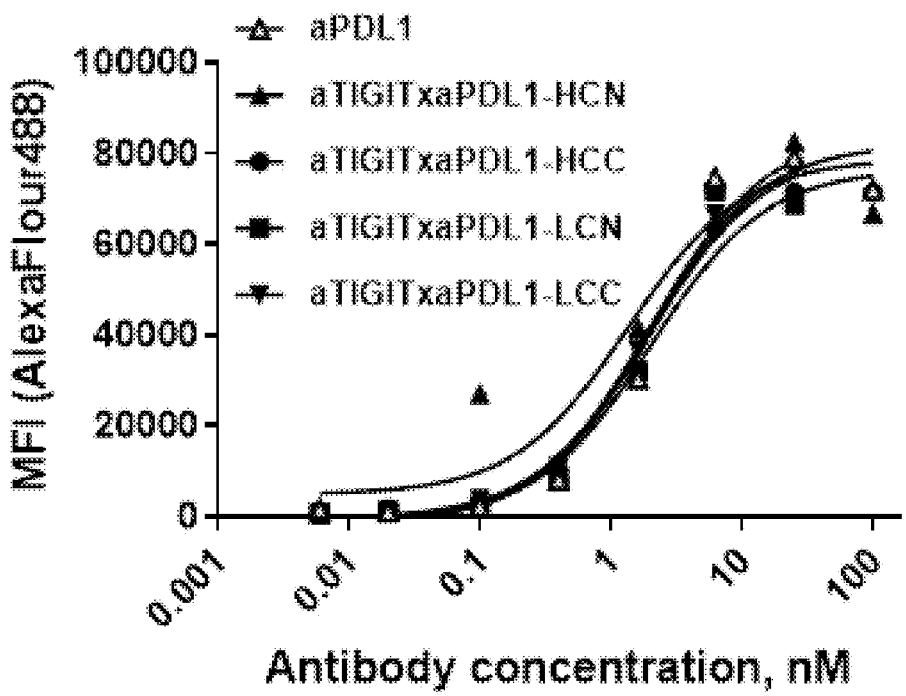
Figure 17D:
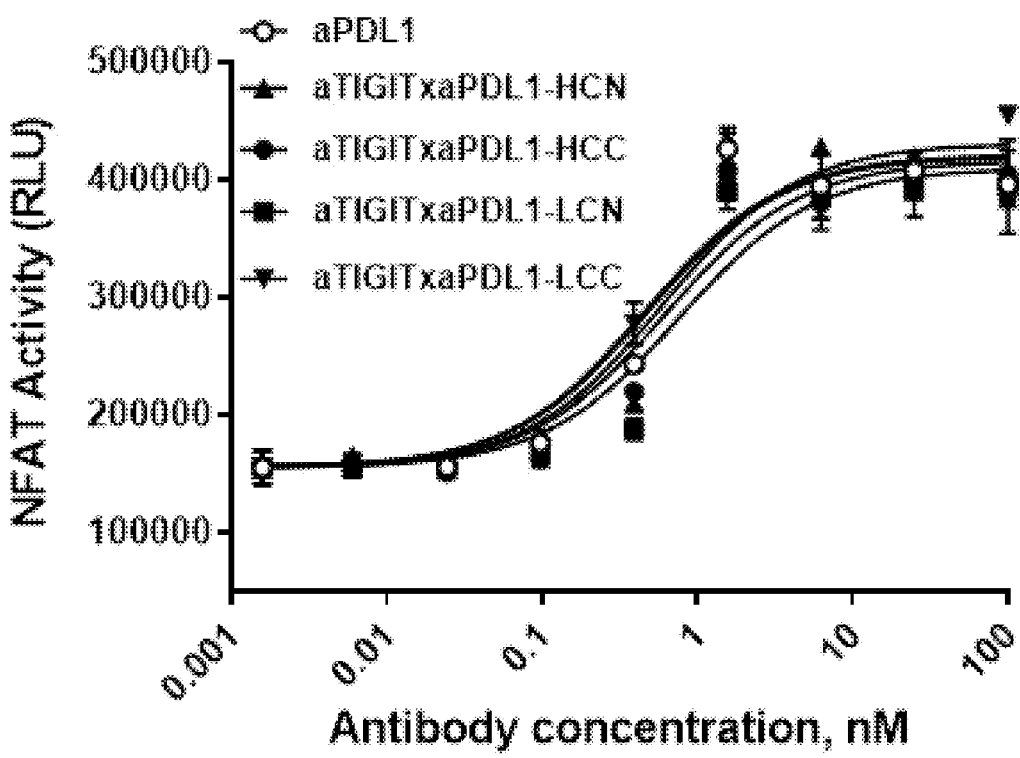

The binding affinity was further examined in whole cell binding assay using flowcytometry. As shown in FIG. 17A, both HCN and LCN kept binding affinity to TIGIT compared to 2A3-Fc mAb, and both HCC and LCC had slightly lower affinities to TIGIT compared to 2A3-Fc mAb. In TIGIT blockade reporter assay, HCN appeared to have the strongest potency in blocking TIGIT among the four BsAbs as shown in FIG. 17B. To human PDL1, the binding affinities of four BsAbs were similar, and the potency of blocking PDL1 in NFAT reporter assay were also similar among four BsAbs, as shown in FIGS. 17C and 17D.

Figure 18:
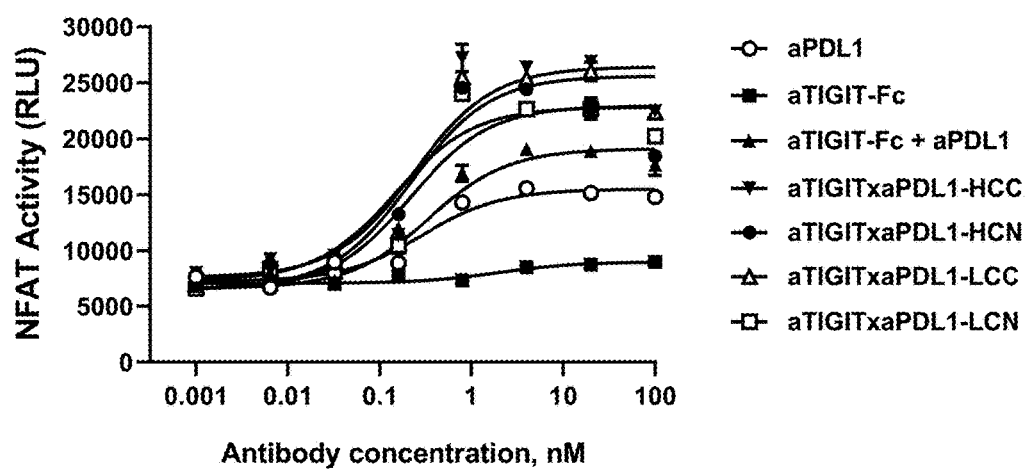
FIG. 18 depicts potency of BsAbs in blocking both TIGIT and PDL1 determined using combination of TIGIT and PD1/PDL1 blockade assay. MAbs and combination of mAbs and BsAbs were cultured with h-TIGIT, h-PD1 & NFAT reporter gene stably transfected Jurkat cells in the presence of PVR and PDL1 stably transfected CHO cells and a low concentration of staphylococcal enterotoxin. TCR-mediated NFAT luciferase reporter activity was measured by a chemiluminescent plate reader and is shown in Y axis in relative luminescence units. Combination of anti-TIGIT mAb (aTIGIT) and anti-PDL1 mAb (aPDL1) was more potent than either mAbs. All BsAbs were more potent than combination treatment.

The function of the four BsAbs was also evaluated using PDL1 and TIGIT double blockade NFAT reporter assay, an assay system mimicking the mechanism of action where both TIGIT and PDL1 are involved in suppressing T cells function. Similar potencies of the four BsAbs in double blockade assay were observed, with HCC, LCC and HCN slightly more potent than the LCN version, as shown in FIG. 18. Combination of anti-TIGIT mAb (aTIGIT) and anti-PDL1 mAb (aPDL1) was more potent than both mAbs used alone. Unexpectedly, all BsAbs were more potent than the combination treatment.

The developability of the four BsAbs was also examined in SDS PAGE gel, size exclusion column (SEC) analysis and Dynamic Light Scattering (DLS) thermostability assessment. Unexpectedly, HCN and HCC exhibited significantly better properties regarding stability and aggregation in SDS PAGE gel, size exclusion column (SEC) analysis and DLS thermostability analysis compared to LCN and LCC BsAbs (summarized in Table 4).

TABLE 4

Summary of in vitro results of BsAbs

| BsAb | Hu-TIGIT WCB | Cyno-TIGIT WCB | PDL1 WCB | TIGIT Blockade Assay | PD1/PDL1 Blockade Assay | TIGIT+PD1 Combination Blockade Assay | SDS PAGE | SEC | DLS |
|---|---|---|---|---|---|---|---|---|---|
| aTIGITx aPDL1-HCN | ++++ | +++ | +++ | ++++ | ++++ | ++++ | +++ | ++++ | +++ |
| aTIGITx aPDL1-HCC | ++ | ++ | +++ | +++ | ++++ | ++++ | +++ | ++++ | +++ |
| aTIGITx aPDL1-LCN | +++ | ++ | +++ | +++ | ++++ | +++ | + | ++ | + |
| aTIGITx aPDL1-LCC | ++ | ++ | +++ | ++ | ++++ | ++++ | ++ | +++ | ++ |

Figure 19A:
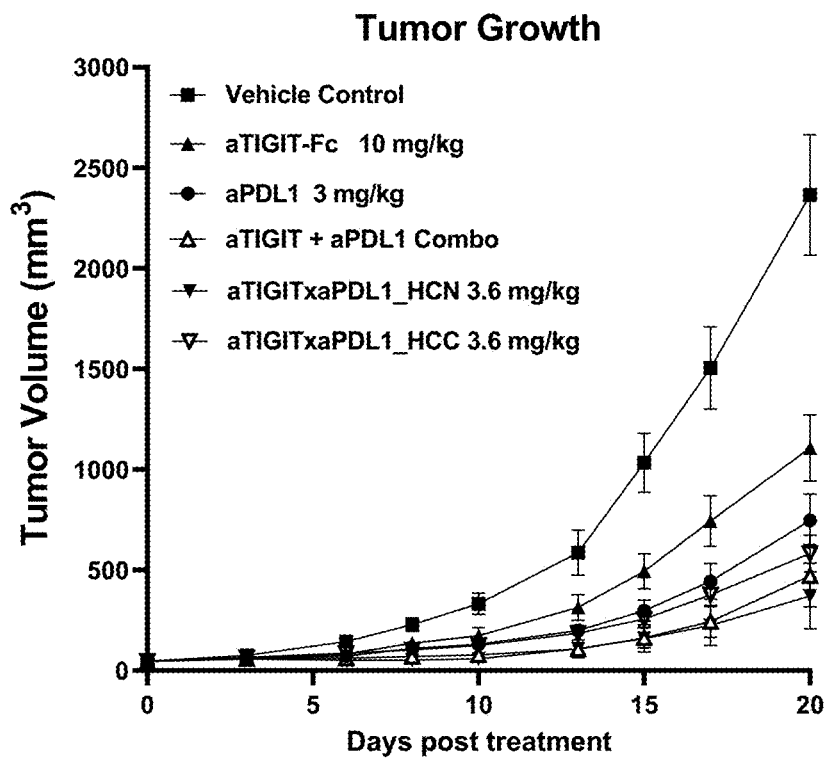
FIGS. 19A and 19B depict in vivo efficacy of BsAbs in MC38 syngeneic tumor model determined using human TIGIT knockin C57BL/6 mice. Mice were inoculated with $0.5 \times 10^6$ MC38 tumor cells subcutaneously one week before treatment. One week later, when the mean tumor size reached approximately 46 mm$^3$, mice were randomly grouped into 6 groups of 8-9 mice/group and treated with vehicle (PBS), anti-TIGIT-Fc (aTIGIT-Fc), anti-PDL1 (aPDL1), combination of aTIGIT-Fc+aPDL1, BsAb HCN or BsAb HCC at dosing shown in figure legends by intraperitoneally (IP). Treatment was performed B.I.W for 6 times in total. and tumor volumes were measured biweekly and shown in Y axis in mm3 in FIG. 19A. Both aTIGIT-Fc and aPDL1 significantly reduced tumor growth. Combo and BsAb HCN were significantly more potent than aPDL1 monotherapy.
Figure 19B:
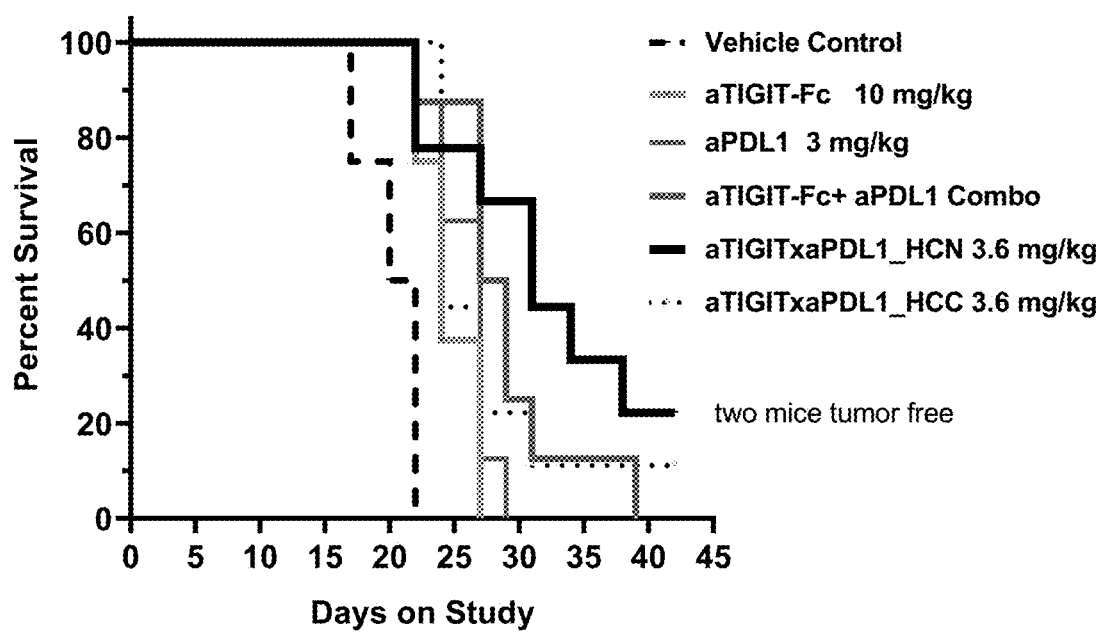
Figure 20A:
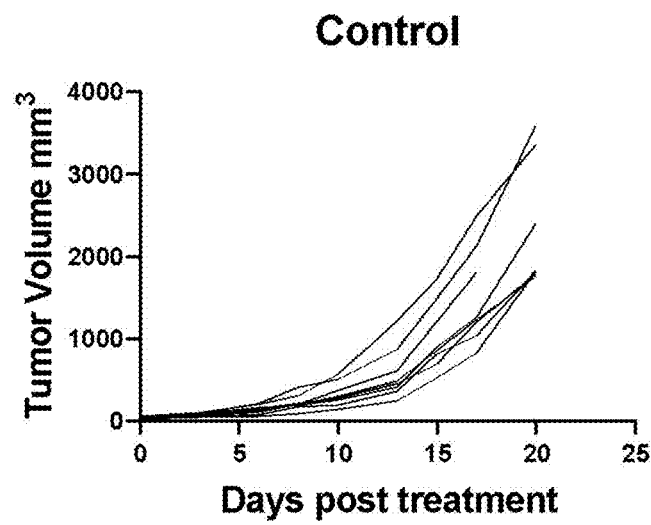
FIGS. 20A-20F depict tumor growth curves of individual animals in the in vivo studies depicted in FIG. 19A.
Figure 20B:
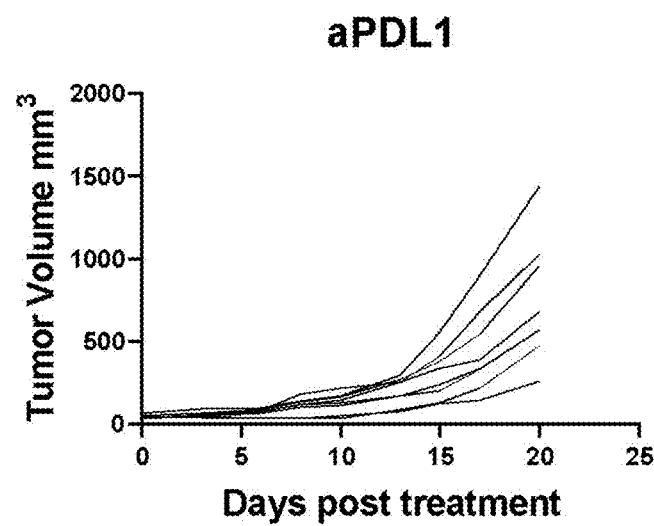
Figure 20C:
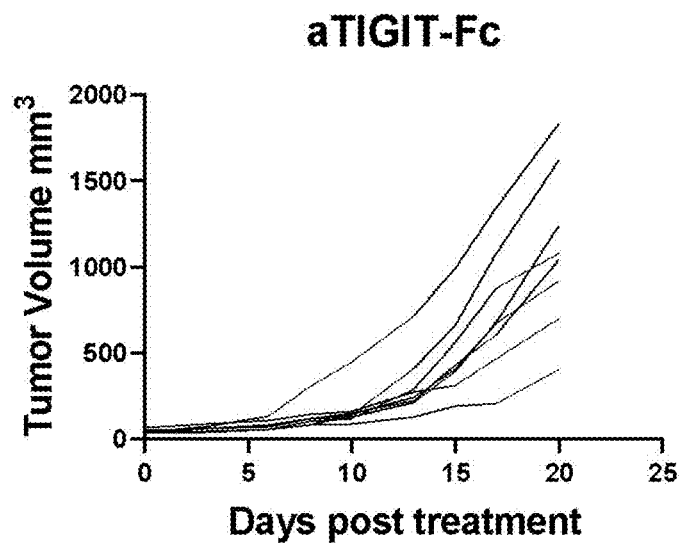
Figure 20D:
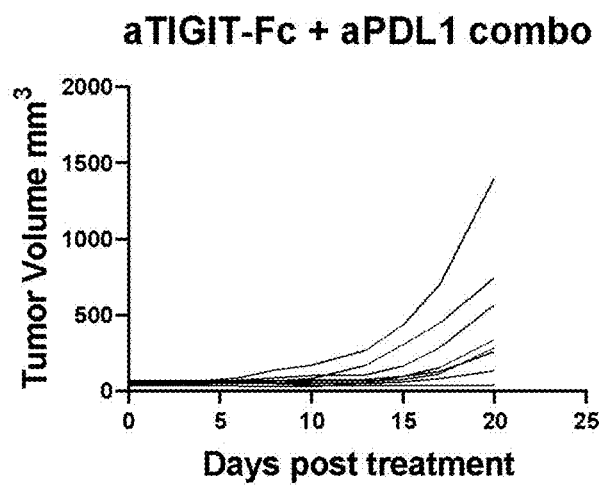
Figure 20E:
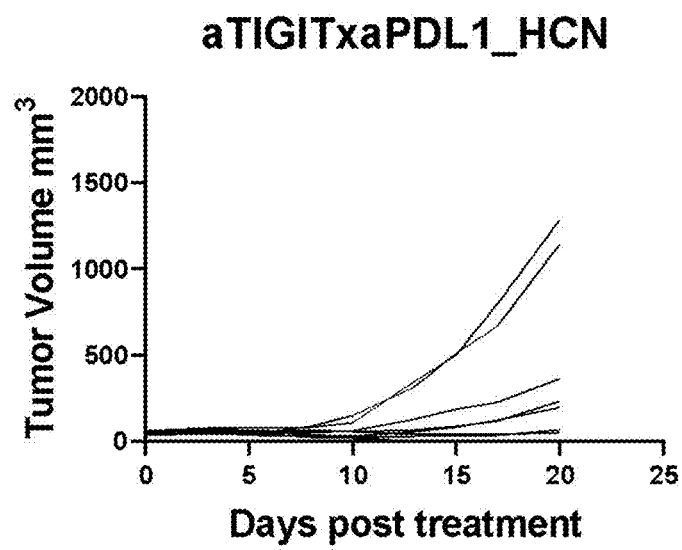
Figure 20F:
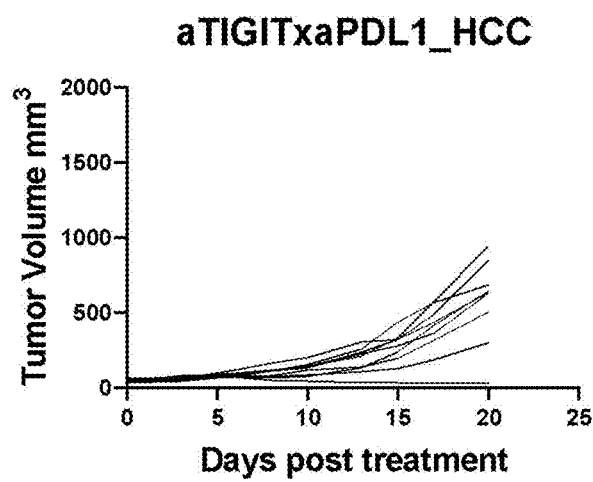

Using h-TIGIT Knock-In mice with MC38 murine colon cancer model, efficacies of BsAb HCN and HCC versions were studied in vivo and compared to anti-PDL1 and anti-TIGIT monotherapy and combination therapy. MC38 tumor cells were implanted one week before treatment. Treatment started when tumor reached about 46 mm$^3$ volume, and drugs were dosed intraperitoneally twice a week for 3 weeks. Both anti-PDL1 and anti-TIGIT monotherapy significantly reduced tumor growth compared to vehicle control with tumor growth inhibition (TGI) of 73% and 52%, respectively at day 17 of post-treatment (Table 5 and FIG. 19A). Combination of anti-PDL1 and anti-TIGIT exhibited higher efficacy compared to monotherapy with TGI of 86% at day 17 post-treatment. BsAbs HCN and HCC also significantly reduced tumor growth with TGI of 88% and 77%, respectively, at day 17 post-treatment. Surprisingly, the treatment with BsAb HCN exhibited significantly improved survival benefit compared to the combination therapy, where complete regression of tumor was observed in two out of nine mice as shown in FIG. 19B. The tumor growth curves of individual animals in the in vivo studies are shown in FIG. 20. No significant difference of body weight was observed among mice from different study groups, indicating the antibodies were well-tolerated.

point inhibitors contribute to immune suppression for tumor immune escape. Gene expression analysis of tumor samples was carried out using RNAseq data from the GEIPA database of Beijing University, which included 9,736 tumors & 8,587 normal tissue samples, which revealed that PVR, the ligand of TIGIT, was highly expressed in many tumor tissues at higher levels than PDL1. Moreover, PVR only co-expressed with PDL1 in a portion of tumor tissues (FIG. 21), whereas in certain tumor tissues only PVR but not PDL1 was expressed, suggesting that PVR plays a broader role in immune suppression for cancer escape. These data indicated that treatment targeting both PDL1 and TIGIT can offer improved antitumor efficacy compared to treatment targeting either molecule.

Figure 21:
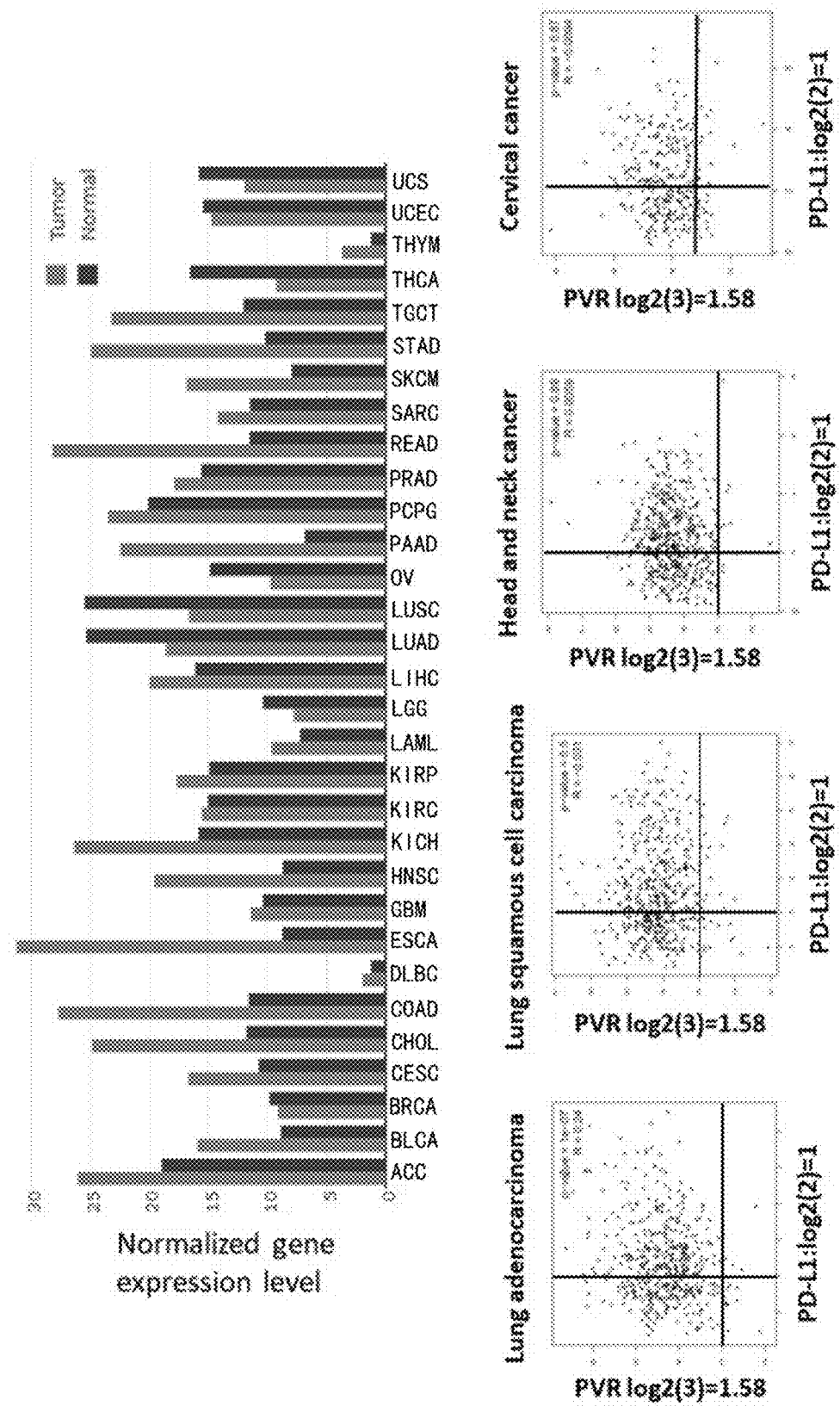
FIG. 21 depicts that TIGIT ligand PVR is highly expressed in many tumor tissues but is only partially co-expressed with PDL1.
Figure 22A:
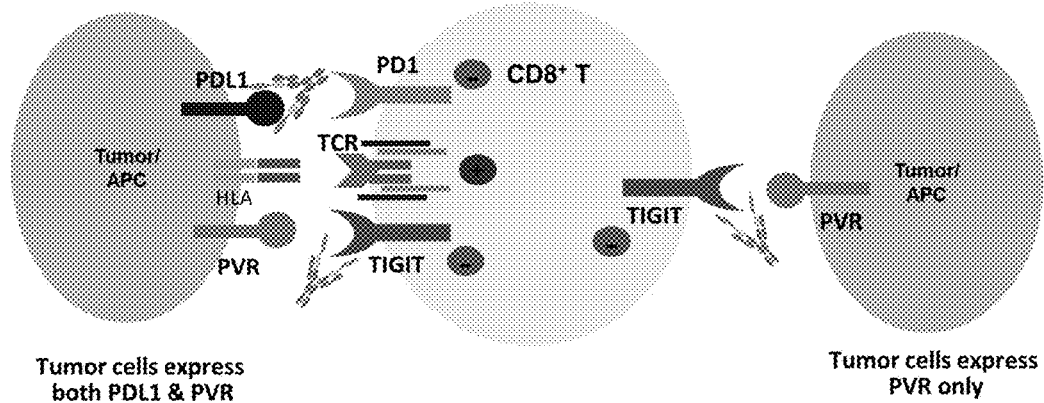
FIGS. 22A-22C depict multiple mechanisms of action of the anti-TIGIT/anti-PDL1 antibodies.

Moreover, bispecific anti-TIGIT/anti-PDL1 antibody can provide superior therapeutic benefits via mechanisms not available to the monotherapy or the combinatory therapy. For example, as illustrated in FIG. 22A, anti-TIGIT/anti-PDL1 BsAb can block inhibitory signals in CD8+ T cells from both PD1 and TIGIT. As the PD1 and TIGIT ligands, PDL1 and PVR, are highly expressed in a portion of tumor tissues as shown in FIG. 21, binding of either PDL1 to PD1 or PVR to TIGIT can suppress TCR signal in CD8+ T cells. As such, blocking PDL1/PD1 and PVR/TIGIT interaction

TABLE 5

Mean Tumor Volumes on Day 17 in MC38 Syngeneic h-TIGIT Mouse Model

| Gps | Treatment | N | TV (mm$^3$)$^a$ | P$^b$ | P$^c$ | P$^d$ | % TGI (Day 17) | Complete Regression |
|---|---|---|---|---|---|---|---|---|
| 1 | Vehicle | 8 | 1504.71 ± 204.73 | — | 0.0003 | 0.0104 | — | 0/8 |
| 2 | Anti-PDL1 | 8 | 444.10 ± 88.56 | 0.0003 | — | 0.1304 | 72.72 | 0/8 |
| 3 | Anti-TIGIT-Fc | 8 | 743.39 ± 126.21 | 0.0104 | 0.1304 | — | 52.20 | 0/8 |
| 4 | aTIGIT-Fc + aPDL1 | 8 | 244.39 ± 79.65 | 0.0002 | 0.083 | 0.007 | 86.40 | 0/8 |
| 5 | aTIGITxaPDL1_HCN | 9 | 224.01 ± 99.68 | <0.0001 | 0.0449 | 0.0078 | 87.79 | 2/9 |
| 6 | aTIGITxaPDL1_HCC | 9 | 375.96 ± 58.92 | <0.0001 | 0.8884 | 0.0111 | 77.36 | 0/9 |

$^a$ Mean ± SEM
$^b$ Compared to vehicle control by Mann-Whitney test on day 17 post-treatment
$^c$ Compared to anti-PDL1 antibody by Mann-Whitney test on day 17 post-treatment
$^d$ Compared to 2A3-Fc by Mann-Whitney test on day 17 post-treatment TIGIT is an immune checkpoint inhibitor similar to PD1 and CTLA4 but has a different expression pattern. It is known that PD1 is expressed at high levels in CD8+ T cells but at low levels in Natural Killer (NK) cells and regulatory T cells (Tregs). In contrast, TIGIT is expressed at high levels in CD8+ T cells, NK cells and Tregs. Both PD1 and TIGIT are up-regulated significantly in tumor infiltrating lymphocytes in tumor tissues, suggesting that both immune checkpoint by the BsAbs can block inhibitory signals from both PD1 and TIGIT and reduce the suppressive effects on immune cells from both PDL1 and PVR double positive tumor cells and antigen presenting cells (APC). In addition, PVR is also expressed in PDL1 negative tumor cells, and the suppressive effect of PVR on CD8+ T cells through binding to TIGIT can also be blocked by the BsAbs.

Figure 22B:
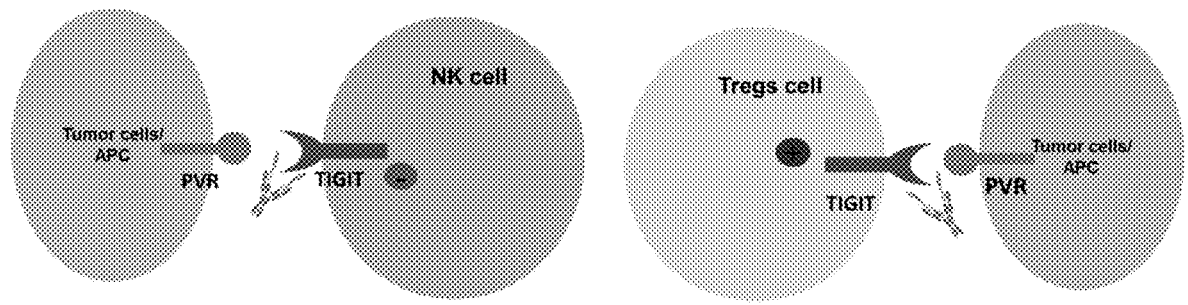

Furthermore, as illustrated in FIG. 22B, anti-TIGIT/anti-PDL1 BsAbs can block inhibitory signal in NK cells and block stimulatory signal in Tregs. PVR expressed on tumor cells or antigen presenting cells (APC) can also bind to TIGIT on NK cells, inducing inhibitory signal and suppressing NK cells function. As such, blocking binding of PVR to TIGIT by the BsAbs can reduce the suppressive effect, leading to enhanced anti-tumor function of NK cells. PVR on tumor cells and APC can also bind to TIGIT on Treg cells, induce stimulatory signal and enhance Tregs function, leading to suppression of anti-tumor activity. As such, blocking TIGIT on Tregs by the BsAbs can reduce Tregs function and enhance anti-tumor activity.

Figure 22C:
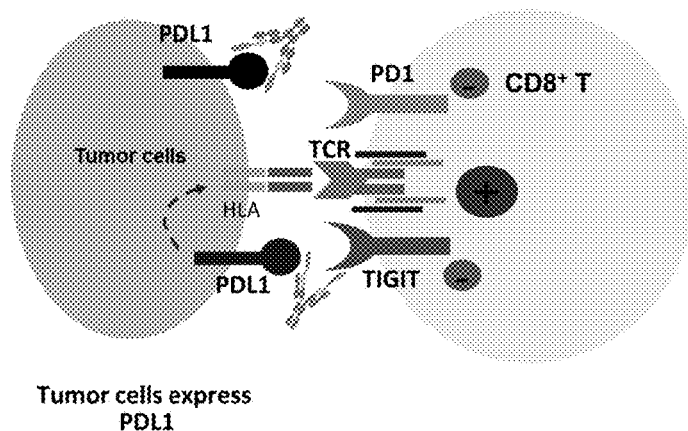

Moreover, anti-TIGITxanti-PDL1 BsAbs can engage T cells towards tumor cells. As illustrated in FIG. 22C, the BsAbs are capable of binding to PDL1 on tumor cells with one arm and binding to TIGIT on T cells with the other arm, and the bridging effect of the BsAb brings CD8+ T cells to the tumor cells, which can lead to enhanced activation of CD8+ T cells, e.g., by increased interaction between HLA-I on the tumor cells and TCRs on the T cells.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the compositions and methods of the disclosed subject matter without departing from the spirit or scope of the disclosed subject matter. Thus, it is intended that the disclosed subject matter include modifications and variations that are within the scope of the appended claims and their equivalents.

Various publications, patents and patent applications are cited herein, the contents of which are hereby incorporated by reference in their entireties.

What is claimed is:

1. A multispecific antibody that binds to T cell immunoreceptor with Ig and ITIM domains (TIGIT) and Programmed cell death ligand-I (PDL1), comprising:
   i) a first antigen-binding moiety comprising an anti-TIGIT antibody comprising a single domain antibody that binds to TIGIT comprising a heavy chain variable region comprising:
   a) a heavy chain variable region CDR1 comprising amino acids having the sequence set forth in SEQ ID NO: 94, a heavy chain variable region CDR2 comprising amino acids having the sequence set forth in SEQ ID NO: 95, and a heavy chain variable region CDR3 comprising amino acids having the sequence set forth in SEQ ID NO: 96,
   b) a heavy chain variable region CDR1 comprising amino acids having the sequence set forth in SEQ ID NO: 98, a heavy chain variable region CDR2 comprising amino acids having the sequence set forth in SEQ ID NO: 99, and a heavy chain variable region CDR3 comprising amino acids having the sequence set forth in SEQ ID NO: 100,
   c) a heavy chain variable region CDR1 comprising amino acids having the sequence set forth in SEQ ID NO: 102, a heavy chain variable region CDR2 comprising amino acids having the sequence set forth in SEQ ID NO: 103, and a heavy chain variable region CDR3 comprising amino acids having the sequence set forth in SEQ ID NO: 104,
   d) a heavy chain variable region CDR1 comprising amino acids having the sequence set forth in SEQ ID NO: 106, a heavy chain variable region CDR2 comprising amino acids having the sequence set forth in SEQ ID NO: 107, and a heavy chain variable region CDR3 comprising amino acids having the sequence set forth in SEQ ID NO: 108,
   e) a heavy chain variable region CDR1 comprising amino acids having the sequence set forth in SEQ ID NO: 110, a heavy chain variable region CDR2 comprising amino acids having the sequence set forth in SEQ ID NO: 111, and a heavy chain variable region CDR3 comprising amino acids having the sequence set forth in SEQ ID NO: 112,
   f) a heavy chain variable region CDR1 comprising amino acids having the sequence set forth in SEQ ID NO: 114, a heavy chain variable region CDR2 comprising amino acids having the sequence set forth in SEQ ID NO: 115, and a heavy chain variable region CDR3 comprising amino acids having the sequence set forth in SEQ ID NO: 116,
   g) a heavy chain variable region CDR1 comprising amino acids having the sequence set forth in SEQ ID NO: 118, a heavy chain variable region CDR2 comprising amino acids having the sequence set forth in SEQ ID NO: 119, and a heavy chain variable region CDR3 comprising amino acids having the sequence set forth in SEQ ID NO: 120,
   h) a heavy chain variable region CDR1 comprising amino acids having the sequence set forth in SEQ ID NO: 122, a heavy chain variable region CDR2 comprising amino acids having the sequence set forth in SEQ ID NO: 123, and a heavy chain variable region CDR3 comprising amino acids having the sequence set forth in SEQ ID NO: 124,
   i) a heavy chain variable region CDR1 comprising amino acids having the sequence set forth in SEQ ID NO: 126, a heavy chain variable region CDR2 comprising amino acids having the sequence set forth in SEQ ID NO: 127, and a heavy chain variable region CDR3 comprising amino acids having the sequence set forth in SEQ ID NO: 128,
   j) a heavy chain variable region CDR1 comprising amino acids having the sequence set forth in SEQ ID NO: 130, a heavy chain variable region CDR2 comprising amino acids having the sequence set forth in SEQ ID NO: 131, and a heavy chain variable region CDR3 comprising amino acids having the sequence set forth in SEQ ID NO: 132,
   k) a heavy chain variable region CDR1 comprising amino acids having the sequence set forth in SEQ ID NO: 134, a heavy chain variable region CDR2 comprising amino acids having the sequence set forth in SEQ ID NO: 135, and a heavy chain variable region CDR3 comprising amino acids having the sequence set forth in SEQ ID NO: 136,
   l) a heavy chain variable region CDR1 comprising amino acids having the sequence set forth in SEQ ID NO: 138, a heavy chain variable region CDR2 comprising amino acids having the sequence set forth in SEQ ID NO: 139, and a heavy chain variable region CDR3 comprising amino acids having the sequence set forth in SEQ ID NO: 140,
   m) a heavy chain variable region CDR1 comprising amino acids having the sequence set forth in SEQ ID NO: 142, a heavy chain variable region CDR2 comprising amino acids having the sequence set forth in SEQ ID NO: 143, and a heavy chain variable region CDR3 comprising amino acids having the sequence set forth in SEQ ID NO: 144,
   n) a heavy chain variable region CDR1 comprising amino acids having the sequence set forth in SEQ ID NO: 146, a heavy chain variable region CDR2 comprising amino acids having the sequence set forth in SEQ ID NO: 147, and a heavy chain variable region CDR3 comprising amino acids having the sequence set forth in SEQ ID NO: 148, o) a heavy chain variable region CDR1 comprising amino acids having the sequence set forth in SEQ ID NO: 150, a heavy chain variable region CDR2 comprising amino acids having the sequence set forth in SEQ ID NO: 151, and a heavy chain variable region CDR3 comprising amino acids having the sequence set forth in SEQ ID NO: 152, p) a heavy chain variable region CDR1 comprising amino acids having the sequence set forth in SEQ ID NO: 154, a heavy chain variable region CDR2 comprising amino acids having the sequence set forth in SEQ ID NO: 155, and a heavy chain variable region CDR3 comprising amino acids having the sequence set forth in SEQ ID NO: 156, q) a heavy chain variable region CDR1 comprising amino acids having the sequence set forth in SEQ ID NO: 158, a heavy chain variable region CDR2 comprising amino acids having the sequence set forth in SEQ ID NO: 159, and a heavy chain variable region CDR3 comprising amino acids having the sequence set forth in SEQ ID NO: 160, r) a heavy chain variable region CDR1 comprising amino acids having the sequence set forth in SEQ ID NO: 162, a heavy chain variable region CDR2 comprising amino acids having the sequence set forth in SEQ ID NO: 163, and a heavy chain variable region CDR3 comprising amino acids having the sequence set forth in SEQ ID NO: 164, s) a heavy chain variable region CDR1 comprising amino acids having the sequence set forth in SEQ ID NO: 166, a heavy chain variable region CDR2 comprising amino acids having the sequence set forth in SEQ ID NO: 167, and a heavy chain variable region CDR3 comprising amino acids having the sequence set forth in SEQ ID NO: 168, t) a heavy chain variable region CDR1 comprising amino acids having the sequence set forth in SEQ ID NO: 170, a heavy chain variable region CDR2 comprising amino acids having the sequence set forth in SEQ ID NO: 171, and a heavy chain variable region CDR3 comprising amino acids having the sequence set forth in SEQ ID NO: 172, u) a heavy chain variable region CDR1 comprising amino acids having the sequence set forth in SEQ ID NO: 174, a heavy chain variable region CDR2 comprising amino acids having the sequence set forth in SEQ ID NO: 175, and a heavy chain variable region CDR3 comprising amino acids having the sequence set forth in SEQ ID NO: 176, v) a heavy chain variable region CDR1 comprising amino acids having the sequence set forth in SEQ ID NO: 178, a heavy chain variable region CDR2 comprising amino acids having the sequence set forth in SEQ ID NO: 179, and a heavy chain variable region CDR3 comprising amino acids having the sequence set forth in SEQ ID NO: 180, w) a heavy chain variable region CDR1 comprising amino acids having the sequence set forth in SEQ ID NO: 182, a heavy chain variable region CDR2 comprising amino acids having the sequence set forth in SEQ ID NO: 183, and a heavy chain variable region CDR3 comprising amino acids having the sequence set forth in SEQ ID NO: 184, x) a heavy chain variable region CDR1 comprising amino acids having the sequence set forth in SEQ ID NO: 186, a heavy chain variable region CDR2 comprising amino acids having the sequence set forth in SEQ ID NO: 187, and a heavy chain variable region CDR3 comprising amino acids having the sequence set forth in SEQ ID NO: 188, or y) a heavy chain variable region CDR1 comprising amino acids having the sequence set forth in SEQ ID NO: 190, a heavy chain variable region CDR2 comprising amino acids having the sequence set forth in SEQ ID NO: 191, and a heavy chain variable region CDR3 comprising amino acids having the sequence set forth in SEQ ID NO: 192; and ii) a second antigen-binding moiety comprising an anti-PDL1 antibody that binds to PDL1, wherein the second antigen-binding moiety comprises:

a) a heavy chain variable domain (VH) sequence comprising (1) a CDR-H1 comprising the amino acid sequence set forth in SEQ ID NO: 221, (2) a CDR-H2 comprising the amino acid sequence set forth in SEQ ID NO: 222, and (3) a CDR-H3 comprising the amino acid sequence set forth in SEQ ID NO: 223; and a light chain variable domain (VL) sequence comprising (1) a CDR-L1 comprising the amino acid sequence set forth in SEQ ID NO: 224, (2) a CDR-L2 comprising the amino acid sequence set forth in SEQ ID NO: 225, and (3) a CDR-L3 comprising the amino acid sequence set forth in SEQ ID NO: 226, b) a heavy chain variable domain (VH) sequence comprising (1) a CDR-H1 comprising the amino acid sequence set forth in SEQ ID NO: 229, (2) a CDR-H2 comprising the amino acid sequence set forth in SEQ ID NO: 230, and (3) a CDR-H3 comprising the amino acid sequence set forth in SEQ ID NO: 231; and a light chain variable domain (VL) sequence comprising (1) a CDR-L1 comprising the amino acid sequence set forth in SEQ ID NO: 232, (2) a CDR-L2 comprising the amino acid sequence set forth in SEQ ID NO: 233, and (3) a CDR-L3 comprising the amino acid sequence set forth in SEQ ID NO: 234, c) a heavy chain variable domain (VH) sequence comprising (1) a CDR-H1 comprising the amino acid sequence set forth in SEQ ID NO: 237, (2) a CDR-H2 comprising the amino acid sequence set forth in SEQ ID NO: 238, and (3) a CDR-H3 comprising the amino acid sequence set forth in SEQ ID NO: 239; and a light chain variable domain (VL) sequence comprising (1) a CDR-L1 comprising the amino acid sequence set forth in SEQ ID NO: 240, (2) a CDR-L2 comprising the amino acid sequence set forth in SEQ ID NO: 241, and (3) a CDR-L3 comprising the amino acid sequence set forth in SEQ ID NO: 242, d) a heavy chain variable domain (VH) sequence comprising (1) a CDR-H1 comprising the amino acid sequence set forth in SEQ ID NO: 245, (2) a CDR-H2 comprising the amino acid sequence set forth in SEQ ID NO: 246, and (3) a CDR-H3 comprising the amino acid sequence set forth in SEQ ID NO: 247; and a light chain variable domain (VL) sequence comprising (1) a CDR-L1 comprising the amino acid sequence set forth in SEQ ID NO: 248, (2) a CDR-L2 comprising the amino acid sequence set forth in SEQ ID NO: 249, and (3) a CDR-L3 comprising the amino acid sequence set forth in SEQ ID NO: 250, e) a heavy chain variable domain (VH) sequence comprising (1) a CDR-H1 comprising the amino acid sequence set forth in SEQ ID NO: 253, (2) a CDR-H2 comprising the amino acid sequence set forth in SEQ ID NO: 254, and (3) a CDR-H3 comprising the amino acid sequence set forth in SEQ ID NO: 255; and a light chain variable domain (VL) sequence comprising (1) a CDR-L1 comprising the amino acid sequence set forth in SEQ ID NO: 256, (2) a CDR-L2 comprising the amino acid sequence set forth in SEQ ID NO: 257, and (3) a CDR-L3 comprising the amino acid sequence set forth in SEQ ID NO: 258, f) a heavy chain variable domain (VH) sequence comprising (1) a CDR-H1 comprising the amino acid sequence set forth in SEQ ID NO: 261, (2) a CDR-H2 comprising the amino acid sequence set forth in SEQ ID NO: 262, and (3) a CDR-H3 comprising the amino acid sequence set forth in SEQ ID NO: 263; and a light chain variable domain (VL) sequence comprising (1) a CDR-L1 comprising the amino acid sequence set forth in SEQ ID NO: 264, (2) a CDR-L2 comprising the amino acid sequence set forth in SEQ ID NO: 265, and (3) a CDR-L3 comprising the amino acid sequence set forth in SEQ ID NO: 266, g) a heavy chain variable domain (VH) sequence comprising (1) a CDR-H1 comprising the amino acid sequence set forth in SEQ ID NO: 269, (2) a CDR-H2 comprising the amino acid sequence set forth in SEQ ID NO: 270, and (3) a CDR-H3 comprising the amino acid sequence set forth in SEQ ID NO: 271; and a light chain variable domain (VL) sequence comprising (1) a CDR-L1 comprising the amino acid sequence set forth in SEQ ID NO: 272, (2) a CDR-L2 comprising the amino acid sequence set forth in SEQ ID NO: 273, and (3) a CDR-L3 comprising the amino acid sequence set forth in SEQ ID NO: 274, h) a heavy chain variable domain (VH) sequence comprising (1) a CDR-H1 comprising the amino acid sequence set forth in SEQ ID NO: 277, (2) a CDR-H2 comprising the amino acid sequence set forth in SEQ ID NO: 278, and (3) a CDR-H3 comprising the amino acid sequence set forth in SEQ ID NO: 279; and a light chain variable domain (VL) sequence comprising (1) a CDR-L1 comprising the amino acid sequence set forth in SEQ ID NO: 280, (2) a CDR-L2 comprising the amino acid sequence set forth in SEQ ID NO: 281, and (3) a CDR-L3 comprising the amino acid sequence set forth in SEQ ID NO: 282, i) a heavy chain variable domain (VH) sequence comprising (1) a CDR-H1 comprising the amino acid sequence set forth in SEQ ID NO: 285, (2) a CDR-H2 comprising the amino acid sequence set forth in SEQ ID NO: 286, and (3) a CDR-H3 comprising the amino acid sequence set forth in SEQ ID NO: 287; and a light chain variable domain (VL) sequence comprising (1) a CDR-L1 comprising the amino acid sequence set forth in SEQ ID NO: 288, (2) a CDR-L2 comprising the amino acid sequence set forth in SEQ ID NO: 289, and (3) a CDR-L3 comprising the amino acid sequence set forth in SEQ ID NO: 290, or i) a heavy chain variable domain (VH) sequence comprising (1) a CDR-H1 comprising the amino acid sequence set forth in SEQ ID NO: 293, (2) a CDR-H2 comprising the amino acid sequence set forth in SEQ ID NO: 294, and (3) a CDR-H3 comprising the amino acid sequence set forth in SEQ ID NO: 295; and a light chain variable domain (VL) sequence comprising (1) a CDR-L1 comprising the amino acid sequence set forth in SEQ ID NO: 296, (2) a CDR-L2 comprising the amino acid sequence set forth in SEQ ID NO: 297, and (3) a CDR-L3 comprising the amino acid sequence set forth in SEQ ID NO: 298.

2. The multispecific antibody of claim 1, wherein the single domain antibody comprises a heavy chain variable region CDR1 comprising amino acids having the sequence set forth in SEQ ID NO: 94, a heavy chain variable region CDR2 comprising amino acids having the sequence set forth in SEQ ID NO: 95, and a heavy chain variable region CDR3 comprising amino acids having the sequence set forth in SEQ ID NO: 96.

3. The multispecific antibody of claim 1, wherein the single domain antibody comprises a heavy chain variable region comprising the amino acid sequence selected from the group consisting of SEQ ID NOs: 97, 101, 105, 109, 113, 117, 121, 125, 129, 133, 137, 141, 145, 149, 153, 157, 161, 165, 169, 173, 177, 181, 185, 189 and 193.

4. The multispecific antibody of claim 1, wherein the single domain antibody comprises a heavy chain variable region comprising the amino acid sequence set forth in SEQ ID NO: 97.

5. The multispecific antibody of claim 1, wherein the second antigen-binding moiety comprises a heavy chain variable domain (VH) sequence comprising (1) a CDR-H1 comprising the amino acid sequence set forth in SEQ ID NO: 293, (2) a CDR-H2 comprising the amino acid sequence set forth in SEQ ID NO: 294, and (3) a CDR-H3 comprising the amino acid sequence set forth in SEQ ID NO: 295; and a light chain variable domain (VL) sequence comprising (1) a CDR-L1 comprising the amino acid sequence set forth in SEQ ID NO: 296, (2) a CDR-L2 comprising the amino acid sequence set forth in SEQ ID NO: 297, and (3) a CDR-L3 comprising the amino acid sequence set forth in SEQ ID NO: 298.

6. The multispecific antibody of claim 1, wherein the anti-PDL1 antibody of the second antigen-binding moiety comprises an Fc region selected from the group consisting of the Fc region of IgG1, IgG2, IgG3 and IgG4.

7. The multispecific antibody of claim 6, wherein the Fc region comprises an IgG1 Fc region.

8. The multispecific antibody of claim 1, wherein the multispecific antibody is a bispecific antibody.

9. The multispecific antibody of claim 1, comprising:
i) a first antigen-binding moiety comprising a single domain anti-TIGIT antibody that comprises a heavy chain variable region CDR1 comprising amino acids having the sequence set forth in SEQ ID NO: 94, a heavy chain variable region CDR2 comprising amino acids having the sequence set forth in SEQ ID NO: 95, and a heavy chain variable region CDR3 comprising amino acids having the sequence set forth in SEQ ID NO: 96; and
ii) a second antigen-binding moiety comprising an anti-PDL1 antibody comprising a heavy chain variable domain (VH) sequence that comprises (1) a CDR-H1 comprising the amino acid sequence set forth in SEQ ID NO: 293, (2) a CDR-H2 comprising the amino acid sequence set forth in SEQ ID NO: 294, and (3) a CDR-H3 comprising the amino acid sequence set forth in SEQ ID NO: 295; and a light chain variable domain (VL) sequence comprising (1) a CDR-L1 comprising the amino acid sequence set forth in SEQ ID NO: 296, (2) a CDR-L2 comprising the amino acid sequence set forth in SEQ ID NO: 297, and (3) a CDR-L3 comprising the amino acid sequence set forth in SEQ ID NO: 298.

10. The multispecific antibody of claim 1, comprising an anti-PDL1 antibody heavy chain linked to an anti-TIGIT antibody comprising the amino acid sequence set forth in SEQ ID NO: 309, and an anti-PDL1 antibody light chain comprising the amino acid sequence set forth in SEQ ID NO: 310.

11. The multispecific antibody of claim 1, comprising an anti-PDL1 antibody heavy chain linked to an anti-TIGIT antibody comprising the amino acid sequence set forth in SEQ ID NO: 313, and an anti-PDL1 antibody light chain comprising the amino acid sequence set forth in SEQ ID NO: 314.

12. An immunoconjugate comprising the multispecific antibody of claim 1, wherein the therapeutic agent is a cytotoxin or a radioactive isotope.

13. A pharmaceutical composition comprising a) the multispecific antibody of claim 1 and b) a pharmaceutically acceptable carrier.

14. A nucleic acid encoding the multispecific antibody of claim 1.

15. A vector comprising the nucleic acid of claim 14.

16. A host cell comprising the nucleic acid of claim 14.

17. A method for preparing an multispecific antibody of claim 1 comprising expressing the multispecific antibody in a host cell comprising the nucleic acid encoding the multispecific antibody of claim 1 and isolating the multispecific antibody from the host cell.

18. A method of reducing tumor burden in a subject, the method comprising administering to the subject an effective amount of the pharmaceutical composition of claim 13.

19. A method of treating a neoplasm, the method comprising administering to the subject an effective amount of the pharmaceutical composition of claim 13.

20. A method of prolonging survival of a subject having a neoplasm, the method comprising administering to the subject an effective amount of the pharmaceutical composition of claim 13.

21. A kit comprising a multispecific antibody of claim 1.

* * * * *

```
                        SEQUENCE LISTING

Sequence total quantity: 318
SEQ ID NO: 1            moltype = AA  length = 8
FEATURE                 Location/Qualifiers
DOMAIN                  1..8
                        note = 4A11 CDR1
source                  1..8
                        mol_type = protein
                        organism = synthetic construct
SEQUENCE: 1
GRPFSNYT                                                                  8

SEQ ID NO: 2            moltype = AA  length = 7
FEATURE                 Location/Qualifiers
DOMAIN                  1..7
                        note = 4A11 CDR2
source                  1..7
                        mol_type = protein
                        organism = synthetic construct
SEQUENCE: 2
AWPSPST                                                                   7

SEQ ID NO: 3            moltype = AA  length = 18
FEATURE                 Location/Qualifiers
DOMAIN                  1..18
                        note = 4A11 CDR3
source                  1..18
                        mol_type = protein
                        organism = synthetic construct
SEQUENCE: 3
AADYKSLTQS WLNAALDY                                                       18

SEQ ID NO: 4            moltype = AA  length = 124
FEATURE                 Location/Qualifiers
DOMAIN                  1..124
                        note = 4A11 VHH
source                  1..124
                        mol_type = protein
                        organism = synthetic construct
SEQUENCE: 4
QVKLEESGGG EAQPGGSLRL SCTASGRPFS NYTMGWFRRA PGKEREFVGL AWPSPSTYVV  60
DSVKGRFTIS RDNAKNTIYL QMNSLKPEDT AIYYCAADYK SLTQSWLNAA LDYWGQGTQV  120
TVSS                                                              124

SEQ ID NO: 5            moltype = AA  length = 8
FEATURE                 Location/Qualifiers
DOMAIN                  1..8
                        note = 4B5 CDR1
source                  1..8
                        mol_type = protein
```

-continued

```
                                    organism = synthetic construct
SEQUENCE: 5
PRTFSTFH                                                                       8

SEQ ID NO: 6            moltype = AA   length = 8
FEATURE                 Location/Qualifiers
DOMAIN                  1..8
                        note = 4B5 CDR2
source                  1..8
                        mol_type = protein
                        organism = synthetic construct
SEQUENCE: 6
FNWSGGRT                                                                       8

SEQ ID NO: 7            moltype = AA   length = 26
FEATURE                 Location/Qualifiers
DOMAIN                  1..26
                        note = 4B5 CDR3
source                  1..26
                        mol_type = protein
                        organism = synthetic construct
SEQUENCE: 7
AAARDRGLHD GTTSDSYLEG SHEYEY                                                  26

SEQ ID NO: 8            moltype = AA   length = 133
FEATURE                 Location/Qualifiers
DOMAIN                  1..133
                        note = 4B5 VHH
source                  1..133
                        mol_type = protein
                        organism = synthetic construct
SEQUENCE: 8
QVKLEESGGR SVLAGGSLRL RCAGTPRTFS TFHIGWFRQA PGKEREFVAA FNWSGGRTYY              60
ADSVKGRFTI SRNNGKNMVY LQMTSLTPED TGLYYCAAAR DRGLHDGTTS DSYLEGSHEY             120
EYWGQGTQVT VSS                                                               133

SEQ ID NO: 9            moltype = AA   length = 8
FEATURE                 Location/Qualifiers
DOMAIN                  1..8
                        note = 4C5 CDR1
source                  1..8
                        mol_type = protein
                        organism = synthetic construct
SEQUENCE: 9
GRSVSTYF                                                                       8

SEQ ID NO: 10           moltype = AA   length = 8
FEATURE                 Location/Qualifiers
DOMAIN                  1..8
                        note = 4C5 CDR2
source                  1..8
                        mol_type = protein
                        organism = synthetic construct
SEQUENCE: 10
IDRGSTVT                                                                       8

SEQ ID NO: 11           moltype = AA   length = 17
FEATURE                 Location/Qualifiers
DOMAIN                  1..17
                        note = 4C5 CDR3
source                  1..17
                        mol_type = protein
                        organism = synthetic construct
SEQUENCE: 11
AAKAITRNFI ATNDYDY                                                            17

SEQ ID NO: 12           moltype = AA   length = 124
FEATURE                 Location/Qualifiers
DOMAIN                  1..124
                        note = 4C5 VHH
source                  1..124
                        mol_type = protein
                        organism = synthetic construct
SEQUENCE: 12
QVQLVDSGGG LVQAGGSLRL SCAVSGRSVS TYFVGWFRQA PGKEREFVAA IDRGSTVTRY              60
DDSVKGRFTI SRDNAKDTVY LQMNSLKPED TAVYYCAAKA ITRNFIATND YDWGQGTQV              120
TVSS                                                                         124

SEQ ID NO: 13           moltype = AA   length = 8
```

```
FEATURE                 Location/Qualifiers
DOMAIN                  1..8
                        note = 4D5 CDR1
source                  1..8
                        mol_type = protein
                        organism = synthetic construct
SEQUENCE: 13
GRAFNEYA                                                                 8

SEQ ID NO: 14           moltype = AA  length = 8
FEATURE                 Location/Qualifiers
DOMAIN                  1..8
                        note = 4D5 CDR2
source                  1..8
                        mol_type = protein
                        organism = synthetic construct
SEQUENCE: 14
ISSDGRFT                                                                 8

SEQ ID NO: 15           moltype = AA  length = 18
FEATURE                 Location/Qualifiers
DOMAIN                  1..18
                        note = 4D5 CDR3
source                  1..18
                        mol_type = protein
                        organism = synthetic construct
SEQUENCE: 15
AARDSGSGYY SRAQWYDY                                                      18

SEQ ID NO: 16           moltype = AA  length = 125
FEATURE                 Location/Qualifiers
DOMAIN                  1..125
                        note = 4D5 VHH
source                  1..125
                        mol_type = protein
                        organism = synthetic construct
SEQUENCE: 16
VDSGGGAVKA GDSLRLVCSA PGRTHGRAFN EYAMAWFRQG PGKERESVAA ISSDGRFTYY         60
AASVKGRFTI SKDNAKSAAF LQMNSLKPED TAVYYCAARD SGSGYYSRAQ WYDYWGQGTQ        120
VTVSS                                                                   125

SEQ ID NO: 17           moltype = AA  length = 8
FEATURE                 Location/Qualifiers
DOMAIN                  1..8
                        note = 4D11 CDR1
source                  1..8
                        mol_type = protein
                        organism = synthetic construct
SEQUENCE: 17
GSISSINA                                                                 8

SEQ ID NO: 18           moltype = AA  length = 7
FEATURE                 Location/Qualifiers
DOMAIN                  1..7
                        note = 4D11 CDR2
source                  1..7
                        mol_type = protein
                        organism = synthetic construct
SEQUENCE: 18
ITNSGST                                                                  7

SEQ ID NO: 19           moltype = AA  length = 10
FEATURE                 Location/Qualifiers
DOMAIN                  1..10
                        note = 4D11 CDR3
source                  1..10
                        mol_type = protein
                        organism = synthetic construct
SEQUENCE: 19
TARRSTWYIS                                                              10

SEQ ID NO: 20           moltype = AA  length = 116
FEATURE                 Location/Qualifiers
DOMAIN                  1..116
                        note = 4D11 VHH
source                  1..116
                        mol_type = protein
                        organism = synthetic construct
SEQUENCE: 20
```

```
QVQLQESGGG LVQPGGSLRL SCAASGSISS INAMGWYRLA PGKHREFVAD ITNSGSTNYA    60
ASVKGRFNIS RDNAKDTVYL QMNSLKFEDT AVYYCTARRS TWYISSGRGT QVTVSS       116

SEQ ID NO: 21           moltype = AA   length = 8
FEATURE                 Location/Qualifiers
DOMAIN                  1..8
                        note = 4E5 CDR1
source                  1..8
                        mol_type = protein
                        organism = synthetic construct
SEQUENCE: 21
GLTSSDIA                                                              8

SEQ ID NO: 22           moltype = AA   length = 8
FEATURE                 Location/Qualifiers
DOMAIN                  1..8
                        note = 4E5 CDR2
source                  1..8
                        mol_type = protein
                        organism = synthetic construct
SEQUENCE: 22
ISSDGRFT                                                              8

SEQ ID NO: 23           moltype = AA   length = 18
FEATURE                 Location/Qualifiers
DOMAIN                  1..18
                        note = 4E5 CDR3
source                  1..18
                        mol_type = protein
                        organism = synthetic construct
SEQUENCE: 23
AARDSGSGYY SRAQWYDY                                                  18

SEQ ID NO: 24           moltype = AA   length = 125
FEATURE                 Location/Qualifiers
DOMAIN                  1..125
                        note = 4E5 VHH
source                  1..125
                        mol_type = protein
                        organism = synthetic construct
SEQUENCE: 24
QVQLVDSGGG VVEVGASLTL SCETSGLTSS DIAVGWFRQG PGKERESVAA ISSDGRFTYY    60
AASVKGRFTI SKDNAKSAAF LQMNSLKPED TAVYYCAARD SGSGYYSRAQ WYDYWGQGTQ   120
VTVSS                                                               125

SEQ ID NO: 25           moltype = AA   length = 8
FEATURE                 Location/Qualifiers
DOMAIN                  1..8
                        note = 4H6 CDR1
source                  1..8
                        mol_type = protein
                        organism = synthetic construct
SEQUENCE: 25
GTIFRLNR                                                              8

SEQ ID NO: 26           moltype = AA   length = 8
FEATURE                 Location/Qualifiers
DOMAIN                  1..8
                        note = 4H6 CDR2
source                  1..8
                        mol_type = protein
                        organism = synthetic construct
SEQUENCE: 26
TIWSGRRT                                                              8

SEQ ID NO: 27           moltype = AA   length = 14
FEATURE                 Location/Qualifiers
DOMAIN                  1..14
                        note = 4H6 CDR3
source                  1..14
                        mol_type = protein
                        organism = synthetic construct
SEQUENCE: 27
NYRRITPWEA SGNY                                                      14

SEQ ID NO: 28           moltype = AA   length = 121
FEATURE                 Location/Qualifiers
DOMAIN                  1..121
                        note = 4H6 VHH
```

```
source                  1..121
                        mol_type = protein
                        organism = synthetic construct
SEQUENCE: 28
QVQLVESGGG LATAGASLIL SCAASGTIFR LNRMGWFRQA PGKERERVAA TIWSGRRTHY    60
ADSVKGRFTI STDNAKKTVY LRMSSLKPED TAVYYCNYRR ITPWEASGNY WGQGTQVTVS   120
S                                                                   121

SEQ ID NO: 29           moltype = AA   length = 8
FEATURE                 Location/Qualifiers
DOMAIN                  1..8
                        note = 4H9 CDR1
source                  1..8
                        mol_type = protein
                        organism = synthetic construct
SEQUENCE: 29
GPIARSRS                                                              8

SEQ ID NO: 30           moltype = AA   length = 10
FEATURE                 Location/Qualifiers
DOMAIN                  1..10
                        note = 4H9 CDR2
source                  1..10
                        mol_type = protein
                        organism = synthetic construct
SEQUENCE: 30
AAISSDGRFT                                                           10

SEQ ID NO: 31           moltype = AA   length = 18
FEATURE                 Location/Qualifiers
DOMAIN                  1..18
                        note = 4H9 CDR3
source                  1..18
                        mol_type = protein
                        organism = synthetic construct
SEQUENCE: 31
AARDSGSGYY SRAQWYDY                                                  18

SEQ ID NO: 32           moltype = AA   length = 127
FEATURE                 Location/Qualifiers
DOMAIN                  1..127
                        note = 4H9 VHH
source                  1..127
                        mol_type = protein
                        organism = synthetic construct
SEQUENCE: 32
QVQLVESGGG AVQAGGSLRL SCTASGPIAR SRSTGMGWFR QGPGKERESV AAISSDGRFT    60
YYAASVKGRF TISKDNAKSA AFLQMNSLKP EDTAVYYCAA RDSGSGYYSR AQWYDYWGQG   120
TQVTVSS                                                             127

SEQ ID NO: 33           moltype = AA   length = 8
FEATURE                 Location/Qualifiers
DOMAIN                  1..8
                        note = 10H5 CDR1
source                  1..8
                        mol_type = protein
                        organism = synthetic construct
SEQUENCE: 33
ETTFKSMA                                                              8

SEQ ID NO: 34           moltype = AA   length = 8
FEATURE                 Location/Qualifiers
DOMAIN                  1..8
                        note = 10H5 CDR2
source                  1..8
                        mol_type = protein
                        organism = synthetic construct
SEQUENCE: 34
TNYNGGRT                                                              8

SEQ ID NO: 35           moltype = AA   length = 17
FEATURE                 Location/Qualifiers
DOMAIN                  1..17
                        note = 10H5 CDR3
source                  1..17
                        mol_type = protein
                        organism = synthetic construct
SEQUENCE: 35
AAKATEGTTF PSRTYEF                                                   17
```

```
SEQ ID NO: 36            moltype = AA   length = 124
FEATURE                  Location/Qualifiers
DOMAIN                   1..124
                         note = 10H5 VHH
source                   1..124
                         mol_type = protein
                         organism = synthetic construct
SEQUENCE: 36
GGGLVQAGGS LRLACTASDP PFANYETTFK SMAMGWVRHI PGKERELVAA TNYNGGRTWY    60
SNSAKARSTI SRDNAKNTVY LQMSSLKPED TAVYYCAAKA TEGTTFPSRT YEFWGQGIQV   120
TVSS                                                                124

SEQ ID NO: 37            moltype = AA   length = 8
FEATURE                  Location/Qualifiers
DOMAIN                   1..8
                         note = 12H7 CDR1
source                   1..8
                         mol_type = protein
                         organism = synthetic construct
SEQUENCE: 37
GNFLSVSD                                                              8

SEQ ID NO: 38            moltype = AA   length = 7
FEATURE                  Location/Qualifiers
DOMAIN                   1..7
                         note = 12H7 CDR2
source                   1..7
                         mol_type = protein
                         organism = synthetic construct
SEQUENCE: 38
VTEHGRT                                                               7

SEQ ID NO: 39            moltype = AA   length = 20
FEATURE                  Location/Qualifiers
DOMAIN                   1..20
                         note = 12H7 CDR3
source                   1..20
                         mol_type = protein
                         organism = synthetic construct
SEQUENCE: 39
KASDVFTDAG AHEAVLIRDY                                                20

SEQ ID NO: 40            moltype = AA   length = 126
FEATURE                  Location/Qualifiers
DOMAIN                   1..126
                         note = 12H7 VHH
source                   1..126
                         mol_type = protein
                         organism = synthetic construct
SEQUENCE: 40
QVQLVDSGGG LVQAGGSLRL SCKVSGNFLS VSDMSWYRQA PGMERDVVAT VTEHGRTTYT    60
DSVKGRFTIS RDNAEHTTYL EMNNLKPEDT AVYFCKASDV FTDAGAHEAV LIRDYWGQGT   120
QVTVSS                                                              126

SEQ ID NO: 41            moltype = AA   length = 8
FEATURE                  Location/Qualifiers
DOMAIN                   1..8
                         note = 13H11 CDR1
source                   1..8
                         mol_type = protein
                         organism = synthetic construct
SEQUENCE: 41
GLTFSMYA                                                              8

SEQ ID NO: 42            moltype = AA   length = 8
FEATURE                  Location/Qualifiers
DOMAIN                   1..8
                         note = 13H11 CDR2
source                   1..8
                         mol_type = protein
                         organism = synthetic construct
SEQUENCE: 42
ISSDGRFT                                                              8

SEQ ID NO: 43            moltype = AA   length = 18
FEATURE                  Location/Qualifiers
DOMAIN                   1..18
                         note = 13H11 CDR3
```

```
source                     1..18
                           mol_type = protein
                           organism = synthetic construct
SEQUENCE: 43
AARDSGSGYY SRAQWYDY                                                      18

SEQ ID NO: 44              moltype = AA  length = 125
FEATURE                    Location/Qualifiers
DOMAIN                     1..125
                           note = 13H11 VHH
source                     1..125
                           mol_type = protein
                           organism = synthetic construct
SEQUENCE: 44
QVQLVESGGG LVQAGGSLRL SCAASGLTFS MYAMGWFRQG PGKERESVAA ISSDGRFTYY        60
AASVKGRFTI SKDNAKSAAF LQMNSLKPED TAVYYCAARD SGSGYYSRAQ WYDYWGQGTQ       120
VTVSS                                                                  125

SEQ ID NO: 45              moltype = AA  length = 8
FEATURE                    Location/Qualifiers
DOMAIN                     1..8
                           note = 15A5 CDR1
source                     1..8
                           mol_type = protein
                           organism = synthetic construct
SEQUENCE: 45
ERTFSSFA                                                                  8

SEQ ID NO: 46              moltype = AA  length = 8
FEATURE                    Location/Qualifiers
DOMAIN                     1..8
                           note = 15A5 CDR2
source                     1..8
                           mol_type = protein
                           organism = synthetic construct
SEQUENCE: 46
IDPSGRYI                                                                  8

SEQ ID NO: 47              moltype = AA  length = 18
FEATURE                    Location/Qualifiers
DOMAIN                     1..18
                           note = 15A5 CDR3
source                     1..18
                           mol_type = protein
                           organism = synthetic construct
SEQUENCE: 47
AARIRGEGYY TRSSFYHY                                                      18

SEQ ID NO: 48              moltype = AA  length = 125
FEATURE                    Location/Qualifiers
DOMAIN                     1..125
                           note = 15A5 VHH
source                     1..125
                           mol_type = protein
                           organism = synthetic construct
SEQUENCE: 48
QVQLVESGGG LVQAGGSLRL SCAASERTFS SFAMGWFRQA PGKEREVVAA IDPSGRYIYY        60
KDSVKGRFTM SRDNAKSTVY LQMNSLKPDD TARYYCAARI RGEGYYTRSS FYHYWGQGTQ       120
VTVSS                                                                  125

SEQ ID NO: 49              moltype = AA  length = 8
FEATURE                    Location/Qualifiers
DOMAIN                     1..8
                           note = 2B7 CDR1
source                     1..8
                           mol_type = protein
                           organism = synthetic construct
SEQUENCE: 49
GRTFSSYP                                                                  8

SEQ ID NO: 50              moltype = AA  length = 8
FEATURE                    Location/Qualifiers
DOMAIN                     1..8
                           note = 2B7 CDR2
source                     1..8
                           mol_type = protein
                           organism = synthetic construct
SEQUENCE: 50
ISSDGRFT                                                                  8
```

```
SEQ ID NO: 51           moltype = AA  length = 18
FEATURE                 Location/Qualifiers
DOMAIN                  1..18
                        note = 2B7 CDR3
source                  1..18
                        mol_type = protein
                        organism = synthetic construct
SEQUENCE: 51
AARDSGSGYY SRAQWYDY                                                    18

SEQ ID NO: 52           moltype = AA  length = 125
FEATURE                 Location/Qualifiers
DOMAIN                  1..125
                        note = 2B7 VHH
source                  1..125
                        mol_type = protein
                        organism = synthetic construct
SEQUENCE: 52
QVQLVESGGG LVQAGGSLRL ACAASGRTFS SYPMGWFRQG PGKERESVAA ISSDGRFTYY       60
AASVKGRFTI SKDNAKSAAF LQMNSLKPED TAVYYCAARD SGSGYYSRAQ WYDYWGQGTQ      120
VTVSS                                                                 125

SEQ ID NO: 53           moltype = AA  length = 8
FEATURE                 Location/Qualifiers
DOMAIN                  1..8
                        note = 2B10 CDR1
source                  1..8
                        mol_type = protein
                        organism = synthetic construct
SEQUENCE: 53
SRIFRRYA                                                                8

SEQ ID NO: 54           moltype = AA  length = 8
FEATURE                 Location/Qualifiers
DOMAIN                  1..8
                        note = 2B10 CDR2
source                  1..8
                        mol_type = protein
                        organism = synthetic construct
SEQUENCE: 54
ITWSGAST                                                                8

SEQ ID NO: 55           moltype = AA  length = 17
FEATURE                 Location/Qualifiers
DOMAIN                  1..17
                        note = 2B10 CDR3
source                  1..17
                        mol_type = protein
                        organism = synthetic construct
SEQUENCE: 55
AADPWGSVIV GTAEYEY                                                     17

SEQ ID NO: 56           moltype = AA  length = 124
FEATURE                 Location/Qualifiers
DOMAIN                  1..124
                        note = 2B10 VHH
source                  1..124
                        mol_type = protein
                        organism = synthetic construct
SEQUENCE: 56
QVKLEESGGG LVQTGDSLRL SCAASSRIFR RYAMGWFRQA PGKEREFVAA ITWSGASTTY       60
TDSVKGRFTI SRDSAENTTY LQMTSLRPED TAVYYCAADP WGSVIVGTAE YEYWGQGTLV      120
TVSS                                                                  124

SEQ ID NO: 57           moltype = AA  length = 8
FEATURE                 Location/Qualifiers
DOMAIN                  1..8
                        note = 3F10 CDR1
source                  1..8
                        mol_type = protein
                        organism = synthetic construct
SEQUENCE: 57
EHTFSNFP                                                                8

SEQ ID NO: 58           moltype = AA  length = 8
FEATURE                 Location/Qualifiers
DOMAIN                  1..8
                        note = 3F10 CDR2
```

```
source                      1..8
                            mol_type = protein
                            organism = synthetic construct
SEQUENCE: 58
IDSSGRLT                                                                  8

SEQ ID NO: 59               moltype = AA   length = 18
FEATURE                     Location/Qualifiers
DOMAIN                      1..18
                            note = 3F10 CDR3
source                      1..18
                            mol_type = protein
                            organism = synthetic construct
SEQUENCE: 59
AARTGGVGYY SRSSFYNY                                                      18

SEQ ID NO: 60               moltype = AA   length = 125
FEATURE                     Location/Qualifiers
DOMAIN                      1..125
                            note = 3F10 VHH
source                      1..125
                            mol_type = protein
                            organism = synthetic construct
SEQUENCE: 60
QVQLVESGGG LVQAGGSLRL SCASSEHTFS NFPMGWFRQA PGKERNVVAA IDSSGRLTYY         60
ADSVKGRFTI SKDNAKSTVY LQMNSLKSED TARYYCAART GGVGYYSRSS FYNYWGQGTL       120
VTVSS                                                                   125

SEQ ID NO: 61               moltype = AA   length = 8
FEATURE                     Location/Qualifiers
DOMAIN                      1..8
                            note = 3G6 CDR1
source                      1..8
                            mol_type = protein
                            organism = synthetic construct
SEQUENCE: 61
GSIFGISV                                                                  8

SEQ ID NO: 62               moltype = AA   length = 7
FEATURE                     Location/Qualifiers
DOMAIN                      1..7
                            note = 3G6 CDR2
source                      1..7
                            mol_type = protein
                            organism = synthetic construct
SEQUENCE: 62
LTRAGLT                                                                   7

SEQ ID NO: 63               moltype = AA   length = 15
FEATURE                     Location/Qualifiers
DOMAIN                      1..15
                            note = 3G6 CDR3
source                      1..15
                            mol_type = protein
                            organism = synthetic construct
SEQUENCE: 63
HANIMESAAS TFGRY                                                         15

SEQ ID NO: 64               moltype = AA   length = 121
FEATURE                     Location/Qualifiers
DOMAIN                      1..121
                            note = 3G6 VHH
source                      1..121
                            mol_type = protein
                            organism = synthetic construct
SEQUENCE: 64
QVQLVESGGG LVQAGGSLSL SCAASGSIFG ISVMGWYRQA PGEQRDLVAT LTRAGLTTYG         60
DSVKGRFSIS RDSAKNTVYL QMNNLKPEDT AVYYCHANIM ESAASTFGRY WGQGTQVTVS       120
S                                                                       121

SEQ ID NO: 65               moltype = AA   length = 8
FEATURE                     Location/Qualifiers
DOMAIN                      1..8
                            note = 3G7 CDR1
source                      1..8
                            mol_type = protein
                            organism = synthetic construct
SEQUENCE: 65
GRTLSTYT                                                                  8
```

```
SEQ ID NO: 66              moltype = AA  length = 7
FEATURE                    Location/Qualifiers
DOMAIN                     1..7
                           note = 3G7 CDR2
source                     1..7
                           mol_type = protein
                           organism = synthetic construct
SEQUENCE: 66
AWPSPST                                                                    7

SEQ ID NO: 67              moltype = AA  length = 18
FEATURE                    Location/Qualifiers
DOMAIN                     1..18
                           note = 3G7 CDR3
source                     1..18
                           mol_type = protein
                           organism = synthetic construct
SEQUENCE: 67
AADYKSLTQS WLNAALDY                                                       18

SEQ ID NO: 68              moltype = AA  length = 124
FEATURE                    Location/Qualifiers
DOMAIN                     1..124
                           note = 3G7 VHH
source                     1..124
                           mol_type = protein
                           organism = synthetic construct
SEQUENCE: 68
QVQLVESGGG LVQAGDSLRL SCEASGRTLS TYTMGWFRRA PGKEREFVGL AWPSPSTYVV          60
DSVKGRFTIS RDNAKNTIYL QMNSLKPEDT AIYYCAADYK SLTQSWLNAA LDYWGQGTQV         120
TVSS                                                                     124

SEQ ID NO: 69              moltype = AA  length = 8
FEATURE                    Location/Qualifiers
DOMAIN                     1..8
                           note = 3H7 CDR1
source                     1..8
                           mol_type = protein
                           organism = synthetic construct
SEQUENCE: 69
GSILSAGV                                                                   8

SEQ ID NO: 70              moltype = AA  length = 8
FEATURE                    Location/Qualifiers
DOMAIN                     1..8
                           note = 3H7 CDR2
source                     1..8
                           mol_type = protein
                           organism = synthetic construct
SEQUENCE: 70
IALDGSTG                                                                   8

SEQ ID NO: 71              moltype = AA  length = 15
FEATURE                    Location/Qualifiers
DOMAIN                     1..15
                           note = 3H7 CDR3
source                     1..15
                           mol_type = protein
                           organism = synthetic construct
SEQUENCE: 71
NANIRTDMRS APFDH                                                          15

SEQ ID NO: 72              moltype = AA  length = 122
FEATURE                    Location/Qualifiers
DOMAIN                     1..122
                           note = 3H7 VHH
source                     1..122
                           mol_type = protein
                           organism = synthetic construct
SEQUENCE: 72
QVKLEESGGG LVQAGGSLRL SCAASGSILS AGVMRWYRQA PGKQRELVAS IALDGSTGYY          60
IDSVKGRFTI SRDNAKNIVY LDMRSLEPAD TAVYLCNANI RTDMRSAPFD HWGHGTQVTV         120
SS                                                                       122

SEQ ID NO: 73              moltype = AA  length = 8
FEATURE                    Location/Qualifiers
DOMAIN                     1..8
                           note = 4C6 CDR1
```

```
source                  1..8
                        mol_type = protein
                        organism = synthetic construct
SEQUENCE: 73
GRTFSSYP                                                                8

SEQ ID NO: 74           moltype = AA   length = 8
FEATURE                 Location/Qualifiers
DOMAIN                  1..8
                        note = 4C6 CDR2
source                  1..8
                        mol_type = protein
                        organism = synthetic construct
SEQUENCE: 74
ISSDGRFT                                                                8

SEQ ID NO: 75           moltype = AA   length = 16
FEATURE                 Location/Qualifiers
DOMAIN                  1..16
                        note = 4C6 CDR3
source                  1..16
                        mol_type = protein
                        organism = synthetic construct
SEQUENCE: 75
AVDPTGWGTI EADFRS                                                      16

SEQ ID NO: 76           moltype = AA   length = 123
FEATURE                 Location/Qualifiers
DOMAIN                  1..123
                        note = 4C6 VHH
source                  1..123
                        mol_type = protein
                        organism = synthetic construct
SEQUENCE: 76
QVQLVESGGG LVQAGGSLRL ACAASGRTFS SYPMGWFRQG PGKERESVAA ISSDGRFTYY       60
AASVKGRFTI SKDNAKSAAF LQMNSLKPED TAVYRCAVDP TGWGTIEADF RSWGQGTQVT      120
VSS                                                                   123

SEQ ID NO: 77           moltype = AA   length = 8
FEATURE                 Location/Qualifiers
DOMAIN                  1..8
                        note = 1C12 CDR1
source                  1..8
                        mol_type = protein
                        organism = synthetic construct
SEQUENCE: 77
SRIFSRYG                                                                8

SEQ ID NO: 78           moltype = AA   length = 8
FEATURE                 Location/Qualifiers
DOMAIN                  1..8
                        note = 1C12 CDR2
source                  1..8
                        mol_type = protein
                        organism = synthetic construct
SEQUENCE: 78
ISWNGAST                                                                8

SEQ ID NO: 79           moltype = AA   length = 17
FEATURE                 Location/Qualifiers
DOMAIN                  1..17
                        note = 1C12 CDR3
source                  1..17
                        mol_type = protein
                        organism = synthetic construct
SEQUENCE: 79
AADPWGAVKL GTAEYEY                                                     17

SEQ ID NO: 80           moltype = AA   length = 124
FEATURE                 Location/Qualifiers
DOMAIN                  1..124
                        note = 1C12 VHH
source                  1..124
                        mol_type = protein
                        organism = synthetic construct
SEQUENCE: 80
QVQLVESGGG LVQTGDSLRL SCAASSRIFS RYGMGWFRQA PGKEREFVAA ISWNGASTTY       60
TDSVKGRFTI SRDSAENTTY LQINSLRPED TAVYYCAADP WGAVKLGTAE YEYWGQGTQV      120
TVSS                                                                  124
```

-continued

```
SEQ ID NO: 81            moltype = AA  length = 8
FEATURE                  Location/Qualifiers
DOMAIN                   1..8
                         note = 1G1 CDR1
source                   1..8
                         mol_type = protein
                         organism = synthetic construct
SEQUENCE: 81
GPSFSSYP                                                                    8

SEQ ID NO: 82            moltype = AA  length = 8
FEATURE                  Location/Qualifiers
DOMAIN                   1..8
                         note = 1G1 CDR2
source                   1..8
                         mol_type = protein
                         organism = synthetic construct
SEQUENCE: 82
ISSDGRFT                                                                    8

SEQ ID NO: 83            moltype = AA  length = 18
FEATURE                  Location/Qualifiers
DOMAIN                   1..18
                         note = 1G1 CDR3
source                   1..18
                         mol_type = protein
                         organism = synthetic construct
SEQUENCE: 83
AARDSGSGYY SRAQWYDY                                                        18

SEQ ID NO: 84            moltype = AA  length = 125
FEATURE                  Location/Qualifiers
DOMAIN                   1..125
                         note = 1G1 VHH
source                   1..125
                         mol_type = protein
                         organism = synthetic construct
SEQUENCE: 84
QVQLVESGGG LVQAGDSLRL SCVASGPSFS SYPMGWFRQG PGKERESVAA ISSDGRFTYY           60
AASVKGRFTI SKDNAKSAAF LQMNSLKPED TAVYYCAARD SGSGYYSRAQ WYDYWGQGTL          120
VTVSS                                                                     125

SEQ ID NO: 85            moltype = AA  length = 125
FEATURE                  Location/Qualifiers
DOMAIN                   1..125
                         note = 1G1-F-G-ERES VHH
source                   1..125
                         mol_type = protein
                         organism = synthetic construct
SEQUENCE: 85
QVQLVESGGG VVQPGRSLRL SCAASGPSFS SYPMGWFRQG PGKERESVAA ISSDGRFTYY           60
ADSVKGRFTI SRDNSKNTLY LQMNSLRAED TAVYYCAARD SGSGYYSRAQ WYDYWGQGTL          120
VTVSS                                                                     125

SEQ ID NO: 86            moltype = AA  length = 125
FEATURE                  Location/Qualifiers
DOMAIN                   1..125
                         note = 1G1-F-A-ERES VHH
source                   1..125
                         mol_type = protein
                         organism = synthetic construct
SEQUENCE: 86
QVQLVESGGG VVQPGRSLRL SCAASGPSFS SYPMGWFRQA PGKERESVAA ISSDGRFTYY           60
ADSVKGRFTI SRDNSKNTLY LQMNSLRAED TAVYYCAARD SGSGYYSRAQ WYDYWGQGTL          120
VTVSS                                                                     125

SEQ ID NO: 87            moltype = AA  length = 125
FEATURE                  Location/Qualifiers
DOMAIN                   1..125
                         note = 1G1-F-A-EREW VHH
source                   1..125
                         mol_type = protein
                         organism = synthetic construct
SEQUENCE: 87
QVQLVESGGG VVQPGRSLRL SCAASGPSFS SYPMGWFRQA PGKEREWVAA ISSDGRFTYY           60
ADSVKGRFTI SRDNSKNTLY LQMNSLRAED TAVYYCAARD SGSGYYSRAQ WYDYWGQGTL          120
VTVSS                                                                     125
```

```
SEQ ID NO: 88              moltype = AA  length = 125
FEATURE                    Location/Qualifiers
DOMAIN                     1..125
                           note = 1G1-F-A-GLEW VHH
source                     1..125
                           mol_type = protein
                           organism = synthetic construct
SEQUENCE: 88
QVQLVESGGG VVQPGRSLRL SCAASGPSFS SYPMGWFRQA PGKGLEWVAA ISSDGRFTYY     60
ADSVKGRFTI SRDNSKNTLY LQMNSLRAED TAVYYCAARD SGSGYYSRAQ WYDYWGQGTL    120
VTVSS                                                                125

SEQ ID NO: 89              moltype = AA  length = 125
FEATURE                    Location/Qualifiers
DOMAIN                     1..125
                           note = 1G1-F-A-GREL VHH
source                     1..125
                           mol_type = protein
                           organism = synthetic construct
SEQUENCE: 89
QVQLVESGGG VVQPGRSLRL SCAASGPSFS SYPMGWFRQA PGKGRELVAA ISSDGRFTYY     60
ADSVKGRFTI SRDNSKNTLY LQMNSLRAED TAVYYCAARD SGSGYYSRAQ WYDYWGQGTL    120
VTVSS                                                                125

SEQ ID NO: 90              moltype = AA  length = 125
FEATURE                    Location/Qualifiers
DOMAIN                     1..125
                           note = 1G1-F-A-GRES VHH
source                     1..125
                           mol_type = protein
                           organism = synthetic construct
SEQUENCE: 90
QVQLVESGGG VVQPGRSLRL SCAASGPSFS SYPMGWFRQA PGKGRESVAA ISSDGRFTYY     60
ADSVKGRFTI SRDNSKNTLY LQMNSLRAED TAVYYCAARD SGSGYYSRAQ WYDYWGQGTL    120
VTVSS                                                                125

SEQ ID NO: 91              moltype = AA  length = 124
FEATURE                    Location/Qualifiers
DOMAIN                     1..124
                           note = 1C12-EREF VHH
source                     1..124
                           mol_type = protein
                           organism = synthetic construct
SEQUENCE: 91
QVQLVESGGG VVQPGRSLRL SCAASSRIFS RYGMGWFRQA PGKEREFVAA ISWNGASTTY     60
TDSVKGRFTI SRDNSKNTLY LQMNSLRAED TAVYYCAADP WGAVKLGTAE YEYWGQGTQV    120
TVSS                                                                 124

SEQ ID NO: 92              moltype = AA  length = 124
FEATURE                    Location/Qualifiers
DOMAIN                     1..124
                           note = 1C12-EREW VHH
source                     1..124
                           mol_type = protein
                           organism = synthetic construct
SEQUENCE: 92
QVQLVESGGG VVQPGRSLRL SCAASSRIFS RYGMGWFRQA PGKEREWVAA ISWNGASTTY     60
TDSVKGRFTI SRDNSKNTLY LQMNSLRAED TAVYYCAADP WGAVKLGTAE YEYWGQGTQV    120
TVSS                                                                 124

SEQ ID NO: 93              moltype = AA  length = 124
FEATURE                    Location/Qualifiers
DOMAIN                     1..124
                           note = 1C12_GLEW VHH
source                     1..124
                           mol_type = protein
                           organism = synthetic construct
SEQUENCE: 93
QVQLVESGGG VVQPGRSLRL SCAASSRIFS RYGMGWFRQA PGKGLEWVAA ISWNGASTTY     60
TDSVKGRFTI SRDNSKNTLY LQMNSLRAED TAVYYCAADP WGAVKLGTAE YEYWGQGTQV    120
TVSS                                                                 124

SEQ ID NO: 94              moltype = AA  length = 8
FEATURE                    Location/Qualifiers
DOMAIN                     1..8
                           note = 2A3 CDR1
source                     1..8
                           mol_type = protein
                           organism = synthetic construct
```

```
SEQUENCE: 94
GGSFSSYP                                                                  8

SEQ ID NO: 95           moltype = AA  length = 8
FEATURE                 Location/Qualifiers
DOMAIN                  1..8
                        note = 2A3 CDR2
source                  1..8
                        mol_type = protein
                        organism = synthetic construct
SEQUENCE: 95
ISSDMRFT                                                                  8

SEQ ID NO: 96           moltype = AA  length = 18
FEATURE                 Location/Qualifiers
DOMAIN                  1..18
                        note = 2A3 CDR3
source                  1..18
                        mol_type = protein
                        organism = synthetic construct
SEQUENCE: 96
AARDSGVGYY SRAQWYDY                                                      18

SEQ ID NO: 97           moltype = AA  length = 125
FEATURE                 Location/Qualifiers
DOMAIN                  1..125
                        note = 2A3 VHH
source                  1..125
                        mol_type = protein
                        organism = synthetic construct
SEQUENCE: 97
QVQLVESGGG VVQPGRSLRL SCAASGGSFS SYPMGWFRQA PGKERESVAA ISSDMRFTYY         60
ADSVKGRFTI SRDNSKNTLY LQMNSLRAED TAVYYCAARD SGVGYYSRAQ WYDYWGQGTL       120
VTVSS                                                                   125

SEQ ID NO: 98           moltype = AA  length = 8
FEATURE                 Location/Qualifiers
DOMAIN                  1..8
                        note = 1A8 CDR1
source                  1..8
                        mol_type = protein
                        organism = synthetic construct
SEQUENCE: 98
GPSFSSYP                                                                  8

SEQ ID NO: 99           moltype = AA  length = 8
FEATURE                 Location/Qualifiers
DOMAIN                  1..8
                        note = 1A8 CDR2
source                  1..8
                        mol_type = protein
                        organism = synthetic construct
SEQUENCE: 99
ISSRGRFT                                                                  8

SEQ ID NO: 100          moltype = AA  length = 18
FEATURE                 Location/Qualifiers
DOMAIN                  1..18
                        note = 1A8 CDR3
source                  1..18
                        mol_type = protein
                        organism = synthetic construct
SEQUENCE: 100
AARDSGSGYY SRAQWYDY                                                      18

SEQ ID NO: 101          moltype = AA  length = 125
FEATURE                 Location/Qualifiers
DOMAIN                  1..125
                        note = 1A8 VHH
source                  1..125
                        mol_type = protein
                        organism = synthetic construct
SEQUENCE: 101
QVQLVESGGG VVQPGRSLRL SCAASGPSFS SYPMGWFRQA PGKERESVAA ISSRGRFTYY         60
ADSVKGRFTI SRDNSKNTLY LQMNSLRAED TAVYYCAARD SGSGYYSRAQ WYDYWGQGTL       120
VTVSS                                                                   125

SEQ ID NO: 102          moltype = AA  length = 8
FEATURE                 Location/Qualifiers
```

```
DOMAIN                  1..8
                        note = 1D11 CDR1
source                  1..8
                        mol_type = protein
                        organism = synthetic construct
SEQUENCE: 102
GPSFSSSP                                                                        8

SEQ ID NO: 103          moltype = AA  length = 8
FEATURE                 Location/Qualifiers
DOMAIN                  1..8
                        note = 1D11 CDR2
source                  1..8
                        mol_type = protein
                        organism = synthetic construct
SEQUENCE: 103
ISSMGRFT                                                                        8

SEQ ID NO: 104          moltype = AA  length = 18
FEATURE                 Location/Qualifiers
DOMAIN                  1..18
                        note = 1D11 CDR3
source                  1..18
                        mol_type = protein
                        organism = synthetic construct
SEQUENCE: 104
AARDSGSGYY SRAQWYDY                                                             18

SEQ ID NO: 105          moltype = AA  length = 125
FEATURE                 Location/Qualifiers
DOMAIN                  1..125
                        note = 1D11 VHH
source                  1..125
                        mol_type = protein
                        organism = synthetic construct
SEQUENCE: 105
QVQLVESGGG VVQPGRSLRL SCAASGPSFS SSPMGWFRQA PGKERESVAA ISSMGRFTYY                60
ADSVKGRFTI SRDNSKNTLY LQMNSLRAED TAVYYCAARD SGSGYYSRAQ WYDYWGQGTL               120
VTVSS                                                                           125

SEQ ID NO: 106          moltype = AA  length = 8
FEATURE                 Location/Qualifiers
DOMAIN                  1..8
                        note = 5E8 CDR1
source                  1..8
                        mol_type = protein
                        organism = synthetic construct
SEQUENCE: 106
GPSFSSYP                                                                        8

SEQ ID NO: 107          moltype = AA  length = 8
FEATURE                 Location/Qualifiers
DOMAIN                  1..8
                        note = 5E8 CDR2
source                  1..8
                        mol_type = protein
                        organism = synthetic construct
SEQUENCE: 107
QSSDGRFT                                                                        8

SEQ ID NO: 108          moltype = AA  length = 18
FEATURE                 Location/Qualifiers
DOMAIN                  1..18
                        note = 5E8 CDR3
source                  1..18
                        mol_type = protein
                        organism = synthetic construct
SEQUENCE: 108
AARDSGSGYY SRAQWYDY                                                             18

SEQ ID NO: 109          moltype = AA  length = 125
FEATURE                 Location/Qualifiers
DOMAIN                  1..125
                        note = 5E8 VHH
source                  1..125
                        mol_type = protein
                        organism = synthetic construct
SEQUENCE: 109
QVQLVESGGG VVQPGRSLRL SCAASGPSFS SYPMGWFRQA PGKERESVAA QSSDGRFTYY                60
```

```
ADSVKGRFTI SRDNSKNTLY LQMNSLRAED TAVYYCAARD SGSGYYSRAQ WYDYWGQGTL   120
VTVSS                                                              125

SEQ ID NO: 110          moltype = AA  length = 8
FEATURE                 Location/Qualifiers
DOMAIN                  1..8
                        note = 2A5 CDR1
source                  1..8
                        mol_type = protein
                        organism = synthetic construct
SEQUENCE: 110
GPSFSSYP                                                           8

SEQ ID NO: 111          moltype = AA  length = 8
FEATURE                 Location/Qualifiers
DOMAIN                  1..8
                        note = 2A5 CDR2
source                  1..8
                        mol_type = protein
                        organism = synthetic construct
SEQUENCE: 111
ISSVGRFT                                                           8

SEQ ID NO: 112          moltype = AA  length = 18
FEATURE                 Location/Qualifiers
DOMAIN                  1..18
                        note = 2A5 CDR3
source                  1..18
                        mol_type = protein
                        organism = synthetic construct
SEQUENCE: 112
AARDSGSGYY SRWQWYDY                                                18

SEQ ID NO: 113          moltype = AA  length = 125
FEATURE                 Location/Qualifiers
DOMAIN                  1..125
                        note = 2A5 VHH
source                  1..125
                        mol_type = protein
                        organism = synthetic construct
SEQUENCE: 113
QVQLVESGGG VVQPGRSLRL SCAASGPSFS SYPMGWFRQA PGKERESVAA ISSVGRFTYY   60
ADSVKGRFTI SRDNSKNTLY LQMNSLRAED TAVYYCAARD SGSGYYSRWQ WYDYWGQGTL   120
VTVSS                                                              125

SEQ ID NO: 114          moltype = AA  length = 8
FEATURE                 Location/Qualifiers
DOMAIN                  1..8
                        note = 5G10 CDR1
source                  1..8
                        mol_type = protein
                        organism = synthetic construct
SEQUENCE: 114
GPRFSSYP                                                           8

SEQ ID NO: 115          moltype = AA  length = 8
FEATURE                 Location/Qualifiers
DOMAIN                  1..8
                        note = 5G10 CDR2
source                  1..8
                        mol_type = protein
                        organism = synthetic construct
SEQUENCE: 115
ISSDGRFT                                                           8

SEQ ID NO: 116          moltype = AA  length = 18
FEATURE                 Location/Qualifiers
DOMAIN                  1..18
                        note = 5G10 CDR3
source                  1..18
                        mol_type = protein
                        organism = synthetic construct
SEQUENCE: 116
AARDSGSGYY SRAQWYDG                                                18

SEQ ID NO: 117          moltype = AA  length = 125
FEATURE                 Location/Qualifiers
DOMAIN                  1..125
                        note = 5G10 VHH
```

```
source                  1..125
                        mol_type = protein
                        organism = synthetic construct
SEQUENCE: 117
QVQLVESGGG VVQPGRSLRL SCAASGPRFS SYPMGWFRQA PGKERESVAA ISSDGRFTYY    60
ADSVKGRFTI SRDNSKNTLY LQMNSLRAED TAVYYCAARD SGSGYYSRAQ WYDGWGQGTL   120
VTVSS                                                               125

SEQ ID NO: 118          moltype = AA   length = 8
FEATURE                 Location/Qualifiers
DOMAIN                  1..8
                        note = 2A6 CDR1
source                  1..8
                        mol_type = protein
                        organism = synthetic construct
SEQUENCE: 118
GPSFSLYP                                                              8

SEQ ID NO: 119          moltype = AA   length = 8
FEATURE                 Location/Qualifiers
DOMAIN                  1..8
                        note = 2A6 CDR2
source                  1..8
                        mol_type = protein
                        organism = synthetic construct
SEQUENCE: 119
ISSDRRFT                                                              8

SEQ ID NO: 120          moltype = AA   length = 18
FEATURE                 Location/Qualifiers
DOMAIN                  1..18
                        note = 2A6 CDR3
source                  1..18
                        mol_type = protein
                        organism = synthetic construct
SEQUENCE: 120
AARDSGSGYY SRAQWYDY                                                  18

SEQ ID NO: 121          moltype = AA   length = 125
FEATURE                 Location/Qualifiers
DOMAIN                  1..125
                        note = 2A6 VHH
source                  1..125
                        mol_type = protein
                        organism = synthetic construct
SEQUENCE: 121
QVQLVESGGG VVQPGRSLRL SCAASGPSFS LYPMGWFRQA PGKERESVAA ISSDRRFTYY    60
ADSVKGRFTI SRDNSKNTLY LQMNSLRAED TAVYYCAARD SGSGYYSRAQ WYDYWGQGTL   120
VTVSS                                                               125

SEQ ID NO: 122          moltype = AA   length = 8
FEATURE                 Location/Qualifiers
DOMAIN                  1..8
                        note = 1G1-1C12 CDR1
source                  1..8
                        mol_type = protein
                        organism = synthetic construct
SEQUENCE: 122
GPSFSSYP                                                              8

SEQ ID NO: 123          moltype = AA   length = 8
FEATURE                 Location/Qualifiers
DOMAIN                  1..8
                        note = 1G1-1C12 CDR2
source                  1..8
                        mol_type = protein
                        organism = synthetic construct
SEQUENCE: 123
ISSDLRFT                                                              8

SEQ ID NO: 124          moltype = AA   length = 18
FEATURE                 Location/Qualifiers
DOMAIN                  1..18
                        note = 1G1-1C12 CDR3
source                  1..18
                        mol_type = protein
                        organism = synthetic construct
SEQUENCE: 124
AARDSGSGYY SRKQWYDY                                                  18
```

```
SEQ ID NO: 125          moltype = AA   length = 125
FEATURE                 Location/Qualifiers
DOMAIN                  1..125
                        note = 1G1-1C12 VHH
source                  1..125
                        mol_type = protein
                        organism = synthetic construct
SEQUENCE: 125
QVQLVESGGG VVQPGRSLRL SCAASGPSFS SYPMGWFRQA PGKERESVAA ISSDLRFTYY    60
ADSVKGRFTI SRDNSKNTLY LQMNSLRAED TAVYYCAARD SGSGYYSRKQ WYDYWGQGTL   120
VTVSS                                                               125

SEQ ID NO: 126          moltype = AA   length = 8
FEATURE                 Location/Qualifiers
DOMAIN                  1..8
                        note = 5B5 CDR1
source                  1..8
                        mol_type = protein
                        organism = synthetic construct
SEQUENCE: 126
GPSFSSYP                                                              8

SEQ ID NO: 127          moltype = AA   length = 8
FEATURE                 Location/Qualifiers
DOMAIN                  1..8
                        note = 5B5 CDR2
source                  1..8
                        mol_type = protein
                        organism = synthetic construct
SEQUENCE: 127
ISSDTRFT                                                              8

SEQ ID NO: 128          moltype = AA   length = 18
FEATURE                 Location/Qualifiers
DOMAIN                  1..18
                        note = 5B5 CDR3
source                  1..18
                        mol_type = protein
                        organism = synthetic construct
SEQUENCE: 128
AARDSGSGYY SRAQWYDR                                                  18

SEQ ID NO: 129          moltype = AA   length = 125
FEATURE                 Location/Qualifiers
DOMAIN                  1..125
                        note = 5B5 VHH
source                  1..125
                        mol_type = protein
                        organism = synthetic construct
SEQUENCE: 129
QVQLVESGGG VVQPGRSLRL SCAASGPSFS SYPMGWFRQA PGKERESVAA ISSDTRFTYY    60
ADSVKGRFTI SRDNSKNTLY LQMNSLRAED TAVYYCAARD SGSGYYSRAQ WYDRWGQGTL   120
VTVSS                                                               125

SEQ ID NO: 130          moltype = AA   length = 8
FEATURE                 Location/Qualifiers
DOMAIN                  1..8
                        note = 6F12 CDR1
source                  1..8
                        mol_type = protein
                        organism = synthetic construct
SEQUENCE: 130
GPSFTSYP                                                              8

SEQ ID NO: 131          moltype = AA   length = 8
FEATURE                 Location/Qualifiers
DOMAIN                  1..8
                        note = 6F12 CDR2
source                  1..8
                        mol_type = protein
                        organism = synthetic construct
SEQUENCE: 131
ISSDGRFK                                                              8

SEQ ID NO: 132          moltype = AA   length = 18
FEATURE                 Location/Qualifiers
DOMAIN                  1..18
                        note = 6F12 CDR3
```

```
source                   1..18
                         mol_type = protein
                         organism = synthetic construct
SEQUENCE: 132
AAEDSGSGYY SRAQWYDY                                                        18

SEQ ID NO: 133           moltype = AA   length = 125
FEATURE                  Location/Qualifiers
DOMAIN                   1..125
                         note = 6F12 VHH
source                   1..125
                         mol_type = protein
                         organism = synthetic construct
SEQUENCE: 133
QVQLVESGGG VVQPGRSLRL SCAASGPSFT SYPMGWFRQA PGKERESVAA ISSDGRFKYY            60
ADSVKGRFTI SRDNSKNTLY LQMNSLRAED TAVYYCAAED SGSGYYSRAQ WYDYWGQGTL           120
VTVSS                                                                      125

SEQ ID NO: 134           moltype = AA   length = 8
FEATURE                  Location/Qualifiers
DOMAIN                   1..8
                         note = 1C7 CDR1
source                   1..8
                         mol_type = protein
                         organism = synthetic construct
SEQUENCE: 134
GPSFSSYP                                                                    8

SEQ ID NO: 135           moltype = AA   length = 8
FEATURE                  Location/Qualifiers
DOMAIN                   1..8
                         note = 1C7 CDR2
source                   1..8
                         mol_type = protein
                         organism = synthetic construct
SEQUENCE: 135
ISSRGRFT                                                                    8

SEQ ID NO: 136           moltype = AA   length = 18
FEATURE                  Location/Qualifiers
DOMAIN                   1..18
                         note = 1C7 CDR3
source                   1..18
                         mol_type = protein
                         organism = synthetic construct
SEQUENCE: 136
AARGSGSGYY SRAQWYDY                                                        18

SEQ ID NO: 137           moltype = AA   length = 125
FEATURE                  Location/Qualifiers
DOMAIN                   1..125
                         note = 1C7 VHH
source                   1..125
                         mol_type = protein
                         organism = synthetic construct
SEQUENCE: 137
QVQLVESGGG VVQPGRSLRL SCAASGPSFS SYPMGWFRQA PGKERESVAA ISSRGRFTYY            60
ADSVKGRFTI SRDNSKNTLY LQMNSLRAED TAVYYCAARG SGSGYYSRAQ WYDYWGQGTL           120
VTVSS                                                                      125

SEQ ID NO: 138           moltype = AA   length = 8
FEATURE                  Location/Qualifiers
DOMAIN                   1..8
                         note = 6E9 CDR1
source                   1..8
                         mol_type = protein
                         organism = synthetic construct
SEQUENCE: 138
GPSRSSYP                                                                    8

SEQ ID NO: 139           moltype = AA   length = 8
FEATURE                  Location/Qualifiers
DOMAIN                   1..8
                         note = 6E9 CDR2
source                   1..8
                         mol_type = protein
                         organism = synthetic construct
SEQUENCE: 139
ISSDGKFT                                                                    8
```

```
SEQ ID NO: 140            moltype = AA   length = 18
FEATURE                   Location/Qualifiers
DOMAIN                    1..18
                          note = 6E9 CDR3
source                    1..18
                          mol_type = protein
                          organism = synthetic construct
SEQUENCE: 140
AARDSGSGYY SRANWYDY                                                       18

SEQ ID NO: 141            moltype = AA   length = 125
FEATURE                   Location/Qualifiers
DOMAIN                    1..125
                          note = 6E9 VHH
source                    1..125
                          mol_type = protein
                          organism = synthetic construct
SEQUENCE: 141
QVQLVESGGG VVQPGRSLRL SCAASGPSRS SYPMGWFRQA PGKERESVAA ISSDGKFTYY          60
ADSVKGRFTI SRDNSKNTLY LQMNSLRAED TAVYYCAARD SGSGYYSRAN WYDYWGQGTL        120
VTVSS                                                                    125

SEQ ID NO: 142            moltype = AA   length = 8
FEATURE                   Location/Qualifiers
DOMAIN                    1..8
                          note = 1A10 CDR1
source                    1..8
                          mol_type = protein
                          organism = synthetic construct
SEQUENCE: 142
GNSFSSYP                                                                   8

SEQ ID NO: 143            moltype = AA   length = 8
FEATURE                   Location/Qualifiers
DOMAIN                    1..8
                          note = 1A10 CDR2
source                    1..8
                          mol_type = protein
                          organism = synthetic construct
SEQUENCE: 143
ISSDGRFS                                                                   8

SEQ ID NO: 144            moltype = AA   length = 18
FEATURE                   Location/Qualifiers
DOMAIN                    1..18
                          note = 1A10 CDR3
source                    1..18
                          mol_type = protein
                          organism = synthetic construct
SEQUENCE: 144
ACRDSGSGYY SRAQWYDY                                                       18

SEQ ID NO: 145            moltype = AA   length = 125
FEATURE                   Location/Qualifiers
DOMAIN                    1..125
                          note = 1A10 VHH
source                    1..125
                          mol_type = protein
                          organism = synthetic construct
SEQUENCE: 145
QVQLVESGGG VVQPGRSLRL SCAASGNSFS SYPMGWFRQA PGKERESVAA ISSDGRFSYY          60
ADSVKGRFTI SRDNSKNTLY LQMNSLRAED TAVYYCACRD SGSGYYSRAQ WYDYWGQGTL        120
VTVSS                                                                    125

SEQ ID NO: 146            moltype = AA   length = 8
FEATURE                   Location/Qualifiers
DOMAIN                    1..8
                          note = 6B11 CDR1
source                    1..8
                          mol_type = protein
                          organism = synthetic construct
SEQUENCE: 146
GPSFPSYP                                                                   8

SEQ ID NO: 147            moltype = AA   length = 8
FEATURE                   Location/Qualifiers
DOMAIN                    1..8
                          note = 6B11 CDR2
```

```
source                      1..8
                            mol_type = protein
                            organism = synthetic construct
SEQUENCE: 147
ISSRGRFT                                                                    8

SEQ ID NO: 148              moltype = AA   length = 18
FEATURE                     Location/Qualifiers
DOMAIN                      1..18
                            note = 6B11 CDR3
source                      1..18
                            mol_type = protein
                            organism = synthetic construct
SEQUENCE: 148
AARDSGSGYY SRLQWYDY                                                         18

SEQ ID NO: 149              moltype = AA   length = 125
FEATURE                     Location/Qualifiers
DOMAIN                      1..125
                            note = 6B11 VHH
source                      1..125
                            mol_type = protein
                            organism = synthetic construct
SEQUENCE: 149
QVQLVESGGG VVQPGRSLRL SCAASGPSFP SYPMGWFRQA PGKERESVAA ISSRGRFTYY            60
ADSVKGRFTI SRDNSKNTLY LQMNSLRAED TAVYYCAARD SGSGYYSRLQ WYDYWGQGTL           120
VTVSS                                                                      125

SEQ ID NO: 150              moltype = AA   length = 8
FEATURE                     Location/Qualifiers
DOMAIN                      1..8
                            note = 6D8 CDR1
source                      1..8
                            mol_type = protein
                            organism = synthetic construct
SEQUENCE: 150
GPSFSSKP                                                                    8

SEQ ID NO: 151              moltype = AA   length = 8
FEATURE                     Location/Qualifiers
DOMAIN                      1..8
                            note = 6D8 CDR2
source                      1..8
                            mol_type = protein
                            organism = synthetic construct
SEQUENCE: 151
RSSDGRFT                                                                    8

SEQ ID NO: 152              moltype = AA   length = 18
FEATURE                     Location/Qualifiers
DOMAIN                      1..18
                            note = 6D8 CDR3
source                      1..18
                            mol_type = protein
                            organism = synthetic construct
SEQUENCE: 152
AARDSGSGRY SRAQWYDY                                                         18

SEQ ID NO: 153              moltype = AA   length = 125
FEATURE                     Location/Qualifiers
DOMAIN                      1..125
                            note = 6D8 VHH
source                      1..125
                            mol_type = protein
                            organism = synthetic construct
SEQUENCE: 153
QVQLVESGGG VVQPGRSLRL SCAASGPSFS SKPMGWFRQA PGKERESVAA RSSDGRFTYY            60
ADSVKGRFTI SRDNSKNTLY LQMNSLRAED TAVYYCAARD SGSGRYSRAQ WYDYWGQGTL           120
VTVSS                                                                      125

SEQ ID NO: 154              moltype = AA   length = 8
FEATURE                     Location/Qualifiers
DOMAIN                      1..8
                            note = 6D12 CDR1
source                      1..8
                            mol_type = protein
                            organism = synthetic construct
SEQUENCE: 154
GPSFSTYP                                                                    8
```

```
SEQ ID NO: 155          moltype = AA  length = 8
FEATURE                 Location/Qualifiers
DOMAIN                  1..8
                        note = 6D12 CDR2
source                  1..8
                        mol_type = protein
                        organism = synthetic construct
SEQUENCE: 155
ISSDGVFT                                                                  8

SEQ ID NO: 156          moltype = AA  length = 18
FEATURE                 Location/Qualifiers
DOMAIN                  1..18
                        note = 6D12 CDR3
source                  1..18
                        mol_type = protein
                        organism = synthetic construct
SEQUENCE: 156
AARDSGSGYY SREQWYDY                                                      18

SEQ ID NO: 157          moltype = AA  length = 125
FEATURE                 Location/Qualifiers
DOMAIN                  1..125
                        note = 6D12 VHH
source                  1..125
                        mol_type = protein
                        organism = synthetic construct
SEQUENCE: 157
QVQLVESGGG VVQPGRSLRL SCAASGPSFS TYPMGWFRQA PGKERESVAA ISSDGVFTYY         60
ADSVKGRFTI SRDNSKNTLY LQMNSLRAED TAVYYCAARD SGSGYYSREQ WYDYWGQGTL        120
VTVSS                                                                   125

SEQ ID NO: 158          moltype = AA  length = 8
FEATURE                 Location/Qualifiers
DOMAIN                  1..8
                        note = 2C5 CDR1
source                  1..8
                        mol_type = protein
                        organism = synthetic construct
SEQUENCE: 158
GPSFSTYP                                                                  8

SEQ ID NO: 159          moltype = AA  length = 8
FEATURE                 Location/Qualifiers
DOMAIN                  1..8
                        note = 2C5 CDR2
source                  1..8
                        mol_type = protein
                        organism = synthetic construct
SEQUENCE: 159
ISSQGRFT                                                                  8

SEQ ID NO: 160          moltype = AA  length = 18
FEATURE                 Location/Qualifiers
DOMAIN                  1..18
                        note = 2C5 CDR3
source                  1..18
                        mol_type = protein
                        organism = synthetic construct
SEQUENCE: 160
AARDSGSGYY SRAQWYDY                                                      18

SEQ ID NO: 161          moltype = AA  length = 125
FEATURE                 Location/Qualifiers
DOMAIN                  1..125
                        note = 2C5 VHH
source                  1..125
                        mol_type = protein
                        organism = synthetic construct
SEQUENCE: 161
QVQLVESGGG VVQPGRSLRL SCAASGPSFS TYPMGWFRQA PGKERESVAA ISSQGRFTYY         60
ADSVKGRFTI SRDNSKNTLY LQMNSLRAED TAVYYCAARD SGSGYYSRAQ WYDYWGQGTL        120
VTVSS                                                                   125

SEQ ID NO: 162          moltype = AA  length = 8
FEATURE                 Location/Qualifiers
DOMAIN                  1..8
                        note = 7F6 CDR1
```

```
source                  1..8
                        mol_type = protein
                        organism = synthetic construct
SEQUENCE: 162
GPMFSSYP                                                                    8

SEQ ID NO: 163          moltype = AA   length = 8
FEATURE                 Location/Qualifiers
DOMAIN                  1..8
                        note = 7F6 CDR2
source                  1..8
                        mol_type = protein
                        organism = synthetic construct
SEQUENCE: 163
ISSDPRFT                                                                    8

SEQ ID NO: 164          moltype = AA   length = 18
FEATURE                 Location/Qualifiers
DOMAIN                  1..18
                        note = 7F6 CDR3
source                  1..18
                        mol_type = protein
                        organism = synthetic construct
SEQUENCE: 164
AARDSGSGYY SRAQWYDY                                                        18

SEQ ID NO: 165          moltype = AA   length = 125
FEATURE                 Location/Qualifiers
DOMAIN                  1..125
                        note = 7F6 VHH
source                  1..125
                        mol_type = protein
                        organism = synthetic construct
SEQUENCE: 165
QVQLVESGGG VVQPGRSLRL SCAASGPMFS SYPMGWFRQA PGKERESVAA ISSDPRFTYY           60
ADSVKGRFTI SRDNSKNTLY LQMNSLRAED TAVYYCAARD SGSGYYSRAQ WYDYWGQGTL          120
VTVSS                                                                     125

SEQ ID NO: 166          moltype = AA   length = 8
FEATURE                 Location/Qualifiers
DOMAIN                  1..8
                        note = 2D5 CDR1
source                  1..8
                        mol_type = protein
                        organism = synthetic construct
SEQUENCE: 166
GPSFSSSP                                                                    8

SEQ ID NO: 167          moltype = AA   length = 8
FEATURE                 Location/Qualifiers
DOMAIN                  1..8
                        note = 2D5 CDR2
source                  1..8
                        mol_type = protein
                        organism = synthetic construct
SEQUENCE: 167
ISWDGRFT                                                                    8

SEQ ID NO: 168          moltype = AA   length = 18
FEATURE                 Location/Qualifiers
DOMAIN                  1..18
                        note = 2D5 CDR3
source                  1..18
                        mol_type = protein
                        organism = synthetic construct
SEQUENCE: 168
AARDSGSGYY SRAQWYVY                                                        18

SEQ ID NO: 169          moltype = AA   length = 125
FEATURE                 Location/Qualifiers
DOMAIN                  1..125
                        note = 2D5 VHH
source                  1..125
                        mol_type = protein
                        organism = synthetic construct
SEQUENCE: 169
QVQLVESGGG VVQPGRSLRL SCAASGPSFS SSPMGWFRQA PGKERESVAA ISWDGRFTYY           60
ADSVKGRFTI SRDNSKNTLY LQMNSLRAED TAVYYCAARD SGSGYYSRAQ WYVYWGQGTL          120
VTVSS                                                                     125
```

```
SEQ ID NO: 170          moltype = AA   length = 8
FEATURE                 Location/Qualifiers
DOMAIN                  1..8
                        note = 7B11 CDR1
source                  1..8
                        mol_type = protein
                        organism = synthetic construct
SEQUENCE: 170
GPSFLIYP                                                                    8

SEQ ID NO: 171          moltype = AA   length = 8
FEATURE                 Location/Qualifiers
DOMAIN                  1..8
                        note = 7B11 CDR2
source                  1..8
                        mol_type = protein
                        organism = synthetic construct
SEQUENCE: 171
ISSDGRFW                                                                    8

SEQ ID NO: 172          moltype = AA   length = 18
FEATURE                 Location/Qualifiers
DOMAIN                  1..18
                        note = 7B11 CDR3
source                  1..18
                        mol_type = protein
                        organism = synthetic construct
SEQUENCE: 172
AARDSGSGYY SRVQWYDY                                                        18

SEQ ID NO: 173          moltype = AA   length = 125
FEATURE                 Location/Qualifiers
DOMAIN                  1..125
                        note = 7B11 VHH
source                  1..125
                        mol_type = protein
                        organism = synthetic construct
SEQUENCE: 173
QVQLVESGGG VVQPGRSLRL SCAASGPSFL IYPMGWFRQA PGKERESVAA ISSDGRFWYY           60
ADSVKGRFTI SRDNSKNTLY LQMNSLRAED TAVYYCAARD SGSGYYSRVQ WYDYWGQGTL          120
VTVSS                                                                     125

SEQ ID NO: 174          moltype = AA   length = 8
FEATURE                 Location/Qualifiers
DOMAIN                  1..8
                        note = 7D12 CDR1
source                  1..8
                        mol_type = protein
                        organism = synthetic construct
SEQUENCE: 174
GPSFLSYP                                                                    8

SEQ ID NO: 175          moltype = AA   length = 8
FEATURE                 Location/Qualifiers
DOMAIN                  1..8
                        note = 7D12 CDR2
source                  1..8
                        mol_type = protein
                        organism = synthetic construct
SEQUENCE: 175
ISSDGRFS                                                                    8

SEQ ID NO: 176          moltype = AA   length = 18
FEATURE                 Location/Qualifiers
DOMAIN                  1..18
                        note = 7D12 CDR3
source                  1..18
                        mol_type = protein
                        organism = synthetic construct
SEQUENCE: 176
AARDWGSGYY SRAQWYDY                                                        18

SEQ ID NO: 177          moltype = AA   length = 125
FEATURE                 Location/Qualifiers
DOMAIN                  1..125
                        note = 7D12 VHH
source                  1..125
                        mol_type = protein
```

```
                          organism = synthetic construct
SEQUENCE: 177
QVQLVESGGG VVQPGRSLRL SCAASGPSFL SYPMGWFRQA PGKERESVAA ISSDGRFSYY  60
ADSVKGRFTI SRDNSKNTLY LQMNSLRAED TAVYYCAARD WGSGYYSRAQ WYDYWGQGTL 120
VTVSS                                                            125

SEQ ID NO: 178            moltype = AA   length = 8
FEATURE                   Location/Qualifiers
DOMAIN                    1..8
                          note = 2A3 ML CDR1
source                    1..8
                          mol_type = protein
                          organism = synthetic construct
SEQUENCE: 178
GGSFSSYP                                                          8

SEQ ID NO: 179            moltype = AA   length = 8
FEATURE                   Location/Qualifiers
DOMAIN                    1..8
                          note = 2A3 ML CDR2
source                    1..8
                          mol_type = protein
                          organism = synthetic construct
SEQUENCE: 179
ISSDLRFT                                                          8

SEQ ID NO: 180            moltype = AA   length = 18
FEATURE                   Location/Qualifiers
DOMAIN                    1..18
                          note = 2A3 ML CDR3
source                    1..18
                          mol_type = protein
                          organism = synthetic construct
SEQUENCE: 180
AARDSGVGYY SRAQWYDY                                               18

SEQ ID NO: 181            moltype = AA   length = 125
FEATURE                   Location/Qualifiers
DOMAIN                    1..125
                          note = 2A3 ML VHH
source                    1..125
                          mol_type = protein
                          organism = synthetic construct
SEQUENCE: 181
QVQLVESGGG VVQPGRSLRL SCAASGGSFS SYPMGWFRQA PGKERESVAA ISSDLRFTYY  60
ADSVKGRFTI SRDNSKNTLY LQMNSLRAED TAVYYCAARD SGVGYYSRAQ WYDYWGQGTL 120
VTVSS                                                            125

SEQ ID NO: 182            moltype = AA   length = 8
FEATURE                   Location/Qualifiers
DOMAIN                    1..8
                          note = 2A3 MI CDR1
source                    1..8
                          mol_type = protein
                          organism = synthetic construct
SEQUENCE: 182
GGSFSSYP                                                          8

SEQ ID NO: 183            moltype = AA   length = 8
FEATURE                   Location/Qualifiers
DOMAIN                    1..8
                          note = 2A3 MI CDR2
source                    1..8
                          mol_type = protein
                          organism = synthetic construct
SEQUENCE: 183
ISSDIRFT                                                          8

SEQ ID NO: 184            moltype = AA   length = 18
FEATURE                   Location/Qualifiers
DOMAIN                    1..18
                          note = 2A3 MI CDR3
source                    1..18
                          mol_type = protein
                          organism = synthetic construct
SEQUENCE: 184
AARDSGVGYY SRAQWYDY                                               18

SEQ ID NO: 185            moltype = AA   length = 125
```

```
FEATURE                 Location/Qualifiers
DOMAIN                  1..125
                        note = 2A3 MI VHH
source                  1..125
                        mol_type = protein
                        organism = synthetic construct
SEQUENCE: 185
QVQLVESGGG VVQPGRSLRL SCAASGGSFS SYPMGWFRQA PGKERESVAA ISSDIRFTYY    60
ADSVKGRFTI SRDNSKNTLY LQMNSLRAED TAVYYCAARD SGVGYYSRAQ WYDYWGQGTL  120
VTVSS                                                              125

SEQ ID NO: 186          moltype = AA  length = 8
FEATURE                 Location/Qualifiers
DOMAIN                  1..8
                        note = 2A3 ML DT CDR1
source                  1..8
                        mol_type = protein
                        organism = synthetic construct
SEQUENCE: 186
GGSFSSYP                                                             8

SEQ ID NO: 187          moltype = AA  length = 8
FEATURE                 Location/Qualifiers
DOMAIN                  1..8
                        note = 2A3 ML DT CDR2
source                  1..8
                        mol_type = protein
                        organism = synthetic construct
SEQUENCE: 187
ISSDLRFT                                                             8

SEQ ID NO: 188          moltype = AA  length = 18
FEATURE                 Location/Qualifiers
DOMAIN                  1..18
                        note = 2A3 ML DT CDR3
source                  1..18
                        mol_type = protein
                        organism = synthetic construct
SEQUENCE: 188
AARTSGVGYY SRAQWYDY                                                 18

SEQ ID NO: 189          moltype = AA  length = 125
FEATURE                 Location/Qualifiers
DOMAIN                  1..125
                        note = 2A3 ML DT VHH
source                  1..125
                        mol_type = protein
                        organism = synthetic construct
SEQUENCE: 189
QVQLVESGGG VVQPGRSLRL SCAASGGSFS SYPMGWFRQA PGKERESVAA ISSDLRFTYY    60
ADSVKGRFTI SRDNSKNTLY LQMNSLRAED TAVYYCAART SGVGYYSRAQ WYDYWGQGTL  120
VTVSS                                                              125

SEQ ID NO: 190          moltype = AA  length = 8
FEATURE                 Location/Qualifiers
DOMAIN                  1..8
                        note = 2A3 ML DE CDR1
source                  1..8
                        mol_type = protein
                        organism = synthetic construct
SEQUENCE: 190
GGSFSSYP                                                             8

SEQ ID NO: 191          moltype = AA  length = 8
FEATURE                 Location/Qualifiers
DOMAIN                  1..8
                        note = 2A3 ML DE CDR2
source                  1..8
                        mol_type = protein
                        organism = synthetic construct
SEQUENCE: 191
ISSDLRFT                                                             8

SEQ ID NO: 192          moltype = AA  length = 18
FEATURE                 Location/Qualifiers
DOMAIN                  1..18
                        note = 2A3 ML DE CDR3
source                  1..18
                        mol_type = protein
```

```
                        -continued
                        organism = synthetic construct
SEQUENCE: 192
AARESGVGYY SRAQWYDY                                              18

SEQ ID NO: 193          moltype = AA   length = 125
FEATURE                 Location/Qualifiers
DOMAIN                  1..125
                        note = 2A3 ML DE VHH
source                  1..125
                        mol_type = protein
                        organism = synthetic construct
SEQUENCE: 193
QVQLVESGGG VVQPGRSLRL SCAASGGSFS SYPMGWFRQA PGKERESVAA ISSDLRFTYY  60
ADSVKGRFTI SRDNSKNTLY LQMNSLRAED TAVYYCAARE SGVGYYSRAQ WYDYWGQGTL 120
VTVSS                                                            125

SEQ ID NO: 194          moltype = AA   length = 357
FEATURE                 Location/Qualifiers
CHAIN                   1..357
                        note = 2A3 LT Fc
source                  1..357
                        mol_type = protein
                        organism = synthetic construct
SEQUENCE: 194
QVQLVESGGG VVQPGRSLRL SCAASGGSFS SYPMGWFRQA PGKERESVAA ISSDLRFTYY  60
ADSVKGRFTI SRDNSKNTLY LQMNSLRAED TAVYYCAART SGVGYYSRAQ WYDYWGQGTL 120
VTVSSEPKSC DKTHTCPPCP APELLGGPSV FLFPPKPKDT LMISRTPEVT CVVVDVSHED 180
PEVKFNWYVD GVEVHNAKTK PREEQYNSTY RVVSVLTVLH QDWLNGKEYK CKVSNKALPA 240
PIEKTISKAK GQPREPQVYT LPPSREEMTK NQVSLTCLVK GFYPSDIAVE WESNGQPENN 300
YKTTPPVLDS DGSFFLYSKL TVDKSRWQQG NVFSCSVMHE ALHNHYTQKS LSLSPGK    357

SEQ ID NO: 195          moltype = AA   length = 12
FEATURE                 Location/Qualifiers
DOMAIN                  1..12
                        note = 195Exemplary linker
source                  1..12
                        mol_type = protein
                        organism = synthetic construct
SEQUENCE: 195
GSGGSGGSGG SG                                                     12

SEQ ID NO: 196          moltype = AA   length = 15
FEATURE                 Location/Qualifiers
DOMAIN                  1..15
                        note = 196Exemplary linker
source                  1..15
                        mol_type = protein
                        organism = synthetic construct
SEQUENCE: 196
GGGGSGGGGS GGGGS                                                  15

SEQ ID NO: 197          moltype = AA   length = 5
FEATURE                 Location/Qualifiers
DOMAIN                  1..5
                        note = 197Exemplary linker
source                  1..5
                        mol_type = protein
                        organism = synthetic construct
SEQUENCE: 197
GGGSG                                                              5

SEQ ID NO: 198          moltype = AA   length = 10
FEATURE                 Location/Qualifiers
DOMAIN                  1..10
                        note = 198Exemplary linker
source                  1..10
                        mol_type = protein
                        organism = synthetic construct
SEQUENCE: 198
GGGSGGGGSG                                                        10

SEQ ID NO: 199          moltype = AA   length = 8
FEATURE                 Location/Qualifiers
DOMAIN                  1..8
                        note = 199Exemplary linker
source                  1..8
                        mol_type = protein
                        organism = synthetic construct
SEQUENCE: 199
```

```
GGSGGGSG                                                                        8

SEQ ID NO: 200         moltype = AA  length = 12
FEATURE                Location/Qualifiers
DOMAIN                 1..12
                       note = 200Exemplary linker
source                 1..12
                       mol_type = protein
                       organism = synthetic construct
SEQUENCE: 200
GGSGGGSGGG SG                                                                  12

SEQ ID NO: 201         moltype = AA  length = 6
FEATURE                Location/Qualifiers
DOMAIN                 1..6
                       note = 201Exemplary linker
source                 1..6
                       mol_type = protein
                       organism = synthetic construct
SEQUENCE: 201
GSGGSG                                                                          6

SEQ ID NO: 202         moltype = AA  length = 9
FEATURE                Location/Qualifiers
DOMAIN                 1..9
                       note = 202Exemplary linker
source                 1..9
                       mol_type = protein
                       organism = synthetic construct
SEQUENCE: 202
GSGGSGGSG                                                                       9

SEQ ID NO: 203         moltype = AA  length = 7
FEATURE                Location/Qualifiers
DOMAIN                 1..7
                       note = 203Exemplary linker
source                 1..7
                       mol_type = protein
                       organism = synthetic construct
SEQUENCE: 203
GSGSGSG                                                                         7

SEQ ID NO: 204         moltype = AA  length = 18
FEATURE                Location/Qualifiers
DOMAIN                 1..18
                       note = 204Exemplary linker
source                 1..18
                       mol_type = protein
                       organism = synthetic construct
SEQUENCE: 204
GGGGSGGGGS GGGGSGGG                                                            18

SEQ ID NO: 205         moltype = AA  length = 5
FEATURE                Location/Qualifiers
DOMAIN                 1..5
                       note = 205Exemplary linker
source                 1..5
                       mol_type = protein
                       organism = synthetic construct
SEQUENCE: 205
PAPAP                                                                           5

SEQ ID NO: 206         moltype = AA  length = 15
FEATURE                Location/Qualifiers
DOMAIN                 1..15
                       note = 206Exemplary linker
source                 1..15
                       mol_type = protein
                       organism = synthetic construct
SEQUENCE: 206
PAPAPPAPAP PAPAP                                                               15

SEQ ID NO: 207         moltype = AA  length = 7
FEATURE                Location/Qualifiers
DOMAIN                 1..7
                       note = 207Exemplary linker
source                 1..7
                       mol_type = protein
                       organism = synthetic construct
```

```
SEQUENCE: 207
IKRTVAA                                                                     7

SEQ ID NO: 208         moltype = AA  length = 7
FEATURE                Location/Qualifiers
DOMAIN                 1..7
                       note = 208Exemplary linker
source                 1..7
                       mol_type = protein
                       organism = synthetic construct
SEQUENCE: 208
VSSASTK                                                                     7

SEQ ID NO: 209         moltype = AA  length = 7
FEATURE                Location/Qualifiers
DOMAIN                 1..7
                       note = 209Exemplary linker
source                 1..7
                       mol_type = protein
                       organism = synthetic construct
SEQUENCE: 209
AEAAAKA                                                                     7

SEQ ID NO: 210         moltype = AA  length = 12
FEATURE                Location/Qualifiers
DOMAIN                 1..12
                       note = 210Exemplary linker
source                 1..12
                       mol_type = protein
                       organism = synthetic construct
SEQUENCE: 210
AEAAAKEAAA KA                                                              12

SEQ ID NO: 211         moltype = AA  length = 10
FEATURE                Location/Qualifiers
DOMAIN                 1..10
                       note = 211Exemplary linker
source                 1..10
                       mol_type = protein
                       organism = synthetic construct
SEQUENCE: 211
GRPGSGRPGS                                                                 10

SEQ ID NO: 212         moltype = AA  length = 20
FEATURE                Location/Qualifiers
DOMAIN                 1..20
                       note = 212Exemplary linker
source                 1..20
                       mol_type = protein
                       organism = synthetic construct
SEQUENCE: 212
GRPGSGRPGS GRPGSGRPGS                                                      20

SEQ ID NO: 213         moltype = AA  length = 10
FEATURE                Location/Qualifiers
DOMAIN                 1..10
                       note = 213Exemplary linker
source                 1..10
                       mol_type = protein
                       organism = synthetic construct
SEQUENCE: 213
GRGGSGRGGS                                                                 10

SEQ ID NO: 214         moltype = AA  length = 20
FEATURE                Location/Qualifiers
DOMAIN                 1..20
                       note = 214Exemplary linker
source                 1..20
                       mol_type = protein
                       organism = synthetic construct
SEQUENCE: 214
GRGGSGRGGS GRGGSGRGGS                                                      20

SEQ ID NO: 215         moltype = AA  length = 10
FEATURE                Location/Qualifiers
DOMAIN                 1..10
                       note = 215Exemplary linker
source                 1..10
                       mol_type = protein
```

```
                                            -continued organism = synthetic construct
SEQUENCE: 215
GKPGSGKPGS                                                                      10

SEQ ID NO: 216          moltype = AA  length = 20
FEATURE                 Location/Qualifiers
DOMAIN                  1..20
                        note = 216Exemplary linker
source                  1..20
                        mol_type = protein
                        organism = synthetic construct
SEQUENCE: 216
GKPGSGKPGS GKPGSGKPGS                                                           20

SEQ ID NO: 217          moltype = AA  length = 10
FEATURE                 Location/Qualifiers
DOMAIN                  1..10
                        note = 217Exemplary linker
source                  1..10
                        mol_type = protein
                        organism = synthetic construct
SEQUENCE: 217
GEPGSGEPGS                                                                      10

SEQ ID NO: 218          moltype = AA  length = 20
FEATURE                 Location/Qualifiers
DOMAIN                  1..20
                        note = 218Exemplary linker
source                  1..20
                        mol_type = protein
                        organism = synthetic construct
SEQUENCE: 218
GEGGSGEGGS GEGGSGEGGS                                                           20

SEQ ID NO: 219          moltype = AA  length = 10
FEATURE                 Location/Qualifiers
DOMAIN                  1..10
                        note = 219Exemplary linker
source                  1..10
                        mol_type = protein
                        organism = synthetic construct
SEQUENCE: 219
GDPGSGDPGS                                                                      10

SEQ ID NO: 220          moltype = AA  length = 20
FEATURE                 Location/Qualifiers
DOMAIN                  1..20
                        note = 220Exemplary linker
source                  1..20
                        mol_type = protein
                        organism = synthetic construct
SEQUENCE: 220
GDPGSGDPGS GDPGSGDPGS                                                           20

SEQ ID NO: 221          moltype = AA  length = 5
FEATURE                 Location/Qualifiers
DOMAIN                  1..5
                        note = PL2#3 CDR-H1
source                  1..5
                        mol_type = protein
                        organism = synthetic construct
SEQUENCE: 221
SYTMN                                                                            5

SEQ ID NO: 222          moltype = AA  length = 17
FEATURE                 Location/Qualifiers
DOMAIN                  1..17
                        note = PL2#3 CDR-H2
source                  1..17
                        mol_type = protein
                        organism = synthetic construct
SEQUENCE: 222
SISSGSDYLY YADSVKG                                                              17

SEQ ID NO: 223          moltype = AA  length = 14
FEATURE                 Location/Qualifiers
DOMAIN                  1..14
                        note = PL2#3 CDR-H3
source                  1..14
```

```
                        mol_type = protein
                        organism = synthetic construct
SEQUENCE: 223
NELRWYPQAG AFDR                                                         14

SEQ ID NO: 224          moltype = AA   length = 13
FEATURE                 Location/Qualifiers
DOMAIN                  1..13
                        note = PL2#3 CDR-L1
source                  1..13
                        mol_type = protein
                        organism = synthetic construct
SEQUENCE: 224
SGSSSYIESS YVG                                                          13

SEQ ID NO: 225          moltype = AA   length = 7
FEATURE                 Location/Qualifiers
DOMAIN                  1..7
                        note = PL2#3 CDR-L2
source                  1..7
                        mol_type = protein
                        organism = synthetic construct
SEQUENCE: 225
DDDMRPS                                                                 7

SEQ ID NO: 226          moltype = AA   length = 10
FEATURE                 Location/Qualifiers
DOMAIN                  1..10
                        note = PL2#3 CDR-L3
source                  1..10
                        mol_type = protein
                        organism = synthetic construct
SEQUENCE: 226
EIWRSGLGGV                                                              10

SEQ ID NO: 227          moltype = AA   length = 123
FEATURE                 Location/Qualifiers
DOMAIN                  1..123
                        note = PL2#3 VH
source                  1..123
                        mol_type = protein
                        organism = synthetic construct
SEQUENCE: 227
EVQLVQSGGG LVKPGGSLRL SCAASGFTFS SYTMNWVRQA PGKGLEWVSS ISSGSDYLYY       60
ADSVKGRFTI SRDNAKNSLY LQMNSLRAED TAVYYCARNE LRWYPQAGAF DRWGQGTMVT       120
VSS                                                                     123

SEQ ID NO: 228          moltype = AA   length = 109
FEATURE                 Location/Qualifiers
DOMAIN                  1..109
                        note = PL2#3 VL
source                  1..109
                        mol_type = protein
                        organism = synthetic construct
SEQUENCE: 228
QSVVTQPPSM SAAPGQRVTI SCSGSSSYIE SSYVGWYQQL PGTAPRLLIY DDDMRPSGIP       60
DRFSGSKSGT SATLAITGLQ TGDEADYYCE IWRSGLGGVF GGGTKLTVL                   109

SEQ ID NO: 229          moltype = AA   length = 5
FEATURE                 Location/Qualifiers
DOMAIN                  1..5
                        note = PL3#7 CDR-H1
source                  1..5
                        mol_type = protein
                        organism = synthetic construct
SEQUENCE: 229
SYPIS                                                                   5

SEQ ID NO: 230          moltype = AA   length = 17
FEATURE                 Location/Qualifiers
DOMAIN                  1..17
                        note = PL3#7 CDR-H2
source                  1..17
                        mol_type = protein
                        organism = synthetic construct
SEQUENCE: 230
RIIPILGIAN YAQKFQG                                                      17

SEQ ID NO: 231          moltype = AA   length = 12
```

```
FEATURE                 Location/Qualifiers
DOMAIN                  1..12
                        note = PL3#7 CDR-H3
source                  1..12
                        mol_type = protein
                        organism = synthetic construct
SEQUENCE: 231
SRDGYAFGAF DI                                                           12

SEQ ID NO: 232          moltype = AA   length = 14
FEATURE                 Location/Qualifiers
DOMAIN                  1..14
                        note = PL3#7 CDR-L1
source                  1..14
                        mol_type = protein
                        organism = synthetic construct
SEQUENCE: 232
TGSSSNIGAG YDVH                                                         14

SEQ ID NO: 233          moltype = AA   length = 7
FEATURE                 Location/Qualifiers
DOMAIN                  1..7
                        note = PL3#7 CDR-L2
source                  1..7
                        mol_type = protein
                        organism = synthetic construct
SEQUENCE: 233
GNSNRPS                                                                 7

SEQ ID NO: 234          moltype = AA   length = 12
FEATURE                 Location/Qualifiers
DOMAIN                  1..12
                        note = PL3#7 CDR-L3
source                  1..12
                        mol_type = protein
                        organism = synthetic construct
SEQUENCE: 234
QTYDSSLSAR VV                                                           12

SEQ ID NO: 235          moltype = AA   length = 121
FEATURE                 Location/Qualifiers
DOMAIN                  1..121
                        note = PL3#7 VH
source                  1..121
                        mol_type = protein
                        organism = synthetic construct
SEQUENCE: 235
QVQLVQSGAE VKKPGSSVKV SCKASGGTFS SYPISWVRQA PGQGLEWIGR IIPILGIANY        60
AQKFQGRVTI TADKSTSTAY MELSSLRSED TAVYYCARSR DGYAFGAFDI WGQGTLVTVS       120
S                                                                      121

SEQ ID NO: 236          moltype = AA   length = 112
FEATURE                 Location/Qualifiers
DOMAIN                  1..112
                        note = PL3#7 VL
source                  1..112
                        mol_type = protein
                        organism = synthetic construct
SEQUENCE: 236
QSVVTQPPPV SGAPGQRVTI SCTGSSSNIG AGYDVHWYQQ LPGTAPKLLI YGNSNRPSGV        60
PDRFSGSKSG TSASLAITGL QAEDEADYYC QTYDSSLSAR VVFGGGTKLT VL               112

SEQ ID NO: 237          moltype = AA   length = 5
FEATURE                 Location/Qualifiers
DOMAIN                  1..5
                        note = PL3#7-19 CDR-H1
source                  1..5
                        mol_type = protein
                        organism = synthetic construct
SEQUENCE: 237
SYPIS                                                                   5

SEQ ID NO: 238          moltype = AA   length = 17
FEATURE                 Location/Qualifiers
DOMAIN                  1..17
                        note = PL3#7-19 CDR-H2
source                  1..17
                        mol_type = protein
                        organism = synthetic construct
```

```
SEQUENCE: 238
RIIPILGIAN YAQKFQG                                                              17

SEQ ID NO: 239          moltype = AA  length = 12
FEATURE                 Location/Qualifiers
DOMAIN                  1..12
                        note = PL3#7-19 CDR-H3
source                  1..12
                        mol_type = protein
                        organism = synthetic construct
SEQUENCE: 239
SRDGYAFGAF DV                                                                   12

SEQ ID NO: 240          moltype = AA  length = 14
FEATURE                 Location/Qualifiers
DOMAIN                  1..14
                        note = PL3#7-19 CDR-L1
source                  1..14
                        mol_type = protein
                        organism = synthetic construct
SEQUENCE: 240
TGSSSNIGGG YDVH                                                                 14

SEQ ID NO: 241          moltype = AA  length = 7
FEATURE                 Location/Qualifiers
DOMAIN                  1..7
                        note = PL3#7-19 CDR-L2
source                  1..7
                        mol_type = protein
                        organism = synthetic construct
SEQUENCE: 241
GNSTRPS                                                                         7

SEQ ID NO: 242          moltype = AA  length = 12
FEATURE                 Location/Qualifiers
DOMAIN                  1..12
                        note = PL3#7-19 CDR-L3
source                  1..12
                        mol_type = protein
                        organism = synthetic construct
SEQUENCE: 242
QTYDSSLSAT VV                                                                   12

SEQ ID NO: 243          moltype = AA  length = 121
FEATURE                 Location/Qualifiers
DOMAIN                  1..121
                        note = PL3#7-19 VH
source                  1..121
                        mol_type = protein
                        organism = synthetic construct
SEQUENCE: 243
QVQLVQSGAE VKKPGSSVKV SCKASGGTFS SYPISWVRQA PGQGLEWMGR IIPILGIANY               60
AQKFQGRVTI TADKSTSTAY MELSSLRSED TAVYYCARSR DGYAFGAFDV WGQGTLVTVS              120
S                                                                             121

SEQ ID NO: 244          moltype = AA  length = 112
FEATURE                 Location/Qualifiers
DOMAIN                  1..112
                        note = PL3#7-19 VL
source                  1..112
                        mol_type = protein
                        organism = synthetic construct
SEQUENCE: 244
QSVVTQPPPV SGAPGQRVTI SCTGSSSNIG GGYDVHWYQQ LPGTAPKLLI YGNSTRPSGV               60
PDRFSGSKSG TSASLAITGL QAEDEADYYC QTYDSSLSAT VVFGGGTKLT VL                     112

SEQ ID NO: 245          moltype = AA  length = 5
FEATURE                 Location/Qualifiers
DOMAIN                  1..5
                        note = PL3#7-43 CDR-H1
source                  1..5
                        mol_type = protein
                        organism = synthetic construct
SEQUENCE: 245
SYPIS                                                                           5

SEQ ID NO: 246          moltype = AA  length = 17
FEATURE                 Location/Qualifiers
DOMAIN                  1..17
```

```
                        note = PL3#7-43 CDR-H2
source                  1..17
                        mol_type = protein
                        organism = synthetic construct
SEQUENCE: 246
RIIPILGIAN YAQKFQG                                                       17

SEQ ID NO: 247          moltype = AA  length = 12
FEATURE                 Location/Qualifiers
DOMAIN                  1..12
                        note = PL3#7-43 CDR-H3
source                  1..12
                        mol_type = protein
                        organism = synthetic construct
SEQUENCE: 247
SRPGYAFGAF DI                                                            12

SEQ ID NO: 248          moltype = AA  length = 14
FEATURE                 Location/Qualifiers
DOMAIN                  1..14
                        note = PL3#7-43 CDR-L1
source                  1..14
                        mol_type = protein
                        organism = synthetic construct
SEQUENCE: 248
TGSSSNVGAG YDVH                                                          14

SEQ ID NO: 249          moltype = AA  length = 7
FEATURE                 Location/Qualifiers
DOMAIN                  1..7
                        note = PL3#7-43 CDR-L2
source                  1..7
                        mol_type = protein
                        organism = synthetic construct
SEQUENCE: 249
GNSNRSS                                                                   7

SEQ ID NO: 250          moltype = AA  length = 12
FEATURE                 Location/Qualifiers
DOMAIN                  1..12
                        note = PL3#7-43 CDR-L3
source                  1..12
                        mol_type = protein
                        organism = synthetic construct
SEQUENCE: 250
QTYDSSGSAR VV                                                            12

SEQ ID NO: 251          moltype = AA  length = 121
FEATURE                 Location/Qualifiers
DOMAIN                  1..121
                        note = PL3#7-43 VH
source                  1..121
                        mol_type = protein
                        organism = synthetic construct
SEQUENCE: 251
QVQLVQSGAE VKKPGSSVKV SCKASGGTFS SYPISWVRQA PGQGLEWMGR IIPILGIANY         60
AQKFQGRVTI TADKSTSTAY MELSSLRSED TAVYYCARSR PGYAFGAFDI WGQGTLVTVS        120
S                                                                       121

SEQ ID NO: 252          moltype = AA  length = 112
FEATURE                 Location/Qualifiers
DOMAIN                  1..112
                        note = PL3#7-43 VL
source                  1..112
                        mol_type = protein
                        organism = synthetic construct
SEQUENCE: 252
QSVVTQPPPV SGAPGQRVTI SCTGSSSNVG AGYDVHWYQQ LPGTAPKLLI YGNSNRSSGV         60
PDRFSGSKSG TSASLAITGL QAEDEADYYC QTYDSSGSAR VVFGGGTKLT VL                112

SEQ ID NO: 253          moltype = AA  length = 5
FEATURE                 Location/Qualifiers
DOMAIN                  1..5
                        note = PL3#7-54 CDR-H1
source                  1..5
                        mol_type = protein
                        organism = synthetic construct
SEQUENCE: 253
SYPIS                                                                     5
```

```
SEQ ID NO: 254          moltype = AA   length = 17
FEATURE                 Location/Qualifiers
DOMAIN                  1..17
                        note = PL3#7-54 CDR-H2
source                  1..17
                        mol_type = protein
                        organism = synthetic construct
SEQUENCE: 254
RIIPILGIAD YAQKFQG                                                      17

SEQ ID NO: 255          moltype = AA   length = 12
FEATURE                 Location/Qualifiers
DOMAIN                  1..12
                        note = PL3#7-54 CDR-H3
source                  1..12
                        mol_type = protein
                        organism = synthetic construct
SEQUENCE: 255
SRPGYAFGAF DI                                                           12

SEQ ID NO: 256          moltype = AA   length = 14
FEATURE                 Location/Qualifiers
DOMAIN                  1..14
                        note = PL3#7-54 CDR-L1
source                  1..14
                        mol_type = protein
                        organism = synthetic construct
SEQUENCE: 256
TGSSSNIGQG YDVH                                                         14

SEQ ID NO: 257          moltype = AA   length = 7
FEATURE                 Location/Qualifiers
DOMAIN                  1..7
                        note = PL3#7-54 CDR-L2
source                  1..7
                        mol_type = protein
                        organism = synthetic construct
SEQUENCE: 257
ANSNRPS                                                                  7

SEQ ID NO: 258          moltype = AA   length = 12
FEATURE                 Location/Qualifiers
DOMAIN                  1..12
                        note = PL3#7-54 CDR-L3
source                  1..12
                        mol_type = protein
                        organism = synthetic construct
SEQUENCE: 258
QTYDSSLSAR VV                                                           12

SEQ ID NO: 259          moltype = AA   length = 121
FEATURE                 Location/Qualifiers
DOMAIN                  1..121
                        note = PL3#7-54 VH
source                  1..121
                        mol_type = protein
                        organism = synthetic construct
SEQUENCE: 259
QVQLVQSGAE VKKPGSSVKV SCKASGGTFS SYPISWVRQA PGQGLEWMGR IIPILGIADY        60
AQKFQGRVTI TADKSTSTAY MELSSLRSED TAVYYCARSR PGYAFGAFDI WGQGTLVTVS       120
S                                                                      121

SEQ ID NO: 260          moltype = AA   length = 112
FEATURE                 Location/Qualifiers
DOMAIN                  1..112
                        note = PL3#7-54 VL
source                  1..112
                        mol_type = protein
                        organism = synthetic construct
SEQUENCE: 260
QSVVTQPPPV SGAPGQRVTI SCTGSSSNIG QGYDVHWYQQ LPGTAPKLLI YANSNRPSGV        60
PDRFSGSKSG TSASLAITGL QAEDEADYYC QTYDSSLSAR VVFGGGTKLT VL               112

SEQ ID NO: 261          moltype = AA   length = 5
FEATURE                 Location/Qualifiers
DOMAIN                  1..5
                        note = PL2#4 CDR-H1
source                  1..5
```

```
SEQUENCE: 261
SYTMN                                                                    5

SEQ ID NO: 262          moltype = AA   length = 17
FEATURE                 Location/Qualifiers
DOMAIN                  1..17
                        note = PL2#4 CDR-H2
source                  1..17
                        mol_type = protein
                        organism = synthetic construct
SEQUENCE: 262
SISSGSDYLY YADSVKG                                                      17

SEQ ID NO: 263          moltype = AA   length = 14
FEATURE                 Location/Qualifiers
DOMAIN                  1..14
                        note = PL2#4 CDR-H3
source                  1..14
                        mol_type = protein
                        organism = synthetic construct
SEQUENCE: 263
NELRWYPLAG AFDI                                                         14

SEQ ID NO: 264          moltype = AA   length = 13
FEATURE                 Location/Qualifiers
DOMAIN                  1..13
                        note = PL2#4 CDR-L1
source                  1..13
                        mol_type = protein
                        organism = synthetic construct
SEQUENCE: 264
SGVSSYIESS YVS                                                          13

SEQ ID NO: 265          moltype = AA   length = 7
FEATURE                 Location/Qualifiers
DOMAIN                  1..7
                        note = PL2#4 CDR-L2
source                  1..7
                        mol_type = protein
                        organism = synthetic construct
SEQUENCE: 265
DDDMRPS                                                                  7

SEQ ID NO: 266          moltype = AA   length = 10
FEATURE                 Location/Qualifiers
DOMAIN                  1..10
                        note = PL2#4 CDR-L3
source                  1..10
                        mol_type = protein
                        organism = synthetic construct
SEQUENCE: 266
KIWDSGLGGV                                                              10

SEQ ID NO: 267          moltype = AA   length = 123
FEATURE                 Location/Qualifiers
DOMAIN                  1..123
                        note = PL2#4 VH
source                  1..123
                        mol_type = protein
                        organism = synthetic construct
SEQUENCE: 267
EVQLVQSGGG LVKPGGSLRL SCAASGFTFS SYTMNWVRQA PGKGLEWVSS ISSGSDYLYY        60
ADSVKGRFTI SRDNAKNSLY LQMNSLRAED TAVYYCARNE LRWYPLAGAF DIWGQGTMVT       120
VSS                                                                    123

SEQ ID NO: 268          moltype = AA   length = 109
FEATURE                 Location/Qualifiers
DOMAIN                  1..109
                        note = PL2#4 VL
source                  1..109
                        mol_type = protein
                        organism = synthetic construct
SEQUENCE: 268
QSVVTQPPSM SAAPGQRVTI SCSGVSSYIE SSYVSWYQQL PGTAPRLLIY DDDMRPSGIP        60
DRFSGSKSGT SATLAITGLQ TGDEADYYCK IWDSGLGGVF GGGTKLTVL                   109

SEQ ID NO: 269          moltype = AA   length = 5
```

```
FEATURE              Location/Qualifiers
DOMAIN               1..5
                     note = PL2#5 CDR-H1
source               1..5
                     mol_type = protein
                     organism = synthetic construct
SEQUENCE: 269
SYTMN                                                                5

SEQ ID NO: 270       moltype = AA  length = 17
FEATURE              Location/Qualifiers
DOMAIN               1..17
                     note = PL2#5 CDR-H2
source               1..17
                     mol_type = protein
                     organism = synthetic construct
SEQUENCE: 270
SISSGSDYLY YADSVKG                                                  17

SEQ ID NO: 271       moltype = AA  length = 14
FEATURE              Location/Qualifiers
DOMAIN               1..14
                     note = PL2#5 CDR-H3
source               1..14
                     mol_type = protein
                     organism = synthetic construct
SEQUENCE: 271
NELRWYPFAG AFDI                                                     14

SEQ ID NO: 272       moltype = AA  length = 13
FEATURE              Location/Qualifiers
DOMAIN               1..13
                     note = PL2#5 CDR-L1
source               1..13
                     mol_type = protein
                     organism = synthetic construct
SEQUENCE: 272
SGSSSYIESS YVS                                                      13

SEQ ID NO: 273       moltype = AA  length = 7
FEATURE              Location/Qualifiers
DOMAIN               1..7
                     note = PL2#5 CDR-L2
source               1..7
                     mol_type = protein
                     organism = synthetic construct
SEQUENCE: 273
DDDMRPS                                                              7

SEQ ID NO: 274       moltype = AA  length = 10
FEATURE              Location/Qualifiers
DOMAIN               1..10
                     note = PL2#5 CDR-L3
source               1..10
                     mol_type = protein
                     organism = synthetic construct
SEQUENCE: 274
EIWDSRLGGV                                                          10

SEQ ID NO: 275       moltype = AA  length = 123
FEATURE              Location/Qualifiers
DOMAIN               1..123
                     note = PL2#5 VH
source               1..123
                     mol_type = protein
                     organism = synthetic construct
SEQUENCE: 275
EVQLVQSGGG LVKPGGSLRL SCAASGFTFS SYTMNWVRQA PGKGLEWVSS ISSGSDYLYY    60
ADSVKGRFTI SRDNAKNSLY LQMNSLRAED TAVYYCARNE LRWYPFAGAF DIWGQGTMVT   120
VSS                                                                123

SEQ ID NO: 276       moltype = AA  length = 109
FEATURE              Location/Qualifiers
DOMAIN               1..109
                     note = PL2#5 VL
source               1..109
                     mol_type = protein
                     organism = synthetic construct
SEQUENCE: 276
```

```
QSVVTQPPSM SAAPGQRVTI SCSGSSSYIE SSYVSWYQQL PGTAPRLLIY DDDMRPSGIP    60
DRFSGSKSGT SATLAITGLQ TGDEADYYCE IWDSRLGGVF GGGTKLTVL              109

SEQ ID NO: 277          moltype = AA  length = 5
FEATURE                 Location/Qualifiers
DOMAIN                  1..5
                        note = PL2#39 CDR-H1
source                  1..5
                        mol_type = protein
                        organism = synthetic construct
SEQUENCE: 277
SYTMN                                                                5

SEQ ID NO: 278          moltype = AA  length = 17
FEATURE                 Location/Qualifiers
DOMAIN                  1..17
                        note = PL2#39 CDR-H2
source                  1..17
                        mol_type = protein
                        organism = synthetic construct
SEQUENCE: 278
SISSGSDYLY YADSVKG                                                  17

SEQ ID NO: 279          moltype = AA  length = 14
FEATURE                 Location/Qualifiers
DOMAIN                  1..14
                        note = PL2#39 CDR-H3
source                  1..14
                        mol_type = protein
                        organism = synthetic construct
SEQUENCE: 279
NELRWYPKAG AFDI                                                     14

SEQ ID NO: 280          moltype = AA  length = 13
FEATURE                 Location/Qualifiers
DOMAIN                  1..13
                        note = PL2#39 CDR-L1
source                  1..13
                        mol_type = protein
                        organism = synthetic construct
SEQUENCE: 280
SGSSSYITSS YVS                                                      13

SEQ ID NO: 281          moltype = AA  length = 7
FEATURE                 Location/Qualifiers
DOMAIN                  1..7
                        note = PL2#39 CDR-L2
source                  1..7
                        mol_type = protein
                        organism = synthetic construct
SEQUENCE: 281
DDDMRPS                                                              7

SEQ ID NO: 282          moltype = AA  length = 10
FEATURE                 Location/Qualifiers
DOMAIN                  1..10
                        note = PL2#39 CDR-L3
source                  1..10
                        mol_type = protein
                        organism = synthetic construct
SEQUENCE: 282
KIWDSGLGGV                                                          10

SEQ ID NO: 283          moltype = AA  length = 123
FEATURE                 Location/Qualifiers
DOMAIN                  1..123
                        note = PL2#39 VH
source                  1..123
                        mol_type = protein
                        organism = synthetic construct
SEQUENCE: 283
EVQLVQSGGG LVKPGGSLRL SCAASGFTFS SYTMNWVRQA PGKGLEWVSS ISSGSDYLYY    60
ADSVKGRFTI SRDNAKNSLY LQMNSLRAED TAVYYCARNE LRWYPKAGAF DIWGQGTMVT   120
VSS                                                                123

SEQ ID NO: 284          moltype = AA  length = 109
FEATURE                 Location/Qualifiers
DOMAIN                  1..109
                        note = PL2#39 VL
```

```
source                      1..109
                            mol_type = protein
                            organism = synthetic construct
SEQUENCE: 284
QSVVTQPPSM SAAPGQRVTI SCSGSSSYIT SSYVSWYQQL PGTAPRLLIY DDDMRPSGIP    60
DRFSGSKSGT SATLAITGLQ TGDEADYYCK IWDSGLGGVF GGGTKLTVL               109

SEQ ID NO: 285              moltype = AA   length = 5
FEATURE                     Location/Qualifiers
DOMAIN                      1..5
                            note = PL3#1 CDR-H1
source                      1..5
                            mol_type = protein
                            organism = synthetic construct
SEQUENCE: 285
SYRIS                                                                 5

SEQ ID NO: 286              moltype = AA   length = 17
FEATURE                     Location/Qualifiers
DOMAIN                      1..17
                            note = PL3#1 CDR-H2
source                      1..17
                            mol_type = protein
                            organism = synthetic construct
SEQUENCE: 286
RIIPILGIAN YAQKFQG                                                   17

SEQ ID NO: 287              moltype = AA   length = 12
FEATURE                     Location/Qualifiers
DOMAIN                      1..12
                            note = PL3#1 CDR-H3
source                      1..12
                            mol_type = protein
                            organism = synthetic construct
SEQUENCE: 287
SRDGYSVGAF DS                                                        12

SEQ ID NO: 288              moltype = AA   length = 14
FEATURE                     Location/Qualifiers
DOMAIN                      1..14
                            note = PL3#1 CDR-L1
source                      1..14
                            mol_type = protein
                            organism = synthetic construct
SEQUENCE: 288
TGSSSNIGAG YDVH                                                      14

SEQ ID NO: 289              moltype = AA   length = 7
FEATURE                     Location/Qualifiers
DOMAIN                      1..7
                            note = PL3#1 CDR-L2
source                      1..7
                            mol_type = protein
                            organism = synthetic construct
SEQUENCE: 289
GNSRRPS                                                               7

SEQ ID NO: 290              moltype = AA   length = 12
FEATURE                     Location/Qualifiers
DOMAIN                      1..12
                            note = PL3#1 CDR-L3
source                      1..12
                            mol_type = protein
                            organism = synthetic construct
SEQUENCE: 290
QTYDSSLSRP VV                                                        12

SEQ ID NO: 291              moltype = AA   length = 121
FEATURE                     Location/Qualifiers
DOMAIN                      1..121
                            note = PL3#1 VH
source                      1..121
                            mol_type = protein
                            organism = synthetic construct
SEQUENCE: 291
QVQLVQSGAE VKKPGSSVKV SCKASGGTFS SYRISWVRQA PGQGLEWMGR IIPILGIANY    60
AQKFQGRVTI TADKSTSTAY MELSSLRSED TAVYYCARSR DGYSVGAFDS WGQGTLVTVS   120
S                                                                  121
```

```
SEQ ID NO: 292          moltype = AA   length = 112
FEATURE                 Location/Qualifiers
DOMAIN                  1..112
                        note = PL3#1 VL
source                  1..112
                        mol_type = protein
                        organism = synthetic construct
SEQUENCE: 292
QSVVTQPPPV SGAPGQRVTI SCTGSSSNIG AGYDVHWYQQ LPGTAPKLLI YGNSRRPSGV    60
PDRFSGSKSG TSASLAITGL QAEDEADYYC QTYDSSLSRP VVFGGGTKLT VL           112

SEQ ID NO: 293          moltype = AA   length = 5
FEATURE                 Location/Qualifiers
DOMAIN                  1..5
                        note = PL3#7-43 D2 CDR-H1
source                  1..5
                        mol_type = protein
                        organism = synthetic construct
SEQUENCE: 293
SYPIS                                                                 5

SEQ ID NO: 294          moltype = AA   length = 17
FEATURE                 Location/Qualifiers
DOMAIN                  1..17
                        note = PL3#7-43 D2 CDR-H2
source                  1..17
                        mol_type = protein
                        organism = synthetic construct
SEQUENCE: 294
RIIPILGIAN YAQKFQG                                                   17

SEQ ID NO: 295          moltype = AA   length = 12
FEATURE                 Location/Qualifiers
DOMAIN                  1..12
                        note = PL3#7-43 D2 CDR-H3
source                  1..12
                        mol_type = protein
                        organism = synthetic construct
SEQUENCE: 295
SRPGYAFGAF DI                                                        12

SEQ ID NO: 296          moltype = AA   length = 14
FEATURE                 Location/Qualifiers
DOMAIN                  1..14
                        note = PL3#7-43 D2 CDR-L1
source                  1..14
                        mol_type = protein
                        organism = synthetic construct
SEQUENCE: 296
TGSSSNVGAG YDVH                                                      14

SEQ ID NO: 297          moltype = AA   length = 7
FEATURE                 Location/Qualifiers
DOMAIN                  1..7
                        note = PL3#7-43 D2 CDR-L2
source                  1..7
                        mol_type = protein
                        organism = synthetic construct
SEQUENCE: 297
GNSQRSS                                                               7

SEQ ID NO: 298          moltype = AA   length = 12
FEATURE                 Location/Qualifiers
DOMAIN                  1..12
                        note = PL3#7-43 D2 CDR-L3
source                  1..12
                        mol_type = protein
                        organism = synthetic construct
SEQUENCE: 298
QTYDSSGSAR VV                                                        12

SEQ ID NO: 299          moltype = AA   length = 121
FEATURE                 Location/Qualifiers
DOMAIN                  1..121
                        note = PL3#7-43 D2 VH
source                  1..121
                        mol_type = protein
                        organism = synthetic construct
SEQUENCE: 299
```

```
QVQLVQSGAE VKKPGSSVKV SCKASGGTFS SYPISWVRQA PGQGLEWMGR IIPILGIANY    60
AQKFQGRVTI TADKSTSTAY MELSSLRSED TAVYYCARSR PGYAFGAFDI WGQGTLVTVS   120
S                                                                  121

SEQ ID NO: 300          moltype = AA  length = 112
FEATURE                 Location/Qualifiers
DOMAIN                  1..112
                        note = PL3#7-43 D2 VL
source                  1..112
                        mol_type = protein
                        organism = synthetic construct
SEQUENCE: 300
QSVVTQPPPV SGAPGQRVTI SCTGSSSNVG AGYDVHWYQQ LPGTAPKLLI YGNSQRSSGV    60
PDRFSGSKSG TSASLAITGL QAEDEADYYC QTYDSSGSAR VVFGGGTKLT VL           112

SEQ ID NO: 301          moltype = AA  length = 5
FEATURE                 Location/Qualifiers
DOMAIN                  1..5
                        note = PL3#7-43 D1 CDR-H1
source                  1..5
                        mol_type = protein
                        organism = synthetic construct
SEQUENCE: 301
SYPIS                                                                5

SEQ ID NO: 302          moltype = AA  length = 17
FEATURE                 Location/Qualifiers
DOMAIN                  1..17
                        note = PL3#7-43 D1 CDR-H2
source                  1..17
                        mol_type = protein
                        organism = synthetic construct
SEQUENCE: 302
RIIPILGIAN YAQKFQG                                                  17

SEQ ID NO: 303          moltype = AA  length = 12
FEATURE                 Location/Qualifiers
DOMAIN                  1..12
                        note = PL3#7-43 D1 CDR-H3
source                  1..12
                        mol_type = protein
                        organism = synthetic construct
SEQUENCE: 303
SRPGYAFGAF DI                                                       12

SEQ ID NO: 304          moltype = AA  length = 14
FEATURE                 Location/Qualifiers
DOMAIN                  1..14
                        note = PL3#7-43 D1 CDR-L1
source                  1..14
                        mol_type = protein
                        organism = synthetic construct
SEQUENCE: 304
TGSSSNVGAG YDVH                                                     14

SEQ ID NO: 305          moltype = AA  length = 7
FEATURE                 Location/Qualifiers
DOMAIN                  1..7
                        note = PL3#7-43 D1 CDR-L2
source                  1..7
                        mol_type = protein
                        organism = synthetic construct
SEQUENCE: 305
GNSNRPS                                                              7

SEQ ID NO: 306          moltype = AA  length = 12
FEATURE                 Location/Qualifiers
DOMAIN                  1..12
                        note = PL3#7-43 D1 CDR-L3
source                  1..12
                        mol_type = protein
                        organism = synthetic construct
SEQUENCE: 306
QTYDSSGSAR VV                                                       12

SEQ ID NO: 307          moltype = AA  length = 121
FEATURE                 Location/Qualifiers
DOMAIN                  1..121
                        note = PL3#7-43 D1 VH
```

```
source                  1..121
                        mol_type = protein
                        organism = synthetic construct
SEQUENCE: 307
QVQLVQSGAE VKKPGSSVKV SCKASGGTFS SYPISWVRQA PGQGLEWMGR IIPILGIANY    60
AQKFQGRVTI TADKSTSTAY MELSSLRSED TAVYYCARSR PGYAFGAFDI WGQGTLVTVS   120
S                                                                   121

SEQ ID NO: 308          moltype = AA  length = 112
FEATURE                 Location/Qualifiers
DOMAIN                  1..112
                        note = PL3#7-43 D1 VL
source                  1..112
                        mol_type = protein
                        organism = synthetic construct
SEQUENCE: 308
QSVVTQPPPV SGAPGQRVTI SCTGSSSNVG AGYDVHWYQQ LPGTAPKLLI YGNSNRPSGV    60
PDRFSGSKSG TSASLAITGL QAEDEADYYC QTYDSSGSAR VVFGGGTKLT VL           112

SEQ ID NO: 309          moltype = AA  length = 588
FEATURE                 Location/Qualifiers
CHAIN                   1..588
                        note = anti-PDL1 HC -Linker- 2A3 (HCC heavy chain)
source                  1..588
                        mol_type = protein
                        organism = synthetic construct
SEQUENCE: 309
QVQLVQSGAE VKKPGSSVKV SCKASGGTFS SYPISWVRQA PGQGLEWMGR IIPILGIANY    60
AQKFQGRVTI TADKSTSTAY MELSSLRSED TAVYYCARSR PGYAFGAFDI WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGSGGSGGSG GSGQVQLVES GGGVVQPGRS   480
LRLSCAASGG SFSSYPMGWF RQAPGKERES VAAISSDMRF TYYADSVKGR FTISRDNSKN   540
TLYLQMNSLR AEDTAVYYCA ARDSGVGYYS RAQWYDYWGQ GTLVTVSS               588

SEQ ID NO: 310          moltype = AA  length = 218
FEATURE                 Location/Qualifiers
CHAIN                   1..218
                        note = anti-PDL1 LC1 (HCC light chain)
source                  1..218
                        mol_type = protein
                        organism = synthetic construct
SEQUENCE: 310
QSVVTQPPPV SGAPGQRVTI SCTGSSSNVG AGYDVHWYQQ LPGTAPKLLI YGNSQRSSGV    60
PDRFSGSKSG TSASLAITGL QAEDEADYYC QTYDSSGSAR VVFGGGTKLT VLGQPKAAPS   120
VTLFPPSSEE LQANKATLVC LISDFYPGAV TVAWKADSSP VKAGVETTTP SKQSNNKYAA   180
SSYLSLTPEQ WKSHKSYSCQ VTHEGSTVEK TVAPTECS                          218

SEQ ID NO: 311          moltype = AA  length = 451
FEATURE                 Location/Qualifiers
CHAIN                   1..451
                        note = anti-PDL1 HC1 (LCC heavy chain)
source                  1..451
                        mol_type = protein
                        organism = synthetic construct
SEQUENCE: 311
QVQLVQSGAE VKKPGSSVKV SCKASGGTFS SYPISWVRQA PGQGLEWMGR IIPILGIANY    60
AQKFQGRVTI TADKSTSTAY MELSSLRSED TAVYYCARSR PGYAFGAFDI WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                 451

SEQ ID NO: 312          moltype = AA  length = 355
FEATURE                 Location/Qualifiers
CHAIN                   1..355
                        note = anti-PDL1 LC-Linker-2A3 (LCC light chain)
source                  1..355
                        mol_type = protein
                        organism = synthetic construct
SEQUENCE: 312
QSVVTQPPPV SGAPGQRVTI SCTGSSSNVG AGYDVHWYQQ LPGTAPKLLI YGNSQRSSGV    60
PDRFSGSKSG TSASLAITGL QAEDEADYYC QTYDSSGSAR VVFGGGTKLT VLGQPKAAPS   120
VTLFPPSSEE LQANKATLVC LISDFYPGAV TVAWKADSSP VKAGVETTTP SKQSNNKYAA   180
```

```
SSYLSLTPEQ WKSHKSYSCQ VTHEGSTVEK TVAPTECSGS GGSGGSGGSG QVQLVESGGG    240
VVQPGRSLRL SCAASGGSFS SYPMGWFRQA PGKERESVAA ISSDMRFTYY ADSVKGRFTI    300
SRDNSKNTLY LQMNSLRAED TAVYYCAARD SGVGYYSRAQ WYDYWGQGTL VTVSS         355

SEQ ID NO: 313              moltype = AA   length = 588
FEATURE                     Location/Qualifiers
CHAIN                       1..588
                            note = 2A3-Linker-anti-PDL1 HC (HCN heavy chain)
source                      1..588
                            mol_type = protein
                            organism = synthetic construct
SEQUENCE: 313
QVQLVESGGG VVQPGRSLRL SCAASGGSFS SYPMGWFRQA PGKERESVAA ISSDMRFTYY    60
ADSVKGRFTI SRDNSKNTLY LQMNSLRAED TAVYYCAARD SGVGYYSRAQ WYDYWGQGTL    120
VTVSSGSGGS GGSGGSGQVQ LVQSGAEVKK PGSSVKVSCK ASGGTFSSYP ISWVRQAPGQ    180
GLEWMGRIIP ILGIANYAQK FQGRVTITAD KSTSTAYMEL SSLRSEDTAV YYCARSRPGY    240
AFGAFDIWGQ GTLVTVSSAS TKGPSVFPLA PSSKSTSGGT AALGCLVKDY FPEPVTVSWN    300
SGALTSGVHT FPAVLQSSGL YSLSSVVTVP SSSLGTQTYI CNVNHKPSNT KVDKKVEPKS    360
CDKTHTCPPC PAPELLGGPS VFLFPPKPKD TLMISRTPEV TCVVVDVSHE DPEVKFNWYV    420
DGVEVHNAKT KPREEQYNST YRVVSVLTVL HQDWLNGKEY KCKVSNKALP APIEKTISKA    480
KGQPREPQVY TLPPSREEMT KNQVSLTCLV KGFYPSDIAV EWESNGQPEN NYKTTPPVLD    540
SDGSFFLYSK LTVDKSRWQQ GNVFSCSVMH EALHNHYTQK SLSLSPGK                 588

SEQ ID NO: 314              moltype = AA   length = 218
FEATURE                     Location/Qualifiers
CHAIN                       1..218
                            note = anti-PDL1 LC2 (HCN light chain)
source                      1..218
                            mol_type = protein
                            organism = synthetic construct
SEQUENCE: 314
QSVVTQPPPV SGAPGQRVTI SCTGSSSNVG AGYDVHWYQQ LPGTAPKLLI YGNSQRSSGV    60
PDRFSGSKSG TSASLAITGL QAEDEADYYC QTYDSSGSAR VVFGGGTKLT VLGQPKAAPS    120
VTLFPPSSEE LQANKATLVC LISDFYPGAV TVAWKADSSP VKAGVETTTP SKQSNNKYAA    180
SSYLSLTPEQ WKSHKSYSCQ VTHEGSTVEK TVAPTECS                            218

SEQ ID NO: 315              moltype = AA   length = 451
FEATURE                     Location/Qualifiers
CHAIN                       1..451
                            note = anti-PDL1 HC2 (LCN heavy chain)
source                      1..451
                            mol_type = protein
                            organism = synthetic construct
SEQUENCE: 315
QVQLVQSGAE VKKPGSSVKV SCKASGGTFS SYPISWVRQA PGQGLEWMGR IIPILGIANY    60
AQKFQGRVTI TADKSTSTAY MELSSLRSED TAVYYCARSR PGYAFGAFDI WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPELLG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRE    360
EMTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                   451

SEQ ID NO: 316              moltype = AA   length = 355
FEATURE                     Location/Qualifiers
CHAIN                       1..355
                            note = 2A3-Linker-anti-PDL1 LC (LCN light chain)
source                      1..355
                            mol_type = protein
                            organism = synthetic construct
SEQUENCE: 316
QVQLVESGGG VVQPGRSLRL SCAASGGSFS SYPMGWFRQA PGKERESVAA ISSDMRFTYY    60
ADSVKGRFTI SRDNSKNTLY LQMNSLRAED TAVYYCAARD SGVGYYSRAQ WYDYWGQGTL    120
VTVSSGSGGS GGSGGSGQSV VTQPPPVSGA PGQRVTISCT GSSSNVGAGY DVHWYQQLPG    180
TAPKLLIYGN SQRSSGVPDR FSGSKSGTSA SLAITGLQAE DEADYYCQTY DSSGSARVVF    240
GGGTKLTVLG QPKAAPSVTL FPPSSEELQA NKATLVCLIS DFYPGAVTVA WKADSSPVKA    300
GVETTTPSKQ SNNKYAASSY LSLTPEQWKS HKSYSCQVTH EGSTVEKTVA PTECS         355

SEQ ID NO: 317              moltype = AA   length = 244
FEATURE                     Location/Qualifiers
CHAIN                       1..244
                            note = Human TIGIT polypeptide
source                      1..244
                            mol_type = protein
                            organism = synthetic construct
SEQUENCE: 317
MRWCLLLIWA QGLRQAPLAS GMMTGTIETT GNISAEKGGS IILQCHLSST TAQVTQVNWE    60
QQDQLLAICN ADLGWHISPS FKDRVAPGPG LGLTLQSLTV NDTGEYFCIY HTYPDGTYTG    120
RIFLEVLESS VAEHGARFQI PLLGAMAATL VVICTAVIVV VALTRKKKAL RIHSVEGDLR    180
```

```
-continued

RKSAGQEEWS PSAPSPPGSC VQAEAAPAGL CGEQRGEDCA ELHDYFNVLS YRSLGNCSFF    240
TETG                                                                244

SEQ ID NO: 318          moltype = AA  length = 138
FEATURE                 Location/Qualifiers
DOMAIN                  1..138
                        note = ECD of Human TIGIT polypeptide
source                  1..138
                        mol_type = protein
                        organism = synthetic construct
SEQUENCE: 318
MRWCLLLIWA QGLRQAPLAS GMMTGTIETT GNISAEKGGS IILQCHLSST TAQVTQVNWE    60
QQDQLLAICN ADLGWHISPS FKDRVAPGPG LGLTLQSLTV NDTGEYFCIY HTYPDGTYTG    120
RIFLEVLESS VAEHGARF                                                  138
```